US010406163B2

(12) United States Patent
Edge et al.

(10) Patent No.: US 10,406,163 B2
(45) Date of Patent: Sep. 10, 2019

(54) COMPOUNDS THAT ENHANCE ATOH1 EXPRESSION

(71) Applicants: Massachusetts Eye & Ear Infirmary, Boston, MA (US); The Brigham & Women s Hospital, Inc., Boston, MA (US)

(72) Inventors: Albert Edge, Brookline, MA (US); Sang-Jun Jeon, Seoul (KP); Kathleen Seyb, Allston, MA (US); Marcie Glicksman, Winchester, MA (US); Lixin Qiao, Tewksbury, MA (US); Gregory D. Cuny, Houston, TX (US)

(73) Assignees: Massachusetts Eye & Ear Infirmary, Boston, MA (US); The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/240,303

(22) Filed: Aug. 18, 2016

(65) Prior Publication Data

US 2017/0095481 A1 Apr. 6, 2017

Related U.S. Application Data

(60) Continuation of application No. 14/511,911, filed on Oct. 10, 2014, now Pat. No. 9,433,610, which is a
(Continued)

(51) Int. Cl.
| | |
|---|---|
| *A61K 31/5377* | (2006.01) |
| *A61K 31/341* | (2006.01) |
| *A61K 31/343* | (2006.01) |
| *A61K 31/381* | (2006.01) |
| *A61K 31/415* | (2006.01) |
| *A61K 31/4184* | (2006.01) |
| *A61K 31/423* | (2006.01) |
| *A61K 31/4245* | (2006.01) |
| *A61K 31/426* | (2006.01) |
| *A61K 31/428* | (2006.01) |
| *A61K 9/00* | (2006.01) |
| *A61K 31/353* | (2006.01) |
| *A61K 31/4436* | (2006.01) |
| *A61K 31/496* | (2006.01) |
| *A61K 31/498* | (2006.01) |
| *A61K 31/517* | (2006.01) |
| *A61K 31/519* | (2006.01) |
| *A61K 35/28* | (2015.01) |
| *A61K 35/545* | (2015.01) |
| *A61K 31/352* | (2006.01) |
| *A61K 31/404* | (2006.01) |
| *A61K 31/4155* | (2006.01) |
| *A61K 31/4192* | (2006.01) |
| *A61K 31/4365* | (2006.01) |
| *A61K 31/437* | (2006.01) |
| *A61K 31/44* | (2006.01) |
| *A61K 31/4439* | (2006.01) |

(52) U.S. Cl.
CPC ........ *A61K 31/5377* (2013.01); *A61K 9/0046* (2013.01); *A61K 31/341* (2013.01); *A61K 31/343* (2013.01); *A61K 31/352* (2013.01); *A61K 31/353* (2013.01); *A61K 31/381* (2013.01); *A61K 31/404* (2013.01); *A61K 31/415* (2013.01); *A61K 31/4155* (2013.01); *A61K 31/4184* (2013.01); *A61K 31/4192* (2013.01); *A61K 31/423* (2013.01); *A61K 31/426* (2013.01); *A61K 31/428* (2013.01); *A61K 31/4245* (2013.01); *A61K 31/437* (2013.01); *A61K 31/4365* (2013.01); *A61K 31/44* (2013.01); *A61K 31/4436* (2013.01); *A61K 31/4439* (2013.01); *A61K 31/496* (2013.01); *A61K 31/498* (2013.01); *A61K 31/517* (2013.01); *A61K 31/519* (2013.01); *A61K 35/28* (2013.01); *A61K 35/545* (2013.01)

(58) Field of Classification Search
None
See application file for complete search history.

(56) References Cited

U.S. PATENT DOCUMENTS

| | | |
|---|---|---|
| 3,429,890 A | 2/1969 | Sletzinger et al. |
| 3,686,110 A | 8/1972 | Fisher et al. |
| | (Continued) | |

FOREIGN PATENT DOCUMENTS

| | | |
|---|---|---|
| CN | 1537136 A | 10/2004 |
| JP | 2004-513882 | 5/2004 |
| | (Continued) | |

OTHER PUBLICATIONS

Anderson (Chem and Biol 10:787-797, 2003).*
(Continued)

*Primary Examiner* — Craig D Ricci
(74) *Attorney, Agent, or Firm* — Fish & Richardson P.C.

(57) ABSTRACT

This invention generally provides compounds, pharmaceutical compositions, and methods for their use, which include methods that result in increased expression in an Atoh1 gene (e.g., Hath1) in a biological cell. More specifically, the invention relates to the treatment of diseases and/or disorders that would benefit from increased Atoh1 expression, e.g., a hearing impairment or imbalance disorder associated with a loss of auditory hair cells, or a disorder associated with abnormal cellular proliferation.

3 Claims, 87 Drawing Sheets
Specification includes a Sequence Listing.

Related U.S. Application Data continuation of application No. 13/454,702, filed on Apr. 24, 2012, now Pat. No. 8,859,597, which is a division of application No. 12/368,173, filed on Feb. 9, 2009, now Pat. No. 8,188,131.

(60) Provisional application No. 61/027,032, filed on Feb. 7, 2008.

(56) References Cited

U.S. PATENT DOCUMENTS

| | | | |
|---|---|---|---|
| 3,743,738 | A | 7/1973 | Hoff et al. |
| 5,140,034 | A | 8/1992 | Baker et al. |
| 5,157,046 | A | 10/1992 | Van Wauwe et al. |
| 5,342,957 | A | 8/1994 | Van Wauwe et al. |
| 5,420,147 | A | 5/1995 | Van Wauwe et al. |
| 5,500,435 | A | 3/1996 | Van Wauwe et al. |
| 5,576,322 | A | 11/1996 | Takase et al. |
| 5,693,652 | A | 12/1997 | Takase et al. |
| 5,780,287 | A | 7/1998 | Kraus et al. |
| 5,801,180 | A | 9/1998 | Takase et al. |
| 6,025,379 | A | 2/2000 | Iyengar et al. |
| 6,111,903 | A | 8/2000 | Isaksson et al. |
| 6,339,782 | B1 | 1/2002 | Gerard et al. |
| 6,855,714 | B2 | 2/2005 | Blume et al. |
| 8,188,131 | B2 | 5/2012 | Edge et al. |
| 8,859,597 | B2 | 10/2014 | Edge et al. |
| 2002/0192665 | A1 | 12/2002 | Zoghbi et al. |
| 2003/0229065 | A1 | 12/2003 | Levy et al. |
| 2004/0106553 | A1 | 6/2004 | Alekshun et al. |
| 2004/0127536 | A1 | 7/2004 | Bhagwat et al. |
| 2004/0166091 | A1 | 8/2004 | Brough |
| 2004/0204461 | A1 | 10/2004 | Karp et al. |
| 2005/0124678 | A1 | 6/2005 | Levy et al. |
| 2006/0160799 | A1 | 7/2006 | Alekshun et al. |
| 2007/0021386 | A1 | 1/2007 | Mjalli et al. |
| 2007/0043043 | A1 | 2/2007 | Chen et al. |
| 2007/0142394 | A1 | 6/2007 | Solomon et al. |
| 2007/0167435 | A1 | 7/2007 | Mutahi et al. |
| 2007/0213347 | A1 | 9/2007 | Mjalli et al. |
| 2009/0005344 | A1 | 1/2009 | Burns et al. |
| 2009/0131401 | A1 | 5/2009 | Levy et al. |
| 2009/0197889 | A1 | 8/2009 | Winfield |

FOREIGN PATENT DOCUMENTS

| | | |
|---|---|---|
| JP | 2004-515496 | 5/2004 |
| JP | 2005-504014 | 2/2005 |
| JP | 2006-117536 | 5/2006 |
| JP | 2006-143746 | 6/2006 |
| JP | 2006-518741 | 8/2006 |
| JP | 2006-522826 | 10/2006 |
| JP | 2006-523721 | 10/2006 |
| WO | WO 1996/019991 | 7/1996 |
| WO | 2001/12627 | 2/2001 |
| WO | WO 0210137 | 2/2002 |
| WO | WO 2002/046168 | 6/2002 |
| WO | WO 02100826 | 12/2002 |
| WO | 2004/076626 | 9/2004 |
| WO | 2004/091502 | 10/2004 |
| WO | WO 2006/076009 | 7/2006 |
| WO | 2007/019416 | 2/2007 |
| WO | WO 2008/056120 | 5/2008 |
| WO | WO 2009/005551 | 1/2009 |

OTHER PUBLICATIONS

Thiel (Nature Biotechnol 2:513-519, 2004).*
Isaacson et al (Am Fam Physician 68:1125-1132, 2003).*
Murphy et al (Indian Drugs 22(5):247-251, 1986—based on the attached STN Summary (Accession No. 1986:129832)).*
Ahluwalia et al (Indian J Chemistry, Section B: Organic Chemistry including Medicinal Chemistry 28B(2):150-153, 1989—based on the attached STN Summary (Accession No. 1990:20958).*
Kidd III et al (Gerentology 58:490-496, 2012) (Year: 2012).*
Ali et al., "Tumor Regression Induced by Intratumor Therapy With a Disabled Infectious Single Cycle (Disc) Herpes Simplex Virus (Hsv) Vector, Disc/Hsv/Murine Granulocyte-Macrophage Colony-Stimulating Factor, Correlates With Antigen-Specific Adaptive Immunity," J. Immunol., 168(7):3512-3519 (2002).
Atar et al., "Therapeutics of Hearing Loss: Expectations Vs Reality," Drug Discov Today, 10(19):1323-1330 (2005).
Chen et al., "The Human Fetal Cochlea Can Be a Source for Auditory Progenitors/Stem Cells Isolation", Hearing Research, 233:23-29 (2007).
Database Pubchem Compound, Bionet1_000639 (2005).
Database Pubchem Compound, Bionet1_000679 (2005).
Drug Design Methodologies, "The Biochemistry of Drugs," Http://Www.Newdrugdesign.Com/Rachel_Theory_02.Html (2002).
Gardiner et al., "Synthesis of 1-Alkoxy-2-Alkyl-Benzimidazoles From 2-Nitroanilines via Tandem N-Alkylation-Cyclization-0-Alkylation", Tetrahedron, 51:4101-4110 (1995).
Gardiner et al., "Synthesis of Novel 2,2- and 1,1-Linked Dimeric 'Head-To-Head' N-Alkoxybenzimidazoles", Tetrahedron Letters, vol. 44, (2003), pp. 511-513.
Ito et al., "A medium-term rat liver bioassay for rapid in vivo detection of carcinogenic potential of chemicals," Cancer Sci., 94(1):3-8 (2003).
Izumikawa et al., "Auditory hair cell replacement and hearing improvement by Atoh1 gene therapy in deaf mammals," Nat. Med., 11(3):271-276 (2005).
Kokare et al., "Design, Synthesis and Utilization of a Novel Coupling Reagent for the Preparation of 0-Alkyl Hydroxamic Acids", Tetrahedron Letters, 48:4437-4440 (2007).
Leow et al., "Hath1, Down-Regulated in Colon Adenocarcinomas, Inhibits Proliferation and Tumorigenesis of Colon Cancer Cells," Cancer Res., 64(17):6050-6057 (2004).
Li et al, "Pluripotent Stem Cells From the Adult Mouse Inner Ear," Nat. Med., 9(10):1293-1299 (2003).
Medvedeva et al., Khimiya Geterotsiklicheskikh Soedinenii, vol. 2, (1979), 9 Pages, and Translation of Article by Park Ip Translations Dated Jul. 25, 2011, Article Entitled "Behaviour of N-Alkoxybenzimidazoles Towards Nucleophilic Reagents. Some Attempts to Synthesize N-Oxy-2-Aminobenzimidazoles", Academy of Science of Latvian Ssr, Chemistry of Heterocyclic Compounds, (1979), 22 Pages.
Office Action issued in Australian Patent Application No. 2009212135 dated Sep. 3, 2013.
Office Action issued in Chinese Patent Application No. 200980121908.5 dated May 31, 2012.
Office Action issued in European Patent Application No. 09708566.6 dated Jun. 28, 2012.
Office Action issued in Japanese Patent Application No. 2010-546093 dated Jul. 2, 2013.
Partial European Search Report issued in EP13182379 dated Mar. 11, 2014 (7 pages).
Sanchez et al., "Mechanistic evidence for a ring-opening pathway in the Pd-catalyzed direct arylation of benzoxazoles," J. Am. Chem. Soc., 129(18):5824-5825 (2007).
Shi et al., "Antitumor benzothiazoles. 3. Synthesis of 2-(4-aminophenyl)benzothiazoles and evaluation of their activities against breast cancer cell lines in vitro and in vivo," J. Med. Chem., 39(17):3375-3384 (1996).
Yamamoto et al., "Inhibition of Notch/Rbp-J Signaling Induces Hair Cell Formation in Neonate Mouse Cochleas," J. Mol. Med., 84(1):37-45 (Jan. 2006).
Decision to Grant in Japanese Application No. 2015-099316, dated Aug. 1, 2017, 13 pages (with English translation).

* cited by examiner

Note: hydrogen atoms to complete valance have been omitted from C, N and O

MEEI-0069961

MEEI-0004116

MEEI-0072720

MEEI-0063182

MEEI-0061401

Note: hydrogen atoms to complete valance have been omitted from C, N and O

MEEI-0110644

MEEI-0064286

MEEI-0039073

MEEI-0105343

MEEI-0122949

Note: hydrogen atoms to complete valance have been omitted from C, N and O

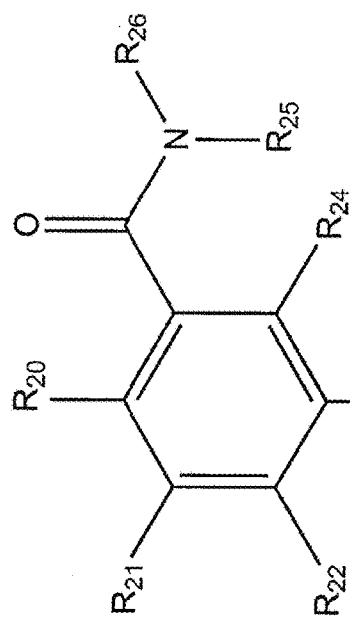
FIG. 2A
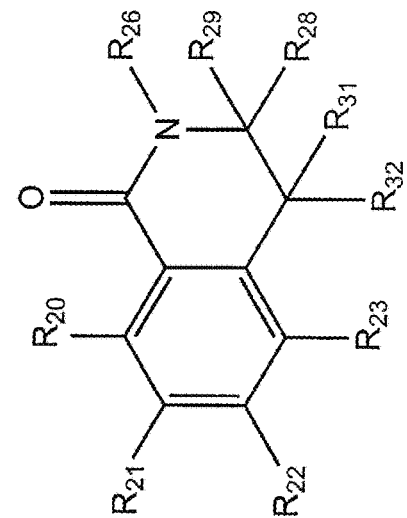
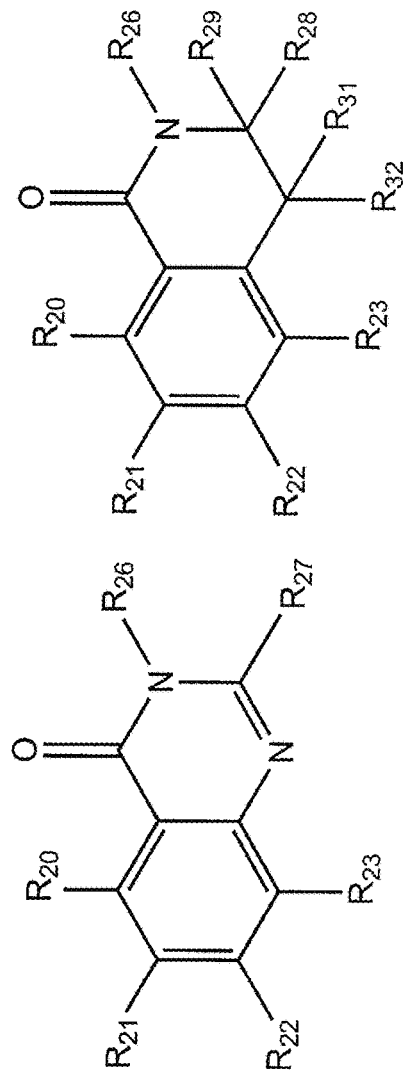
FIG. 2D
FIG. 2C
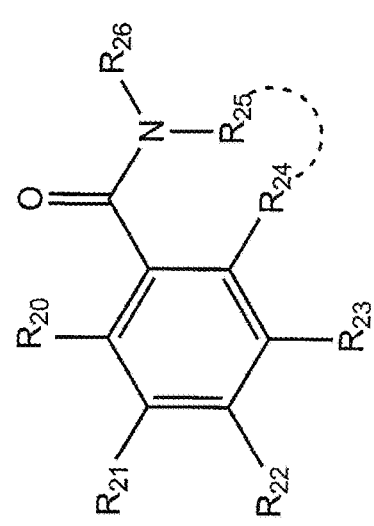
FIG. 2B

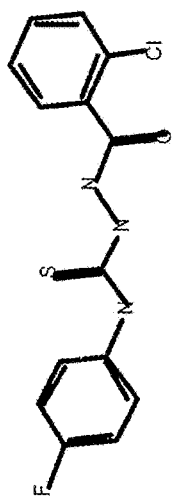
MEEI-0005186
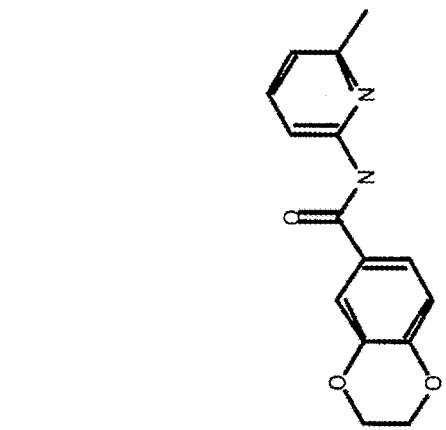
MEEI-0034360
MEEI-0029278
FIG. 2G
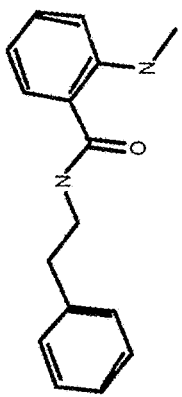
MEEI-0007991
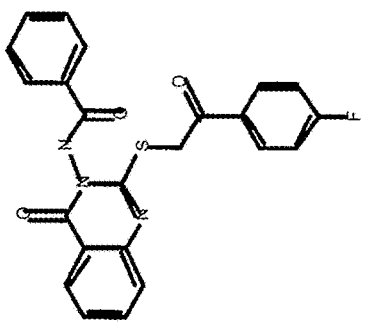
MEEI-0036187
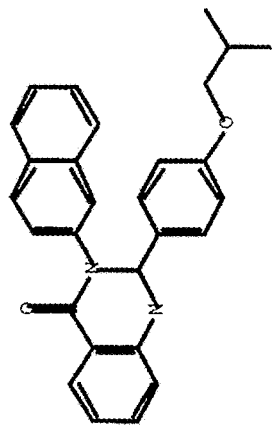
Note: hydrogen atoms to complete valance have been omitted from C, N and O

MEEI-0060729

MEEI-0104765

MEEI-0065665

MEEI-0061566

MEEI-0066008

Note: hydrogen atoms to complete valance have been omitted from C, N and O

MEEI-0130665

MEEI-0110352

Note: hydrogen atoms to complete valance have been omitted from C, N and O

MEEI-0007994

MEEI-0051092

MEEI-0062030

MEEI-0008545

MEEI-0063375

Note: hydrogen atoms to complete valance have been omitted from C, N and O

Note: hydrogen atoms to complete valance have been omitted from C, N and O

MEEI-0079642

MEEI-0079810

MEEI-0075627

MEEI-0067246

MEEI-0104904

MEEI-0099289

Note: hydrogen atoms to complete valance have been omitted from C, N and O

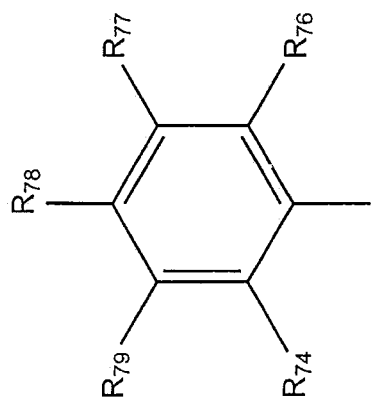
FIG. 4A
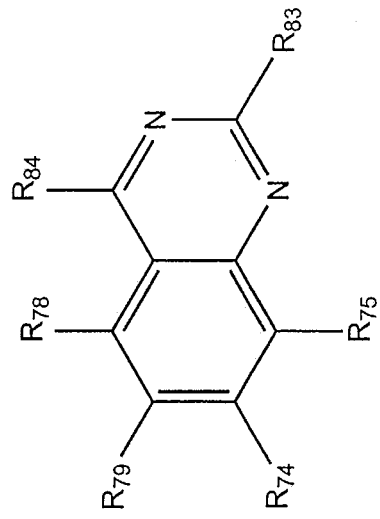
FIG. 4D
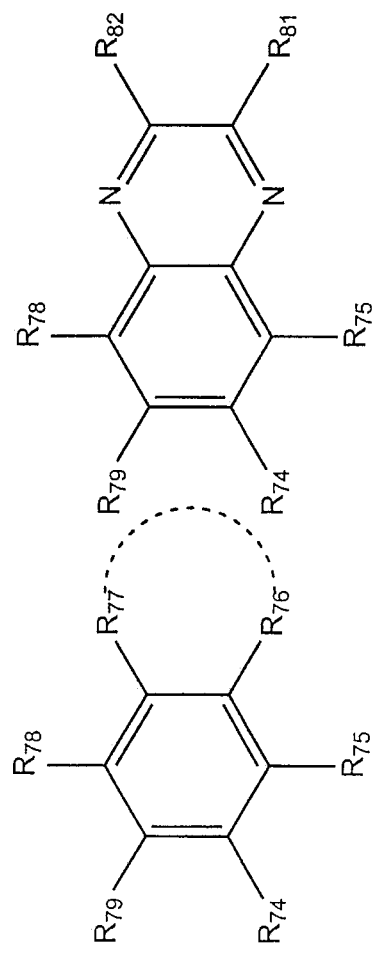
FIG. 4C
FIG. 4B

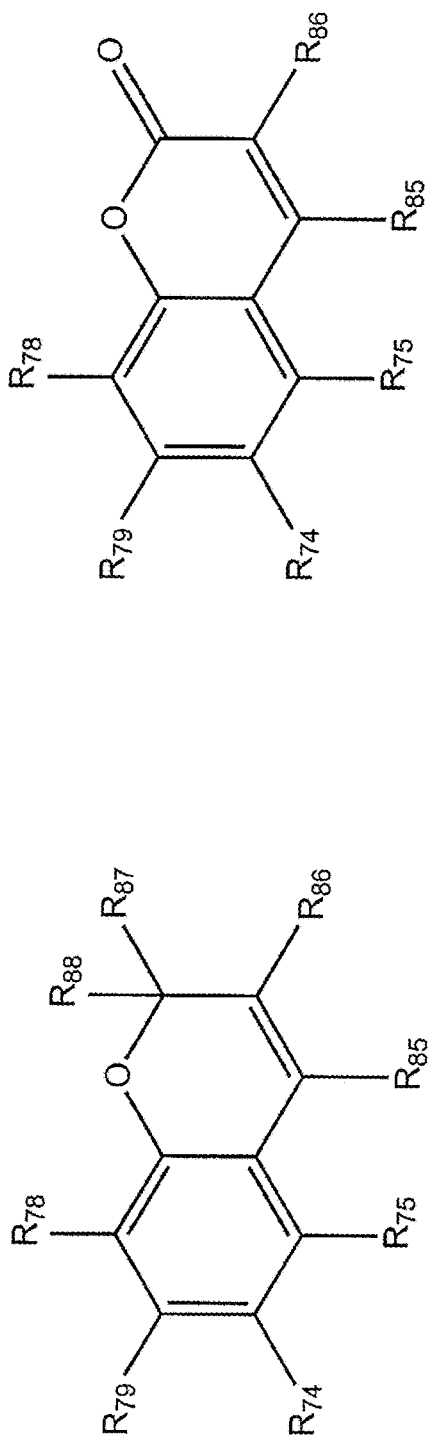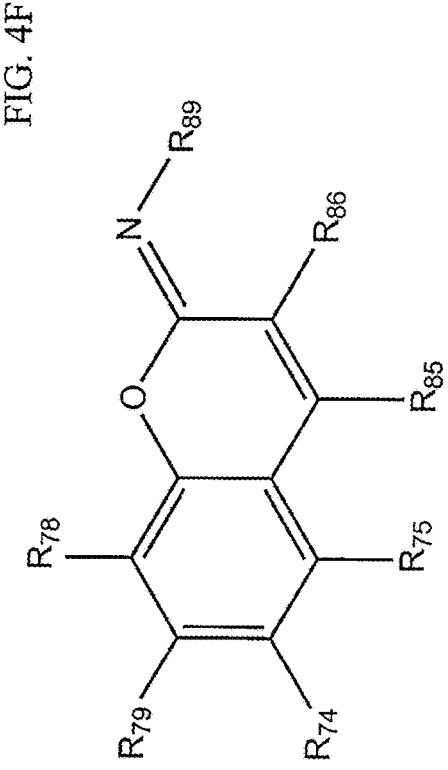
FIG. 4F
FIG. 4G
FIG. 4E

MEEI-0045061

MEEI-0064382

MEEI-0000928

MEEI-0063508

Note: hydrogen atoms to complete valance have been omitted from C, N and O

MEEI-0076627

MEEI-0091818

MEEI-0067053

Note: hydrogen atoms to complete valance have been omitted from C, N and O

MEEI-0072253

MEEI-0105777

MEEI-0070886

MEEI-0072156

Note: hydrogen atoms to complete valance have been omitted from C, N and O

Note: hydrogen atoms to complete valance have been omitted from C, N and O

MEEI-0029300

MEEI-0047659

MEEI-0010539

MEEI-0059563

MEEI-0050095

Note: hydrogen atoms to complete valance have been omitted from C, N and O

Note: hydrogen atoms to complete valance have been omitted from C, N and O

MEEI-0068577

MEEI-0070871

MEEI-0068578

MEEI-0078448

MEEI-0072096

Note: hydrogen atoms to complete valance have been omitted from C, N and O

MEEI-0079983

MEEI-0103014

MEEI-0080773

MEEI-0087336

MEEI-0103978

Note: hydrogen atoms to complete valance have been omitted from C, N and O

Note: hydrogen atoms to complete valance have been omitted from C, N and O

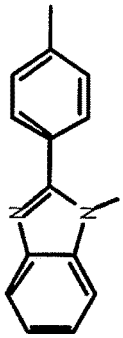 MEEI-00000489
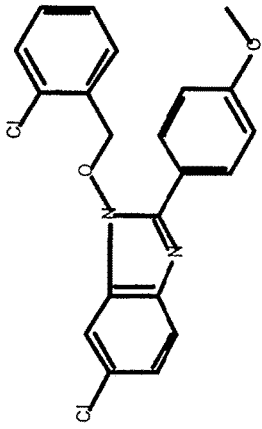 MEEI-00000550
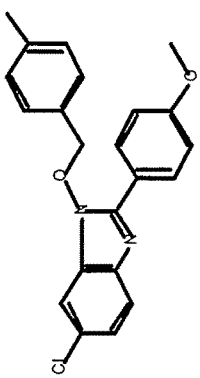 MEEI-00000553
FIG. 6U
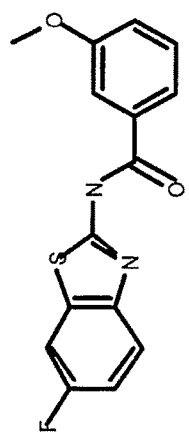 MEEI-01107060
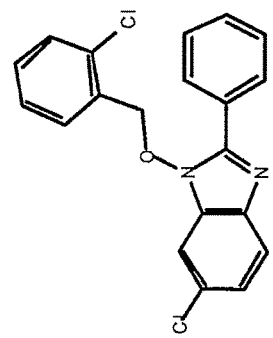 MEEI-00000540
Note: hydrogen atoms to complete valance have been omitted from C, N and O

MEEI-00000557

MEEI-00000554

MEEI-00000477

MEEI-00000571

Note: hydrogen atoms to complete valance have been omitted from C, N and O

MEEI-0070367

MEEI-0059547

MEEI-0072092

MEEI-0066751

MEEI-0067108

Note: hydrogen atoms to complete valance have been omitted from C, N and O

Note: hydrogen atoms to complete valance have been omitted from C, N and O

Note: hydrogen atoms to complete valance have been omitted from C, N and O

COMPOUNDS THAT ENHANCE ATOH1 EXPRESSION

CLAIM OF PRIORITY

This application is a continuation of U.S. patent application Ser. No. 14/511,911, filed on Oct. 10, 2014, which is a continuation of U.S. patent application Ser. No. 13/454,702, filed Apr. 24, 2012, now U.S. Pat. No. 8,859,597, which is a divisional of U.S. patent application Ser. No. 12/368,173, filed Feb. 9, 2009, now U.S. Pat. No. 8,188,131, which claims the benefit under 35 U.S.C. § 119(e) of U.S. Provisional Patent Application Ser. No. 61/027,032, filed on Feb. 7, 2008, the entire contents of each of these prior filed applications is incorporated herein by reference.

TECHNICAL FIELD

This invention generally provides compounds, pharmaceutical compositions, and methods for their use, which include methods that result in increased expression in an Atoh1 gene (e.g., Hath1) in a biological cell. More specifically, the invention relates to the treatment of diseases and/or disorders that would benefit from increased Atoh1 expression.

BACKGROUND

One of the most common types of hearing loss is sensorineural deafness which is caused by the loss of hair cells, sensory cells in the cochlea that are responsible for transduction of sound into an electrical signal. The human inner ear contains only about 15,000 hair cells per cochlea at birth, and, although these cells can be lost as a result of various genetic or environmental factors, the lost or damaged cells cannot be replaced. However, overexpression of the transcription factor, Atoh1, can induce the differentiation of hair cells from epithelial cells in the sensory organ of the cochlea, the organ of Corti ((Zheng and Gao, Nat Neurosci 2000; 3:580-586; Kawamoto et al., J Neurosci 2003; 23:4395-4400; Gubbels et al., Nature 2008; 455:537-541). Atoh-1 expression also plays a role in driving other cells, e.g., intestinal cells, into a differentiated state (Aragaki et al., Biochem. Biophys. Res. Comm. 2008 April; 368(4):923-929), and overexpression of Atoh-1 reduces proliferation of colon cancer cells (Leow et al., Ann N Y Acad Sci. 2005 November; 1059:174-83).

SUMMARY

The present invention features the compounds described herein, and compositions containing them. For example, the present invention features a pharmaceutical composition including one or more compounds capable of increasing Atoh1 expression in a cell, as disclosed herein, or a pharmaceutically acceptable salt thereof, and a pharmaceutically acceptable carrier. The compositions can be formulated for administration to a patient. Thus, pharmaceutical compositions are within the present invention, as are concentrated stocks and compositions suitable for application to cells or tissues maintained in tissue culture, and methods of use of the compounds and compositions.

Where the composition is pharmaceutically acceptable (i.e., non-toxic), it can include a pharmaceutically acceptable carrier such as a buffer (e.g., a phosphate buffer), an amino acid, urea, an alcohol, ascorbic acid, a phospholipid, a polypeptide, EDTA, sodium chloride (e.g., normal saline), a liposome, mannitol, sorbitol, water, glycerol, or a combination thereof. Preservatives and dyes may also be included. In some embodiments, the composition is sterile.

The compounds described herein can be used to alter the characteristics of a cell maintained in cell culture (e.g., in vitro), and the compounds and/or the treated cells can be administered to a patient in need of treatment. For example, a method of treating a patient can be carried out by a method including the steps of (a) selecting a patient in need of treatment, and (b) administering to the patient a therapeutically effective amount of a compound described herein (e.g., a compound formulated for administration). The pharmaceutical composition can be administered systemically (e.g., orally or parenterally). More specifically, the composition can be administered intravenously, intramuscularly, intraperitoneally, sublingually, rectally, vaginally, transdermally, subcutaneously, or by inhalation. When administered orally, the composition can be formulated as a tablet (e.g., a compressed tablet), pill, syrup, suspension, emulsion, or capsule. When administered parenterally, the composition can be formulated as a lozenge, drop (e.g., ear drops), solution, enema, suppository, or spray. The compositions can also be administered using a catheter or pump.

The present compositions can also be administered locally (e.g., to the ear or other site where cellular differentiation and/or Atoh1 expression is desired). For administration to the ear, the pharmaceutical composition can be administered by injection into the luminae of the cochlea, into the auditory nerve trunk in the internal auditory meatus, and/or into the scala tympani. More specifically, the pharmaceutical composition can be administered by intratympanic injection, application to (e.g., injection into) the outer, middle, or inner ear, an injection through the round window of the ear, or an injection through the cochlear capsule. The pharmaceutical composition can also be administered to the patient (e.g., locally to the middle and/or inner ear) using a catheter or pump.

The patient in need of treatment can have, or have a risk of developing, a hearing impairment or imbalance disorder associated with loss of auditory hair cells. While the invention is not limited to compounds that work by any particular mechanism, the present compositions may be used where the treatment effectively increases the expression of an Atoh1 gene in cells in the patient's inner ear (or other target tissue (e.g., a tumor)) or effectively increases the number of cells in the patient's inner ear that have characteristics of auditory hair cells. The auditory hair cells can be outer or inner auditory hair cells.

The patient in need of treatment can also have, or be at risk of developing, cancer. The cancer can be a gastrointestinal cancer (e.g., cancer of the esophagus, gallbladder, liver, pancreas, stomach, small intestine, large intestine, colon, or rectum).

The patient in need of treatment can also have, or be at risk of developing, cerebellar granule neuron deficiencies, joint disease, and/or osteoarthritis.

In one embodiment, the method of treating a patient who has a hearing impairment or imbalance disorder can be carried out by a method that includes the steps of: (a) optionally selecting a patient in need of treatment, (b) obtaining a population of cells capable of differentiating into auditory hair cells, (c) contacting the population of cells in vitro with an effective amount of one or more of the compounds described herein for a time sufficient to increase the number cells in the population that have characteristics of a differentiated auditory hair cell, and (d) administering the population of cells, or a subset thereof (e.g., a subset of more highly differentiated cells), to the patient's ear. The population of cells capable of differentiating into auditory hair cells can include stem cells, induced pluripotent stem (iPS) cells, progenitor cells, support cells, Deiters' cells, pillar cells, inner phalangeal cells, tectal cells, Hensen's cells, and germ cells. The stem cells can be adult stem cells (e.g., stem cells derived from the inner ear, bone marrow, mesenchyme, skin, fat, liver, muscle, or blood), embryonic stem cells, or stem cells obtained from a placenta or umbilical cord. Like the stem cells, the progenitor cells can be derived from the inner ear, bone marrow, mesenchyme, skin, fat, liver, muscle, or blood. Administering the population of cells can be accomplished by (a) injecting the cells into the luminae of the cochlea, into the auditory nerve trunk in the internal auditory meatus, or into the scala tympani or (b) implanting the cells within a cochlear implant. In any method where the patient is treated with cells, they may, in addition, be treated with one or more of the present compounds, and vice-versa. The pharmaceutical compositions can be administered systemically or locally, as described above.

Other methods of the invention include methods of increasing the number of cells with the characteristics of auditory hair cells in a population of cells in vitro. These methods can be carried out by obtaining a population of cells capable of differentiating into auditory hair cells, contacting the population of cells in vitro (e.g., in cell culture) with an effective amount of one or more of the compounds described herein for a time sufficient to increase the number of cells with the characteristics of auditory hair cells in the population of cells. The population of cells capable of differentiating into hair cells includes cells selected from the group consisting of stem cells, iPS cells, inner ear stem cells, adult stem cells, bone marrow derived stem cells, embryonic stem cells, mesenchymal stem cells, skin stem cells, fat derived stem cells, progenitor cells, inner ear progenitor cells, support cells, Deiters' cells, pillar cells, inner phalangeal cells, tectal cells, Hensen's cells, and germ cells.

Also within the invention is the use of the compounds described herein as a medicament, and in the manufacture of a medicament for the treatment or prevention of a condition described herein. For example, the medicament can be used in a method for treating or preventing hearing loss or imbalance associated with hair cell loss, or a condition associated with unwanted cellular proliferation. Also within the present invention is the use of the described compounds in the treatment of a condition described herein, e.g., hearing loss or imbalance associated with hear cell loss, or a condition associated with unwanted cellular proliferation. The medicament can be in any form described herein, and can be administered alone or in combination with another treatment or active agent.

Also provided herein are kits (e.g., a kit comprising the pharmaceutical compositions described above with informational material or a kit comprising a compound described herein and informational material). The cells within the kits can be made by the methods described above, and any of the kits can include additional materials such as a device suitable for administration of the pharmaceutical composition or the population of cells, e.g., a sterile flexible cannula that is adapted for insertion into the inner ear of a subject.

Further, the invention encompasses a cell or a population of cells made by the methods described herein.

The present disclosure also includes using one or more of the compounds described herein as a medicament, e.g., that can be used for the treatment of a hearing impairment or imbalance disorder associated with a loss of auditory hair cells and/or a condition associated with abnormal cellular proliferation.

The use of one or more of the compounds described herein for the treatment of a hearing impairment or imbalance disorder associated with a loss of auditory hair cells and/or a disorder associated with abnormal cellular proliferation is also encompassed by the present disclosure.

DEFINITIONS

The term "abnormal proliferation" as used herein is defined as any unwanted hyperproliferation of any type of cell, wherein said cell is not under the constraints of normal cell cycle progression and wherein said proliferation can result in a tumor or any cancerous development.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present invention.

The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome.

Effective amounts of one or more compounds or a pharmaceutical composition for use in the present invention include amounts that promote increased Atoh1 expression, promote complete or partial differentiation of one or more cells to treat a disease that would benefit from increased Atoh1 expression, e.g., prevent or delay the onset, delay the progression, ameliorate the effects of, or generally improve the prognosis of a patient diagnosed with one or more diseases that would benefit from increased Atoh1 expression, e.g., one or more of the diseases described herein. For example, in the treatment of hearing impairment, a compound which improves hearing to any degree or arrests any symptom of hearing impairment would be therapeutically effective. In the treatment of abnormal proliferation of cells, a compound which reduces proliferation would be therapeutically effective. In the treatment of abnormal cell proliferation, a compound which reduces proliferation of the cells, reduces tumor size, reduces metastases, reduces proliferation of blood vessels to said cancer would be therapeutically effective, for example. A therapeutically effective amount of a compound is not required to cure a disease but will provide a treatment for a disease.

The term "patient" is used throughout the specification to describe an animal, human or non-human, to whom treatment according to the methods of the present invention is provided. Veterinary and non-veterinary applications are contemplated. The term includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Typical patients include humans, farm animals, and domestic pets such as cats and dogs.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more subsitutents (e.g., such as those delineated in any definition of $R^a$ described herein). Examples of alkyl groups include without limitation methyl, ethyl, n-propyl, isopropyl, and tert-butyl.

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents (e.g., such as those delineated in any definition of $R^b$ described herein).

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents (e.g., such as those delineated in any definition of $R^c$ described herein). Non-limiting examples of "aralkyl" include benzyl, 2-phenylethyl, and 3-phenylpropyl groups.

The term "heteroaralkyl" refers to an alkyl moiety in which an alkyl hydrogen atom is replaced by a heteroaryl group. One of the carbons of the alkyl moiety serves as the point of attachment of the aralkyl group to another moiety. Heteroaralkyl includes groups in which more than one hydrogen atom on an alkyl moiety has been replaced by a heteroaryl group. Any ring or chain atom can be optionally substituted e.g., by one or more substituents (e.g., such as those delineated in any definition of $R^c$ described herein). Heteroaralkyl can include, for example, 2-pyridylethyl.

The terms "alkoxy" and "haloalkoxy" refer to —O-alkyl and —O-haloalkyl radicals, respectively. The term "phenoxy" refers to an —O-phenyl radical.

The term "heterocyclyl" refers to a fully saturated monocyclic, bicyclic, tricyclic or other polycyclic ring system having one or more (e.g., 1-4) heteroatom ring atoms independently selected from O, N, or S. The heteroatom or ring carbon is the point of attachment of the heterocyclyl substituent to another moiety. Any atom can be optionally substituted, e.g., by one or more substituents (e.g., such as those delineated in any definition of $R^c$ described herein). Heterocyclyl groups can include, e.g., tetrahydrofuryl, tetrahydropyranyl, piperidyl (piperidino), piperazinyl, morpholinyl (morpholino), pyrrolinyl, and pyrrolidinyl.

The term "cycloalkyl" refers to a fully saturated monocyclic, bicyclic, tricyclic, or other polycyclic hydrocarbon groups. Any atom can be optionally substituted, e.g., by one or more substituents (e.g., such as those delineated in any definition of $R^c$ described herein). A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents (e.g., such as those delineated in any definition of $R^c$ described herein). Cycloalkenyl moieties can include, e.g., cyclohexenyl, cyclohexadienyl, or norbornenyl.

The term "aryl" refers to an aromatic monocyclic or bicyclic hydrocarbon ring system, wherein any ring atom can be optionally substituted, e.g., by one or more substituents (e.g., such as those delineated in any definition of $R^d$ described herein). Aryl moieties can include phenyl and naphthyl.

The term "heteroaryl" refers to an aromatic monocyclic or bicyclic hydrocarbon groups having one or more (e.g., 1-6) heteroatom ring atoms independently selected from O, N, or S (and mono and dioxides thereof, e.g., N→O⁻, S(O), SO₂). Any atom can be optionally substituted, e.g., by one or more substituents (e.g., such as those delineated in any definition of $R^d$ described herein). Heteroaryl groups can include pyridyl, thienyl, furyl (furanyl), imidazolyl, isoquinolyl, quinolyl and pyrrolyl.

The descriptor C(O) refers to a carbon atom that is doubly bonded to an oxygen atom. The term "oxo" refers to doubly bonded oxygen, i.e., =O.

The term "substituent" refers to a group "substituted" on, e.g., an alkyl, haloalkyl, cycloalkyl, aralkyl, heteroaralkyl, heterocyclyl, cycloalkenyl, aryl, or heteroaryl group at any atom of that group. In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

Descriptors such as "$C_6$-$C_{10}$ aryl which is optionally substituted with from 1-5 $R^d$" (and the like) is intended to include both an unsubstituted $C_6$-$C_{10}$ aryl group and a $C_6$-$C_{10}$ aryl group that is substituted with from 1-5 $R^d$. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

For ease of exposition, it is also understood that where in this specification (including the claims), a group is defined by "as defined anywhere herein" (or the like), the definitions for that particular group include the first occurring and broadest generic definition as well as any sub-generic and specific definitions delineated anywhere in this specification.

This application is related to U.S. Provisional Application Ser. No. 60/605,746, filed on Aug. 31, 2004, International Application No. PCT/US2005/030714, filed on Aug. 30, 2005, U.S. application Ser. No. 10/989,649, filed on Nov. 15, 2004, U.S. application Ser. No. 11/953,797, filed on Dec. 12, 2007, U.S. application Ser. No. 12/187,543, filed on Aug. 7, 2008, U.S. Provisional Application Ser. No. 60/859,041, filed on Nov. 15, 2006, International Application No. PCT/US2007/084654, filed on Nov. 14, 2007, U.S. application Ser. No. 12/233,017, filed Sep. 18, 2008, and U.S. Provisional Application Ser. No. 60/859,041, filed Nov. 24, 2008, the entire contents of each of which are incorporated herein by reference.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-2F are generalized structures of benzamide compounds or related compounds.

FIGS. 2G-2I are structures of specific benzamide compounds or related compounds.

FIGS. 4A-4G are generalized structures of compounds that include one or more phenyl rings.

FIGS. 7A-7C are generalized structures of pyridine compounds, while

FIGS. 121A and 121B are photographs of untreated cells (A) and cells contacted with compound (Cp) Cp.-0000540 (B). Cell populations that stained positive for the hair cell specific markers Math1-GFP and myosin 7a are indicated by arrows.

DETAILED DESCRIPTION

Figure 1C:
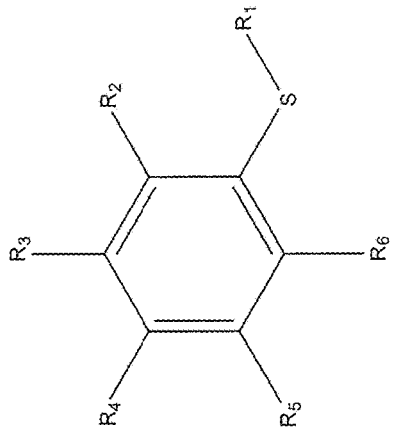
FIGS. 1A-1H are generalized structures of phenolic compounds or derivatives thereof.
Figure 1B:
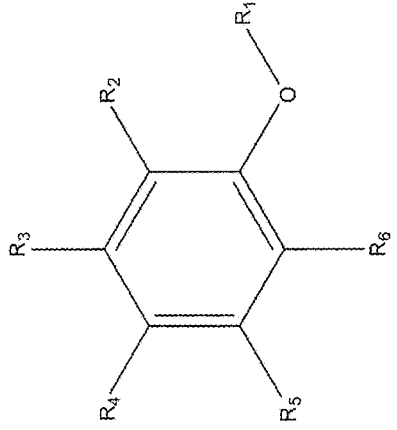

The present invention provides, inter alia, compounds and methods related to compounds and/or pharmaceutical compositions for treating patients for the conditions described herein. While the treatment methods are not limited to those in which particular underlying cellular events occur, the present compounds and compositions may increase the expression of an Atoh1 gene in a subject and/or a cell, thereby causing the cell to differentiate, e.g., into an auditory hair cell.

Atoh-1

Atonal protein homologue 1 (Atoh1 or atonal) is a proneural gene that encodes a basic helix-loop-helix (bHLH) domain-containing protein that seems to play an important role in cell fate determination in the development of the *Drosophila* nervous system (Jarman et al., *Cell*, 73:1307-1321, 1993). Atoh1 is evolutionarily conserved, with homologs identified in *Tribolium castenium* (the red flour beetle), *Fugu rubripes* (puffer fish), chicken (Cath1), mouse (Math1), and human (Hath1) (Ben-Arie et al., *Hum. Mol. Gene.*, 5:1207-1216, 1996). Each of these homologs contain a bHLH domain that is identical in length and have high sequence identity to the Atoh1 bHLH domain. For example, the Hath1 and Math1 genes are almost identical in length. These molecules also have highly similar nucleotide sequences (86% identity) and highly similar bHLH amino acid sequences (89%). The bHLH domain of Cath1 is 97% and 95% identical to the bHLH domain of Hath1 and Math1, respectively. The bHLH of Cath1 is 67% identical to the Atoh1 bHLH domain. In contrast, the bHLH domains of other *Drosophila* encoded proteins share only 40-50% sequence identity.

Each of the mammalian Atoh1 homologs functions as a transcription factor that activates E box (CANNTG (SEQ ID NO: 1)) dependent transcription (Arie et al., Hum. Mol. Genet., 9:1207-1216, 1996; Akazawa et al., J. Biol. Chem., 270:8730-8738, 1995) and functions as a critical positive regulator of cell fate determination in neural tissue and the gastrointestinal (GI) tract (Helms et al., Development, 125: 919-928, 1998; Isaka et al., Eur. J. Neurosci., 11:2582-2588, 1999; Ben-Arie et al., Development, 127:1039-1048, 2000).

The use of nucleic acids encoding the Atoh1 homologues described above for the treatment of deafness, osteoarthritis, and abnormal cell proliferation was described by Zoghbi et al., (U.S. Publication No. 2004/0237127).

As used herein, "Atoh1" refers to any and all Atoh1-associated nucleic acid or protein sequences and includes any sequence that is orthologous or homologous to, or has significant sequence similarity to, an Atoh1 nucleic acid or amino acid sequence, respectively, and thus the term "Atoh1" includes other mammalian homologues, e.g., human, mouse, rat, etc. The sequence can be present in any animal including mammals (e.g., humans). Examples of Atoh1 nucleic acid and amino sequences include, but are not limited to Atoh1 (e.g., NM_001012432.1 and NP_001012434.1, respectively)(Pan troglodytes), Hath1 (e.g., NM_005172.1 and NP_005163.1)(*Homo sapiens*), Math1 (e.g., NM_007500.4 and NP_031526.1)(*Mus musculus*), Atoh1 (NM_001109238.1 and NP_001102708.1) (*Rattus norvegicus*); Atoh1 (XM_001102247.1 and XP_001102247.1)(*Macaca mulatta*); Atoh1 (NM_001098099.1 and NP_001091568.1)(*Bos taurus*); Atoh1 (XM_544986.2 and XP_544986.2)(*Canis lupus familiaris*); and Cath1 (e.g., U61149.1 and AF467292.1) (*Gallus gallus*), as well as all other synonyms that may be used to refer to this protein, e.g., atonal, atonal homolog 1, Ath1, and helix-loop-helix protein Hath1. Furthermore, multiple homologous or similar sequences can exist in an animal. See, e.g., GeneID: 474 (*Homo sapiens*); GeneID: 11921 (*mus musculus*); GeneID: 461380 (Pan troglodytes); GeneID: 500156 (*Rattus norvegicus*); GeneID: 704893 (*Macaca mulatta*); GeneID: 539158 (*Bos taurus*); and GeneID: 487864 (*Canis lupus familiaris*).

Any sequence with significant sequence similarity (i.e., similarity greater than 80%, e.g., is at least 85%, 90%, 95%, 99%, or more, across the entire sequence) to the human Atoh1 sequence (found at Genbank Acc. Nos. NM_005172.1 and NP_005163.1) can be used in the present methods. To determine the percent identity of two nucleic acid sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Compounds

The present invention provides compounds that are capable of increasing Atoh1 expression in a cell. In some embodiments, the increase in Atoh1 expression is a significant increase. In some embodiments, the increase in Atoh1 expression can be, e.g., between about 1-10% above baseline, 11-20%, 21-30%, 31-40%, 41-50%, 51-60%, 61-70%, 71-80%, 81-90%, 91-100%, 101-200%, 201-300%, 301-400%, 401-500%, 501-1000%, 1001-10000%, 10001-100000% or more. Increases in Atoh1 can also be expressed as a fold increase, e.g., wherein a increase of 100% is a 1-fold increase, an increase of 1000% is a 10-fold increase and so forth. Alternatively or in addition, the increase in Atoh1 expression is sufficient to promote the differentiation of a cell, e.g., of a non-auditory hair cell (i.e., a cell other than an auditory hair cell, e.g., a progenitor or stem cell) to or towards an auditory hair cell.

The compounds that can be utilized in any of the methods described herein are phenolic compounds (or their sulfur analogs, e.g., phenyl thiols), or compounds that are derived from such compounds, such as phenyl ethers (or thioethers), e.g., straight chain or cyclic phenyl ethers. For example, such compounds can be generally represented by those structures shown in FIGS. 1A-1H, and specifically exemplified in those structures shown in FIGS. 1I-1K. Any phenolic compound (or sulfur analog) can be in neutral or salt form, e.g., a lithium, sodium, potassium or calcium salt thereof.

Figure 1A:
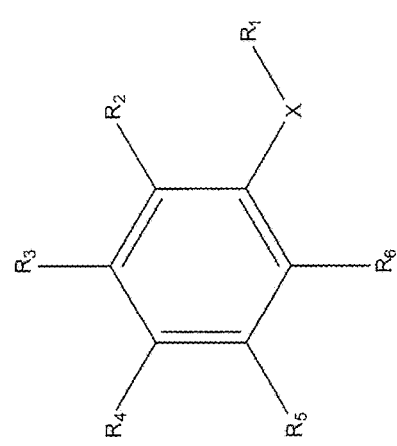
Figure 1E:
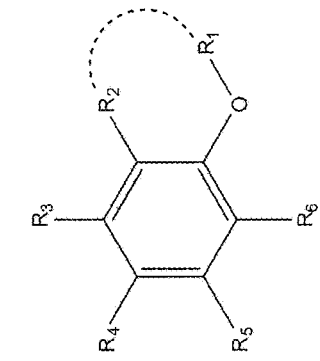

Such phenolic compounds and derivatives (or their sulfur analogs) are described by the structures of FIG. 1A, in which $R_2$, $R_3$, $R_4$, $R_5$ and $R_6$ are each independently H, F, Cl, Br, I, OH, CN, $NO_2$, or a moiety that includes up to 16 carbon atoms and, optionally, one or more N, O, S or F atoms; X is O (see FIG. 1B) or S (see FIG. 1C); and $R_1$ is H or a moiety that includes up to 16 carbon atoms and, optionally, one or more N, O, S or F atoms. For example, the moiety that includes up to 16 carbon atoms and, optionally, one or more N, O, S or F atoms can be an alkoxy group or a trifluoromethyl group.

Figure 1D:
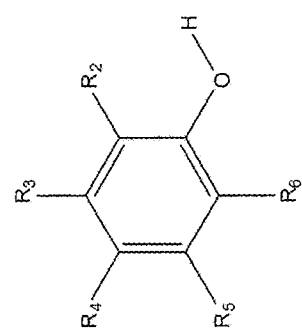

Referring to FIG. 1D, in particular embodiments, $R_1$ and $R_2$ together define one or more ring systems that each include up to 16 carbon atoms and, optionally, one or more N, O, S or F atoms.

Referring to FIG. 1E, in particular embodiments, $R_1$ is H; that is, the compounds are phenols.

Figure 1H:
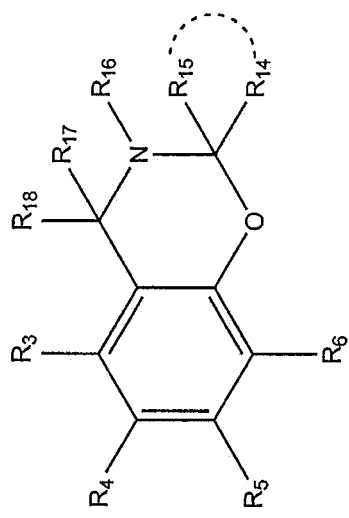
Figure 1G:
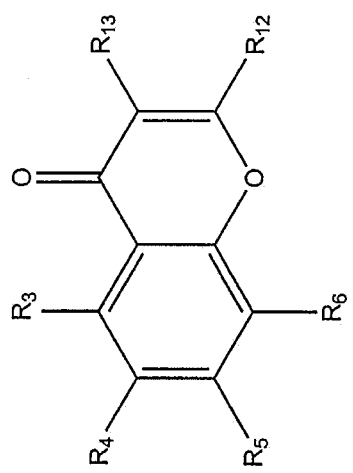
Figure 1F:
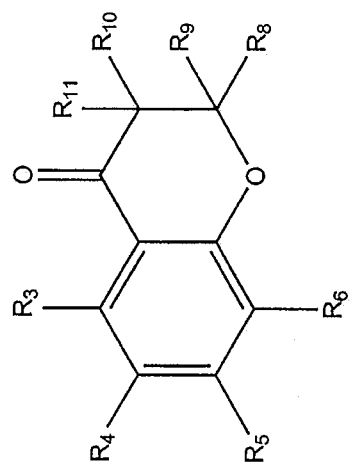
Figure 1I:
FIGS. 1I-1K are structures of specific phenolic compounds or derivatives thereof.
Figure 1I:
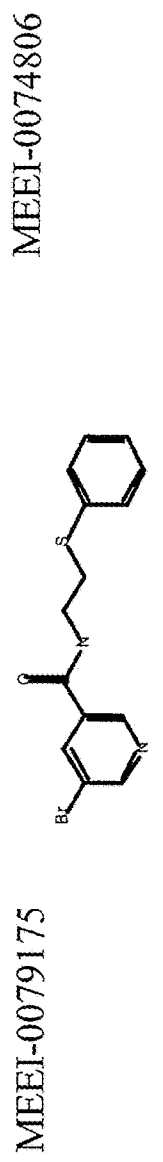
Figure 1I:
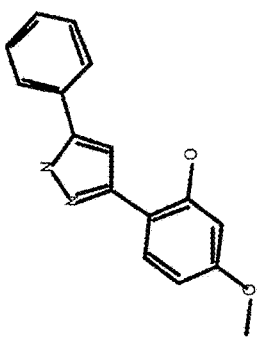
Figure 1J:
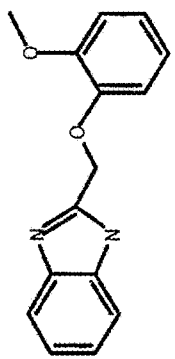
Figure 1J:
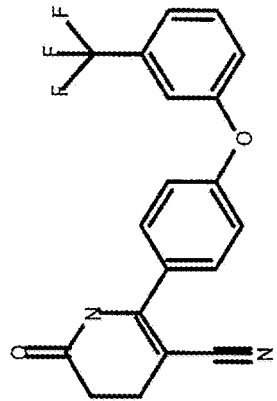
Figure 1J:
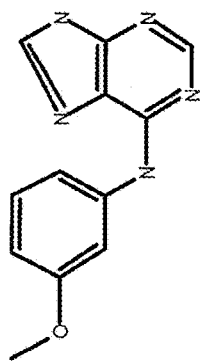
Figure 1J:
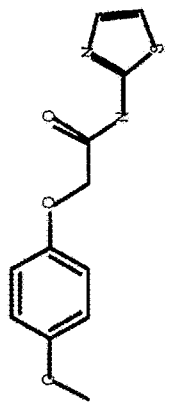
Figure 1J:
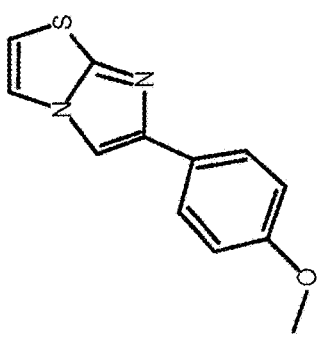
Figure 1K:
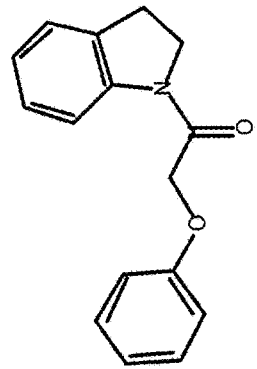
Figure 1K:
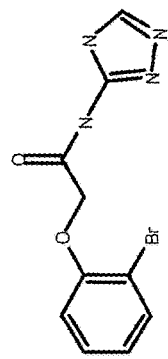
Figure 1K:
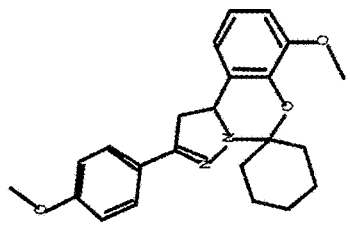
Figure 1K:
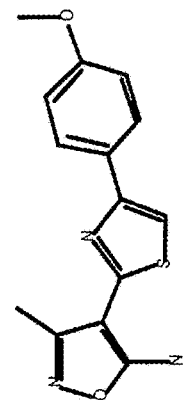
Figure 1K:
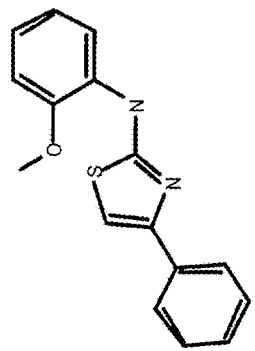

Referring to FIGS. 1F-1H, in certain embodiments, the phenolic derivatives are cyclic ether derivatives. For example, the cyclic ether portion of the molecules can be made rigid by incorporating a carbonyl group (see FIG. 1F) and/or a carbon-carbon double bond (see FIG. 1G, which contains both). In other embodiments, such cyclic ether derivatives can be made rigid by incorporating a second ring system about the cyclic ether system. In particular embodiments, the cyclic ether derivatives are represented by the structure of FIG. 1F in which $R_8$, $R_9$, $R_{10}$ and $R_{11}$ are each independently H, F, Cl, Br, I, OH, CN, $NO_2$, or a moiety that includes up to 16 carbon atoms and, optionally, one or more N, O, S or F atoms. In other particular embodiments, the cyclic ether derivatives are represented by the structure of FIG. 1G, in which $R_{12}$ and $R_{13}$ are each independently H, F, Cl, Br, I, OH, or a moiety that includes up to 16 carbon atoms and, optionally, one or more N, O, S or F atom. In other particular embodiments, the cyclic ether derivatives are represented by the structure of FIG. 1H, in which $R_{14}$ and $R_{15}$ together define one or more ring systems that each include up to 16 carbon atoms and, optionally, one or more N, O, S or F atoms, $R_{16}$, $R_{17}$ and $R_{18}$ each are each independently H, F, Cl, Br, I, OH, or a moiety that includes up to 16 carbon atoms and, optionally, one or more N, O, S or F atoms.

The present compounds are benzamide compounds and/or related compounds. Such compounds can be generally represented by those structures shown in FIGS. 2A-2F, and specifically exemplified in those structures shown in FIGS. 2G-2I. Any of the present benzamide or related compounds can be in neutral or salt form.

The present benzamide compounds and/or derivatives can be described by the structure of FIG. 2A, in which $R_{20}$, $R_{21}$, $R_{22}$, $R_{23}$ and $R_{24}$ are each independently H, F, Cl, Br, I, OH, CN, NO$_2$, or a moiety that includes up to 16 carbon atoms and, optionally, one or more N, O, S or F atoms; and $R_{24}$ and $R_{26}$ are each independently H or a moiety that includes up to 16 carbon atoms and, optionally, one or more N, O, S or F atoms.

In the compounds of FIG. 2A, $R_{24}$ and $R_{25}$ can together define one or more ring systems that each include up to 16 carbon atoms and, optionally, one or more N, O, S or F atoms. Such compounds can be represented by the structures of FIG. 2B. For example, such compounds can have the structures shown in FIGS. 2C and 2D in which $R_{27}$, $R_{28}$, $R_{29}$, $R_{31}$ and $R_{32}$ are each independently H, F, Cl, Br, I, OH, CN, NO$_2$, or a moiety that includes up to 16 carbon atoms and, optionally, one or more N, O, S or F atoms; and $R_{26}$ is H or a moiety that includes up to 16 carbon atoms and, optionally, one or more N, O, S or F atoms.

Figure 2E:
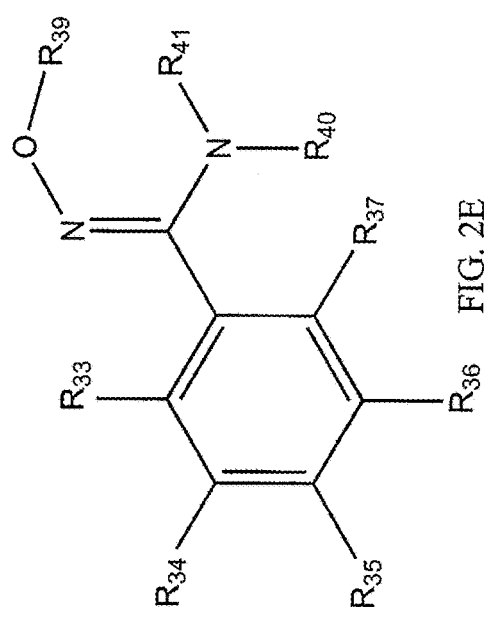
Figure 2F:
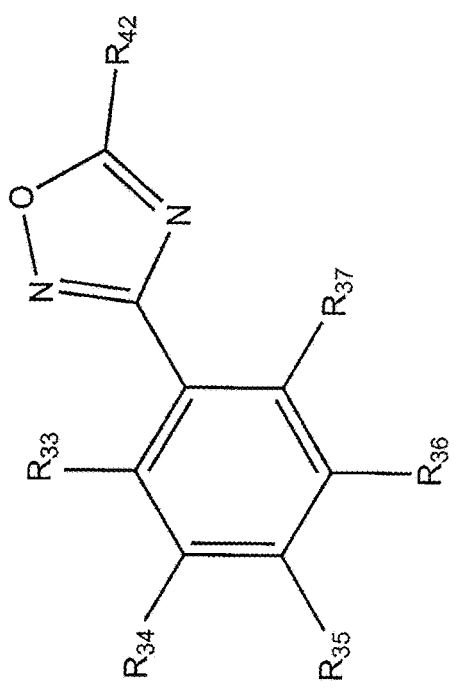
Figure 2H:
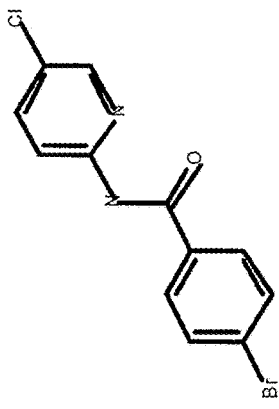
Figure 2H:
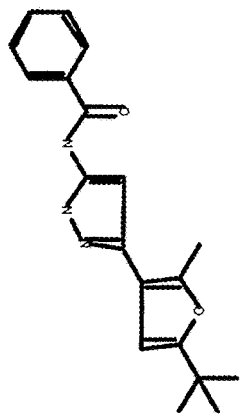
Figure 2H:
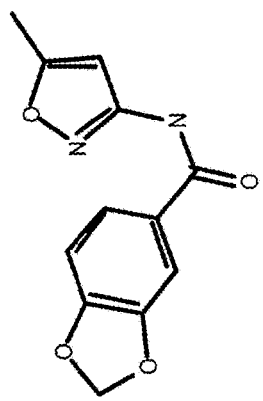
Figure 2H:
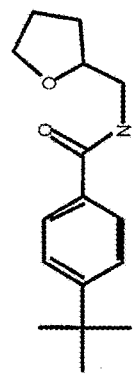
Figure 2H:
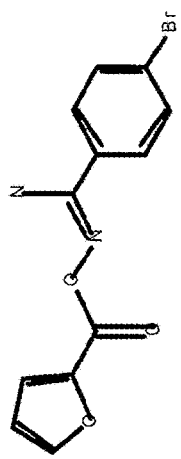
Figure 2I:
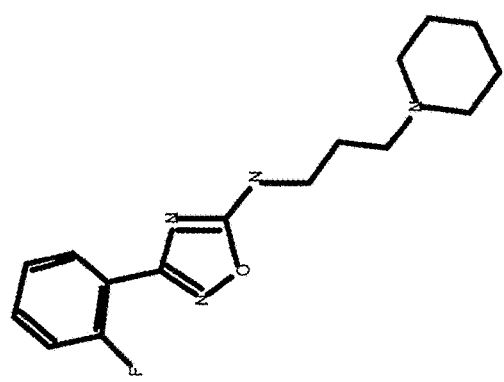
Figure 2I:
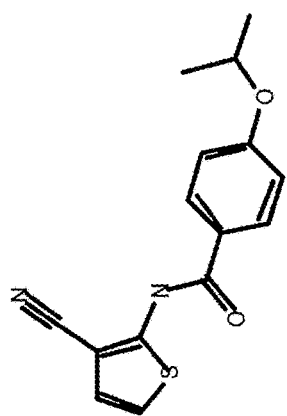

Other benzamide-related compounds and derivatives are described by the structures of FIGS. 2E and 2F, in which $R_{33}$, $R_{34}$, $R_{35}$, $R_{36}$ and $R_{37}$ are each independently H, F, Cl, Br, I, OH, CN, NO$_2$, or a moiety that includes up to 16 carbon atoms and, optionally, one or more N, O, S or F atoms; $R_{39}$, $R_{40}$, $R_{41}$ and $R_{42}$ are each independently H or a moiety that includes up to 16 carbon atoms and, optionally, one or more N, O, S or F atoms.

The present compounds are, or can include, one or more heterocyclic ring systems, such as a 3, 4, 5, 6, or 7-membered ring system that includes one more heteroatoms, such as O, S or N. For example, the one or more ring systems can include 1, 2, 3, 4 or even 5 heteroatoms, such as O, S or N. In many embodiments, the rings systems are aromatic. For example, such compounds can be generally represented by those structures shown in FIGS. 3A-3X, and specifically exemplified in those structures shown in FIGS. 3Y-3ZZ. Any described compound that is or that includes the one or more ring system can be in neutral or salt form.

Figure 3A:
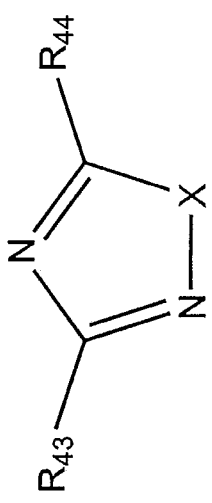
FIGS. 3A-3X are generalized structures of compounds that include one or more heterocyclic rings.
Figure 3C:
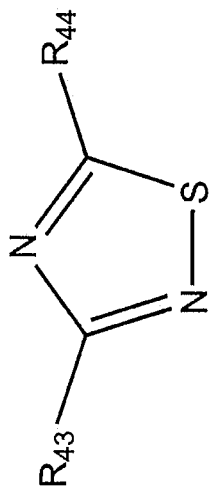
FIGS. 3Y-3ZZ are structures of specific compounds that include one or more heterocyclic rings.
Figure 3B:
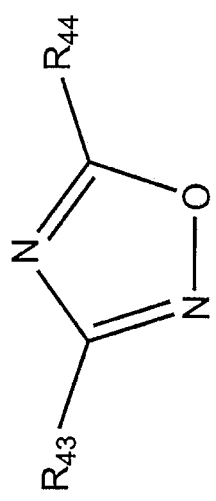

The compounds that are, or that include, one or more heterocyclic ring systems are described by the structures of FIG. 3A, in which $R_{43}$ and $R_{44}$ are each independently H, F, Cl, Br, I, OH, CN, NO$_2$, or a moiety that includes up to 16 carbon atoms and, optionally, one or more N, O, S or F atoms; and X is O (FIG. 3B) or S (FIG. 3C).

Figure 3D:
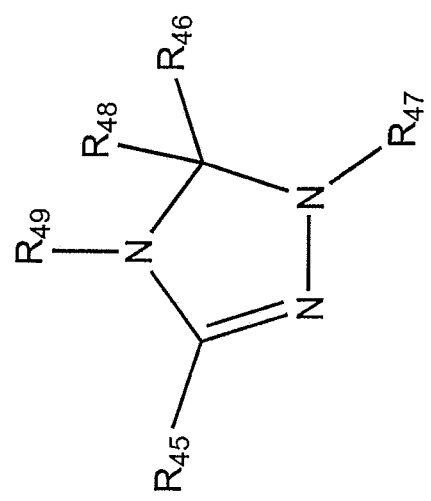

Compounds that are or include one or more heterocyclic ring systems are described by the structures of FIG. 3D, in which $R_{45}$, $R_{46}$ and $R_{48}$ are each independently H, F, Cl, Br, I, OH, CN, NO$_2$, or a moiety that includes up to 16 carbon atoms and, optionally, one or more N, O, S or F atoms; and $R_{47}$ and $R_{49}$ are each independently H, or a moiety that includes up to 16 carbon atoms and, optionally, one or more N, O, S or F atoms.

Figure 3E:
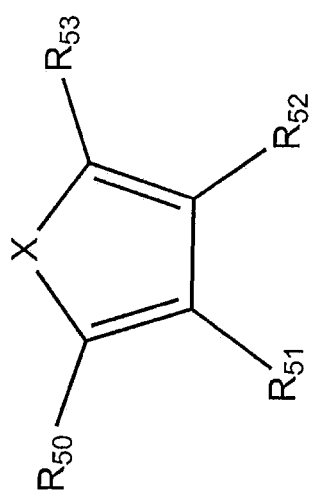
Figure 3G:
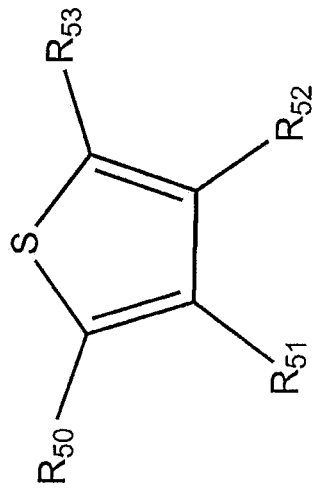
Figure 3F:
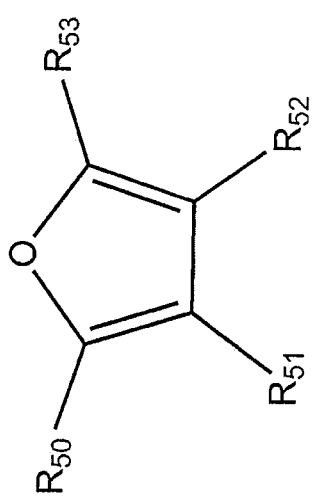

Compounds that are or include one or more heterocyclic ring systems are described by the structures of FIG. 3E, in which $R_{50}$, $R_{51}$, $R_{52}$ and $R_{53}$ are each independently H, F, Cl, Br, I, OH, CN, NO$_2$, or a moiety that includes up to 16 carbon atoms and, optionally, one or more N, O, S or F atoms; and X is O (FIG. 3F) or S (FIG. 3G).

Figure 3H:
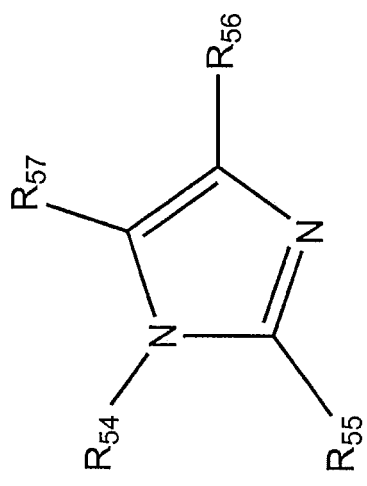
Figure 3I:
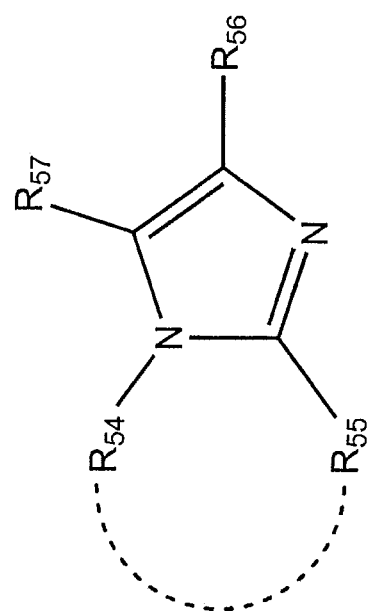

Compounds that are or include one or more heterocyclic ring systems are described by the structures of FIG. 3H, in which $R_{55}$, $R_{56}$ and $R_{57}$ are each independently H, F, Cl, Br, I, OH, CN, NO$_2$, or a moiety that includes up to 16 carbon atoms and, optionally, one or more N, O, S or F atoms; and $R_{54}$ is H or a moiety that includes up to 16 carbon atoms and, optionally, one or more N, O, S or F atoms. For example, in specific embodiments, $R_{54}$ and $R_{55}$ can together define one or more ring systems that each includes up to 16 carbon atoms and, optionally, one or more N, O, S or F atoms, as shown in FIG. 3I.

Figure 3J:
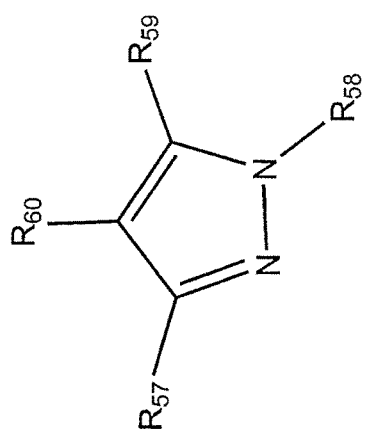
Figure 3L:
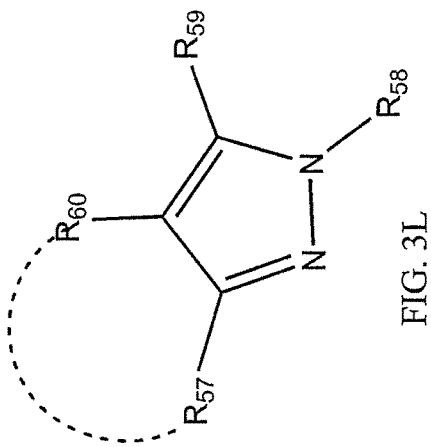
Figure 3M:
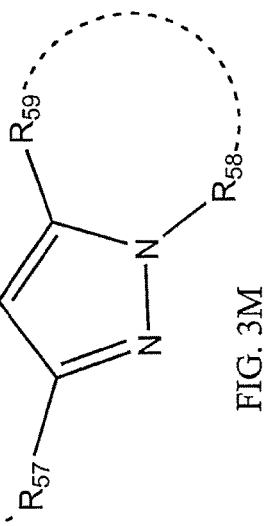
Figure 3K:
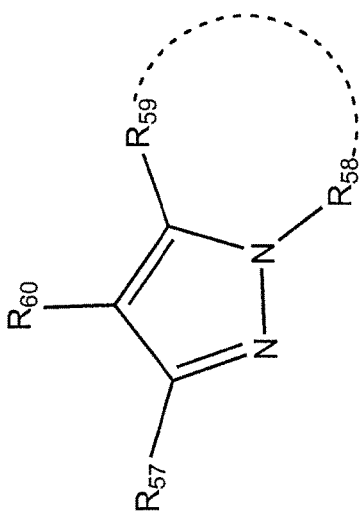

Compounds that are or include one or more heterocyclic ring systems are described by the structures of FIG. 3J, in which $R_{57}$, $R_{59}$ and $R_{60}$ are each independently H, F, Cl, Br, I, OH, CN, NO$_2$ or a moiety that includes up to 16 carbon atoms and, optionally, one or more N, O, S or F atoms; and $R_{58}$ is H or a moiety that includes up to 16 carbon atoms and, optionally, one or more N, O, S or F atoms. For example, in specific embodiments, $R_{58}$ and $R_{59}$ can together define one or more ring systems that each includes up to 16 carbon atoms and, optionally, one or more N, O, S or F atoms, as shown in FIG. 3K. For example, in specific embodiments, $R_{57}$ and $R_{60}$ can together define one or more ring systems that each includes up to 16 carbon atoms and, optionally, one or more N, O, S or F atoms, as shown in FIG. 3L. For example, in specific embodiments, $R_{57}$ and $R_{60}$ and $R_{58}$ and $R_{59}$ can together each define one or more ring systems that each includes up to 16 carbon atoms and, optionally, one or more N, O, S or F atoms, as shown in FIG. 3M.

Figure 3N:
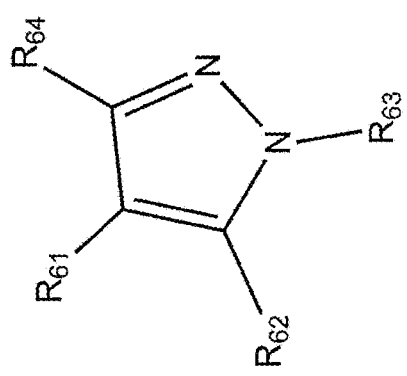
Figure 3O:
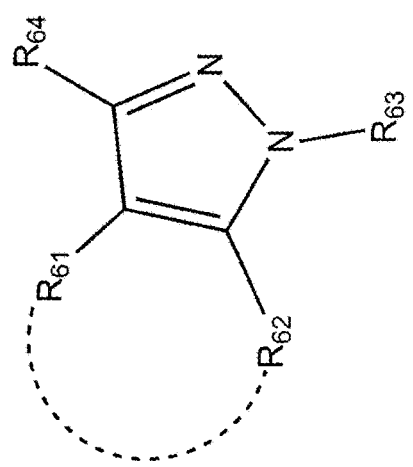

Compounds that are or include one or more heterocyclic ring systems are described by the structures of FIG. 3N, in which $R_{61}$, $R_{62}$, and $R_{64}$ are each independently H, F, Cl, Br, I, OH, CN, NO$_2$, or a moiety that includes up to 16 carbon atoms and, optionally, one or more N, O, S or F atoms; and $R_{63}$ is H or a moiety that includes up to 16 carbon atoms and, optionally, one or more N, O, S or F atoms. For example, in specific embodiments, $R_{61}$ and $R_{62}$ can together define one or more ring systems that each includes up to 16 carbon atoms and, optionally, one or more N, O, S or F atoms, as shown in FIG. 3O.

Figure 3P:
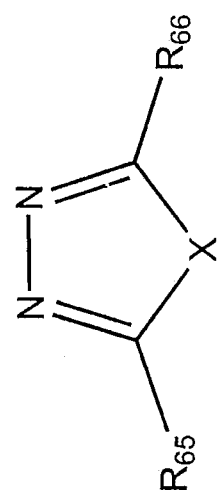
Figure 3R:
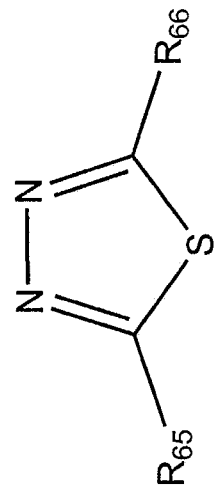
Figure 3Q:
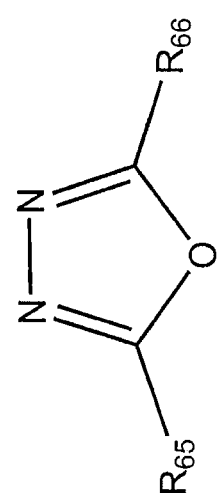

Compounds that are or include one or more heterocyclic ring systems are described by the structures of FIG. 3P, in which $R_{65}$ and $R_{66}$ are each independently H, F, Cl, Br, I, OH, CN, NO$_2$, or a moiety that includes up to 16 carbon atoms and, optionally, one or more N, O, S or F atoms; and X is O (FIG. 3Q) or S (FIG. 3R).

Figure 3S:
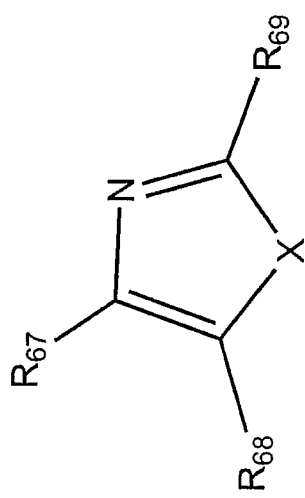
Figure 3U:
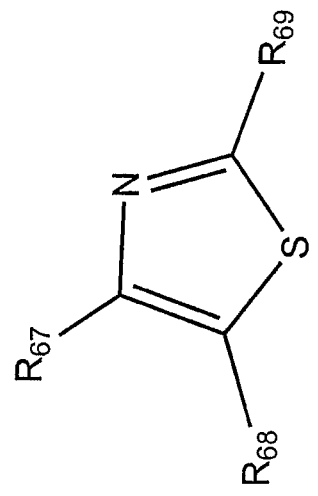
Figure 3T:
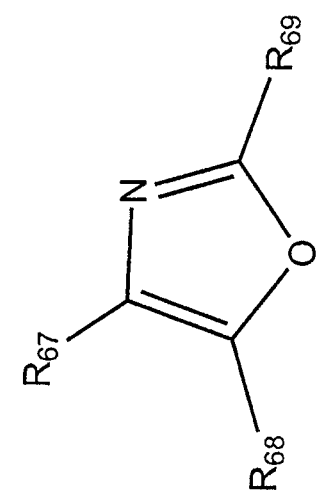

Compounds that are or include one or more heterocyclic ring systems are described by the structures of FIG. 3S, in which $R_{67}$, $R_{68}$, and $R_{69}$ are each independently H, F, Cl, Br, I, OH, CN, NO$_2$ or a moiety that includes up to 16 carbon atoms and, optionally, one or more N, O, S or F atoms; and X is O (FIG. 3T) or S (FIG. 3U).

Figure 3V:
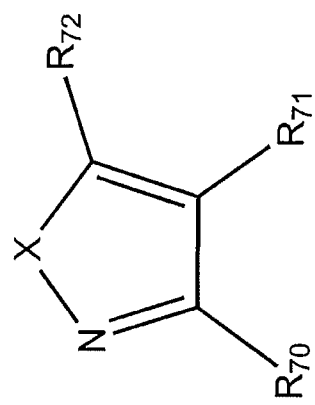
Figure 3X:
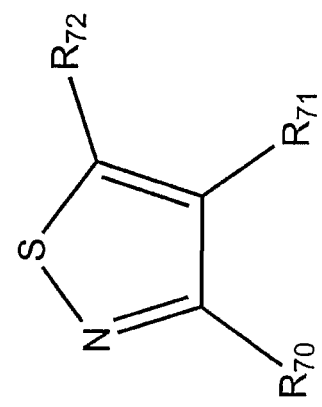
Figure 3W:
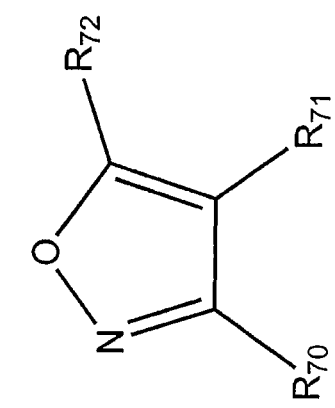
Figure 3Y:
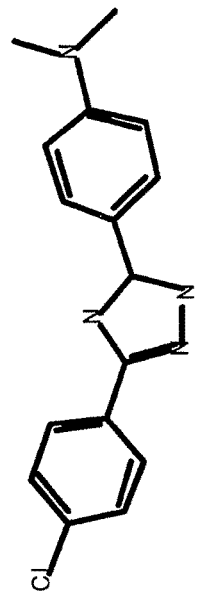
Figure 3Y:
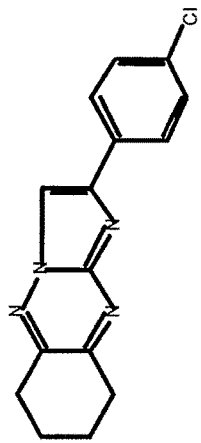
Figure 3Y:
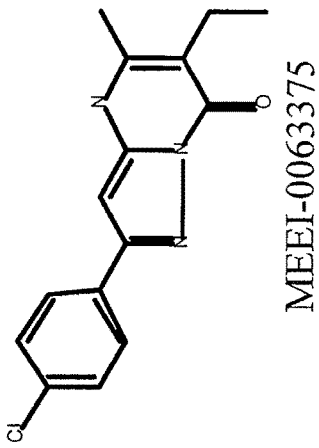
Figure 3Y:
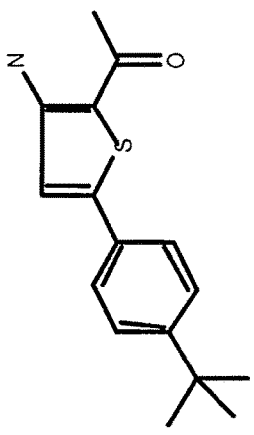
Figure 3Z:
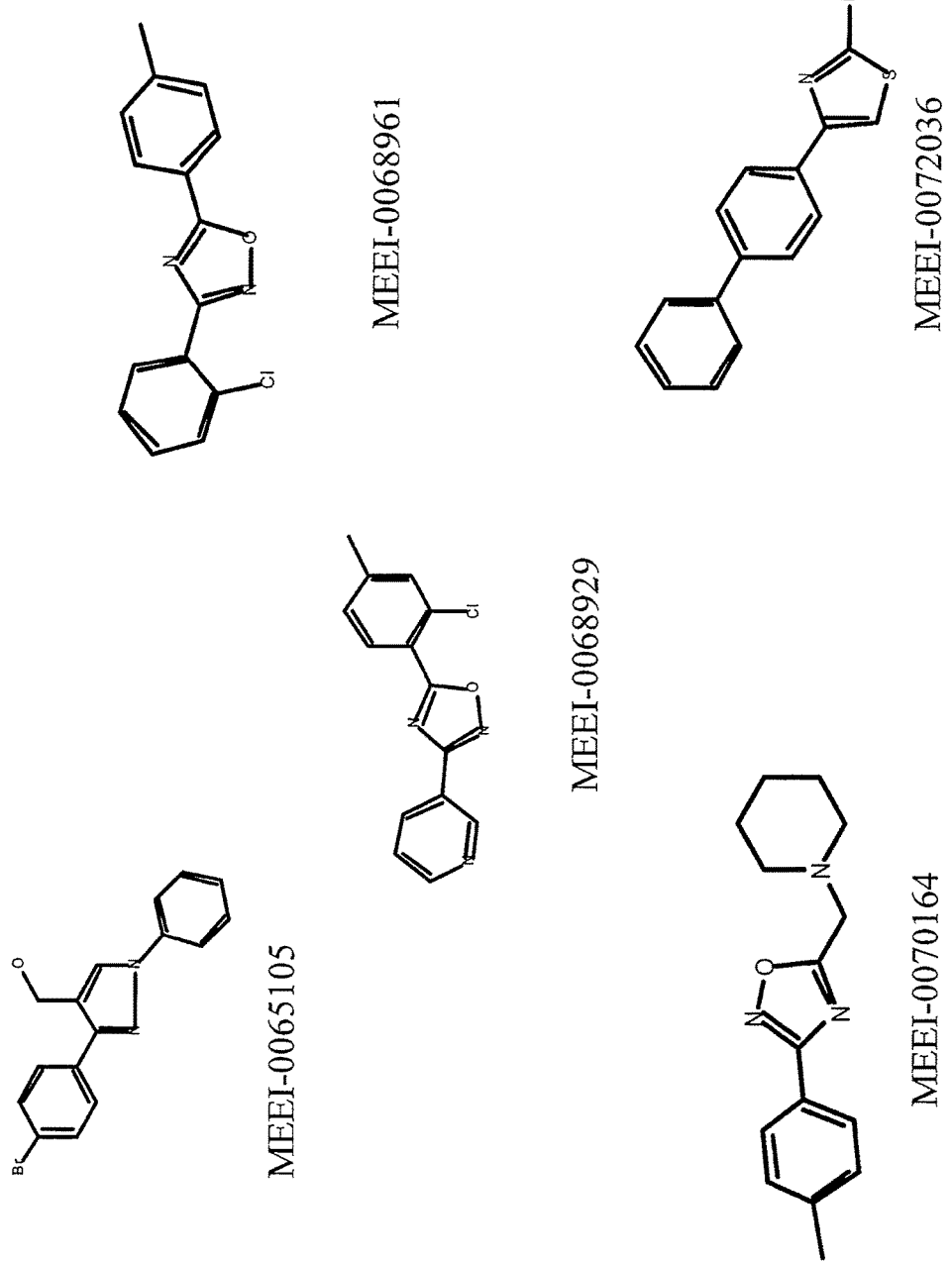
Figure 3Z:
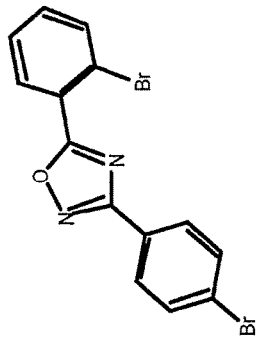
Figure 3Z:
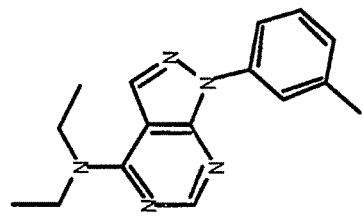
Figure 3Z:
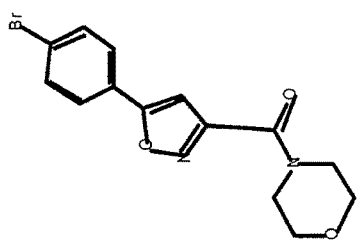
Figure 3Z:
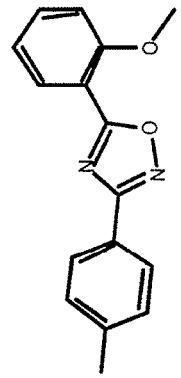
Figure 3Z:
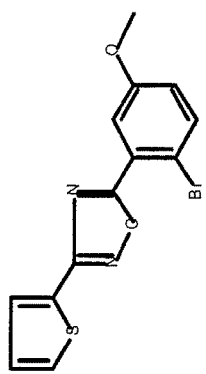
Figure 3Z:
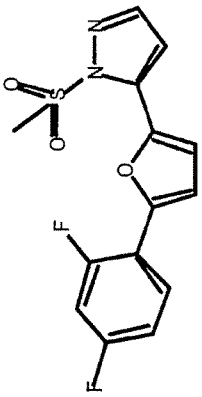

Compounds that are or include one or more heterocyclic ring systems are described by the structures of FIG. 3V, in which $R_{70}$, $R_{71}$, and $R_{72}$ are each independently H, F, Cl, Br, I, OH, CN, NO$_2$ or a moiety that includes up to 16 carbon atoms and, optionally, one or more N, O, S or F atoms; and X is O (FIG. 3W) or S (FIG. 3X).

Figure 4H:
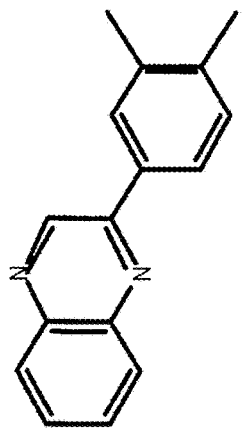
FIGS. 4H-4I are structures of specific compounds that include one or more phenyl rings.
Figure 4H:
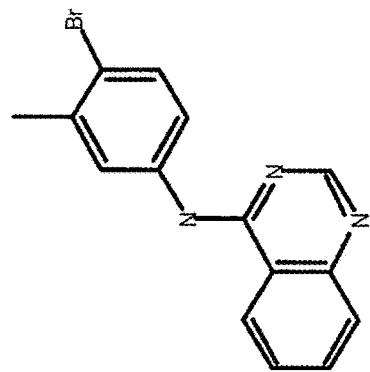
Figure 4H:
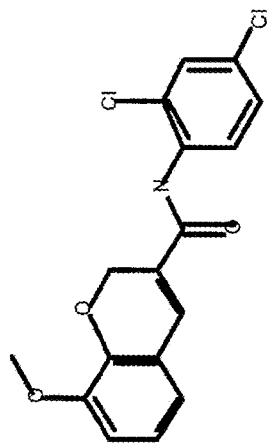
Figure 4H:
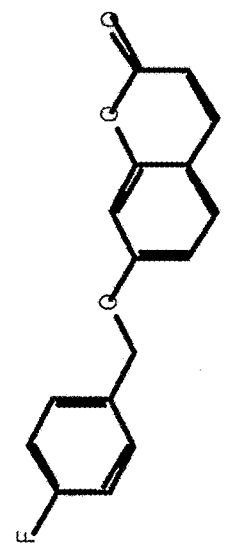
Figure 4I:
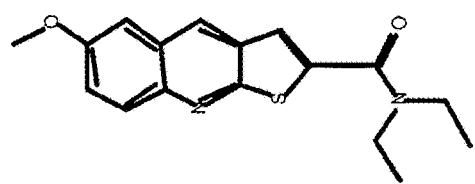
Figure 4I:
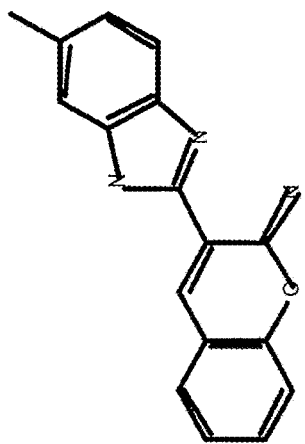
Figure 4I:
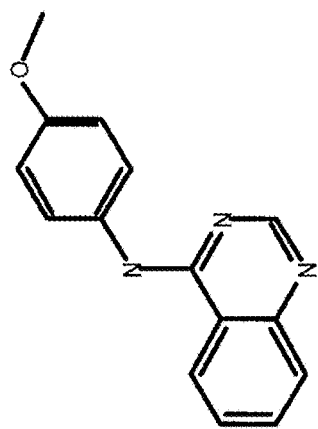

The present compounds, which can be utilized in any method described herein, are or include one or more phenyl rings, such as a fused phenyl ring system, e.g., one that is part of a flavonoid, coumarin or other similar system. For example, such compounds can be generally represented by those structures shown in FIGS. 4A-4G, and specifically exemplified in those structures shown in FIGS. 4H and 4I. Any described compound that is or that includes the one or more ring system can be in neutral or salt form.

Compounds that are or include one or more phenyl rings are described by the structures of FIG. 4A, in which $R_{74}$, $R_{75}$, $R_{76}$, $R_{77}$, $R_{78}$ and $R_{79}$ are each independently H, F, Cl, Br, I, OH, CN, $NO_2$ or a moiety that includes up to 16 carbon atoms and, optionally, one or more N, O, S or F atoms. For example, in specific embodiments, $R_{76}$ and $R_{77}$ can together define one or more ring systems that each includes up to 16 carbon atoms and, optionally, one or more N, O, S or F atoms, as shown in FIG. 4B. For example, the compounds of FIG. 4B, can be described by the compounds of FIGS. 4C and 4D in which $R_{81}$, $R_{82}$, $R_{83}$ and $R_{84}$ are each independently H, F, Cl, Br, I, OH, CN, $NO_2$ or a moiety that includes up to 16 carbon atoms and, optionally, one or more N, O, S or F atoms. For example, in other specific embodiments in which $R_{76}$ and $R_{77}$ together define one or more ring systems, the compounds can be represented by those structures of FIGS. 4E-4G, in which $R_{85}$, $R_{86}$, $R_{87}$ and $R_{88}$ are each independently H, F, Cl, Br, I, OH, CN, $NO_2$ or a moiety that includes up to 16 carbon atoms and, optionally, one or more N, O, S or F atoms; and $R_{89}$ is H or a moiety that includes up to 16 carbon atoms and, optionally, one or more N, O, S or F atoms.

In some embodiments, the compounds that can be utilized in any method described herein include an amide group bonded to a 5-membered heterocyclic ring system, such as one that that includes one more heteroatoms, such as O, S or N. For example, the one or more ring systems can include 1, 2, 3, 4 or even 5 heteroatoms, such as O, S or N. In many embodiments, the rings systems are aromatic. For example, such compounds can be generally represented by those structures shown in FIGS. 5A-5E, and specifically exemplified in those structures shown in FIGS. 5F-5G. Any described compound that is or that includes the one or more ring system can be in neutral or salt form.

Figure 5A:
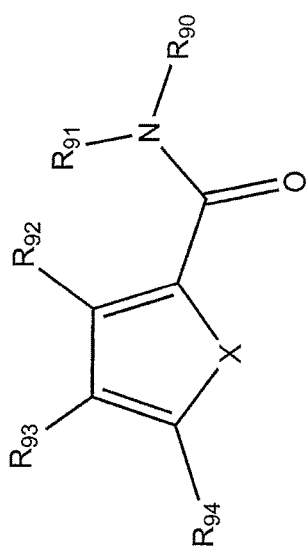
FIGS. 5A-5E are generalized structures of compounds that include an amide group attached to a 5-membered heterocyclic ring system.
Figure 5C:
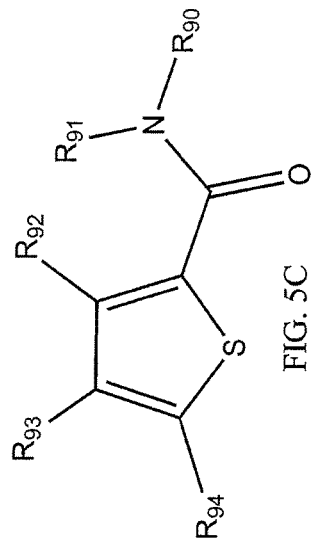

In certain embodiments, such compounds that include an amide group bonded to a 5-membered heterocyclic ring system are described by the structure of FIG. 5A, in which $R_{92}$, $R_{93}$ and $R_{94}$ are each independently H, F, Cl, Br, I, OH, CN, $NO_2$ or a moiety that includes up to 16 carbon atoms and, optionally, one or more N, O, S or F atoms; and $R_{90}$ and $R_{91}$ are each independently H or a moiety that includes up to 16 carbon atoms and, optionally, one or more N, O, S or F atoms; and X is O (FIG. 5B) or S (FIG. 5C). For example, in some specific embodiments, $R_{90}$ and $R_{91}$ can together define one or more ring systems that includes up to 16 carbon atoms, optionally, substituted with one or more N, O, S or F atoms (see FIG. 5D).

Figure 5E:
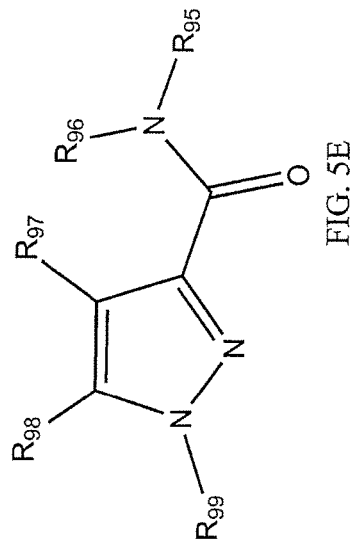
Figure 5B:
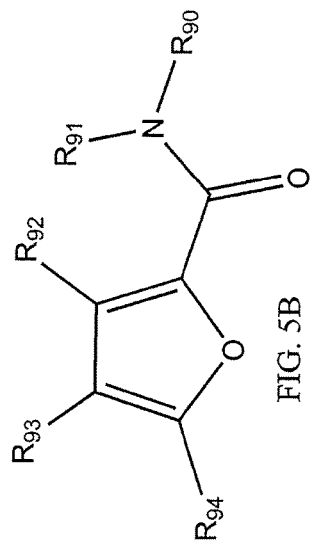
Figure 5D:
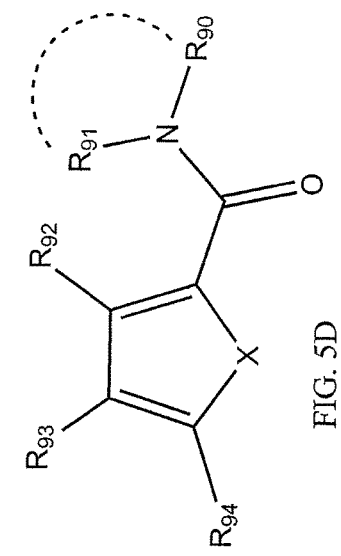
Figure 5F:
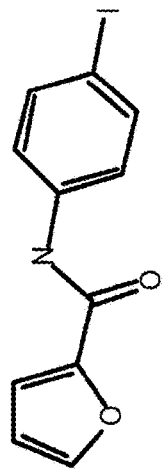
FIGS. 5F and 5G are structures of specific compounds that include an amide group attached to a 5-membered heterocyclic ring system.
Figure 5F:
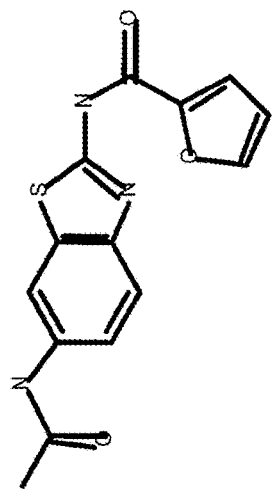
Figure 5F:
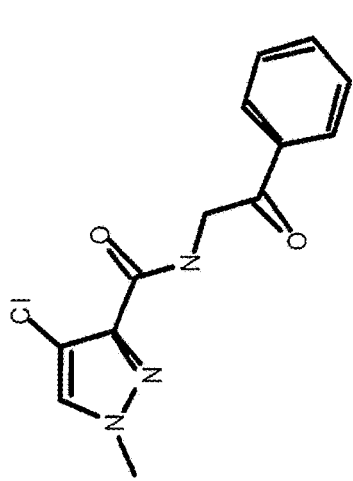
Figure 5F:
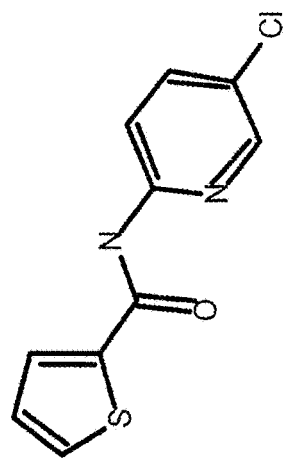
Figure 5G:
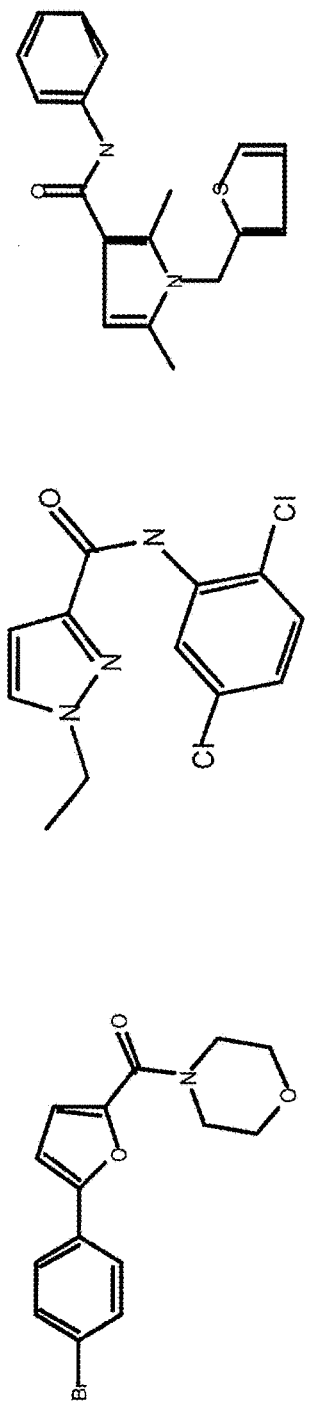
Figure 5G:
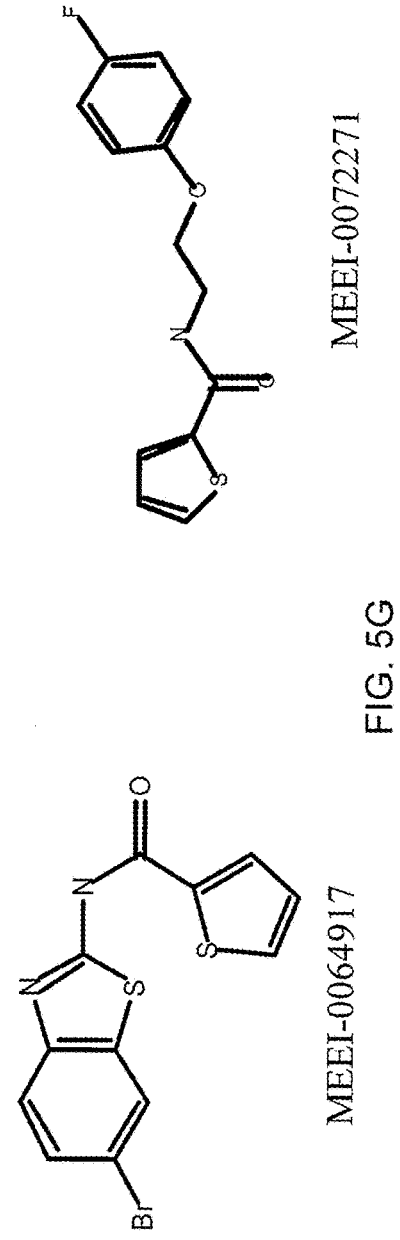

In other certain embodiments, such compounds that include an amide group bonded to a 5-membered heterocyclic ring system are described by the structure of FIG. 5E, in which $R_{97}$ and $R_{98}$ are each independently H, F, Cl, Br, I, OH, CN, $NO_2$ or a moiety that includes up to 16 carbon atoms and, optionally, one or more N, O, S or F atoms; and $R_{95}$, $R_{96}$ and $R_{99}$ are each independently H or a moiety that includes up to 16 carbon atoms and, optionally, one or more N, O, S or F atoms.

In some embodiments, the compounds that can be utilized in any method described herein include a 5-membered heterocyclic ring system fused to one or more other ring systems, e.g., that defines one or more 4-, 5-, 6-, 7- or 8-membered ring system. For example, such compounds can be generally represented by those structures shown in FIGS. 6A-6O, and specifically exemplified in those structures shown in FIGS. 6P-6V. Any described compound that is or that includes the one or more ring system can be in neutral or salt form.

Figure 6A:
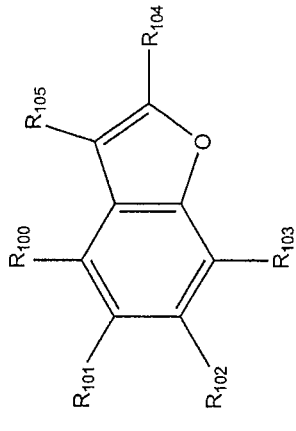
FIGS. 6A-6O are generalized structures of compounds that include a 5-membered heterocyclic ring system fused to another ring system.
Figure 6D:
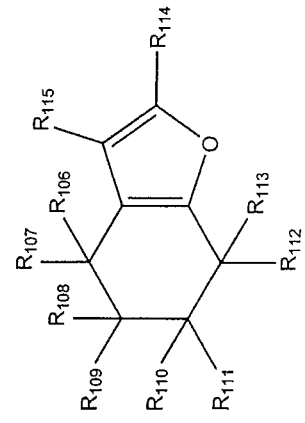
FIGS. 6P-6V are structures of specific compounds that include a 5-membered heterocyclic ring system fused to another ring system.
Figure 6B:
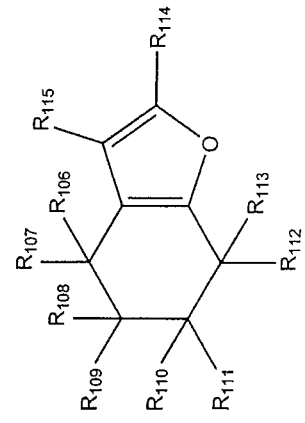
Figure 6E:
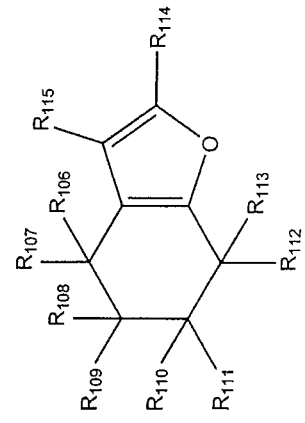
Figure 6C:
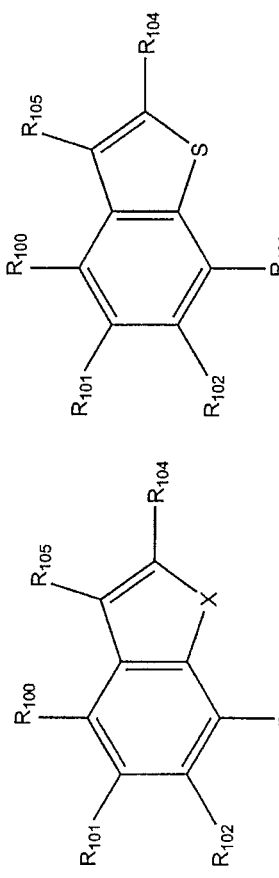

In some embodiments, the compounds that include a 5-membered heterocyclic ring system fused to one or more other ring systems are described by FIG. 6A, in which $R_{100}$, $R_{101}$, $R_{102}$, $R_{103}$, $R_{104}$ and $R_{105}$ are each independently H, F, Cl, Br, I, OH, CN, $NO_2$ or a moiety that includes up to 16 carbon atoms and, optionally, one or more N, O, S or F atoms; and X is S (see FIG. 6B) or O (see FIG. 6C).

Figure 6F:
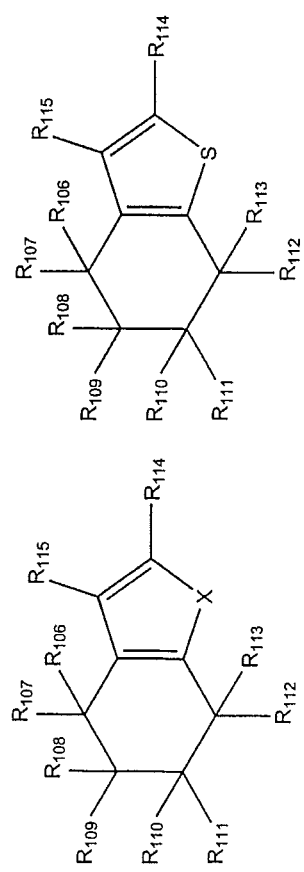

In other embodiments, the compounds that include a 5-membered heterocyclic ring system fused to one or more other ring systems are described by FIG. 6D, in which $R_{106}$, $R_{107}$, $R_{108}$, $R_{109}$, $R_{110}$, $R_{111}$, $R_{112}$, $R_{113}$, $R_{114}$ and $R_{115}$ are each independently H, F, Cl, Br, I, OH, CN, $NO_2$ or a moiety that includes up to 16 carbon atoms and, optionally, one or more N, O, S or F atoms; and X is S (see FIG. 6E) or O (see FIG. 6F).

Figure 6H:
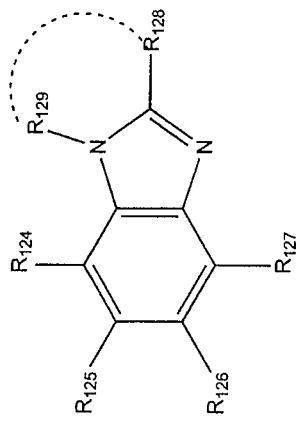
Figure 6G:
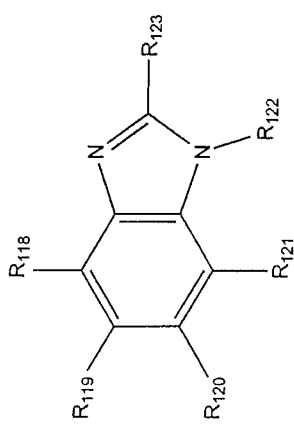

In certain embodiments, the compounds that include a 5-membered heterocyclic ring system fused to one or more other ring systems are described by FIG. 6G, in which $R_{118}$, $R_{119}$, $R_{120}$, $R_{121}$, $R_{123}$ are each independently H, F, Cl, Br, I, OH, CN, $NO_2$ or a moiety that includes up to 16 carbon atoms and, optionally, one or more N, O, S or F atoms; and $R_{123}$ is H or a moiety that includes up to 16 carbon atoms and, optionally, one or more N, O, S or F atoms.

In certain embodiments, the compounds that include a 5-membered heterocyclic ring system fused to one or more other ring systems are described by FIG. 6H, in which $R_{124}$, $R_{125}$, $R_{126}$ and $R_{127}$ are each independently H, F, Cl, Br, I, OH, CN, $NO_2$ or a moiety that includes up to 16 carbon atoms and, optionally, one or more N, O, S or F atoms; and $R_{128}$ and $R_{129}$ together define one or more rings that each include up to 16 carbon atoms and, optionally, one or more N, O, S or F atoms. For example, the compounds of FIG. 6H can be described by FIG. 6I, in which $R_{130}$, $R_{131}$, $R_{132}$ and $R_{128'}$ are each independently H, F, Cl, Br, I, OH, CN, $NO_2$ or a moiety that includes up to 16 carbon atoms and, optionally, one or more N, O, S or F atoms; and $R_{129'}$ is H, or a moiety that includes up to 16 carbon atoms and, optionally, one or more N, O, S or F atoms.

Figure 6K:
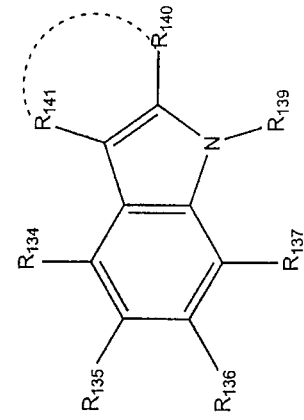
Figure 6J:
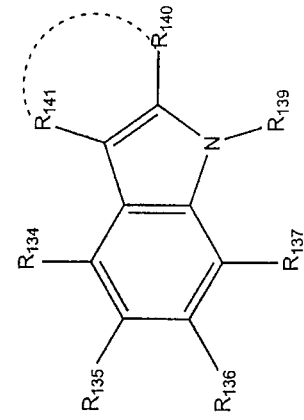

In other certain embodiments, the compounds that include a 5-membered heterocyclic ring system fused to one or more other ring systems are described by FIG. 6J, in which $R_{134}$, $R_{135}$, $R_{136}$, $R_{137}$, $R_{140}$ and $R_{141}$ are each independently H, F, Cl, Br, I, OH, CN, $NO_2$ or a moiety that includes up to 16 carbon atoms and, optionally, one or more N, O, S or F atoms; and $R_{139}$ is H or a moiety that includes up to 16 carbon atoms and, optionally, one or more N, O, S or F atoms. For example and by reference to FIG. 6K, in specific embodiments, $R_{140}$ and $R_{141}$ together define a one or more rings that each include up to 16 carbon atoms and, optionally, one or more N, O, S or F atoms.

Figure 6I:
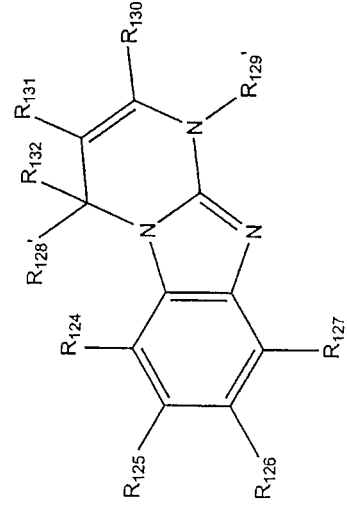
Figure 6N:
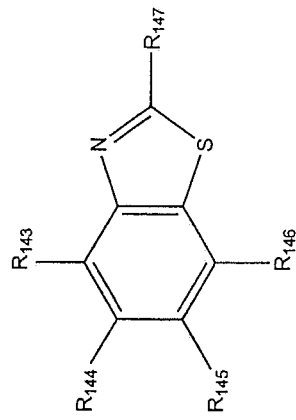
Figure 6M:
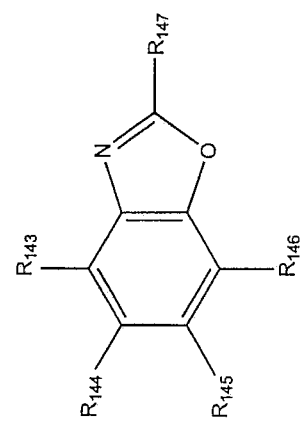
Figure 6O:
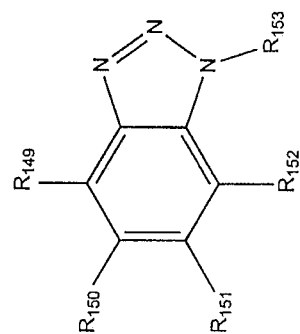
Figure 6L:
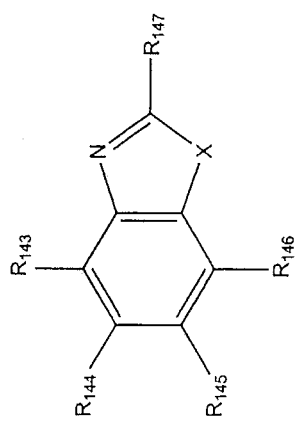
Figure 6P:
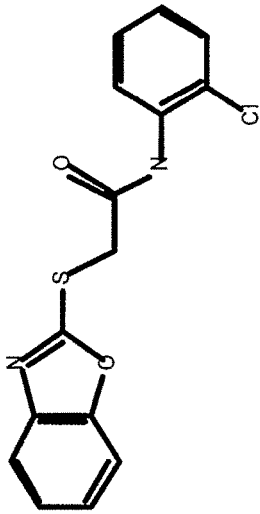
Figure 6P:
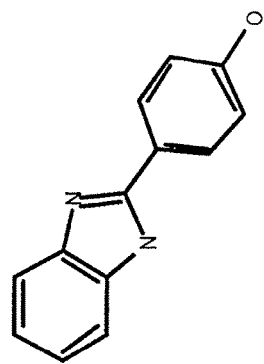
Figure 6P:
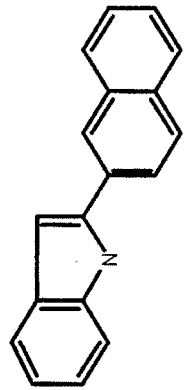
Figure 6P:
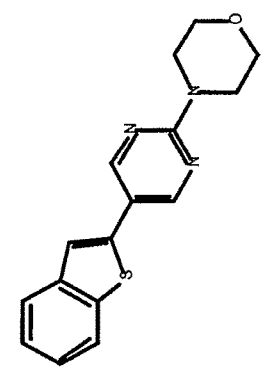
Figure 6P:
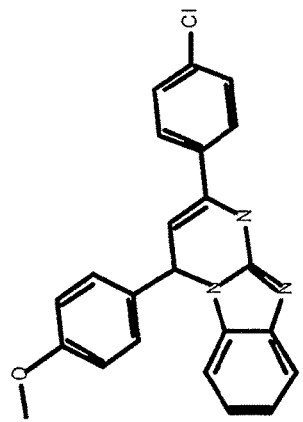
Figure 6Q:
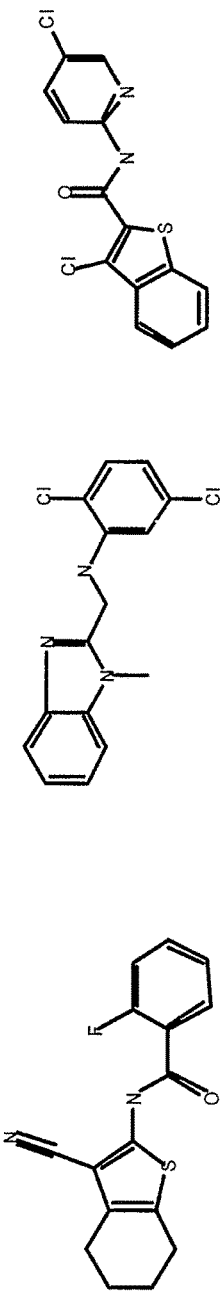
Figure 6Q:
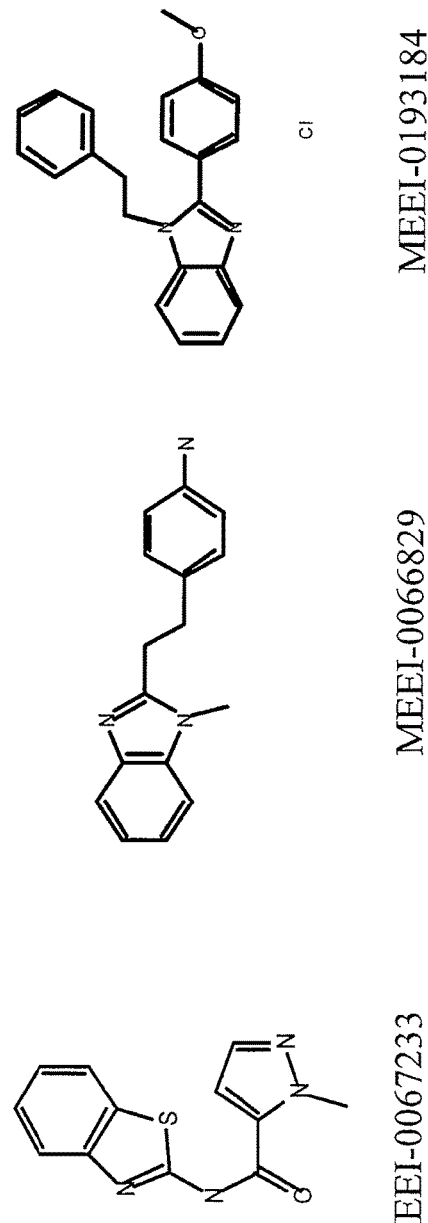
Figure 6R:
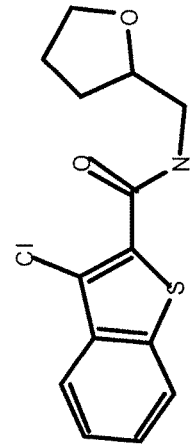
Figure 6R:
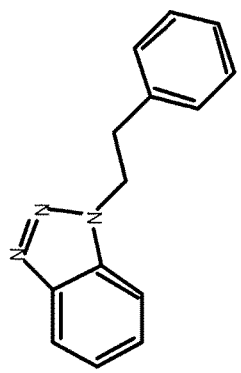
Figure 6R:
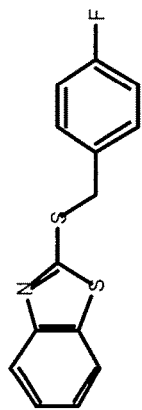
Figure 6R:
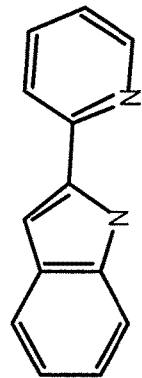
Figure 6S:
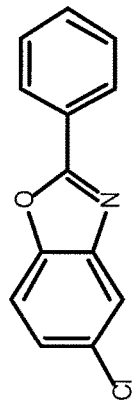
Figure 6S:
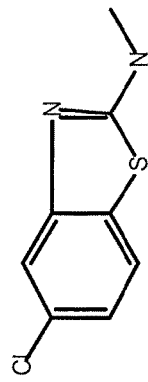
Figure 6S:
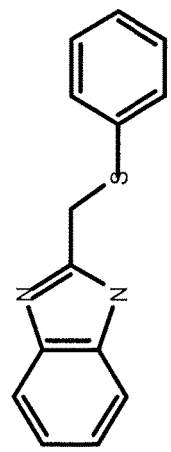
Figure 6S:
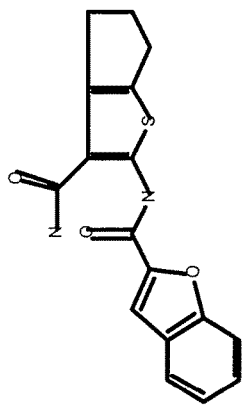
Figure 6S:
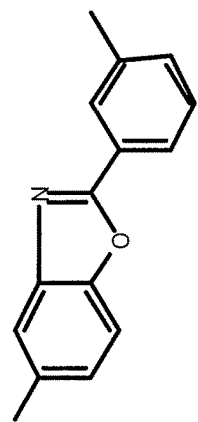
Figure 6T:
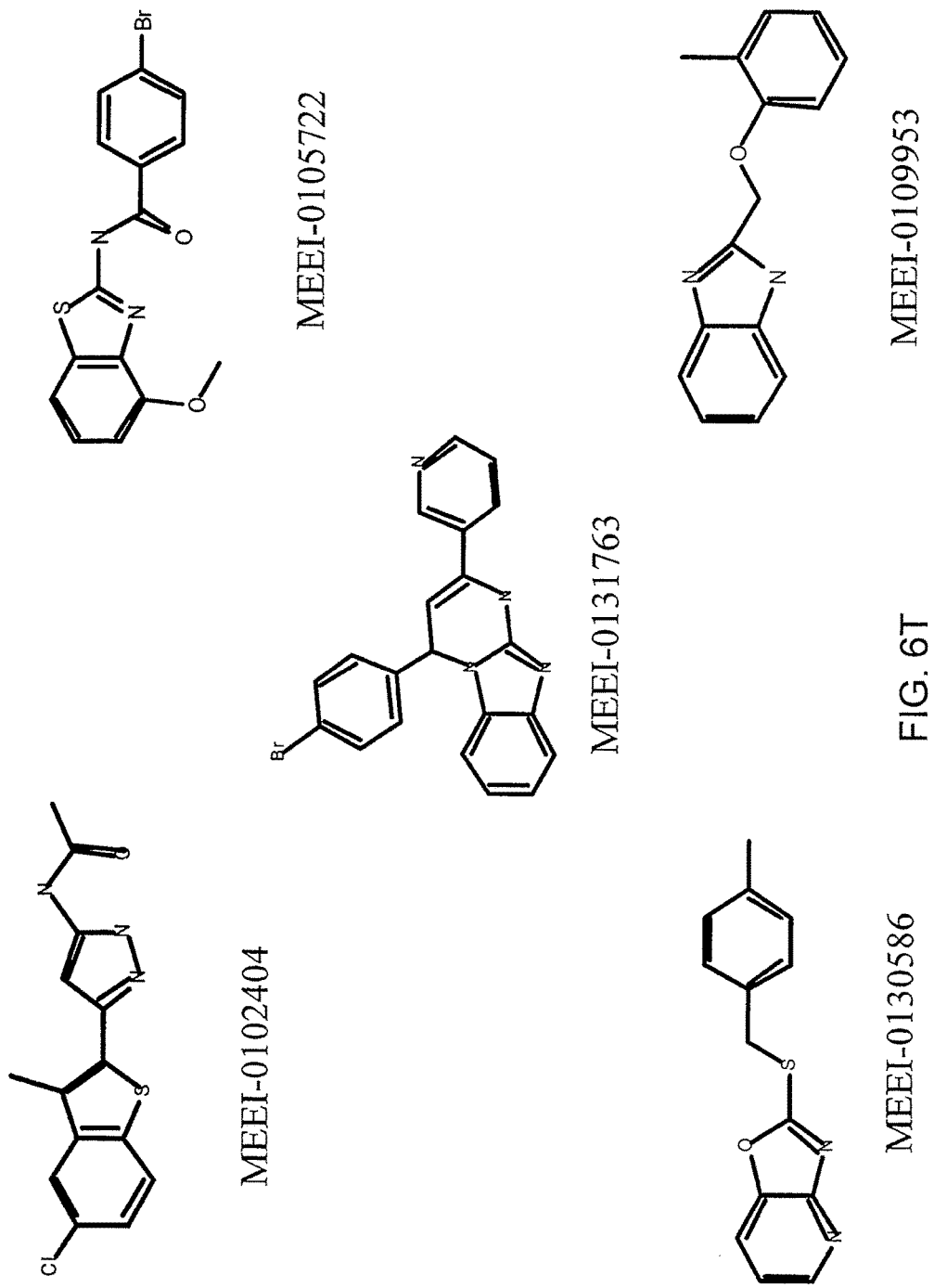
Figure 6V:
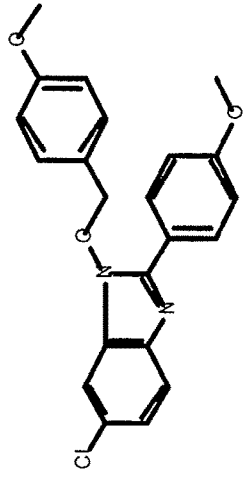
Figure 6V:
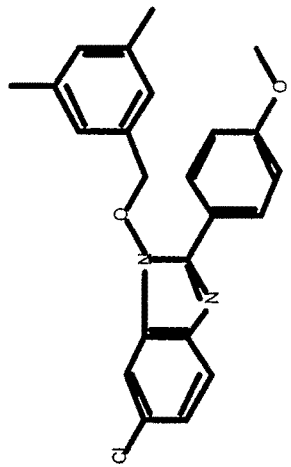
Figure 6V:
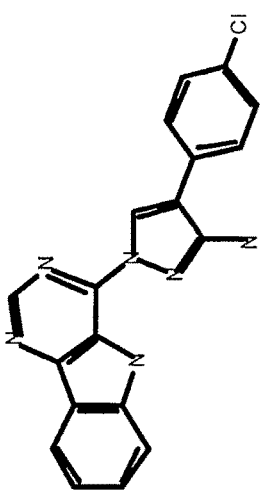
Figure 6V:
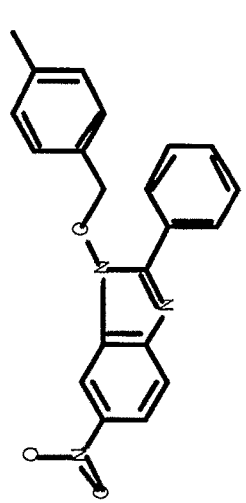

In some embodiments, the compounds that include a 5-membered heterocyclic ring system fused to one or more other ring systems are described by FIG. 6L, in which $R_{143}$, $R_{144}$, $R_{145}$, $R_{146}$ and $R_{147}$ are each independently H, F, Cl, Br, I, OH, CN, $NO_2$ or a moiety that includes up to 16 carbon atoms and, optionally, one or more N, O, S or F atoms; and X is O (see FIG. 6M) or S (see FIG. 6N).

In still other embodiments, the compounds that include a 5-membered heterocyclic ring system fused to one or more other ring systems are described by FIG. 6O, in which $R_{149}$, $R_{150}$, $R_{151}$ and $R_{152}$ are each independently H, F, Cl, Br, I, OH, CN, $NO_2$ or a moiety that includes up to 16 carbon atoms and, optionally, one or more N, O, S or F atoms; and $R_{153}$ is H or a moiety that includes up to 16 carbon atoms and, optionally, one or more N, O, S or F atoms.

In some embodiments, the compounds that can be utilized in any method described herein are pyridines or pyrimidines. For example, such compounds can be generally represented by those structures shown in FIGS. 7A-7D, and specifically exemplified in those structures shown in FIGS. 7E and 7F. Any described compound that is a pyridine or a pyrimidine can be in neutral or salt form, e.g., a hydrochloride salt thereof.

Figure 7C:
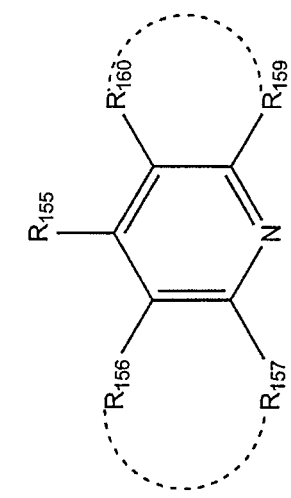
Figure 7B:
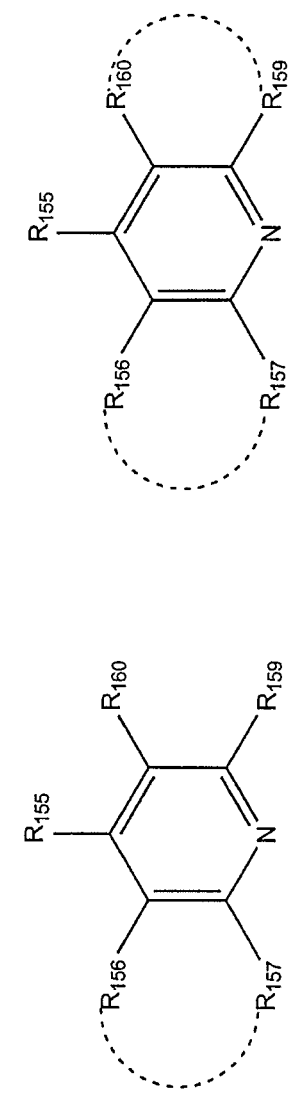
Figure 7A:
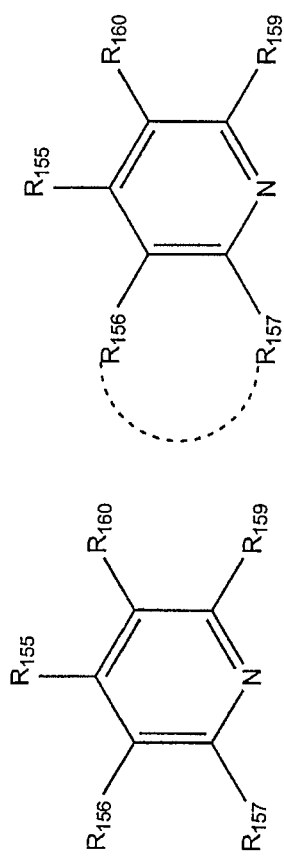

In some embodiments, the pyridine compounds are described by FIG. 7A, in which $R_{155}$, $R_{156}$, $R_{157}$, $R_{159}$ and $R_{160}$ are each independently H, F, Cl, Br, I, OH, CN, $NO_2$ or a moiety that includes up to 16 carbon atoms and, optionally, one or more N, O, S or F atoms. In some specific embodiments, $R_{156}$ and $R_{157}$ (see FIG. 7B), or $R_{156}$ and $R_{157}$ and $R_{159}$ and $R_{160}$ (see FIG. 7C) together define a one or more rings that each include up to 16 carbon atoms and, optionally, one or more N, O, S or F atoms.

Figure 7D:
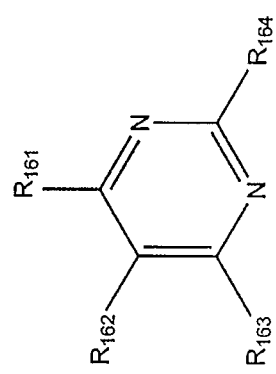
FIG. 7D is a generalized structure of pyrimidine compounds.

In some embodiments, the pyrimidine compounds are described by FIG. 7D, in which $R_{161}$, $R_{162}$, $R_{163}$ and $R_{164}$ are each independently H, F, Cl, Br, I, OH, CN, $NO_2$ or a moiety that includes up to 16 carbon atoms and, optionally, one or more N, O, S or F atoms.

Figure 8B:
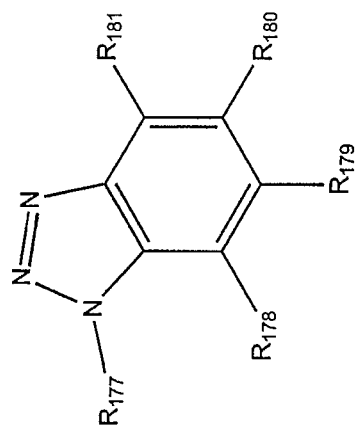
FIGS. 8A and 8B are generalized structures of aniline compounds or aniline derivatives.

In some embodiments, the compounds that can be utilized in any method described herein are anilines or aniline derivatives. For example, such compounds can be generally represented by those structures shown in FIGS. 8A and 8B, and specifically exemplified in those structures shown in FIG. 8C. Any described compound that is a pyridine or a pyrimidine can be in neutral or salt form.

Figure 8A:
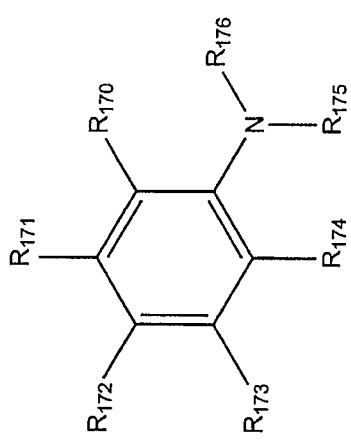
Figure 8C:
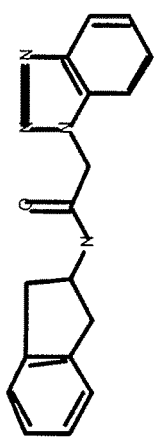
FIG. 8C are structures of specific structures of anilines or aniline derivatives.
Figure 8C:
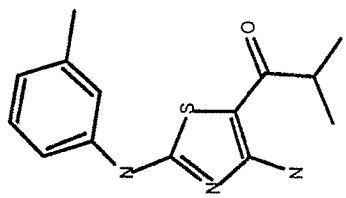
Figure 8C:
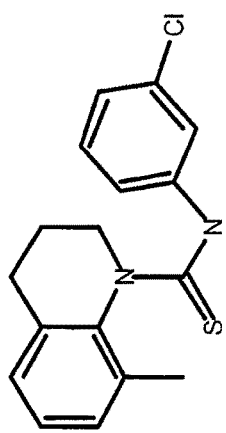
Figure 8C:
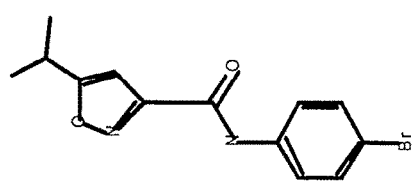

In some embodiments, the aniline compounds are described by FIG. 8A, in which $R_{170}$, $R_{171}$, $R_{172}$, $R_{173}$ and $R_{174}$ are each independently H, F, Cl, Br, I, OH, CN, $NO_2$ or a moiety that includes up to 16 carbon atoms and, optionally, one or more N, O, S or F atoms; and $R_{175}$ and $R_{176}$ are each independently H or a moiety that includes up to 16 carbon atoms and, optionally, one or more N, O, S or F atoms.

In some embodiments, the aniline derivative compounds are described by FIG. 8B, in which $R_{178}$, $R_{179}$, $R_{180}$ and $R_{181}$ are each independently H, F, Cl, Br, I, OH, CN, $NO_2$, or a moiety that includes up to 16 carbon atoms and, optionally, one or more N, O, S or F atoms; and $R_{177}$ is H or a moiety that includes up to 16 carbon atoms and, optionally, one or more N, O, S or F atoms.

In some embodiments, the compounds can have the formula delineated in FIG. 6G:

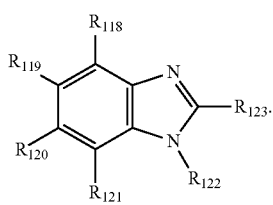

In some embodiments:
each of $R_{118}$, $R_{119}$, $R_{120}$, and $R_{121}$ is, independently selected from H, halo, OH, CN, $NO_2$, $C_1$-$C_3$ alkyl, $C_1$-$C_3$ haloalkyl, $C_1$-$C_3$ alkoxy, and $C_1$-$C_3$ haloalkoxy;
$R_{122}$ is hydrogen or —Z—$R^a$; wherein:
Z is O or a bond; and
$R^a$ is:

(i) $C_1$-$C_6$ alkyl or $C_1$-$C_6$ haloalkyl, each of which is optionally substituted with from 1-3 $R^b$; or
(ii) $C_3$-$C_{10}$ cycloalkyl, $C_3$-$C_{10}$ cycloalkenyl, each of which is optionally substituted with from 1-5 $R^c$; or
(iii) $C_7$-$C_{11}$ aralkyl, or heteroaralkyl including 6-11 atoms, each of which is optionally substituted with from 1-5 $R^c$;
(iv) $C_6$-$C_{10}$ aryl or heteroaryl including 5-10 atoms, each of which is
optionally substituted with from 1-5 $R^d$;
$R_{123}$ is:
(i) hydrogen; or
(ii) $C_1$-$C_6$ alkyl or $C_1$-$C_6$ haloalkyl, each of which is optionally substituted with from 1-3 $R^b$; or
(iii) $C_6$-$C_{10}$ aryl or heteroaryl including 5-10 atoms, each of which is optionally substituted with from 1-5 $R^d$; or
(iv) $C_7$-$C_{11}$ aralkyl, or heteroaralkyl including 6-11 atoms, each of which is optionally substituted with from 1-5 $R^c$; or
(v) —($C_1$-$C_6$ alkyl)-$Z^1$—($C_6$-$C_{10}$ aryl), wherein $Z^1$ is O, S, NH, or N($CH_3$); the alkyl portion is optionally substituted with from 1-3 $R^b$; and the aryl portion is optionally substituted with from 1-5 $R^d$; or
(vi) —($C_1$-$C_6$ alkyl)-$Z^2$-(heteroaryl including 5-10 atoms), wherein $Z^2$ is O, S, NH, or N($CH_3$); the alkyl portion is optionally substituted with from 1-3 $R^b$; and the heteroaryl portion is optionally substituted with from 1-5 $R^d$; or
(vii) —($C_1$-$C_6$ alkyl)-$Z^3$—($C_3$-$C_{10}$ cycloalkyl), wherein $Z^3$ is O, S, NH, or N($CH_3$); the alkyl portion is optionally substituted with from 1-3 $R^b$; and the cycloalkyl portion is optionally substituted with from 1-5 $R^c$;
$R^b$ at each occurrence is, independently:
(i) $NH_2$; $NH(C_1$-$C_3$ alkyl); $N(C_1$-$C_3$ alkyl$)_2$; hydroxy; $C_1$-$C_6$ alkoxy or $C_1$-$C_6$ haloalkoxy; or
(ii) $C_3$-$C_7$ cycloalkyl optionally substituted with from 1-3 substituents independently selected from $C_1$-$C_6$ alkyl, $NH_2$; $NH(C_1$-$C_3$ alkyl); $N(C_1$-$C_3$ alkyl$)_2$; hydroxy; $C_1$-$C_6$ alkoxy or $C_1$-$C_6$ haloalkoxy;
$R^c$ at each occurrence is, independently:
(i) halo; $NH_2$; $NH(C_1$-$C_3$ alkyl); $N(C_1$-$C_3$ alkyl$)_2$; hydroxy; $C_1$-$C_6$ alkoxy; $C_1$-$C_6$ haloalkoxy; or oxo; or
(ii) $C_1$-$C_6$ alkyl or $C_1$-$C_6$ haloalkyl; and
$R^d$ at each occurrence is, independently:
(i) halo; $NH_2$; $NH(C_1$-$C_3$ alkyl); $N(C_1$-$C_3$ alkyl$)_2$; hydroxy; $C_1$-$C_6$ alkoxy or $C_1$-$C_6$ haloalkoxy; nitro; —NHC(O)($C_1$-$C_3$ alkyl); or cyano; or
(ii) $C_1$-$C_6$ alkyl or $C_1$-$C_6$ haloalkyl.

Embodiments can include one or more of the following features.

Variables $R_{118}$, $R_{119}$, $R_{120}$, and $R_{121}$

In certain embodiments, each of $R_{118}$, $R_{119}$, $R_{120}$, and $R_{121}$ is hydrogen. In other embodiments, each of $R_{118}$, $R_{119}$, $R_{120}$, and $R_{121}$ is independently selected from H, halo and $NO_2$. In still other embodiments, one of $R_{118}$, $R_{119}$, $R_{120}$, and $R_{121}$ (e.g., $R_{120}$) is halo, OH, CN, $NO_2$, $C_1$-$C_3$ alkyl, $C_1$-$C_3$ haloalkyl, $C_1$-$C_3$ alkoxy, or $C_1$-$C_3$ haloalkoxy (e.g., halo, e.g., chloro; or $NO_2$); and the others are hydrogen (e.g., one of $R_{118}$, $R_{119}$, $R_{120}$, and $R_{121}$ (e.g., $R_{120}$) is halo and $NO_2$, and the others are hydrogen).

Variable $R_{122}$

In certain embodiments, $R_{122}$ can be —Z—$R^a$. Embodiments can include one or more of the following features.

Z can be O.
Z can be a bond.
$R^a$ can be:

(i) $C_1$-$C_6$ alkyl or $C_1$-$C_6$ haloalkyl, each of which is optionally substituted with from 1-3 $R^b$; or (iii) $C_7$-$C_{11}$ aralkyl, or heteroaralkyl including 6-11 atoms, each of which is optionally substituted with from 1-5 $R^c$.

For example, $R^a$ can be:

(i) $C_1$-$C_6$ alkyl, each of which is optionally substituted with from 1-3 $R^b$; or (iii) $C_7$-$C_{11}$ aralkyl, which is optionally substituted with from 1-5 $R^c$.

$R^a$ can be $C_7$-$C_{11}$ aralkyl, or heteroaralkyl including 6-11 atoms, each of which is optionally substituted with from 1-5 $R^c$ (e.g., $C_7$-$C_{11}$ aralkyl, which is optionally substituted with from 1-5 $R^c$). For example, $R^a$ can be benzyl or phenethyl, in which the phenyl portion is optionally substituted with from 1-5 (e.g., 1-4, 1-3, 1-2, or 1, e.g., 1-2 or 1) $R^c$ (e.g., halo (e.g., chloro); $C_1$-$C_6$ alkoxy (e.g., $OCH_3$); or $C_1$-$C_6$ alkyl (e.g., $CH_3$). In certain embodiments, Z can be O.

$R^a$ can be $C_1$-$C_6$ alkyl or $C_1$-$C_6$ haloalkyl, each of which is optionally substituted with from 1-3 $R^b$ (e.g., $C_1$-$C_6$ alkyl, each of which is optionally substituted with from 1-3 $R^b$). For example, $R^a$ can be $CH_3$. In certain embodiments, Z can be a bond.

In certain embodiments, $R_{122}$ can be hydrogen.

Variable $R_{123}$

In certain embodiments, $R_{123}$ can be:

(iii) $C_6$-$C_{10}$ aryl or heteroaryl including 5-10 atoms, each of which is optionally substituted with from 1-5 $R^d$; or (iv) $C_7$-$C_{11}$ aralkyl, or heteroaralkyl including 6-11 atoms, each of which is optionally substituted with from 1-5 $R^c$; or (v) —($C_1$-$C_6$ alkyl)-$Z^1$—($C_6$-$C_{10}$ aryl), wherein $Z^1$ is O, S, NH, or N($CH_3$); the alkyl portion is optionally substituted with from 1-3 $R^b$; and the aryl portion is optionally substituted with from 1-5 $R^d$.

For example, $R_{123}$ can be:

(iii) $C_6$-$C_{10}$ aryl, which is optionally substituted with from 1-5 $R^d$; or (iv) $C_7$-$C_{11}$ aralkyl, which is optionally substituted with from 1-5 $R^c$; or (v) —($C_1$-$C_6$ alkyl)-$Z^1$—($C_6$-$C_{10}$ aryl), wherein $Z^1$ is O, S, NH, or N($CH_3$); the alkyl portion is optionally substituted with from 1-3 $R^a$; and the aryl portion is optionally substituted with from 1-5 $R^d$.

In embodiments, $R_{123}$ can be $C_6$-$C_{10}$ aryl or heteroaryl including 5-10 atoms, each of which is optionally substituted with from 1-5 $R^d$ (e.g., $C_6$-$C_{10}$ aryl, which is optionally substituted with from 1-5 $R^d$). For example, $R_{123}$ can be phenyl, is optionally substituted with from 1-5 (e.g., 1-4, 1-3, 1-2, or 1) $R^d$ (e.g., $C_1$-$C_6$ alkoxy, e.g., $OCH_3$).

In embodiments, $R_{123}$ can be $C_7$-$C_{11}$ aralkyl, or heteroaralkyl including 6-11 atoms, each of which is optionally substituted with from 1-5 $R^c$ (e.g., $C_7$-$C_{11}$ aralkyl, which is optionally substituted with from 1-5 $R^c$). For example, $R_{123}$ can be benzyl or phenethyl, in which the phenyl portion is optionally substituted with from 1-5 (e.g., 1-4, 1-3, 1-2, or 1) $R^c$ (e.g., halo (e.g., chloro); $C_1$-$C_6$ alkoxy (e.g., $OCH_3$); $C_1$-$C_6$ alkyl (e.g., $CH_3$); $NH_2$; or hydroxyl).

In embodiments, $R_{123}$ can be —($C_1$-$C_6$ alkyl)-Z—($C_6$-$C_{10}$ aryl), wherein $Z^1$ is O, S, NH, or N($CH_3$); the alkyl portion is optionally substituted with from 1-3 $R^b$; and the aryl portion is optionally substituted with from 1-5 $R^d$. For example, $R_{123}$ can be —($CH_2$)—$Z^1$-(phenyl), in which the phenyl portion is optionally substituted with from 1-5 (e.g., 1-4, 1-3, 1-2, or 1) $R^d$ (e.g., halo (e.g., chloro); $C_1$-$C_6$ alkoxy (e.g., $OCH_3$); $C_1$-$C_6$ alkyl (e.g., $CH_3$); $NH_2$; or hydroxyl).

A subset of compounds includes those in which:

$R_{122}$ is —Z—$R^a$, in which $R^a$ can be $C_7$-$C_{11}$ aralkyl, or heteroaralkyl including 6-11 atoms, each of which is optionally substituted with from 1-5 $R^c$ (e.g., $C_7$-$C_{11}$ aralkyl, e.g., benzyl or phenethyl, which is optionally substituted with from 1-5 $R^c$); and $R_{123}$ can be $C_6$-$C_{10}$ aryl or heteroaryl including 5-10 atoms, each of which is optionally substituted with from 1-5 $R^d$ (e.g., $C_6$-$C_{10}$ aryl, e.g., phenyl, which is optionally substituted with from 1-5 $R^d$).

Embodiments can include one or more of the following features:

$R^c$ and $R^d$ can be as defined anywhere herein.

Z can be O.

Each of $R_{118}$, $R_{119}$, $R_{120}$, and $R_{121}$ is hydrogen. In other embodiments, each of $R_{118}$, $R_{119}$, $R_{120}$, and $R_{121}$ is independently selected from H, halo and $NO_2$. In still other embodiments, one of $R_{118}$, $R_{119}$, $R_{120}$, and $R_{121}$ (e.g., $R_{120}$) is halo, OH, CN, $NO_2$, $C_1$-$C_3$ alkyl, $C_1$-$C_3$ haloalkyl, $C_1$-$C_3$ alkoxy, or $C_1$-$C_3$ haloalkoxy (e.g., halo, e.g., chloro; or $NO_2$); and the others are hydrogen (e.g., one of $R_{118}$, $R_{119}$, $R_{120}$, and $R_{121}$ (e.g., $R_{120}$) is halo and $NO_2$, and the others are hydrogen); e.g., one of is halo (e.g., chloro) or nitro, e.g., halo (e.g., chloro), and the others are hydrogen.

For example:

$R_{122}$ is —Z—$R^a$, wherein Z is O, and $R^a$ is $C_7$-$C_{11}$ aralkyl, which is optionally substituted with from 1-5 $R^c$; and $R_{123}$ is $C_6$-$C_{10}$ aryl, which is optionally substituted with from 1-5 $R^d$; and each of $R_{118}$, $R_{119}$, $R_{120}$, and $R_{121}$ can be hydrogen; or each of $R_{118}$, $R_{119}$, $R_{120}$, and $R_{121}$ can be, independently halo (e.g., chloro) or nitro, e.g., halo (e.g., chloro); or one of $R_{118}$, $R_{119}$, $R_{120}$, and $R_{121}$ can be halo (e.g., chloro) or $NO_2$, e.g., halo (e.g., chloro); and the others are hydrogen.

As another example, Z is a bond, and the definitions in the above example apply.

Examples of compounds having the formula delineated in FIG. 6G include: CP-0000489, CP-0000540, CP-0000550, CP-0000553, CP-0000554, CP-0000557, CP-0000571, CP-0047659, CP-0064483, CP-0066829, CP-0069961, CP-0074806, CP-0080773, CP-0091818, CP-0109953, CP-0105772, and CP-0193184.

Other examples of compounds having the formula delineated in FIG. 6G include:

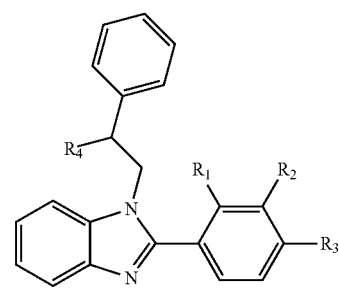

1 $R_1$ = H, $R_2$ = H, $R_3$ = H, $R_4$ = H
2 $R_1$ = H, $R_2$ = OMe, $R_3$ = OMe, $R_4$ = H
3 $R_1$ = H, $R_2$ = H, $R_3$ = H, $R_4$ = OH

-continued

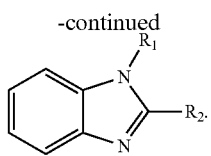

4 $R_1$ = $CH_2Ph$, $R_2$ = Ph
5 $R_1$ = Ph, $R_2$ = Ph
6 $R_1$ = $CH_2$-2-ClPh, $R_2$ = Ph
7 $R_1$ = $CH_2Ph$, $R_2$ = 4-OMePh
8 $R_1$ = $CH_2CH_2$-c-hex, $R_2$ = 4-OMePh
9 $R_1$ = H, $R_2$ = 4-OMePh
10 $R_1$ = Me, $R_2$ = 4-OMePh
11 $R_1$ = $CH_2CH_2Ph$, $R_2$ = H
12 $R_1$ = $CH_2CH_2Ph$, $R_2$ = Me
13 $R_1$ = $CH_2CH_2Ph$, $R_2$ = 2-thienyl
14 $R_1$ = $CH_2CH_2Ph$, $R_2$ = $CH_2Ph$ In some embodiments, the compounds can have the formula delineated in FIG. 6L:

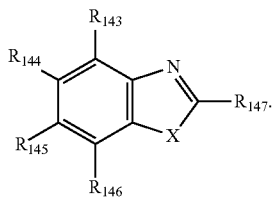

In some embodiments:

X is O or S;

each of $R_{143}$, $R_{144}$, $R_{145}$, and $R_{146}$ is, independently selected from H, halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; and —NHC(O)($C_1$-$C_3$ alkyl);

$R_{147}$ is $NR^eR^f$, wherein one of $R^e$ and $R^f$ is hydrogen or $C_1$-$C_3$ alkyl; and the other of $R^e$ and $R^f$ is:
(i) —C(O)$R^g$; wherein $R^g$ is $C_6$-$C_{10}$ aryl or heteroaryl including 5-10 atoms, each of which is optionally substituted with from 1-5 $R^h$; or
(ii) $C_1$-$C_3$ alkyl;
or $R_{147}$ is $C_6$-$C_{10}$ aryl or heteroaryl including 5-10 atoms, each of which is optionally substituted with from 1-5 $R^h$; or $R_{147}$ is —$SCH_2R^i$, wherein $R^i$ is:
(i) $C_6$-$C_{10}$ aryl or heteroaryl including 5-10 atoms, each of which is optionally substituted with from 1-5 $R^h$; or
(ii) —C(O)$NR^eR^f$, wherein one of $R^e$ and $R^f$ is hydrogen or $C_1$-$C_3$ alkyl; and the other of $R^e$ and $R^f$ is —C(O)$R^g$; wherein $R^g$ is $C_6$-$C_{10}$ aryl or heteroaryl including 5-10 atoms, each of which is optionally substituted with from 1-5 $R^h$; and $R^h$ at each occurrence is, independently:
(i) halo; $NH_2$; $NH(C_1$-$C_3$ alkyl); $N(C_1$-$C_3$ alkyl$)_2$; hydroxy; $C_1$-$C_6$ alkoxy or $C_1$-$C_6$ haloalkoxy; nitro; or cyano; or
(ii) $C_1$-$C_6$ alkyl or $C_1$-$C_6$ haloalkyl.

Embodiments can include one or more of the following features.

Variable X
X can be S.
X can be O.
Variables $R_{143}$, $R_{144}$, $R_{145}$, and $R_{146}$
In certain embodiments, each of $R_{143}$, $R_{144}$, $R_{145}$, and $R_{146}$ is hydrogen. In other embodiments, one of $R_{143}$, $R_{144}$, $R_{145}$, and $R_{146}$ is halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; or —NHC(O)($C_1$-$C_3$ alkyl); and the others are hydrogen.

Variable $R_{147}$

In certain embodiments, $R_{147}$ can be $NR^eR^f$, wherein one of $R^e$ and $R^f$ is hydrogen or $C_1$-$C_3$ alkyl (e.g., hydrogen); and the other of $R^e$ and $R^f$ is:
(i) —C(O)$R^g$; wherein $R^g$ is $C_6$-$C_{10}$ aryl or heteroaryl including 5-10 atoms, each of which is optionally substituted with from 1-5 $R^h$; or
(ii) $C_1$-$C_3$ alkyl.

In embodiments, $R_{147}$ can be $NR^eR^f$, wherein one of $R^e$ and $R^f$ is hydrogen or $C_1$-$C_3$ alkyl (e.g., hydrogen); and the other of $R^e$ and $R^f$ is —C(O)$R^g$; wherein $R^g$ is $C_6$-$C_{10}$ aryl or heteroaryl including 5-10 atoms, each of which is optionally substituted with from 1-5 $R^h$.

By way of example, $R^g$ can be phenyl, which is optionally substituted with from 1-5 (e.g., 1-4, 1-3, 1-2, or 1) $R^h$ (e.g., halo (e.g., chloro); $C_1$-$C_6$ alkoxy (e.g., $OCH_3$); or $C_1$-$C_6$ alkyl (e.g., $CH_3$)).

As another example, $R^g$ can be heteroaryl including 5-6 (e.g., 5) atoms, which is optionally substituted with from 1-2 (e.g., 1) $R^h$ (e.g., $C_1$-$C_6$ alkyl (e.g., $CH_3$)).

In certain embodiments:
X can be S; and
$R_{147}$ can be $NR^eR^f$, wherein one of $R^e$ and $R^f$ is hydrogen or $C_1$-$C_3$ alkyl (e.g., hydrogen); and the other of $R^e$ and $R^f$ is:
(i) —C(O)$R^g$; wherein $R^g$ is $C_6$-$C_{10}$ aryl or heteroaryl including 5-10 atoms, each of which is optionally substituted with from 1-5 $R^h$; or
(ii) $C_1$-$C_3$ alkyl;
(e.g., one of $R^e$ and $R^f$ is hydrogen or $C_1$-$C_3$ alkyl (e.g., hydrogen); and the other of $R^e$ and $R^f$ is —C(O)$R^g$; wherein $R^g$ is $C_6$-$C_{10}$ aryl or heteroaryl including 5-10 atoms, each of which is optionally substituted with from 1-5 $R^h$).

$R^g$ and $R^h$ can be as defined anywhere herein.

In certain embodiments, each of $R_{143}$, $R_{144}$, $R_{145}$, and $R_{146}$ is hydrogen. In other embodiments, one of $R_{143}$, $R_{144}$, $R_{145}$, and $R_{146}$ is halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; or —NHC(O)($C_1$-$C_3$ alkyl); and the others are hydrogen.

Examples of compounds having the formula delineated in FIG. 6L include: CP-0064917, CP-0067233, CP-0068578, CP-0103014, CP-0105777, CP-0107060, CP-0029300, CP-0079983, and CP-0103978.

In some embodiments, the compounds can have the formula delineated in FIG. 6A:

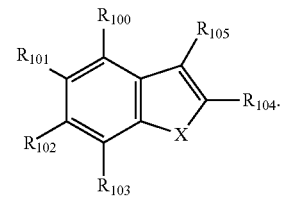

In some embodiments:
X is O or S;
each of $R_{100}$, $R_{101}$, $R_{102}$, and $R_{103}$, is, independently selected from H, halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; or
any two adjacent pairs of $R_{100}$, $R_{101}$, $R_{102}$, and $R_{103}$, together with the carbon atoms to which they are attached form a fused heterocyclic ring including 5 or 6 total ring atoms; wherein the heterocyclic ring is optionally substituted with from 1-3 substituents independently selected from $C_1$-$C_3$ alkyl and oxo;

$R_{104}$ is —C(O)NR$^j$R$^k$, wherein one of R$^j$ and R$^k$ is hydrogen or $C_1$-$C_3$ alkyl; and the other of R$^j$ and R$^k$ is:
(i) $C_1$-$C_8$ alkyl, optionally substituted with a 5-6 heterocyclyl; or
(ii) heteroaryl including 5-6 atoms, which is optionally substituted with from 1-5 substituents independently selected from halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; —C(O)$NH_2$; —NHC(O)($C_1$-$C_3$ alkyl); and a fused $C_5$-$C_6$ cycloalkyl ring;
or
$R_{104}$ is heteroaryl including 5-6 atoms, which is optionally substituted with from 1-5 substituents independently selected from halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; —C(O)$NH_2$; —NHC(O)($C_1$-$C_3$ alkyl); and
$R_{105}$ is halo or $C_1$-$C_3$ alkyl.

Embodiments can include one or more of the following features.

Variable X

X can be S.

X can be O.

Variables $R_{100}$, $R_{101}$, $R_{102}$, and $R_{103}$

In certain embodiments, each of $R_{100}$, $R_{101}$, $R_{102}$, and $R_{103}$ is hydrogen. In other embodiments, one of $R_{100}$, $R_{101}$, $R_{102}$, and $R_{103}$ is halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; or —NHC(O)($C_1$-$C_3$ alkyl); and the others are hydrogen.

Variable $R_{104}$

In certain embodiments, $R_{104}$ is —C(O)NR$^j$R$^k$, wherein one of R$^j$ and R$^k$ is hydrogen or $C_1$-$C_3$ alkyl (e.g., hydrogen); and the other of R$^j$ and R$^k$ is:
(i) $C_1$-$C_5$ alkyl, optionally substituted with a 5-6 heterocyclyl; or
(ii) heteroaryl including 5-6 atoms, which is optionally substituted with from 1-5 substituents independently selected from halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; cyano; —C(O)$NH_2$; —NHC(O)($C_1$-$C_3$ alkyl); $C_1$-$C_3$ alkyl; $C_1$-$C_3$ alkyl; and a fused $C_5$-$C_6$ cycloalkyl ring.

By way of example, one of R$^j$ and R$^k$ is hydrogen or $C_1$-$C_3$ alkyl (e.g., hydrogen); and the other of R$^j$ and R$^k$ is heteroaryl including 5-6 atoms, which is optionally substituted with from 1-5 substituents independently selected from halo, OH, CN, $NO_2$, $C_1$-$C_3$ alkyl, $C_1$-$C_3$ haloalkyl, $C_1$-$C_3$ alkoxy, $C_1$-$C_3$ haloalkoxy; —C(O)$NH_2$; —NHC(O)($C_1$-$C_3$ alkyl); and a fused $C_5$-$C_6$ cycloalkyl ring.

Variable $R_{105}$ $R_{105}$ can be chloro or $CH_3$.

Examples of compounds having the formula delineated in FIG. 6A include: CP-0079175, CP-0087336, CP-0064314, CP-0068577, and CP-0102404.

In some embodiments, the compounds can have the formula delineated in FIG. 3A:

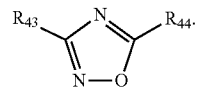

In some embodiments:

$R_{43}$ is $C_6$-$C_{10}$ aryl or heteroaryl including 5-10 atoms, each of which is optionally substituted with from 1-5 R$^m$;

$R_{44}$ is:
(i) $C_6$-$C_{10}$ aryl or heteroaryl including 5-10 atoms, each of which is optionally substituted with from 1-5 R$^m$; or
(ii) —$Z^4$—($C_1$-$C_6$ alkyl), wherein:
$Z^4$ is a bond or NH; and
the $C_1$-$C_6$ alkyl is substituted with one of the following:
(a) heterocyclyl including 5-6 atoms, which is optionally substituted with from 1-3 substituents independently selected from oxo and $C_1$-$C_6$ alkyl; or
(b) phenoxy, which is optionally substituted with from 1-5 R$^m$; and R$^m$ at each occurrence is, independently:
(i) halo; $NH_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; or cyano; or
(ii) $C_1$-$C_6$ alkyl or $C_1$-$C_6$ haloalkyl.

Embodiments can include one or more of the following features.

Variable $R_{43}$

In certain embodiments, $R_{43}$ can be $C_6$-$C_{10}$ aryl, which is optionally substituted with from 1-5 R$^m$. For example, $R_{43}$ can be phenyl, which is optionally substituted with from 1-5 (e.g., 1-4, 1-3, 1-2, or 1) R$^m$ (e.g., $C_1$-$C_6$ alkyl (e.g., $CH_3$)).

In certain embodiments, $R_{43}$ can be heteroaryl including 5-6 atoms, each of which is optionally substituted with from 1-5 R$^m$.

Variable $R_{44}$

In certain embodiments, $R_{44}$ can be $C_6$-$C_{10}$ aryl, which is optionally substituted with from 1-5 R$^m$. For example, $R_{44}$ can be phenyl, which is optionally substituted with from 1-5 (e.g., 1-4, 1-3, 1-2, or 1) R$^m$ (e.g., halo (e.g., chloro); $C_1$-$C_6$ alkoxy (e.g., $OCH_3$); or $C_1$-$C_6$ alkyl (e.g., $CH_3$)).

Examples of compounds having the formula delineated in FIG. 3A include: CP-0067108, CP-0067246, CP-0068395, CP-0068929, CP-0068961, CP-0070164, CP-0070367, CP-0079642, CP-0104904, and CP-0130665.

In some embodiments, the compounds can have the formula delineated in FIG. 3U:

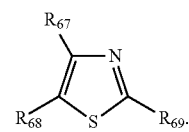

In some embodiments:

Each of $R_{67}$ and $R_{68}$ is, independently:
(i) hydrogen; or
(ii) $C_6$-$C_{10}$ aryl or heteroaryl including 5-10 atoms, each of which is optionally substituted with from 1-5 R$^n$; or
(iii) $NH_2$; or
(iv) —C(O)($C_1$-$C_6$ alkyl);

$R_{69}$ is NR$^o$R$^p$, wherein one of R$^o$ and R$^p$ is hydrogen or $C_1$-$C_3$ alkyl; and the other of R$^o$ and R$^p$ is:
(i) hydrogen; or
(ii) $C_6$-$C_{10}$ aryl or heteroaryl including 5-6 atoms, which is optionally substituted with from 1-5 R$^n$; or
(iii) —C(O)($C_1$-$C_6$ alkyl), wherein the $C_1$-$C_6$ alkyl is substituted with phenoxy that is optionally substituted with from 1-5 R$^n$;

R$^n$ at each occurrence is, independently:
(i) halo; $NH_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; or cyano; or
(ii) $C_1$-$C_6$ alkyl or $C_1$-$C_6$ haloalkyl; or
(iii) phenyl.

Embodiments can include one or more of the following features.

Variables $R_{67}$ and $R_{68}$

In certain embodiments, one of $R_{67}$ and $R_{68}$ is $C_6$-$C_{10}$ aryl or heteroaryl including 5-10 atoms, each of which is optionally substituted with from 1-5 $R''$; and the other is hydrogen.

Variable $R_{69}$

In certain embodiments, one of $R^o$ and $R^p$ is hydrogen or $C_1$-$C_3$ alkyl (e.g., hydrogen); and the other of $R^o$ and $R^p$ is $C_6$-$C_{10}$ aryl or heteroaryl including 5-6 atoms, which is optionally substituted with from 1-5 $R''$.

Examples of compounds having the formula delineated in FIG. 3U include: CP-0063182, CP-0071862, CP-0072036, CP-0105343, CP-0122949, and CP-0134381.

In some embodiments, the compounds can have the formula delineated in FIG. 3E:

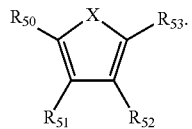

In some embodiments:

X is O or S;

$R_{50}$ and $R_{53}$ are each, independently:
(i) hydrogen; or
(ii) —C(O)$R^q$; or
(iii) $C_6$-$C_{10}$ aryl or heteroaryl including 5-10 atoms, each of which is optionally substituted with from 1-5 $R^r$;
provided that at least one of $R_{50}$ and $R_{53}$ is other than hydrogen;

$R_{51}$ and $R_{52}$ are each, independently, hydrogen or halo;

$R^q$ is:
(i) $C_1$-$C_6$ alkyl; or
(ii) —NR$^s$R$^t$, wherein:
  (a) one of $R^s$ and $R^t$ is hydrogen, and the other is $C_6$-$C_{10}$ aryl or heteroaryl including 5-10 atoms, each of which is optionally substituted with from 1-5 $R^r$; $C_1$-$C_6$ alkyl, which is substituted with phenoxy that is optionally substituted with from 1-5 $R^r$; or —O—N=C(NH$_2$)($C_6$-$C_{10}$ aryl), wherein the aryl portion is optionally substituted with from 1-5 $R^r$; or
  (b) $R^s$ and $R^t$, together with the nitrogen atom to which each is attached forms a heterocyclyl including 5-6 atoms; or
(iii) —NH—C(O)($C_6$-$C_{10}$ aryl), wherein the aryl portion is optionally substituted with from 1-5 $R^r$; and $R^r$ at each occurrence is, independently:
(i) halo; NH$_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; or cyano; or
(ii) $C_1$-$C_6$ alkyl or $C_1$-$C_6$ haloalkyl.

In certain embodiments, one of $R_{50}$ and $R_{53}$ is —C(O)$R^q$; and the other of $R_{50}$ and $R_{53}$ is hydrogen or $C_6$-$C_{10}$ aryl or heteroaryl including 5-10 atoms, each of which is optionally substituted with from 1-5 $R^r$. In embodiments, $R^q$ can be —NR$^s$R$^t$.

Examples of compounds having the formula delineated in FIG. 3E include: CP-0061777, CP-0066008, CP-0072253, CP-0099289, CP-0008545, CP-0060852, CP-0072156, CP-0072271, CP-0104766, and CP-0110352.

In some embodiments, the compounds can have the formula delineated in FIG. 3N:

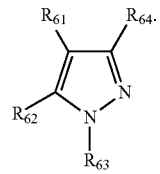

In some embodiments:

each of $R_{61}$, $R_{62}$, and $R_{64}$ is, independently:
(i) hydrogen; or
(ii) $C_6$-$C_{10}$ aryl or heteroaryl including 5-10 atoms, each of which is optionally substituted with from 1-5 $R^u$; or
(iii) —NH—C(O)($C_6$-$C_{10}$ aryl), wherein the aryl portion is optionally substituted with from 1-5 $R^u$; or
(iv) —C(O)NR'R$^w$, wherein one of $R^v$ and $R^w$ is hydrogen; and the other of $R^v$ and $R^w$ is $C_6$-$C_{10}$ aryl, which is optionally substituted with from 1-5 $R^u$; or $C_7$-$C_{11}$ aralkyl, which is optionally substituted with oxo; or
(v) NH$_2$ or hydroxymethyl;

$R_{63}$ is:
(i) hydrogen; or
(ii) $C_6$-$C_{10}$ aryl or heteroaryl including 5-10 atoms, each of which is optionally substituted with from 1-5 $R^u$; or
(iii) $C_1$-$C_6$ alkyl; and $R^u$ at each occurrence is, independently:
(i) halo; NH$_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; or cyano; or
(ii) $C_1$-$C_6$ alkyl or $C_1$-$C_6$ haloalkyl.

In certain embodiments, two of $R_{61}$, $R_{62}$, and $R_{64}$ are other than hydrogen.

Examples of compounds having the formula delineated in FIG. 3N include: CP-0000477, CP-0063375, CP-0064231, CP-0065105, CP-0070844, CP-0070886, and CP-0104765.

In some embodiments, the compounds can have the formula delineated in FIG. 3V.

In certain embodiments, $R_{70}$ can be an amide (i.e., having the general formula —C(O)NRR') or reverse amide (i.e., having the general formula —NR''C(O)R''') as described anywhere herein.

In certain embodiments, $R_{71}$ can be hydrogen.

In certain embodiments, $R_{72}$ can be:
(i) $C_1$-$C_6$ alkyl; or
(ii) $C_6$-$C_{10}$ aryl or heteroaryl including 5-10 atoms, each of which is optionally substituted with from 1-5 substituents independently selected from halo; NH$_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; cyano; $C_1$-$C_6$ alkyl; and $C_1$-$C_6$ haloalkyl.

Examples of compounds having the formula delineated in FIG. 3V include: CP-0065665, CP-0075627, and CP-0075656.

In some embodiments, the compounds can have the formula delineated in FIG. 7D.

In certain embodiments, the pyrimidine ring can be substituted with 1-2 substituents independently selected from:
(i) heterocyclyl including 5-6 atoms; or
(ii) $C_6$-$C_{10}$ aryl or heteroaryl including 5-10 atoms, each of which is optionally substituted with from 1-5 substituents independently selected from halo; NH$_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; cyano; $C_1$-$C_6$ alkyl; and $C_1$-$C_6$ haloalkyl.

In other embodiments, the pyrimidine ring can be substituted with a fused ring.

Examples of compounds having the formula delineated in FIG. 7D include: CP-0059547, CP-0059563, CP-0059642, CP-0064382, CP-0067053, CP-0072720, and CP-0079810.

In some embodiments, the compounds can have the formula delineated in FIG. 7A.

In certain embodiments, the pyridine ring can be substituted with an amide or reverse amide as described anywhere herein.

In other embodiments, the pyrimidine ring can be substituted with one or more fused ring.

Examples of compounds having the formula delineated in FIG. 7A include: CP-0060729, CP-0066751, CP-0069934, CP-0076627, CP-0080276, CP-0089966, CP-0029278, and CP-0130586.

Mixtures of any of the compounds described herein can also be utilized in any method described herein.

Methods of Synthesis

The compounds of the present invention can be obtained commercially from suppliers such as Bionet, Maybridge, Chemdiv, ChemBridge, Peakdale, IFLAB/Life Chemicals, Enamine, Microsource, or Timtec. Alternatively or in addition, the compounds described herein can be synthesized according to methods described herein (or variations thereof) and/or conventional, organic chemical synthesis methods from commercially available starting materials and reagents or from starting materials and reagents that can be prepared according to conventional organic chemical synthesis methods. The compounds described herein can be separated from a reaction mixture and further purified by a method such as column chromatography, high-performance liquid chromatography (HPLC), or recrystallization. As can be appreciated by the skilled artisan, further methods of synthesizing the compounds of the formulae herein will be evident to those skilled in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in Larock, *Comprehensive Organic Transformations*, 2d. ed., Wiley-VCH Publishers (1999); Wuts and Greene, Protective Groups in Organic Synthesis, 4th Ed., John Wiley and Sons (2007); Fieser and Fieser, *Fieser and Fieser's Reagents for Organic Synthesis*, John Wiley and Sons (1994); and Paquette, ed., *Encyclopedia of Reagents for Organic Synthesis*, John Wiley and Sons (1995), and subsequent editions thereof.

Benzimidazole-Containing Compounds

Compounds having the formula delineated in FIG. 6G can be obtained commercially or synthesized using conventional synthetic methods. For example, compounds CP-0000489, CP-0000540, CP-0000550, CP-0000553, CP-0000554, CP-0000557, CP-0000571, CP-0047659, CP-0064483, CP-0066829, CP-0069961, CP-0074806, CP-0080773, CP-0091818, CP-0105772, and CP-0109953 were obtained commercially from the suppliers provided in Table 1 (Entries 1-17). Other benzimidazoles 1-14 (Scheme 1) described in the present disclosure can be obtained commercially.

Scheme 1

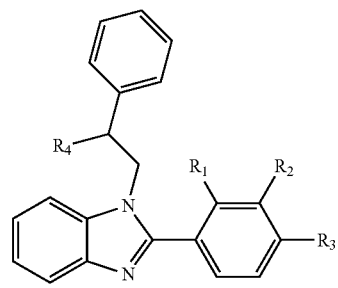

1 $R_1 = H, R_2 = H, R_3 = H, R_4 = H$
2 $R_1 = H, R_2 = OMe, R_3 = OMe, R_4 = H$
3 $R_1 = H, R_2 = H, R_3 = H, R_4 = OH$

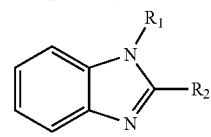

4 $R_1 = CH_2Ph, R_2 = Ph$
5 $R_1 = Ph, R_2 = Ph$
6 $R_1 = CH_2$-2-ClPh, $R_2 = Ph$
7 $R_1 = CH_2Ph, R_2 = $ 4-OMePh
8 $R_1 = CH_2CH_2$-c-hex, $R_2 = $ 4-OMePh
9 $R_1 = H, R_2 = $ 4-OMePh
10 $R_1 = Me, R_2 = $ 4-OMePh
11 $R_1 = CH_2CH_2Ph, R_2 = H$
12 $R_1 = CH_2CH_2Ph, R_2 = Me$
13 $R_1 = CH_2CH_2Ph, R_2 = $ 2-thienyl
14 $R_1 = CH_2CH_2Ph, R_2 = CH_2Ph$ Other compounds having the formula delineated in FIG. 6G can be obtained, e.g., using the chemistries described in Kokare et al., Protein & Peptide Letters, 14:259-263, 2007 which describes the synthesis of CP-0000540. Benzimidazole analogs incorporating changes to the specific portions of the molecule can be prepared according to Scheme 2 utilizing well established chemistry. In cases where a 1H-benzimidazole intermediate is commercially available, alkylation reactions can be carried out to introduce the $R_1$ substituent (Route A). Other elaborations of the commercial benzimidazoles can be utilized to install various substituents at different positions of the molecule. However, for unsymmetrically substituted 1H-benzimidazoles two other routes can be used. In cases of where $R_3$ is an electron-withdrawing group, nucleophilic aromatic substitution of 2-fluoronitrobenzenes can be utilized (Route B) to give 2-aminonitrobenzene intermediates. For other analogs, alkylation of 2-aminonitrobenzenes (Route C) to introduce the $R_1$ group can be pursued to give the same intermediate. The reduction of the nitro group to the amino group can be carried out with established reduction protocols. Oxidative cyclization of such 1,2-diamines with aldehydes or condensations with carboxylic acids will give the desired benzimidazole analogs.

Scheme 2: Synthesis of benzimidazole analogs

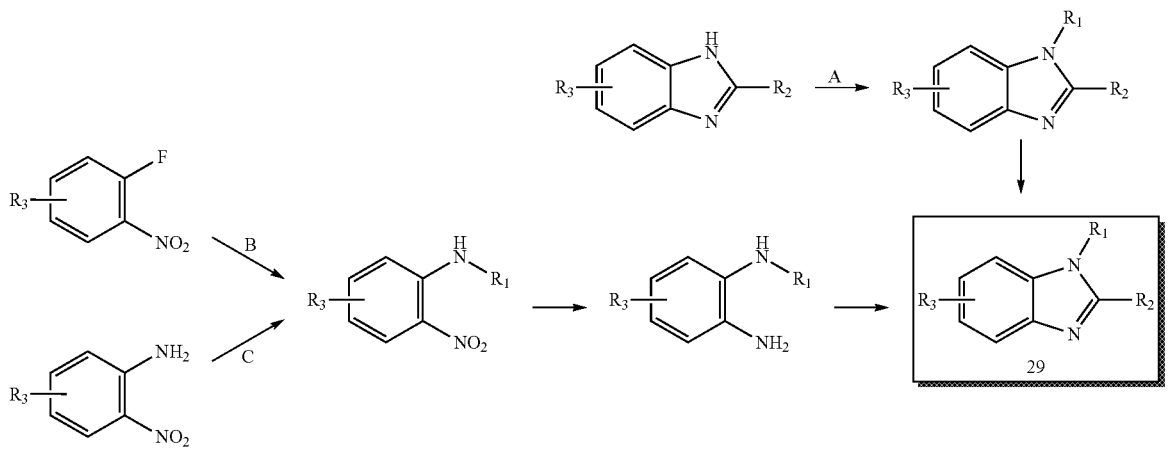

Benzothiazole-Containing Compounds

Compounds having the formula delineated in FIG. 6L (X=S) can be obtained commercially or synthesized using conventional synthetic methods. For example, compounds CP-0064917, CP-0067233, CP-0068578, CP-0103014, CP-0105777, and CP-0107060 were obtained commercially from the suppliers provided in Table 1 (Entries 18-23). Compounds having the formula delineated in FIG. 6L (X=S) can be obtained, e.g., by the cyclization of ortho-halo benzamides using Lawesson's reagent or via the oxidation of thioanilides. Other compounds having the formula delineated in FIG. 6L (X=S) can also be obtained, e.g., using the chemistries described in Song et al., Eur. J. Med. Chem. 43(7):1519-1524, 2008.

Benzoxazole-Containing Compounds

Compounds having the formula delineated in FIG. 6L (X=O) can be obtained commercially or synthesized using conventional synthetic methods. For example, compounds CP-0029300, CP-0079983, and CP-0103978 were obtained commercially from the suppliers provided in Table 1 (Entries 24-27). Other compounds having the formula delineated in FIG. 6L (X=O) can be obtained, e.g., using the chemistries described in Boyd, Sci. Synth. 11:481-492, 2002.

Quinazolinone-Containing Compounds

Quinazolinone derivatives included in the FIG. 2G, can be obtained commercially or synthesized using conventional synthetic methods. For example, compounds CP-0034360 and CP-0036187 were obtained commercially from the suppliers provided in Table 1 (Entries 27-28). Other compounds having the formula delineated in FIG. 2C can be obtained, e.g., using the chemistries described in Connolly et al., Tetrahedron 61(43):10153-10202, 2005.

Benzimidazopyrimidine-Containing Compounds

Benzimidazopyrimidine compounds having the formula delineated in FIG. 6I can be obtained commercially or synthesized using conventional synthetic methods. For example, compounds CP-0050095 and CP-0131763 were obtained commercially from the suppliers provided in Table 1 (Entries 29-30).

Benzofuran-Containing Compounds

Compounds having the formula delineated in FIG. 6A (X=O) can be obtained commercially or synthesized using conventional synthetic methods. For example, compounds CP-0079175 and CP-0087336 were obtained commercially from the suppliers provided in Table 1 (Entries 31-32). Other compounds having the formula delineated in FIG. 6A (X=O) can be obtained, e.g., using the chemistries described in Hou, et al., Progress in Heterocyclic Chemistry 17:142-171, 2005.

Benzothiophene-Containing Compounds

Compounds having the formula delineated in FIG. 6A (X=S) can be obtained commercially or synthesized using conventional synthetic methods. For example, compounds CP-0064314, CP-0068577, and CP-0102404 were obtained commercially from the suppliers provided in Table 1 (Entries 33-35). Other compounds having the formula delineated in FIG. 6A (X=S) can be obtained, e.g., using the chemistries described in either Bravo et al., J. Heterocyclic Chem., 7(4):967-8, 1970, or Rayner et al., Sci. Synth. 10:155-181, 2005.

Indole-Containing Compounds

Compounds having the formula delineated in FIG. 6J can be obtained commercially or synthesized using conventional synthetic methods. For example, compounds CP-0010539, CP-0072096, CP-0078448, and CP-0103978 were obtained commercially from the suppliers provided in Table 1 (Entries 36-38). Other compounds having the formula delineated in FIG. 6J can be obtained, e.g., using the chemistries described in Humphrey et al., Chem. Rev., 106(7):2875-2911, 2006.

Quinoline-Containing Compounds

Figure 7E:
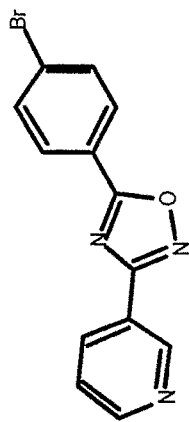
FIGS. 7E-7F are structures of specific pyridine or pyrimidine compounds.
Figure 7E:
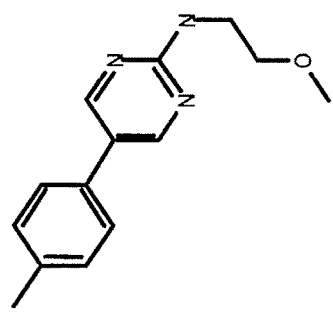
Figure 7E:
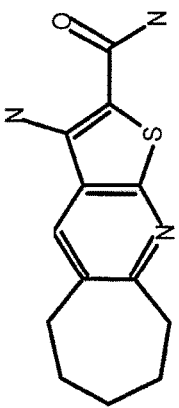
Figure 7E:
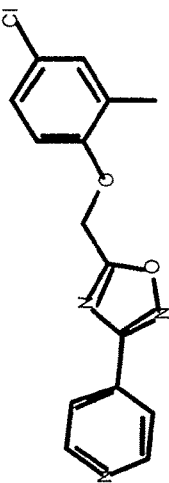
Figure 7F:
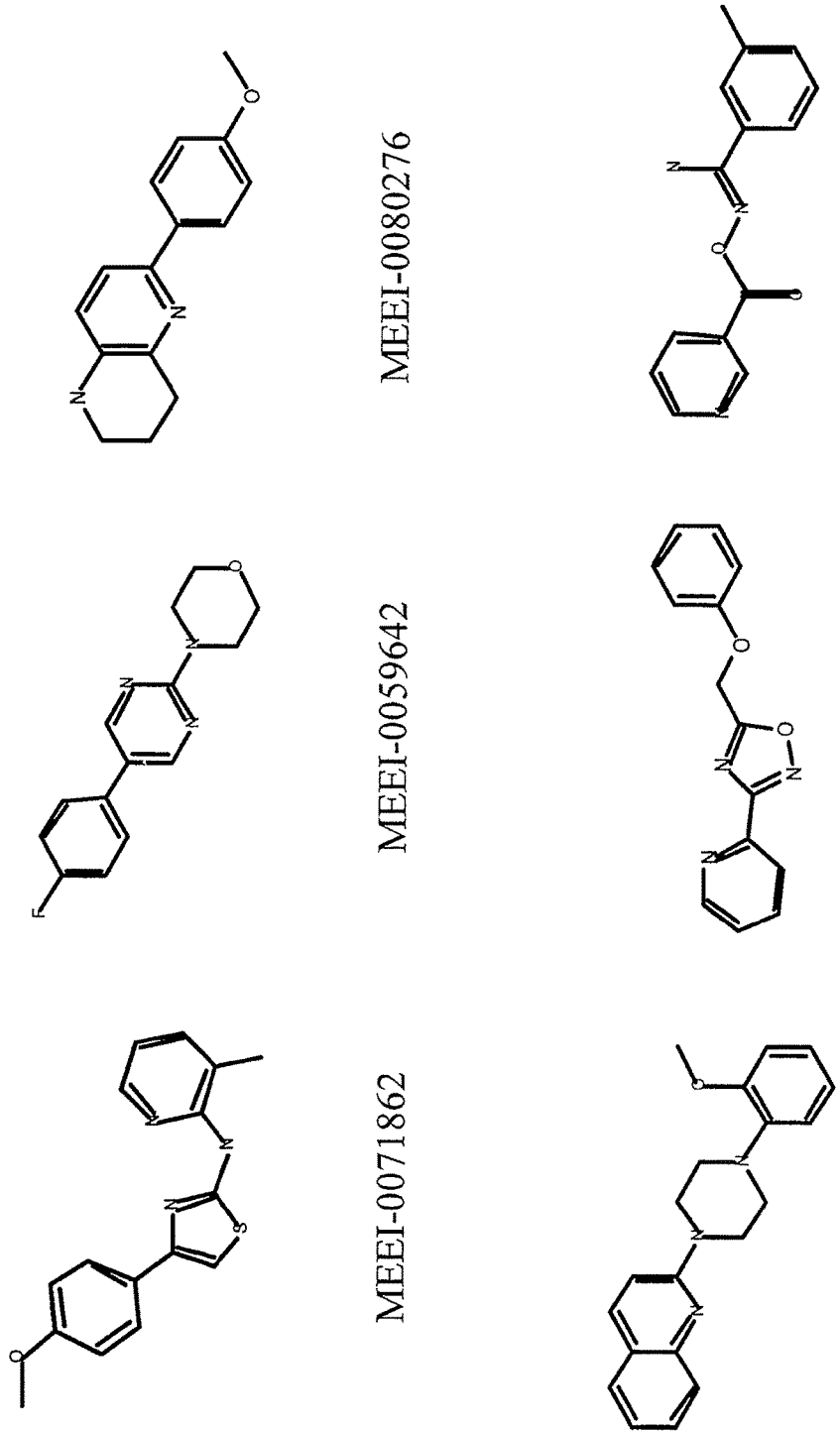

Quinolines derivatives included in the FIGS. 7E and 7F, can be obtained commercially or synthesized using conventional synthetic methods. For example, compounds CP-0072092 and CP-0087799 were obtained commercially from the suppliers provided in Table 1 (Entries 39-40). Other quinoline compounds can be obtained, e.g., using the chemistries described in Larsen et al., Sci. Synth. 15:389-549, 2005.

Benzotriazole-Containing Compounds

Compounds having the formula delineated in FIG. 6O can be obtained commercially or synthesized using conventional synthetic methods. For example, compounds CP-0009883 and CP-0070871 were obtained commercially from the suppliers provided in Table 1 (Entries 41-42). Other compounds having the formula delineated in FIG. 6O can be obtained, e.g., using the chemistries described in Katritzky et al., Chem. Rev. 98(2):409-548, 1998.

The coumarin-, benzopyran-, tetrahydroquinoline-, benzopyranone-, and benzopyrazine-containing compounds of the invention can be obtained commercially or synthesized using conventional synthetic methods. For example, compounds CP-0063508, CP-0000928, CP-0005069, CP-0096433, and CP-0045061 included in the FIG. 1, were obtained from the suppliers provided in Table 1 (Entries 43-47). Other coumarin-, benzopyran-, tetrahydroquinoline-, benzopyranone-, and benzopyrazine-containing compounds can be obtained, e.g., using the chemistries described in Borges et al., Curr. Med. Chem. 12(8):887-916, 2005; Schweizer et al., Chemistry of Heterocyclic Compounds 31:11-139, 1977; Katritzky et al., Tetrahedron 52(48): 15031-15070, 1996; Williams et al., Sci. Synth. 14:347-638, 2003; Kress et al., Progress in Heterocyclic Chemistry 4:186-203, 1992.

Pyridine-Containing Compounds

Compounds having the formula delineated in FIG. 7A can be obtained commercially or synthesized using conventional synthetic methods. For example, compounds CP-0060729, CP-0066751, CP-0069934, CP-0076627, CP-0080276, CP-0089966, CP-0029278, and CP-0130586 were obtained commercially from the suppliers provided in Table 1 (Entries 48-55). Other compounds having the formula delineated in FIG. 7A can be obtained, e.g., using the chemistries described in either Li et al., Bioorg. & Med. Chem. Lett. 17(8):2347-2350, 2007, or in Spitzner et al., Sci. Synth. 15:11-255, 2005.

Pyrimidine-Containing Compounds

Compounds having the formula delineated in FIG. 7D can be obtained commercially or synthesized using conventional synthetic methods. For example, compounds CP-0059547, CP-0059563, CP-0059642, CP-0064382, CP-0067053, CP-0072720, and CP-0079810 were obtained commercially from the suppliers provided in Table 1 (Entries 56-62). Other compounds having the formula delineated in FIG. 7D can be obtained, e.g., using the chemistries described in either Luo et al., Tetrahedron Lett. 43(33), 5739-5742, 2002, or von Angerer et al., Sci. Synth. 16:379-572, 2004.

Furan-Containing Compounds

Compounds having the formula delineated in FIG. 3E (X=O) can be obtained commercially or synthesized using conventional synthetic methods. For example, compounds CP-0061777, CP-0066008, CP-0072253, and CP-0099289 were obtained commercially from the suppliers provided in Table 1 (Entries 63-66). Other compounds having the formula delineated in FIG. 3E (X=O) can be obtained, e.g., using the chemistries described in either Kort et al., J. Med. Chem. 51(3):407-416, 2008, or Konig et al., Sci. Synth. 9:183-286, 2001.

Thiophene-Containing Compounds

Compounds having the formula delineated in FIG. 3E (X=S) can be obtained commercially or synthesized using conventional synthetic methods. For example, compounds CP-0008545, CP-0060852, CP-0072156, CP-0072271, CP-0104766, and CP-0110352 were obtained commercially from the suppliers provided in Table 1 (Entries 67-72). Other compounds having the formula delineated in FIG. 3E (X=S) can be obtained, e.g., using the chemistries described in either Kaizerman et al., J. Med. Chem. 46(18): 3914-3929, 2003, or Schatz et a., Sci. Synth. 10:287-392, 2001.

Thiazole-Containing Compounds

Compounds having the formula delineated in FIG. 3U can be obtained commercially or synthesized using conventional synthetic methods. For example, compounds CP-0063182, CP-0071862, CP-0072036, CP-0105343, CP-0122949, and CP-0134381 were obtained commercially from the suppliers provided in Table 1 (Entries 73-78). Other compounds having the formula delineated in FIG. 3U can be obtained, e.g., using the chemistries described in either Narayana et al., Phosphorus, Sulfur and Silicon and the Related Elements 181(6): 1381-1389, 2006, or Kikelj et al., Sci. Synth. 11:627-806, 2002.

Pyrazole-Containing Compounds

Compounds having the formula delineated in FIG. 3N can be obtained commercially or synthesized using conventional synthetic methods. For example, compounds CP-0000477, CP-0063375, CP-0064231, CP-0065105, CP-0070844, CP-0070886, and CP-0104765 were obtained commercially from the suppliers provided in Table 1 (Entries 79-85). Other compounds having the formula delineated in FIG. 3N can be obtained, e.g., using the chemistries described in either McKeown et al., Bioorg. & Med. Chem. Lett., 16(18):4767-4771, 2006, or Stanovnik, et al., Sci. Synth. 12:15-226, 2003.

Isoxazole-Containing Compounds

Compounds having the formula delineated in FIG. 3V can be obtained commercially or synthesized using conventional synthetic methods. For example, compounds CP-0065665, CP-0075627, and CP-0075656 were obtained commercially from the suppliers provided in Table 1 (Entries 86-88). Other compounds having the formula delineated in FIG. 3V can be obtained, e.g., using the chemistries described in Wakefield, Sci. Synth. 11:229-288, 2002.

Oxadiazole-Containing Compounds

Compounds having the formula delineated in FIG. 3A can be obtained commercially or synthesized using conventional synthetic methods. For example, compounds CP-0067108, CP-0067246, CP-0068395, CP-0068929, CP-0068961, CP-0070164, CP-0070367, CP-0079642, CP-0104904, and CP-0130665 were obtained commercially from the suppliers provided in Table 1 (Entries 89-98). Other compounds having the formula delineated in FIG. 3A can be obtained, e.g., using the chemistries described in either Grant et al., J. Org. Chem. 73(18):7219-7223, 2008, or Hemming, et al., Sci. Synth. 13:127-184, 2004.

Benzamide-Containing Compounds

Compounds having the formula delineated in FIG. 2A can be obtained commercially or synthesized using conventional synthetic methods. For example, compounds CP-0005186, CP-0007991, and CP-0061566 were obtained commercially from the suppliers provided in Table 1 (Entries 99-101). Other compounds having the formula delineated in FIG. 2A can be obtained using the methods known to one skilled in the art e.g., by a condensation of the corresponding benzoic acid and an amine.

The 1,3,4-oxadiazole-, triazoline-, pyrazoline-, dihydropyridone-, triazole-, indoline-, and imidazotriazine-containing compounds can be obtained commercially or synthesized using conventional synthetic methods. For example, compounds CP-0062030, CP-0007994, CP-0039073, CP-0004116, CP-0061401, CP-0064286, CP-0110644, and CP-0051092 were obtained commercially from the suppliers provided in Table 1 (Entries 102-109).

TABLE 1

| Compound | Structure | Entry Number and Name[A] | Supplier (Supplier ID) |
|---|---|---|---|
| CP-0000489 | 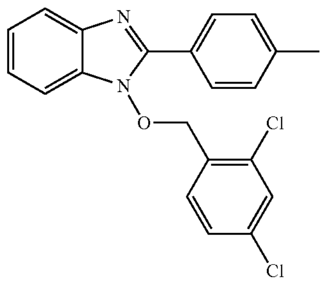 [SMILES: Cc1ccc(-c2nc3ccccc3n2OCc2ccc(Cl)cc2Cl)cc1] | 1. 4-(4-chlorophenyl)-1-(5H-pyrimido[5,4-b]indol-4-yl)-1H-pyrazol-3-amine | BIONET (bionet-7F-307S) |
| CP-0000540 | 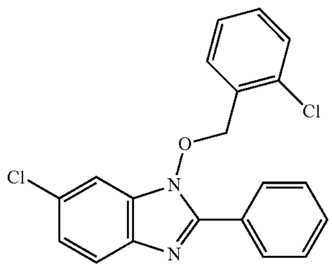 [SMILES: Clc1ccc2nc(-c3ccccc3)n(OCc3ccccc3Cl)c2c1] | 2. 6-chloro-1-(2-chlorobenzyloxy)-2-phenyl-1H-benzo[d]imidazole | BIONET (bionet-9F-327S) |
| CP-0000550 | 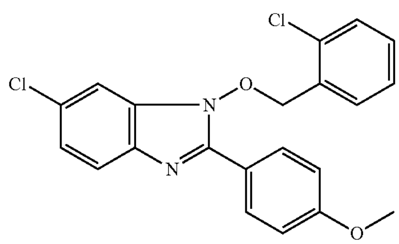 [SMILES: COc1ccc(-c2nc3ccc(Cl)cc3n2OCc2ccccc2Cl)cc1] | 3. 6-chloro-1-(2-chlorobenzyloxy)-2-(4-methoxyphenyl)-1H-benzo[d]imidazole | BIONET (bionet-10F-310S) |
| CP-0000553 | 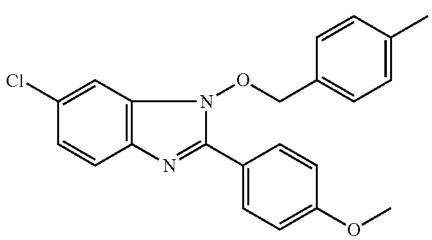 [SMILES: COc1ccc(-c2nc3ccc(Cl)cc3n2OCc2ccc(C)cc2)cc1] | 4. 6-chloro-2-(4-methoxyphenyl)-1-(4-methylbenzyloxy)-1H-benzo[d]imidazole | BIONET (bionet-10F-324S) |
| CP-0000554 | 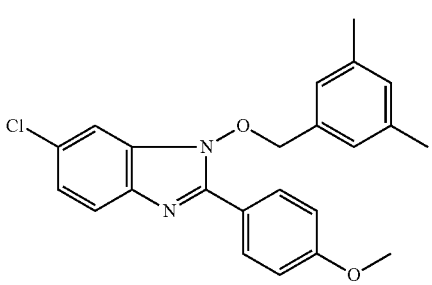 [SMILES: COc1ccc(-c2nc3ccc(Cl)cc3n2OCc2cc(C)cc(C)c2)cc1] | 5. 6-chloro-1-(3,5-dimethylbenzyloxy)-2-(4-methoxyphenyl)-1H-benzo[d]imidazole | BIONET (bionet-10F-325S) |
| CP-0000557 | 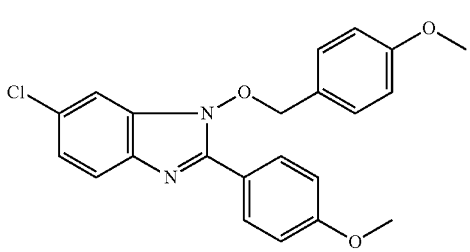 [SMILES: COc1ccc(COn2c(-c3ccc(OC)cc3)nc3ccc(Cl)cc32)cc1] | 6. 6-chloro-1-(4-methoxybenzyloxy)-2-(4-methoxyphenyl)-1H-benzo[d]imidazole | BIONET (bionet-10F-350S) |

TABLE 1-continued

| Compound | Structure | Entry Number and Name[A] | Supplier (Supplier ID) |
|---|---|---|---|
| CP-0000571 | 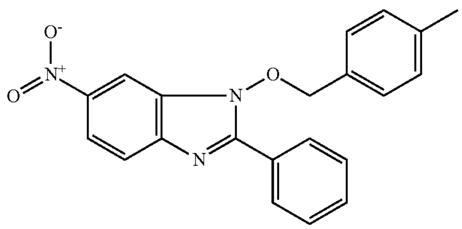 [SMILES: Cc1ccc(COn2c(-c3ccccc3)nc3ccc([N+](=O)[O-])cc32)cc1] | 7. 1-(4-methylbenzyloxy)-6-nitro-2-phenyl-1H-benzo[d]imidazole | BIONET (bionet-11F-314S) |
| CP-0047659 | 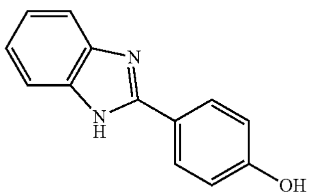 [SMILES: Oc1ccc(-c2nc3ccccc3[nH]2)cc1] | 8. 4-(1H-benzo[d]imidazol-2-yl)phenol | CHEMDIV (4385-2057) |
| CP-0064483 | 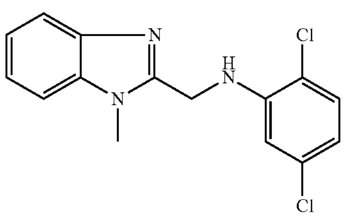 [SMILES: Cn1c(CNc2cc(Cl)ccc2Cl)nc2ccccc21] | 9. 2,5-dichloro-N-((1-methyl-1H-benzo[d]imidazol-2-yl)methyl)aniline | CHEMDIV (3546-0621) |
| CP-0066829 | 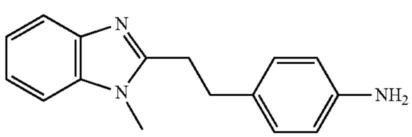 [SMILES: Cn1c(CCc2ccc(N)cc2)nc2ccccc21] | 10. 4-(2-(1-methyl-1H-benzo[d]imidazol-2-yl)ethyl)aniline | CHEMDIV (4432-2284) |
| CP-0069961 | 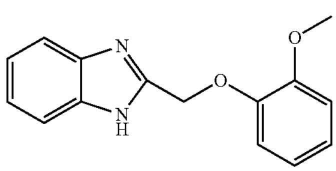 [SMILES: COc1ccccc1OCc1nc2ccccc2[nH]1] | 11. 2-((2-methoxyphenoxy)methyl)-1H-benzo[d]imidazole | CHEMDIV (G6856-0617) |
| CP-0074806 | 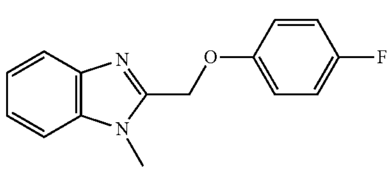 [SMILES: Cn1c(COc2ccc(F)cc2)nc2ccccc21] | 12. 2-((4-fluorophenoxy)methyl)-1-methyl-1H-benzo[d]imidazole | CHEMDIV (C147-0180) |
| CP-0080773 | 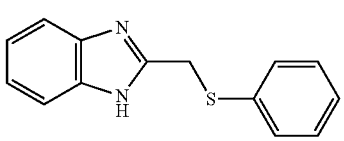 [SMILES: c1ccc(SCc2nc3ccccc3[nH]2)cc1] | 13. 2-(phenylthiomethyl)-1H-benzo[d]imidazole | BIONET (bionet_8J-311S) |
| CP-0091818 | 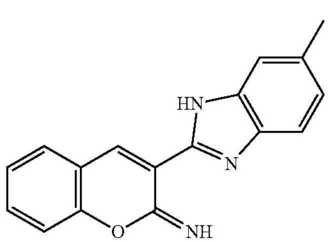 [SMILES: Cc1ccc2nc(-c3cc4ccccc4oc3=N)[nH]c2c1] | 14. 3-(6-methyl-1H-benzo[d]imidazol-2-yl)-2H-chromen-2-imine | CHEMDIV (4285-2380) |

TABLE 1-continued

| Compound | Structure | Entry Number and Name | Supplier (Supplier ID) |
|---|---|---|---|
| CP-0105772 | 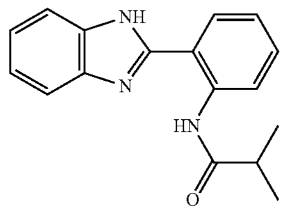 [SMILES: CC(C)C(=O)Nc1ccccc1-c1nc2ccccc2[nH]1] | 15. N-(2-(1H-benzo[d]imidazol-2-yl)phenyl)isobutyramide | IFLAB/LIFECHEMICALS (F0015-0753) |
| CP-0109953 | 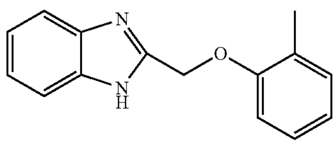 [SMILES: Cc1ccccc1OCc1nc2ccccc2[nH]1] | 16. 2-(o-tolyloxymethyl)-1H-benzo[d]imidazole | CHEMDIV (6286-0428) |
| CP-0193184 | 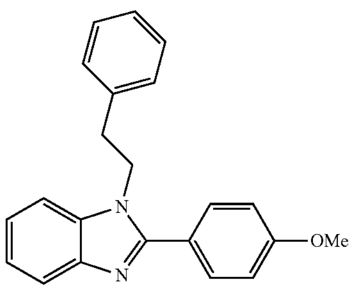 [SMILES: COc1ccc(-c2nc3ccccc3n2CCc2ccccc2)cc1] | 17. 2-(4-methoxyphenyl)-1-phenethyl-1H-benzo[d]imidazole | LDDN |
| CP-0064917 | 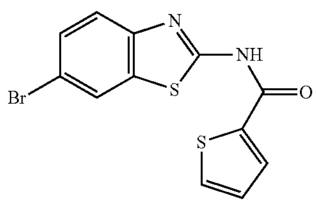 [SMILES: O=C(Nc1nc2ccc(Br)cc2s1)c1cccs1] | 18. N-(6-bromobenzo[d]thiazol-2-yl)thiophene-2-carboxamide | CHEMDIV (2769-2060) |
| CP-0067233 | 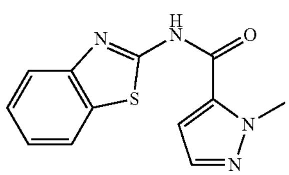 [SMILES: Cn1nccc1C(=O)Nc1nc2ccccc2s1] | 19. N-(benzo[d]thiazol-2-yl)-1-methyl-1H-pyrazole-5-carboxamide | CHEMDIV (4487-0569) |
| CP-0068578 | 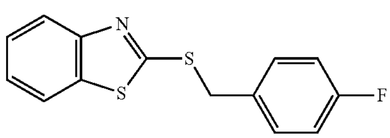 [SMILES: Fc1ccc(CSc2nc3ccccc3s2)cc1] | 20. 2-(4-fluorobenzylthio)benzo[d]thiazole | CHEMDIV (5222-1038) |
| CP-0103014 | 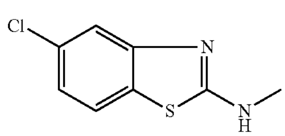 | 21. 5-chloro-N-methylbenzo[d]thiazol-2-amine | MAYBRIDGE (RF 04015) |
| CP-0105777 | 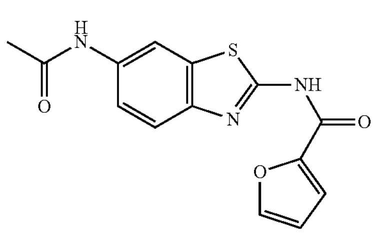 [SMILES: CC(=O)Nc1ccc2nc(NC(=O)c3ccco3)sc2c1] | 22. N-(6-acetamidobenzo[d]thiazol-2-yl)furan-2-carboxamide | IFLAB/LIFE-CHEMICALS (F0018-0056) |

TABLE 1-continued

| Compound | Structure | Entry Number and Name[A] | Supplier (Supplier ID) |
|---|---|---|---|
| CP-0107060 | 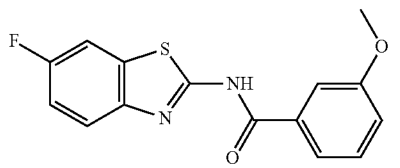 [SMILES: COc1cccc(C(=O)Nc2nc3ccc(F)cc3s2)c1] | 23. N-(6-fluorobenzo[d]thiazol-2-yl)-3-methoxybenzamide | IFLAB/LIFECHEMICALS (F0412-0020) |
| CP-0029300 | 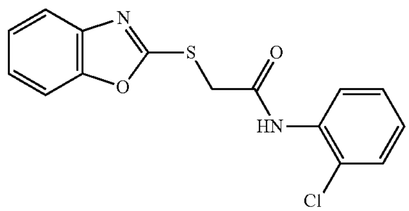 [SMILES: O=C(CSc1nc2ccccc2o1)Nc1ccccc1Cl] | 24. 2-(benzo[d]oxazol-2-ylthio)-N-(2-chlorophenyl)acetamide | CHEMDIV (3627-0019) |
| CP-0079983 | 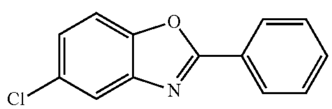 | 25. 5-chloro-2-phenylbenzo[d]oxazole | CHEMDIV (K780-0060) |
| CP-0103978 | 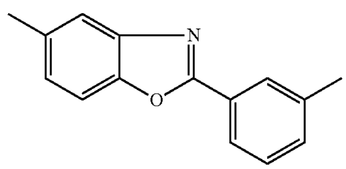 | 26. 5-methyl-2-m-tolylbenzo[d]oxazole | MAYBRIDGE (S 15553) |
| CP-0034360 | 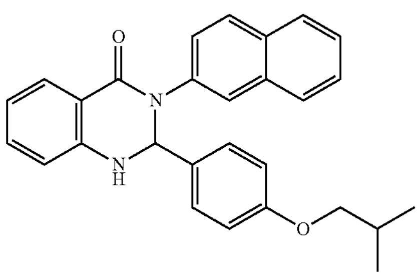 [SMILES: CC(C)COc1ccc(C2Nc3ccccc3C(=O)N2c2ccc3ccccc3c2)cc1] | 27. 2-(4-isobutoxyphenyl)-3-(naphthalen-2-yl)-2,3-dihydroquinazolin-4(1H)-one | CHEMDIV (8008-6354) |
| CP-0036187 | 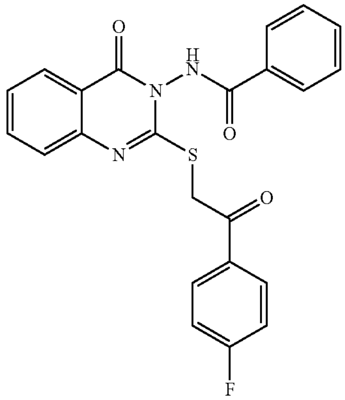 [SMILES: O=C(CSc1nc2ccccc2c(=O)n1NC(=O)c1ccccc1)c1ccc(F)cc1] | 28. N-(2-(2-(4-fluorophenyl)-2-oxoethylthio)-4-oxoquinazolin-3(4H)-yl)benzamide | CHEMDIV (K284-2447) |

TABLE 1-continued

| Compound | Structure | Entry Number and Name[a] | Supplier (Supplier ID) |
|---|---|---|---|
| CP-0050095 | 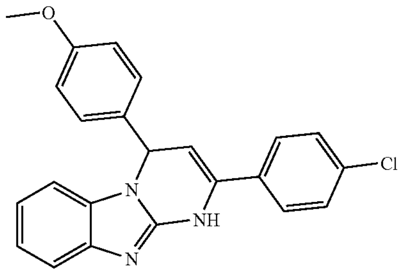 [SMILES: COc1ccc(C2C=C(c3ccc(Cl)cc3)Nc3nc4ccccc4n32)cc1] | 29. 2-(4-chlorophenyl)-4-(4-methoxyphenyl)-1,4-dihydrobenzo[4,5]imidazol[1,2-a]pyrimidine | CHEMDIV (K832-2696) |
| CP-0131763 | 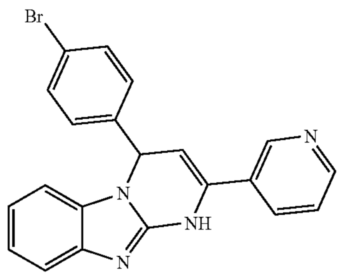 [SMILES: Brc1ccc(C2C=C(c3cccnc3)Nc3nc4ccccc4n32)cc1] | 30. 2-(3-pyridyl)-4-(4-bromophenyl)-1,4-dihydrobenzo[4,5]imidazol[1,2-a]pyrimidine | CHEMDIV (K832-2426) |
| CP-0079175 | 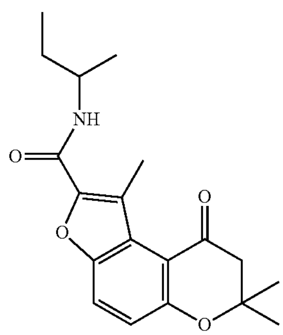 [SMILES: CCC(C)NC(=O)c1oc2ccc3c(c2c1C)C(=O)CC(C)(C)O3] | 31. N-sec-butyl-1,7,7-trimethyl-9-oxo-8,9-dihydro-7H-furo[3,2-f]chromen-2-carboxamide | CHEMDIV (C795-0478) |
| CP-0087336 | 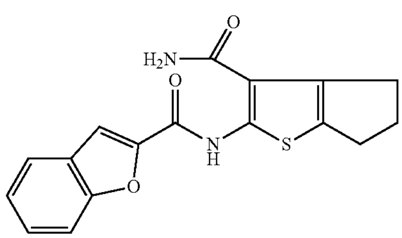 [SMILES: NC(=O)c1c(NC(=O)c2cc3ccccc3o2)sc2c1CCC2] | 32. N-(3-carbamoyl-5,6-dihydro-4H-cyclopenta[b]thiophen-2-yl)benzofuran-2-carboxamide | ENAMINE (T0516-9815) |
| CP-0064314 | 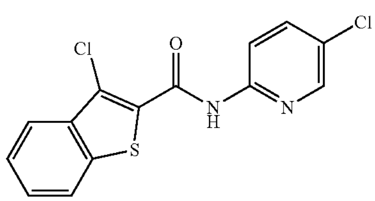 [SMILES: O=C(Nc1ccc(Cl)cn1)c1sc2ccccc2c1Cl] | 33. 3-chloro-N-(5-chloropyridin-2-yl)benzo[b]thiophene-2-carboxamide | CHEMDIV (3616-0520) |
| CP-0068577 | 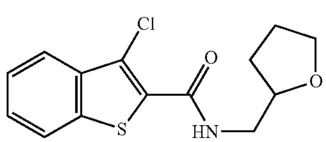 [SMILES: O=C(NCC1CCCO1)c1sc2ccccc2c1Cl] | 34. 3-chloro-N-((tetrahydrofuran-2-yl)methyl)benzo[b]thiophene-2-carboxamide | CHEMDIV (5067-0367) |

TABLE 1-continued

| Compound | Structure | Entry Number and Name | Supplier (Supplier ID) |
|---|---|---|---|
| CP-0102404 | 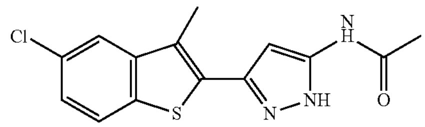 [SMILES: CC(=O)Nc1cc(-c2sc3ccc(Cl)cc3c2C)n[nH]1] | 35. N-(3-(5-chloro-3-methylbenzo[b]thiophen-2-yl)-1H-pyrazol-5-yl)acetamide | MAYBRIDGE (MWP 00596) |
| CP-0010539 | 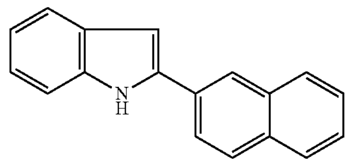 [SMILES: c1ccc2cc(-c3cc4ccccc4[nH]3)ccc2c1] | 36. 2-(naphthalen-2-yl)-1H-indole | MAYBRIDGE (RDR 01160) |
| CP-0072096 | 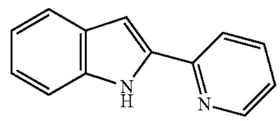 [SMILES: c1ccc(-c2cc3ccccc3[nH]2)nc1] | 37. 2-(pyridin-2-yl)-1H-indole | CHEMDIV (8005-4453) |
| CP-0078448 | 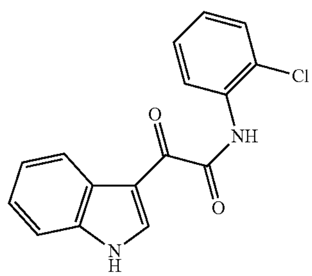 [SMILES: O=C(Nc1ccccc1Cl)C(=O)c1c[nH]c2ccccc12] | 38. N-(2-chlorophenyl)-2-(1H-indol-3-yl)-2-oxoacetamide | CHEMDIV (C730-0133) |
| CP-0072092 | 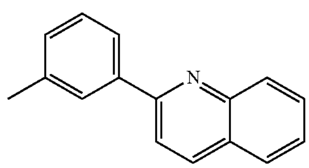 [SMILES: Cc1cccc(-c2ccc3ccccc3n2)c1] | 39. 2-m-tolylquinoline | CHEMDIV (8005-4434) |
| CP-0087799 | 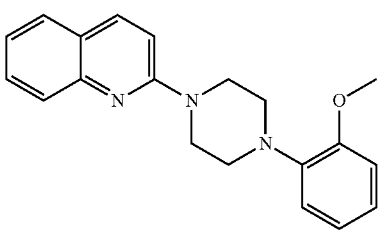 [SMILES: COc1ccccc1N1CCN(c2ccc3ccccc3n2)CC1] | 40. 2-(4-(2-methoxyphenyl)piperazin-1-yl)quinoline | ENAMINE (T0503-7528) |
| CP-0009883 | 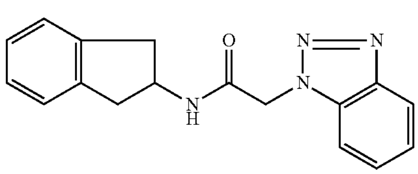 [SMILES: O=C(Cn1nnc2ccccc21)NC1Cc2ccccc2C1] | 41. 2-(1H-benzo[d][1,2,3]triazol-1-yl)-N-(2,3-dihydro-1H-inden-2-yl)acetamide | MAYBRIDGE (KM 10562) |
| CP-0070871 | 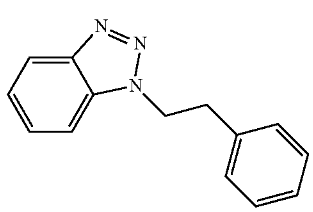 [SMILES: c1ccc(CCn2nnc3ccccc32)cc1] | 42. 1-phenethyl-1H-benzo[d][1,2,3]triazole | ChemBridge (7653692) |

TABLE 1-continued

| Compound | Structure | Entry Number and Name | Supplier (Supplier ID) |
|---|---|---|---|
| CP-0063508 | 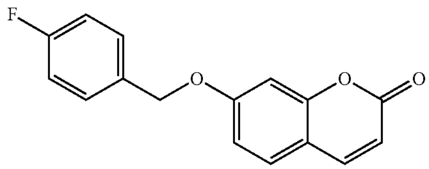 [SMILES: O=c1ccc2ccc(OCc3ccc(F)cc3)cc2o1] | 43. 7-(4-fluorobenzyloxy)-2H-chromen-2-one | CHEMDIV (3330-4085) |
| CP-0000928 | 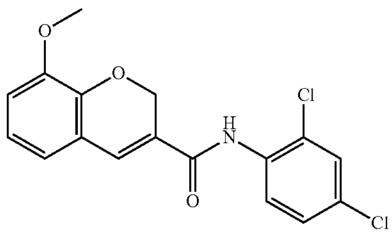 [SMILES: COc1cccc2c1OCC(C(=O)Nc1ccc(Cl)cc1Cl)=C2] | 44. N-(2,4-dichlorophenyl)-8-methoxy-2H-chromene-3-carboxamide | BIONET (bionet-5G-331S) |
| CP-0005069 | 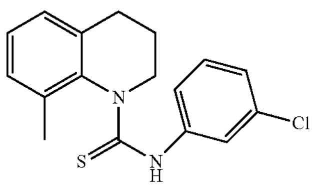 [SMILES: Cc1cccc2c1N(C(=S)Nc1cccc(Cl)c1)CCC2] | 45. N-(3-chlorophenyl)-8-methyl-3,4-dihydroquinoline-1(2H)-carbothioamide | MAYBRIDGE (BTB 01026) |
| CP-0096433 | 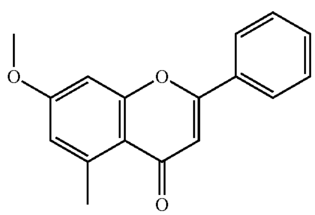 [SMILES: COc1cc(C)c2c(=O)cc(-c3ccccc3)oc2c1] | 46. 7-methoxy-5-methyl-2-phenyl-4H-chromen-4-one | MICROSOURCE (01400666) |
| CP-0045061 | 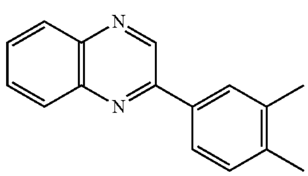 [SMILES: Cc1ccc(-c2cnc3ccccc3n2)cc1C] | 47. 2-(3,4-dimethylphenyl)quinoxaline | CHEMDIV (3257-1451) |
| CP-0060729 | 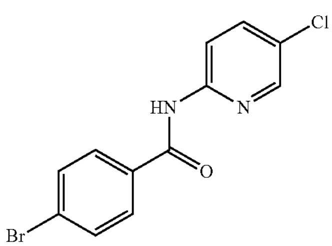 [SMILES: O=C(Nc1ccc(Cl)cn1)c1ccc(Br)cc1] | 48. 4-bromo-N-(5-chloropyridin-2-yl)benzamide | CHEMDIV (0868-0014) |
| CP-0066751 | 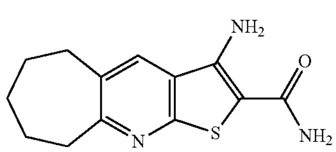 [SMILES: NC(=O)c1sc2nc3c(cc2c1N)CCCCC3] | 49. 3-amino-6,7,8,9-tetrahydro-5H-cyclohepta[e]thieno[2,3-b]pyridine-2-carboxamide | CHEMDIV (4365-0051) |
| CP-0069934 | 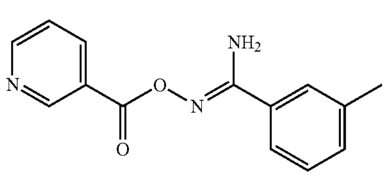 [SMILES: Cc1cccc(/C(N)=N/OC(=O)c2cccnc2)c1] | 50. (Z)-3-methyl-N'-(nicotinoyloxy)benzimidamide | CHEMDIV (5906-1071) |

TABLE 1-continued

| Compound | Structure | Entry Number and Name[A] | Supplier (Supplier ID) |
|---|---|---|---|
| CP-0076627 | 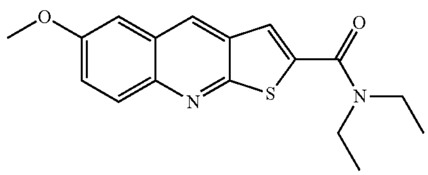 [SMILES: CCN(CC)C(=O)c1cc2cc3cc(OC)ccc3nc2s1] | 51. N,N-diethyl-6-methoxythieno[2,3-b]quinoline-2-carboxamide | CHEMDIV (C303-0565) |
| CP-0080276 | 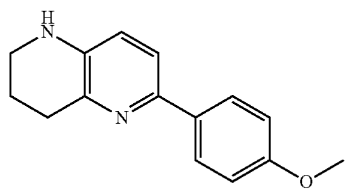 [SMILES: COc1ccc(-c2ccc3c(n2)CCCN3)cc1] | 52. 6-(4-methoxyphenyl)-1,2,3,4-tetrhydro-1,5-naphthyridine | Reference for Symethesis: Lahue, B.R. et al. J. Org. Chem. 2004, 69, 7171-7182. |
| CP-0089966 | 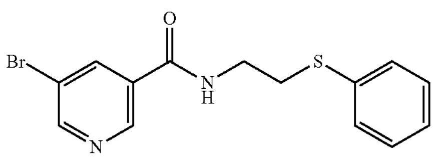 [SMILES: O=C(NCCSc1ccccc1)c1cncc(Br)c1] | 53. 5-bromo-N-(2-(penylthio)ethyl)nicotinamide | CHEMDIV (8011-8572) |
| CP-0029278 | 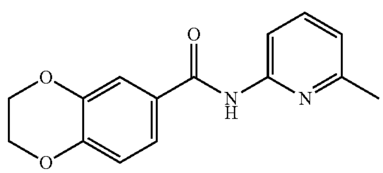 [SMILES: Cc1cccc(NC(=O)c2ccc3c(c2)OCCO3)n1] | 54. N-(6-methylpyridin-2-yl)-2,3-dihydrobenzo[b][1,4]dioxine-6-carboxamide | CHEMDIV (3617-0256) |
| CP-0130586 | 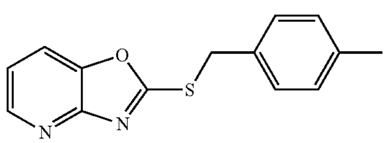 [SMILES: Cc1ccc(CSc2nc3ncccc3o2)cc1] | 55. 2-(4-methylbenzylthio)oxazolo[4,5-b]pyridine | CHEMDIV (G293-0009) |
| CP-0059547 | 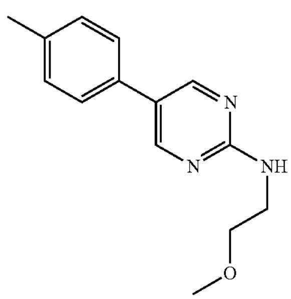 [SMILES: COCCNc1ncc(-c2ccc(C)cc2)cn1] | 56. N-(2-methoyethyl)-5-p-tolylpyrimidin-2-amine | PEAK-DALE (1000119) |
| CP-0059563 | 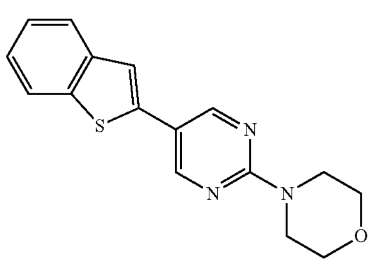 [SMILES: c1ccc2sc(-c3cnc(N4CCOCC4)nc3)cc2c1] | 57. 4-(5-(benzo[b]thiophen-2-yl)pyrimidin-2-yl)morpholine | PEAK-DALE (1000166) |

TABLE 1-continued

| Compound | Structure | Entry Number and Name | Supplier (Supplier ID) |
|---|---|---|---|
| CP-0059642 | 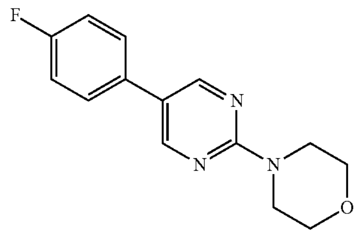 [SMILES: Fc1ccc(-c2cnc(N3CCOCC3)nc2)cc1] | 58. 4-(5-(4-fluorophenyl)pyrimidin-2-yl)morpholine | PEAKDALE (1000143) |
| CP-0064382 | 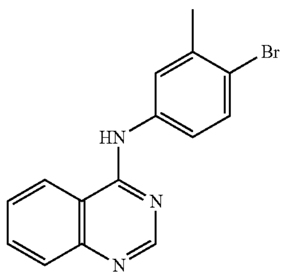 [SMILES: Cc1cc(Nc2ncnc3ccccc23)ccc1Br] | 59. N-(4-bromo-3-methylphenyl)quinazolin-4-amine | CHEMDIV (3651-6031) |
| CP-0067053 | 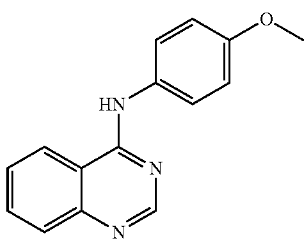 [SMILES: COc1ccc(Nc2ncnc3ccccc23)cc1] | 60. N-(4-methoxyphenyl)quinazolin-4-amine | CHEMDIV (4491-0691) |
| CP-0072720 | 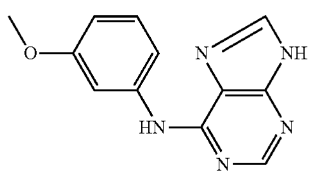 [SMILES: COc1cccc(Nc2ncnc3[nH]cnc23)c1] | 61. N-(3-methoxyphenyl)-9H-purin-6-amine | CHEMDIV (8009-2985) |
| CP-0079810 | 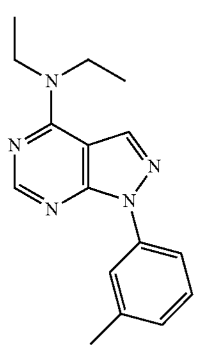 [SMILES: CCN(CC)c1ncnc2c1cnn2-c1cccc(C)c1] | 62. N,N-diethyl-1-m-tolyl-1H-pyrazolo[3,4-d]pyrimidin-4-amine | CHEMDIV (K402-0503) or IFLAB/LIFE-CHEMICALS (F0518-0004) |
| CP-0061777 | 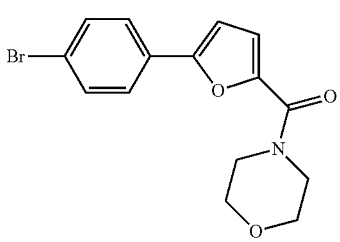 [SMILES: O=C(c1ccc(-c2ccc(Br)cc2)o1)N1CCOCC1] | 63. (5-(4-bromophenyl)furan-2-yl)(morpholino)methanone | CHEMDIV (1975-0198) |

TABLE 1-continued

| Compound | Structure | Entry Number and Name[A] | Supplier (Supplier ID) |
|---|---|---|---|
| CP-0066008 | 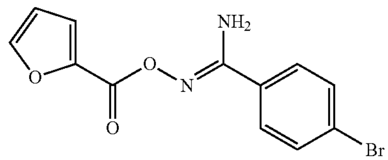 [SMILES: N/C(=N\OC(=O)c1ccco1)c1ccc(Br)cc1] | 64. (Z)-4-bromo-N'-(furan-2-carbonyloxy)benzimidamide | CHEMDIV (4260-1000) |
| CP-0072253 | 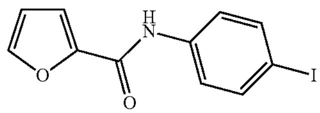 [SMILES: O=C(Nc1ccc(I)cc1)c1ccco1] | 65. N-(4-iodophenyl)furan-2-carboxamide | CHEMDIV (8002-5214) |
| CP-0099289 | 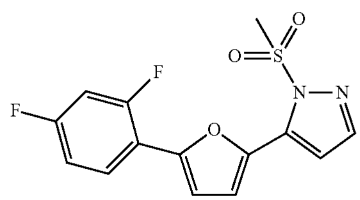 [SMILES: CS(=O)(=O)n1nccc1-c1ccc(-c2ccc(F)cc2F)o1] | 66. 5-(5-(2,4-difluorophenyl)furan-2-yl)-1-(methylsulfonyl)-1H-pyrazole | MAY-BRIDGE (CD 10941) |
| CP-0008545 | 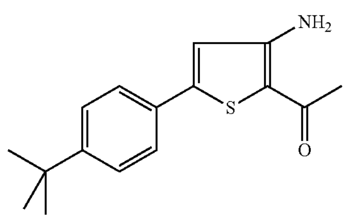 [SMILES: CC(=O)c1sc(-c2ccc(C(C)(C)C)cc2)cc1N] | 67. 1-(3-amino-5-(4-tert-butylphenyl)thiophen-2-yl)ethanone | MAY-BRIDGE (GK 03407) |
| CP-0060852 | 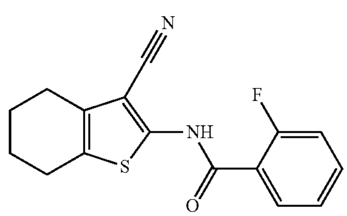 [SMILES: N#Cc1c(NC(=O)c2ccccc2F)sc2c1CCCC2] | 68. N-(3-cyano-4,5,6,7-tetrahydrobenzo[b]thiophen-2-yl)-2-fluorobenzamide | CHEMDIV (1000-0399) |
| CP-0072156 | 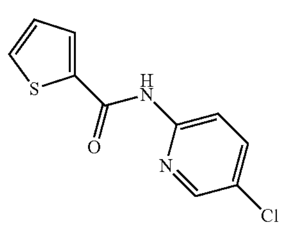 [SMILES: O=C(Nc1ccc(Cl)cn1)c1cccs1] | 69. N-(5-chloropyridin-2-yl)thiophene-2-carboxamide | CHEMDIV (8005-8364) |
| CP-0072271 | 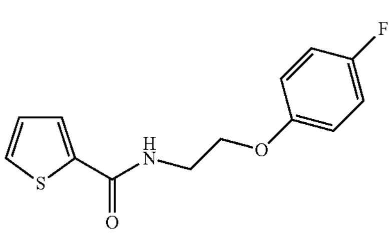 [SMILES: O=C(NCCOc1ccc(F)cc1)c1cccs1] | 70. N-(2-(4-fluorophenoxy)ethyl)thiophene-2-carboxamide | CHEMDIV (8003-7471) |

TABLE 1-continued

| Compound | Structure | Entry Number and Name^A | Supplier (Supplier ID) |
|---|---|---|---|
| CP-0104766 | 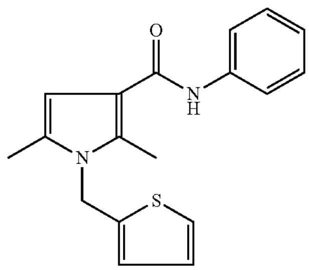 [SMILES: Cc1cc(C(=O)Nc2ccccc2)c(C)n1Cc1cccs1] | 71. 2,5-dimethyl-N-phenyl-1-(thiophen-2-ylmethyl)-1H-pyrrole-3-carboxamide | MAYBRIDGE (SP 00299) |
| CP-0110352 | 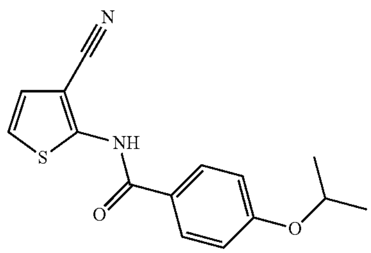 [SMILES: CC(C)Oc1ccc(C(=O)Nc2sccc2C#N)cc1] | 72. N-(3-cyanothiophen-2-yl)-4-isopropoxybenzamide | IFLAB/LIFE-CHEMICALS (F1385-0110) |
| CP-0063182 | 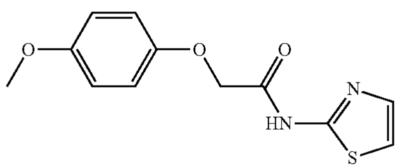 [SMILES: COc1ccc(OCC(=O)Nc2nccs2)cc1] | 73. 2-(4-methoxyphenoxy)-N-(thiazol-2-yl)acetamide | CHEMDIV (3297-0008) |
| CP-0071862 | 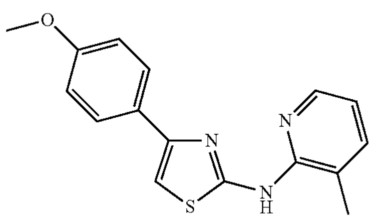 [SMILES: COc1ccc(-c2csc(Nc3ncccc3C)n2)cc1] | 74. 4-(4-methoxyphenyl)-N-(3-methylpyridin-2-yl)thiazol-2-amine | CHEMDIV (7100-0567) |
| CP-0072036 | 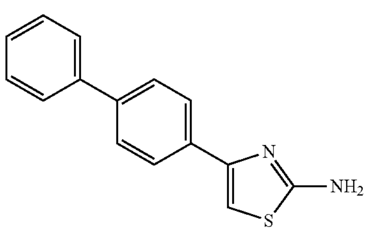 [SMILES: Nc1nc(-c2ccc(-c3ccccc3)cc2)cs1] | 75. 4-(biphenyl-4-yl)thiazol-2-amine | CHEMDIV (8005-3411) |
| CP-0105343 | 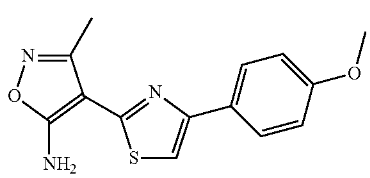 [SMILES: COc1ccc(-c2csc(-c3c(C)noc3N)n2)cc1] | 76. 4-(4-(4-methoxyphenyl)thiazol-2-yl)-3-methylisoxazol-5-amine | MAYBRIDGE (SPB 05463) |

TABLE 1-continued

| Compound | Structure | Entry Number and Name[A] | Supplier (Supplier ID) |
|---|---|---|---|
| CP-0122949 | 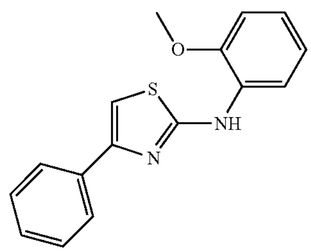 [SMILES: COc1ccccc1Nc1nc(-c2ccccc2)cs1] | 77. N-(2-methoxyphenyl)-4-phenylthiazol-2-amine | CHEMDIV (0896-3691) |
| CP-0134381 | 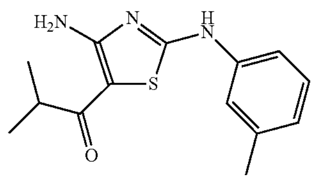 [SMILES: Cc1cccc(Nc2nc(N)c(C(=O)C(C)C)s2)c1] | 78. 1-(4-amino-2-(m-tolylamino)thiazol-5-yl)-2-methylpropan-1-one | CHEMDIV (F091-0329) |
| CP-0000477 | 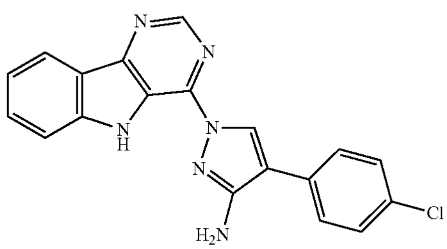 [SMILES: Nc1nn(-c2ncnc3c2[nH]c2ccccc23)cc1-c1ccc(Cl)cc1] | 79. 4-(4-chlorophenyl)-1-(5H-pyrimido[5,4-b]indol-4-yl)-1H-pyrazol-3-amine | BIONET (bionet-5F-909) |
| CP-0063375 | 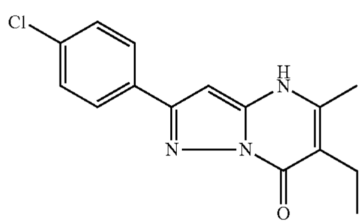 [SMILES: CCc1c(C)[nH]c2cc(-c3ccc(Cl)cc3)nn2c1=O] | 80. 2-(4-chlorophenyl)-6-ethyl-5-methylpyrazolo[1,5-a]pyrimidin-7(4H)-one | CHEMDIV (3270-0084) |
| CP-0064231 | 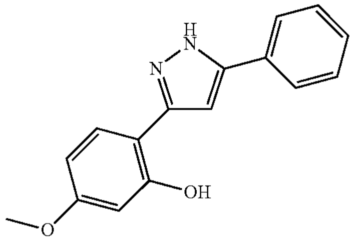 [SMILES: COc1ccc(-c2cc(-c3ccccc3)[nH]n2)c(O)c1] | 81. 5-methoxy-2-(5-phenyl-1H-pyrazol-3-yl)phenol | CHEMDIV (3486-0181) |
| CP-0065105 | 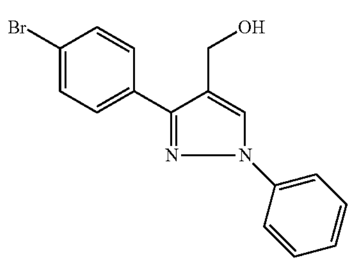 [SMILES: OCc1cn(-c2ccccc2)nc1-c1ccc(Br)cc1] | 82. (3-(4-bromophenyl)-1-phenyl-1H-pyrazol-4-yl)methanol) | CHEMDIV (3935-0218) |

TABLE 1-continued

| Compound | Structure | Entry Number and Name[A] | Supplier (Supplier ID) |
|---|---|---|---|
| CP-0070844 | 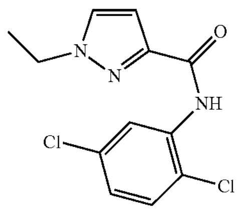 [SMILES: CCn1ccc(C(=O)Nc2cc(Cl)ccc2Cl)n1] | 83. N-(2,5-dichlorophenyl)-1-ethyl-1H-pyrazole-3-carboxamide | CHEMDIV (6228-1918) |
| CP-0070886 | 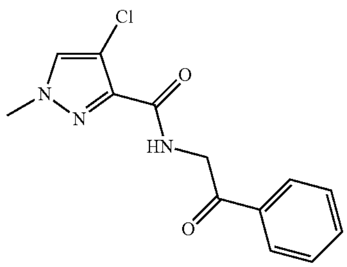 [SMILES: Cn1cc(Cl)c(C(=O)NCC(=O)c2ccccc2)n1] | 84. 4-chloro-1-methyl-N-(2-oxo-2-phenylethyl)-1H-pyrazol-3-carboxamide | Chem-Bridge (7528295) |
| CP-0104765 | 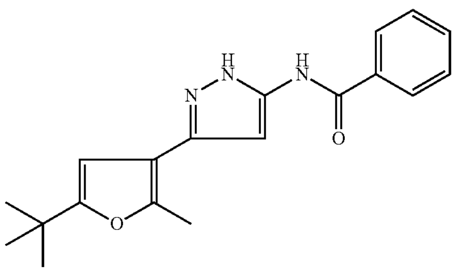 [SMILES: Cc1oc(C(C)(C)C)cc1-c1cc(NC(=O)c2ccccc2)[nH]n1] | 85. N-(3-(5-tert-butyl-2-methylfuran-3-yl)-1H-pyrazol-5-yl)benzamide | MAYBRIDGE (SP 00221) |
| CP-0065665 | 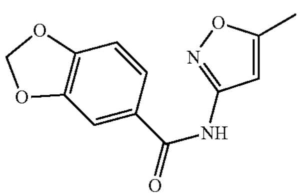 [SMILES: Cc1cc(NC(=O)c2ccc3c(c2)OCO3)no1] | 86. N-(5-methylisoxazol-3-yl)benzo[d][1,3]dioxole-5-carboxamide | CHEMDIV (4100-3780) |
| CP-0075627 | 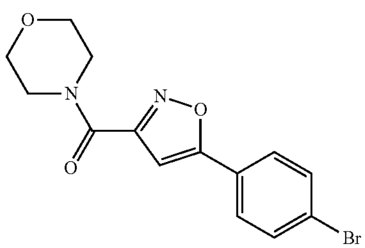 [SMILES: O=C(c1cc(-c2ccc(Br)cc2)on1)N1CCOCC1] | 87. (5-(4-bromophenyl)isoxazol-3-yl)(morpholino)methanone | CHEMDIV (C226-0488) |
| CP-0075656 | 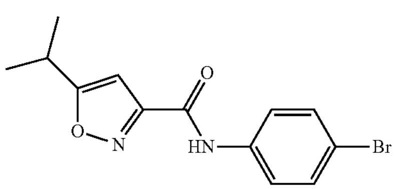 [SMILES: CC(C)c1cc(C(=O)Nc2ccc(Br)cc2)no1] | 88. N-(4-bromophenyl)-5-isopropylisoxazole-5-carboxamide | CHEMDIV (C226-292) |
| CP-0067108 | 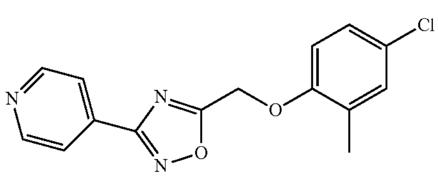 [SMILES: Cc1cc(Cl)ccc1OCc1nc(-c2ccncc2)no1] | 89. 5-((4-chloro-2-methylphenoxy)methyl)-3-(pyridin-4-yl)-1,2,4-oxadiazole | CHEMDIV (4534-3904) |

TABLE 1-continued

| Compound | Structure | Entry Number and Name[A] | Supplier (Supplier ID) |
|---|---|---|---|
| CP-0067246 | 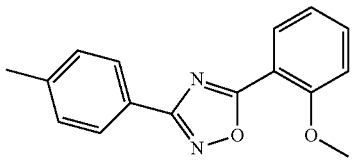 | 90. 5-(2-methoxyphenyl)-3-p-tolyl-1,2,4-oxadiazole | CHEMDIV (4534-1114) |
| CP-0068395 | 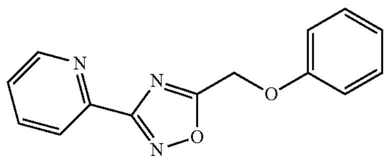 [SMILES: c1ccc(OCc2nc(-c3ccccn3)no2)cc1] | 91. 5-(phenoxymethyl)-3-(pyridin-2-yl)-1,2,4-oxadiazole | CHEMDIV (4951-0941) |
| CP-0068929 | 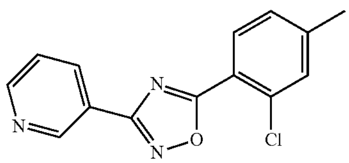 [SMILES: Cc1ccc(-c2nc(-c3cccnc3)no2)c(Cl)c1] | 92. 5-(2-chloro-4-methylphenyl)-3-(pyridin-3-yl)-1,2,4-oxadiazole | CHEMDIV (5235-0410) |
| CP-0068961 | 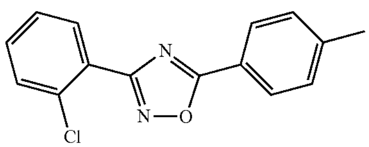 [SMILES: Cc1ccc(-c2nc(-c3ccccc3Cl)no2)cc1] | 93. 3-(2-chlorophenyl)-5-p-tolyl-1,2,4-oxadiazole | CHEMDIV (5235-2061) |
| CP-0070164 | 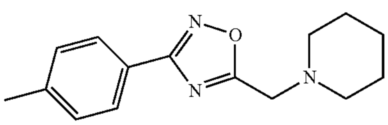 [SMILES: Cc1ccc(-c2noc(CN3CCCCC3)n2)cc1] | 94. 5-(piperidin-1-ylmethyl)-3-p-tolyl-1,2,4-oxadiazole | CHEMDIV (5927-0188) |
| CP-0070367 | 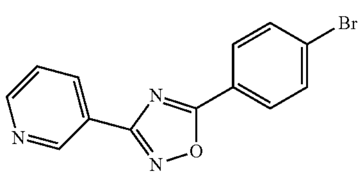 [SMILES: Brc1ccc(-c2nc(-c3cccnc3)no2)cc1] | 95. 5-(4-bromophenyl)-3-(pyridin-3-yl)-1,2,4-oxadiazole | CHEMDIV (6018-0130) |
| CP-0079642 | 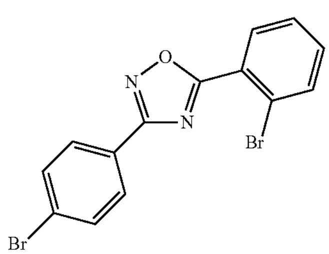 [SMILES: Brc1ccc(-c2noc(-c3ccccc3Br)n2)cc1] | 96. 5-(2-bromophenyl)-3-(4-bromophenyl)-1,2,4-oxadiazole | CHEMDIV (K086-0188) |
| CP-0104904 | 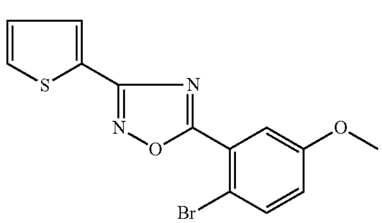 [SMILES: COc1ccc(Br)c(-c2nc(-c3cccs3)no2)c1] | 97. 5-(2-bromo-5-methoxyphenyl)-3-(thiophen-2-yl)-1,2,4-oxadiazole | MAYBRIDGE (SP 00905) |

TABLE 1-continued

| Compound | Structure | Entry Number and Name | Supplier (Supplier ID) |
|---|---|---|---|
| CP-0130665 | 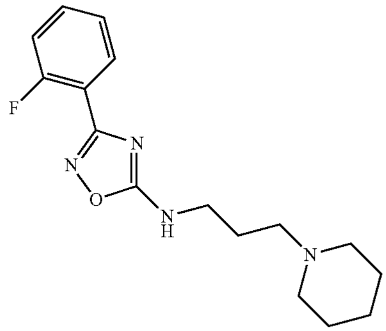 [SMILES: Fc1ccccc1-c1noc(NCCCN2CCCCC2)n1] | 98. 3-(2-fluorophenyl)-N-(3-(piperidin-1-yl)propyl)-1,2,4-oxadiazol-5-amine | CHEMDIV (G349-0769) |
| CP-0005186 | 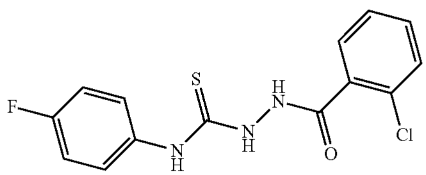 [SMILES: O=C(NNC(=S)Nc1ccc(F)cc1)c1ccccc1Cl] | 99. 2-(2-chlorobenzoyl)-N-(4-fluorophenyl)hydrazinecarbothioamide | MAYBRIDGE (BTB 01235) |
| CP-0007991 | 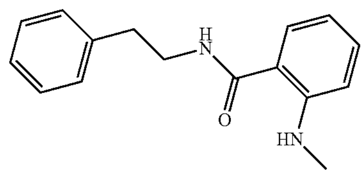 [SMILES: CNc1ccccc1C(=O)NCCc1ccccc1] | 100. 2-(methylamino)-N-phenethylbenzamide | MAYBRIDGE (DP 01029) |
| CP-0061566 | 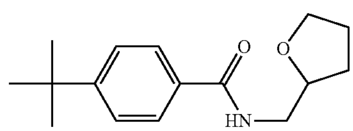 [SMILES: CC(C)(C)c1ccc(C(=O)NCC2CCCO2)cc1] | 101. 4-tert-butyl-N-((tetrahydrofuran-2-yl)methyl)benzamide | CHEMDIV (1786-0077) |
| CP-0062030 | 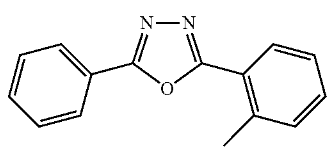 [SMILES: Cc1ccccc1-c1nnc(-c2ccccc2)o1] | 102. 2-phenyl-5-o-tolyl-1,3,4-oxadiazole | CHEMDIV (2089-0007) |
| CP-0007994 | 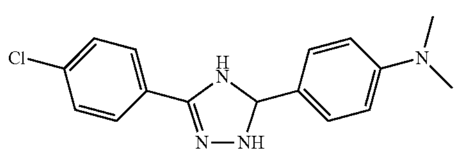 [SMILES: CN(C)c1ccc(C2NN=C(c3ccc(Cl)cc3)N2)cc1] | 103. 4-(3-(4-chlorophenyl)-4,5-dihydro-1H-1,2,4-triazol-5-yl)-N,N-dimethylaniline | MAYBRIDGE (DP 01118) |
| CP-0039073 | 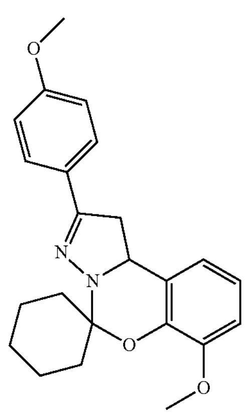 [SMILES: COc1ccc(C2=NN3C(C2)c2cccc(OC)c2OC32CCCCC2)cc1] | 104. 7-methoxy-2-(4-methoxyphenyl)-1,10b-dihydrospiro[benzo[e]pyrazolo[1,5-c][1,3]oxazine-5,1'-cyclohexane] | CHEMDIV (K0805-0823) |

TABLE 1-continued

| Compound | Structure | Entry Number and Name[A] | Supplier (Supplier ID) |
|---|---|---|---|
| CP-0004116 | 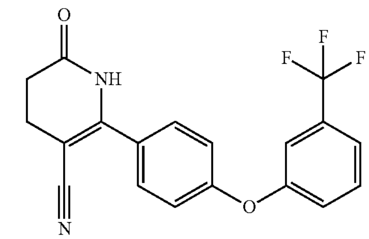 [SMILES: N#CC1=C(c2ccc(Oc3cccc(C(F)(F)F)c3)cc2)NC(=O)CC1] | 105. 6-oxo-2-(4-(3-(trifluoromethyl)phenoxy)phenyl)-1,4,5,6-tetrahydropyridine-3-carbonitrile | BIONET (bionet-8P-057) |
| CP-0061401 | 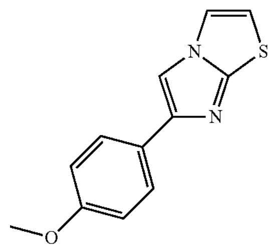 [SMILES: COc1ccc(-c2cn3ccsc3n2)cc1] | 106. 6-(4-methoxyphenyl)imidazo[2,1-b]thiazole | CHEMDIV (1487-1266) |
| CP-0064286 | 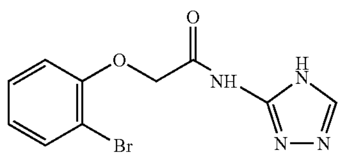 [SMILES: O=C(COc1ccccc1Br)Nc1nnc[nH]1] | 107. 2-(2-bromophenoxy)-N-(4H-1,2,4-triazol-3-yl)acetamide | CHEMDIV (3643-3466) |
| CP-0110644 | 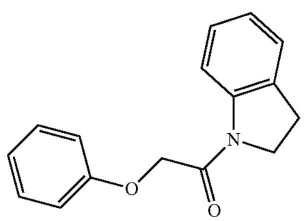 [SMILES: O=C(COc1ccccc1)N1CCc2ccccc21] | 108. 1-(indolin-1-yl)-2-phenoxyethanone | TIMTEC (ST040751) |
| CP-0051092 | 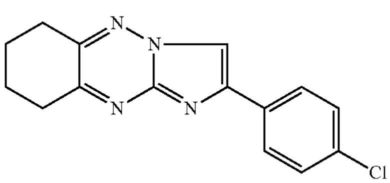 [SMILES: Clc1ccc(-c2cn3nc4c(nc3n2)CCCC4)cc1] | 109. 2-(4-chlorophenyl)-6,7,8,9-tetrahydrobenzo[e]imidazo[1,2-b][1,2,4]triazine | CHEMDIV (8011-7131) |

[A]The systematic names provided in Table 1 were generated using ChemDraw Ultra Version 9.0.1 software as follows. The systematic names were generated by inputting each of the chemical structures shown in Table 1 in the ChemDraw drawing window, selecting the compound, and selecting the "convert structure to name" tool under the Structure menu.

Methods of Treatment

The present invention provides methods related to the use of the compounds described herein for treating diseases and/or disorders that would benefit from increased Atoh1 expression. In general, the methods of treatment involve the use of one or more of the compounds described herein to increase Atoh1 expression levels, and thereby promote partial or complete differentiation of a target cell. Diseases that can benefit from such treatment are those in which increased levels of Atoh1 treat one or more symptoms of the disease, e.g., those diseases in which the completely or partially differentiated cells that result from increased Atoh1 expression (1) serve to replace lost or damaged cells or tissue, e.g., functional cells, e.g., auditory hair cells, and/or (2) prevent expansion of a damaging population of cells, e.g., cancer cells.

In general, the present invention provides steps whereby one or more of the compounds described herein are administered to a patient. Alternatively or in addition, the present invention provides steps whereby one or more target cells e.g., stem cells, iPS cells, progenitor cells, and/or support cells are contacted, e.g., in vitro, with one or more of the compounds described herein to promote complete or partial differentiation of those cells to or toward a mature cell type, e.g., a hair cell, steps whereby one or more cells, e.g., cells, progenitor cells, and/or support cells that have been contacted with one or more of the compounds described herein, e.g., in vitro, is administered to a patient, and/or steps whereby one or more cells, e.g., cells, progenitor cells, and/or support cells that have been contacted with one or more of the compounds described herein, e.g., in vitro are administered to a patient in combination with one or more of the compounds.

Auditory Hair Cell Loss

It is widely accepted that although cells capable of generating hair cells are present in the inner ear, natural hair cell regeneration in the inner ear is low (Li et al., Trends Mol. Med., 10, 309-315 (2004); Li et al., Nat. Med., 9, 1293-1299 (2003); Rask-Andersen et al., Hear. Res., 203, 180-191 (2005)). As a result, lost or damaged hair cells may not be adequately replaced by natural physiological processes (e.g., cell differentiation) and a loss of hair cells occurs. In many individuals, such hair cell loss can result in, e.g., sensorineural hearing loss, hearing impairment, and imbalance disorders. Therapeutic strategies that increase the number of hair cells in the inner ear will benefit a patient with hair cell loss, e.g., with one or more of these conditions.

The importance of Atoh1 in hair cell genesis is well documented. For example, Math1 is required for hair cell development and the differentiation of inner ear progenitor cells to inner ear support cells and/or hair cells (Bermingham et al., Science, 284:1837-1841, 1999). In addition, adenovirus mediated Math1 overexpression in the endolymph of the mature guinea pig results in the differentiation of non-sensory cells in the mature cochlea into immature hair cells (Kawamoto et al., J. Neurosci., 23:4395-4400, 2003). The implications of these studies are twofold. First, they demonstrate that non-sensory cells of the mature cochlear retain the ability to differentiate into sensory cells, e.g., hair cells. Second, they demonstrate that Math1 overexpression is necessary and sufficient to direct hair cell differentiation from non-sensory cells. A later study furthered these findings by demonstrating that adenovirus mediated Atoh1 overexpression induces hair cell regeneration and substantially improves hearing thresholds in an experimentally deafened animal model (Izumikawa et al., Nat. Med., 11:271-276, 2005).

Provided herein are compounds capable of increasing Atoh1 levels in a subject and/or cell or tissue. As described herein, these compounds promote increased Atoh1 expression and thereby promote differentiation of a target cell or cells to or toward sensory cell or cells of the inner ear, e.g., a hair cell. The use of these compounds to promote hair cell differentiation from cells located in the ear, or from cells capable of differentiating into a hair cell is well supported at least by the experimental data described by Bermingham et al., supra, Kawamoto et al., supra, and Izumikawa et al., supra. Consequently, the compounds described herein can be used to treat those diseases and disorders that result from hair cell loss in a patient.

The present invention provides compounds and methods for treating patients who have, or who are at risk for developing, an auditory disorder resulting from a loss of hair cells. In some embodiments, the methods of treatment include steps whereby one or more of the compounds described herein are administered to a patient to promote the formation of auditory hair cells, e.g., in the ear of the patient (e.g., the inner ear) and/or increase the number of auditory hair cells in the ear (e.g., the inner ear) of a patient by promoting complete or partial auditory hair cell differentiation from non-hair cell types naturally present in the inner ear of a patient.

In some embodiments, the methods of treatment include steps whereby one or more of the compounds described herein are administered to a patient to promote the formation of auditory hair cells in the patient's inner ear (e.g., an inner and/or outer auditory hair cells) and/or increase the number of auditory hair cells (e.g., an inner and/or outer auditory hair cells) in the inner ear of a patient by promoting complete or partial auditory hair cell differentiation from non-hair cell types naturally present in the inner ear of a patient.

Examples of cells that are capable of differentiating into hair cells (e.g., an inner and/or outer hair cells) include but are not limited to inner ear stem cells, iPS cells, progenitor cells, and/or support cells (e.g., Deiters' cells, pillar cells, inner phalangeal cells, tectal cells and Hensen's cells).

The present invention also include steps whereby one or more cells that are capable of differentiating completely or partially into a hair cell are contacted, e.g., in vitro, with one or more of the compounds described herein to promote complete or partial differentiation of those cells to or toward a mature cell type of the inner ear, e.g., a hair cell (e.g., an inner and/or outer hair cell). Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat derived stem cells), progenitor cells (e.g., inner ear progenitor cells), support cells (e.g., Deiters' cells, pillar cells, inner phalangeal cells, tectal cells and Hensen's cells), and/or germ cells.

Alternatively or in addition, the methods include steps whereby one or more cells that are capable of differentiating into a hair cell (e.g., an inner and/or outer hair cell) and that have been contacted with one or more of the compounds described herein, e.g., in vitro, are administered to the ear (e.g., the inner ear) of the patient (cell therapy). Finally, the methods include steps whereby one or more cells that are capable of differentiating into a hair cell (e.g., an inner and/or outer hair cell) and that have been contacted with one or more of the compounds described herein, e.g., in vitro are administered to the ear (e.g., inner ear) of a patient in combination with one or more of the compounds (combination therapy).

The present invention can be used to treat hair cell loss and any disorder that arises as a consequence of cell loss in the ear, such as hearing impairments, deafness, and vestibular disorders, for example, by promoting differentiation (e.g., complete or partial differentiation) of one or more cells into one or more cells capable of functioning as sensory cells of the ear, e.g., hair cells.

In some embodiments, the methods include steps of selecting a patient at risk of hair cell loss and/or a patient with hair cell loss. Alternatively or in addition, the methods include steps of selecting a patient at risk of sensorineural hearing loss and/or a patient with sensorineural hearing loss. For example, any human experiencing or at risk for developing hearing loss is a candidate for the treatment methods described herein. A human having or at risk for developing a hearing loss can hear less well than the average human being, or less well than a human before experiencing the hearing loss. For example, hearing can be diminished by at least 5, 10, 30, 50% or more.

The subject can a hearing loss associated with hair cell loss for any reason, or as a result of any type of event. For example, a human can be deaf because of a genetic or congenital defect; for example, a human can have been deaf since birth, or can be deaf or hard-of-hearing as a result of a gradual loss of hearing due to a genetic or congenital defect. In another example, a human can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss. A human can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants. A human can have a hearing disorder that results from aging, or the human can have tinnitus (characterized by ringing in the ears).

A human suitable for the treatment using the compounds and methods featured in the invention can include a human having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

Alternatively or in addition, the compounds and methods featured in the invention can be used prophylactically, such as to prevent, reduce or delay progression of hearing loss, deafness, or other auditory disorders associated with loss of inner ear function. For example, a composition containing one or more compounds can be administered with (e.g., before, after or concurrently with) a second therapeutic, such as a therapeutic that may affect a hearing disorder. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine. For example, a human undergoing chemotherapy can be treated using the compounds and methods described herein. The chemotherapeutic agent cisplatin, for example, is known to cause hearing loss. Therefore, a composition containing one or more compounds can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

The compounds and methods featured in the invention are appropriate for the treatment of hearing disorders resulting from sensorineural hair cell loss. Patients with sensorineural hair cell loss experience the degeneration of cochlear hair cells, which frequently results in the loss of spiral ganglion neurons in regions of hair cell loss. Such patients may also experience loss of supporting cells in the organ of Corti, and degeneration of the limbus, spiral ligament, and stria vascularis in the temporal bone material. These patients can receive treatment with an agent that causes cells to differentiate into hair cells, or a tissue transplant containing hair cells grafted or injected into the inner ear.

Methods of generating cells of the inner ear are provided below. Ear cells or ear cell progenitors can be generated from stem cells isolated from a mammal, such as a mouse or human, and the cells can be embryonic stem cells or stem cells derived from mature (e.g., adult) tissue, such as the inner ear, central nervous system, blood, skin, eye or bone marrow. Any of the methods described below for culturing stem cells and inducing differentiation into ear cells (e.g., hair cells) can be used.

In general, the compounds and methods described herein can be used to generate hair cell growth in the ear and/or to increase the number of hair cells in the ear (e.g., in the inner, middle, and/or outer ear). For example, the number of hair cells in the ear can be increased about 2-, 3-, 4-, 6-, 8-, or 10-fold, or more, as compared to the number of hair cells before treatment. This new hair cell growth can effectively restore or establish at least a partial improvement in the subject's ability to hear. For example, administration of an agent can improve hearing loss by about 5, 10, 15, 20, 40, 60, 80, 100% or more.

Where appropriate, following treatment, the human can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlear hair cells, and electro-cochleography provides information about the functioning of the cochlea and the first part of the nerve pathway to the brain. In some embodiments, treatment can be continued with or without modification or can be stopped.

Abnormal Cell Proliferation

Cell proliferation is normally a tightly regulated process that is governed by multiple checkpoints and safeguards. Abnormal cell proliferation occurs when one or more of these checkpoints or safeguards are bypassed or breakdown, e.g., through genetic mutation. The result of abnormal cell proliferation is the formation of cancerous growths or tumors. The most aggressive cancerous growths are typically invasive and metastatic. Less aggressive benign growths are not invasive or metastatic, although they frequently retain the potential to become metastatic.

In some embodiments, the present invention is directed to methods and compositions for the treatment of abnormal cell proliferation and/or cancer, which would benefit from increased Atoh1 expression. Abnormally proliferating or cancerous cells that can benefit from increased Atoh1 expression can be identified by determining Atoh1 expression levels within the cells, e.g., using real-time PCR and other techniques that can be readily performed by one of skill in the art. Such determinations can be performed by obtaining a sample of abnormally proliferating or cancerous cells from a subject; isolating the genetic material from the sample (e.g., DNA and RNA); reverse transcribing the mRNA from the sample; and amplifying a Atoh1 sequence using oligonucleotides that have been designed to hybridize to a Atoh1 sequence. Abnormally proliferating cells or cancer cells that can benefit from increased Atoh1 expression will have undetectable Atoh1 expression in the cell sample. Alternatively or in addition, the above determination will be repeated using a non-cancerous cell control. Atoh1 expression in the control will then be compared to Atoh1 expression in the cancerous sample. Abnormally proliferating cells or cancer cells that can benefit from increased Atoh1 expression will have less Atoh1 expression than the non-cancerous control. In general, abnormally proliferating cells or cancer cells that can benefit from increased Atoh1 expression will have low or undetectable Atoh1 expression levels.

In some embodiments, the present invention is directed to methods and compositions for the treatment of abnormal cell proliferation and/or cancer in the gastrointestinal system. Exemplary cancers include but are not limited to cancers of the esophagus, gallbladder, liver, pancreas, stomach, small intestine, large intestine (colon) and rectum.

Support for the use of the present invention for the treatment of abnormal cell proliferation and/or cancer of the gastrointestinal system is provided by the following studies: Normally, the intestinal epithelium consists of four main cell types that derived from one multipotent stem cell during embryogenesis. The first cell type is the absorptive enterocyte or columnar cell; the second cell type is the mucous secreting goblet cell; the third cell type is the regulatory peptide-secreting enteroendocrine cell; and the fourth cell type is the antimicrobial peptide-secreting Paneth cell. A healthy animal will have each of these four cell types. Math1 null transgenic mice, however, have depleted goblet, enteroendocrine, and paneth cells. This observation has lead to the conclusion that Math1 is required for cell fate determination (e.g., differentiation) towards these three cell types in the developing gut (Yang et al., Science, 294:2155-2158, 2001). It has also been demonstrated that Hath1 expression is absent in five gastric cancer cell lines compared with normal gastric mucosae. This supports the fact that the loss of Hath1 expression may play a role in gastric carcinogenesis (Sekine et al., Biochem. Biophys., Res. Comm., 344:1166-1171, 2006). Decreased Hath1 and Math1 expression in colon cancer cell lines is also reported elsewhere (Leow et al., Cancer Res., 64:6050-6057, 2004 and Leow et al., Ann. N.Y. Acad. Sci., 1059:174-183, 2005). These studies, however, also demonstrate that Hath1 overexpression in an aggressive colon cancer cell line results in a significant inhibition of cell proliferation, and that this decreased proliferation occurs because the aggressive colon cancer cells differentiate to or towards goblet cells, which are not cancerous. These data, therefore, clearly suggest that gastrointestinal cancer will benefit from increased Atoh1 expression, for example, by reducing the number of proliferating gastric cancer cells by promoting the differentiation of such cells to or towards a non-cancerous cell of the intestinal epithelium. Consequently, a patient with gastrointestinal cancer can be treated with one or more of the compounds described herein.

In general, the present invention provides compounds and methods for treating patients who have, or who are at risk for developing gastrointestinal cancer. Methods for identifying such a patient are described below. The methods of treatment include steps whereby one or more of the compounds described herein are administered to a patient to treat gastrointestinal cancer (direct therapy).

In some embodiments, the methods include methods of selecting a patient at risk of gastrointestinal cancer and/or a patient with gastrointestinal cancer.

Methods for identifying a patient with gastrointestinal cancer are known in the art. For example, screens can include the use of endoscopy (e.g., oral and/or rectal). Screens can also include tests to detect various immunohistochemical markers, including but not limited to, e.g., CK20, MUC2, MUC5A, MUC6, DAS-1, and CDX2.

The present invention is useful for providing treatment for patients who have or who are at risk for developing gastrointestinal cancer using one or more of the compounds described herein. The methods of treatment include steps whereby one or more of the compounds described herein are administered to a patient to promote complete or partial differentiation of gastric cancer cells.

In some embodiments, the present invention is directed to methods and compositions for the treatment of colorectal cancer. Screens for identifying individuals with colorectal cancer are known in the art. For example, screens for colorectal cancer include: fecal occult blood test (FOBT), which checks for blood in the stool, digital rectal exam (DRE), which checks for tactile abnormalities in the rectum, sigmoidoscopy, which looks for visual abnormality in the rectum and lower part of the colon, colonoscopy, which allows visualization of the rectum and entire colon, and double contrast barium enema (DCBE), which allows radiographic examination of the rectum and colon. Frequently, a biopsy or polypectomy of abnormal colorectal tissue is examined to confirm that the tissue is cancerous.

Individuals with colorectal cancer can be classified according to cancer stage scales, such as the Dukes, Astler-Coller, and AJCC/TNM scales. An individual's grade of cancer indicates the degree of de-differentiation the cancer cells have undergone, i.e., how much the tumor's cells still retain the characteristics of a colon or rectal cell. Stage groupings are indicative of person's overall disease stage. In some systems, stage groupings are expressed as Roman numerals from 0 (the earliest stage) to IV (the most advanced stage). In stage 0, the cancer is found only in the inner lining of the colon or rectum. In stage I, the cancer has spread to more of the inner wall of the colon or rectum. In stage II, the cancer has spread outside the colon or rectum to nearby tissue, but has not spread to the lymph nodes. In stage III, the cancer has spread to nearby lymph nodes but not to other parts of the body. In stage IV, the cancer has spread to other parts of the body. Colorectal cancer tends to spread to the liver and/or lungs. (Stages 0 and IV, just described, correspond to stages A and D, respectively, in the Duke scale). Further information on the screening, diagnosis, and staging of colorectal cancer can be found in Frei et al., *Cancer Medicine*, BC Decker Inc., Hamilton, Ontario (2003).

The present invention is useful for providing treatment for patients who have (e.g., stages 0 to IV), or who are at risk for developing, colorectal cancer using one or more of the compounds described herein. The methods of treatment include steps whereby one or more of the compounds described herein are administered to a patient to promote complete or partial differentiation of colorectal cancer cells.

In some embodiments, a patient undergoing treatment or having completed treatment for colon cancer may be reevaluated, e.g., using the methods described above, to determine the effectiveness of therapy. In some embodiments, treatment can be continued with or without modification or can be stopped.

Other Conditions

Atoh1 expression is also reported in the cerebellum and dorsal spinal cord and has an important role, e.g., in development (Bermingham et al., supra and Helms et al., supra). Atoh1 clearly has a role in promoting cell differentiation in neural cells and tissues beyond those found in the inner ear. The compounds and pharmaceutical compositions described herein, therefore, can also be used for the treatment of diseases and/or disorders of such tissues that would benefit from increased Atoh1 expression.

Alternatively or in addition, the present invention can be used to treat cerebellar granule neuron deficiencies, joint disease, and osteoarthritis.

Conditions that can benefit from increased Atoh1 expression can be identified by determining Atoh1 expression levels within a cell using, e.g., the RT-PCR methods described above. In general, conditions that can benefit from increased Atoh1 expression will have low or undetectable Atoh1 expression levels.

Routes of Administration for the Treatment of Auditory Hair Cell Loss

Direct Therapy

The route of administration will vary depending on the disease being treated. Hair cell loss and/or sensorineural hearing loss can be treated using direct therapy using systemic administration and/or local administration. In some embodiments, the route of administration can be determined by a patient's health care provider or clinician, for example following an evaluation of the patient. In some embodiments, a individual patient's therapy may be customized, e.g., one or more compounds, the routes of administration, and the frequency of administration can be personalized. Alternatively, therapy may be performed using a standard course of treatment, e.g., using one or more pre-selected compounds and pre-selected routes of administration and frequency of administration.

In some embodiments, one or more of the compounds described herein can be administered to a patient, e.g., a patient identified as being in need of treatment for hair cell loss, using a systemic route of administration. Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

Alternatively or in addition, one or more of the compounds described herein can be administered to a patient, e.g., a patient identified as being in need of treatment for hair cell loss, using a local route of administration. Such local routes of administration include administering one or more of the compounds described herein into the ear of a patient and/or the inner ear of a patient, for example, by injection and/or using a pump.

In some embodiments, a pharmaceutical composition can be injected into the ear (e.g., auricular administration), such as into the luminae of the cochlea (e.g., the Scala media, Sc vestibulae, and Sc tympani), e.g., using a syringe, e.g., a single-dose syringe. For example, one or more of the compounds described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, Drug Discovery Today, 10:1299-1306, 2005).

In another mode of administration, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described by McKenna et al., (U. S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a patient during a surgical procedure. In some embodiments, a catheter or pump can be positioned, e.g., in the ear (e.g., the outer, middle, and/or inner ear) of a patient without the need for a surgical procedure.

Alternatively or in addition, one or more of the compounds described herein can be administered in combination with a mechanical device such as a cochlear implant or a hearing aid, which is worn in the outer ear. An exemplary cochlear implant that is suitable for use with the present invention is described by Edge et al., (U.S. Publication No. 2007/0093878).

In some embodiments, the modes of administration described above may be combined in any order and can be simultaneous or interspersed.

Alternatively or in addition, the present invention may be administered according to any of the Food and Drug Administration approved methods, for example, as described in CDER Data Standards Manual, version number 004 (which is available at fda.give/cder/dsm/DRG/drg00301.htm).

Cell Therapy

In general, the cell therapy methods described herein can be used to promote complete or partial differentiation of a cell to or towards a mature cell type of the inner ear (e.g., a hair cell) in vitro. Cells resulting from such methods can then be transplanted or implanted into a patient in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cell Selection

Cells suitable for use in the present invention include, but are not limited to, cells that are capable of differentiating completely or partially into a mature cell of the inner ear, e.g., a hair cell (e.g., an inner and/or outer hair cell), when contacted, e.g., in vitro, with one or more of the compounds described herein. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described in Li et al., (U.S. Publication No. 2005/0287127) and Li et al., (U.S. patent Ser. No. 11/953, 797). The use of bone marrow derived stem cells for the replacement of inner ear sensory cells is described in Edge et al., PCT/US2007/084654. iPS cells are described, e.g., at Takahashi et al., Cell, Volume 131, Issue 5, Pages 861-872 (2007); Takahashi and Yamanaka, Cell 126, 663-76 (2006); Okita et al., Nature 448, 260-262 (2007); Yu, J. et al., Science 318(5858):1917-1920 (2007); Nakagawa et al., Nat. Biotechnol. 26:101-106 (2008); and Zaehres and Schöler, Cell 131(5):834-835 (2007).

Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

Tissue-specific gene expression can also be assayed by detection of RNA transcribed from the gene. RNA detection methods include reverse transcription coupled to polymerase chain reaction (RT-PCR), Northern blot analysis, and RNAse protection assays.

Exemplary tissue specific genes that may be used to identify a stem cell (e.g., an undifferentiated cell) include, but are not limited to, e.g., nestin, sox1, sox2, or musashi, NeuroD, Atoh1, and neurogenin1. Alternatively or in addition, stem cells can be selected based on one or more of the unique properties that such cell types present in vitro. For example, in vitro, stem cells often show a distinct potential for forming spheres by proliferation of single cells. Thus, the identification and isolation of spheres can aid in the process of isolating stem cells from mature tissue for use in making differentiated cells of the inner ear. For example, stem cells can be cultured in serum free DMEM/high-glucose and F12 media (mixed 1:1), and supplemented with N2 and B27 solutions and growth factors. Growth factors such as EGF, IGF-1, and bFGF have been demonstrated to augment sphere formation in culture.

Exemplary tissue specific genes that may be used to identify a progenitor cells and/or an inner ear progenitor cell (e.g., a less than fully differentiated or partially differentiated cell) include but are not limited to, e.g., nestin, sox2, and musashi, in addition to certain inner-ear specific marker genes such as Brn3c, islet1 and Pax2 Exemplary tissue specific genes that may be used to identify fully differentiated cells (e.g., support cells) include, but are not limited to, e.g., $p27_{kip}$, p75, S100A, Jagged-1, and Prox1.

Exemplary tissue specific genes that may be used to identify fully differentiated cells capable of functioning as inner ear sensory cells include, but are not limited to, e.g., myosin VIIa, Math1, α9 acetylcholine receptor, espin, parvalbumin 3, and F-actin (phalloidin).

Alternatively or in addition, cells suspected as being fully differentiated (e.g., cells capable of functioning as inner ear sensory cells) may be subjected to physiological testing to determine whether conductance channels that would be present in mature hair cells are present and active.

Alternatively or in addition, inner ear hair cells may be distinguished from other fully differentiated cells of the inner ear (e.g., spiral ganglia) by analyzing the expression of markers that are specific to spiral ganglia, which include but are not limited to ephrinB2, ephrinB3, trkB, trkC, GATA3, and BF1.

In some embodiments, suitable cells can be derived from a mammal, such as a human, mouse, rat, pig, sheep, goat, or non-human primate. For example, stem cells have been identified and isolated from the mouse utricular macula (Li et al., Nature Medicine 9:1293-1299, 2003). The cells can also be obtained from a patient to whom they will subsequently be re-administered.

In some embodiments, suitable cells (e.g., a stem cell, progenitor cell, and/or support cell) may be isolated from the inner ear of an animal. More specifically, a suitable cells can be obtained from the cochlear organ of Corti, the modiolus (center) of the cochlea, the spiral ganglion of the cochlea, the vestibular sensory epithelia of the saccular macula, the utricular macula, or the cristae of the semicircular canals. The stem cell, progenitor cell, and/or support cells can also be obtained, however, from other tissues such as bone marrow, blood, skin, or an eye. The cells employed can be obtained from a single source (e.g., the ear or a structure or tissue within the ear) or a combination of sources (e.g., the ear and one or more peripheral tissues (e.g., bone marrow, blood, skin, or an eye)).

Alternatively or in addition, methods include obtaining tissue from the inner ear of the animal, where the tissue includes at least a portion of the utricular maculae. The animal can be a mammal, such as a mouse, rat, pig, rabbit, goat, horse, cow, dog, cat, primate, or human. The isolated tissue can be suspended in a neutral buffer, such as phosphate buffered saline (PBS), and subsequently exposed to a tissue-digesting enzyme (e.g., trypsin, leupeptin, chymotrypsin, and the like) or a combination of enzymes, or a mechanical (e.g., physical) force, such as trituration, to break the tissue into smaller pieces. Alternatively, or in addition, both mechanisms of tissue disruption can be used. For example, the tissue can be incubated in about 0.05% enzyme (e.g., about 0.001%, 0.01%, 0.03%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 μm or less, about 70 μm or less, about 60 μm or less, about 50 μm or less, about 40 μm or less, about 30 μm or less, about 35 μm or less, or about 20 μm or less.

The cells obtained may constitute an enriched population of stem cells and/or progenitor cells; isolation from all (or essentially all) differentiated cells or other cellular material within the tissue may be achieved but is not required to meet the definition of "isolated." Absolute purity is not required. The invention encompasses cells obtained by the isolation procedures described herein. The cells may be mixed with a cryoprotectant and stored or packaged into kits. Once obtained, the stem cells and/or progenitor cells can be expanded in culture.

Where a mixed population of cells is used, the proportion of stem cells within the test population can vary. For example, the population can contain few stem cells (e.g., about 1-10%) a moderate proportion of stem cells (e.g., about 10-90% (e.g., about 20, 25, 30, 40, 50, 60, 70, 75, 80, or 85% stem cells)) or many stem cells (e.g., at least 90% of the population (e.g., 92, 94, 96, 97, 98, or 99%) can be stem cells). The cells will have the potential to differentiate into a completely or partially differentiated cell of the inner ear (e.g., the cell can be a pluripotent stem cell that differentiates into a cell that expresses one or more auditory proteins). Partially differentiated cells are useful in the treatment methods (whether therapeutic or prophylactic) so long as they express a sufficient number and type of auditory-specific proteins to confer a benefit on the patient (e.g., improved hearing).

Differentiation Methods

In general, differentiation can be promoted by contacting a suitable target cell and/or cell population with one or more of the compounds described herein for a time sufficient to promote complete or partial differentiation of the cells to or towards a mature sensory cell of the inner ear, e.g., a hair cell.

Suitable cells, e.g., identified according to the methods described above, can be cultured in vitro. In general, standard culture methods are used in the methods described herein. Appropriate culture medium is described in the art, such as in Li et al. Nature Medicine 9:1293-1299, 2003. The growth medium for cultured stem cells can contain one or more or any combination of growth factors. For example, growth media can contain leukemia inhibitory factor (LIF), which prevents stem cells from differentiating.

Cells can be separated into individual well of a culture dish and cultured. Formation of spheres (clonal floating colonies) from the isolated cells can be monitored, and the spheres can be amplified by disrupting them (e.g., by physically means) to separate the cells, and the cells can be cultured again to form additional spheres. Such cultured cells can then be contacted with one or more of the compounds described herein.

Alternatively or in addition, cells may be contacted with one or more of the compounds described herein in combination with an additional induction protocol. There are a number of induction protocols known in the art for inducing differentiation of stem cells with neurogenic potential into neural progenitor cells, including growth factor treatment (e.g., treatment with EGF, FGF, and IGF, as described herein) and neurotrophin treatment (e.g., treatment with NT3 and BDNF, as described herein). Other differentiation protocols are known in the art; see, e.g., Corrales et al., J. Neurobiol. 66(13):1489-500 (2006); Kim et al., Nature 418:50-6 (2002); Lee et al., Nat. Biotechnol. 18:675-9 (2000); and Li et al., Nat. Biotechnol. 23:215-21 (2005).

As one example of an additional induction protocol, suitable cells are grown in the presence of supplemental growth factors that induce differentiation into progenitor cells. These supplemental growth factors are added to the culture medium. The type and concentration of the supplemental growth factors is be adjusted to modulate the growth characteristics of the cells (e.g., to stimulate or sensitize the cells to differentiate) and to permit the survival of the differentiated cells such as neurons, glial cells, supporting cells or hair cells.

Exemplary supplementary growth factors include, but are not limited to basic fibroblast growth factor (bFGF), insulin-like growth factor (IGF), and epidermal growth factor (EGF). Alternatively, the supplemental growth factors can include the neurotrophic factors neurotrophin-3 (NT3) and brain derived neurotrophic factor (BDNF). Exemplary concentrations of growth factors can range, e.g., from about 100 ng/mL to about 0.5 ng/mL (e.g., from about 80 ng/mL to about 3 ng/mL, such as about 60 ng/mL, about 50 ng/mL, about 40 ng/mL, about 30 ng/mL, about 20 ng/mL, about 10 ng/mL, or about 5 ng/mL).

Alternatively or in addition, the medium can be exchanged for medium lacking growth factors. For example, the medium can be serum-free DMEM/high glucose and F12 media (mixed 1:1) supplemented with N2 and B27 solutions. Equivalent alternative media and nutrients can also be used. Culture conditions can be optimized using methods known in the art.

In some embodiments, a compound can be tested for its ability to promote differentiation using stem cells that have been engineered to express a reporter gene that facilitates detection of cells converted into inner ear cells. These engineered stem cells make up a reporter cell line. A reporter gene is any gene whose expression may be assayed; such genes include, without limitation, green fluorescent protein (GFP), α-glucuronidase (GUS), luciferase, chloramphenicol transacetylase (CAT), horseradish peroxidase (HRP), alkaline phosphatase, acetylcholinesterase and β-galactosidase. Other optional fluorescent reporter genes include but are not limited to red fluorescent protein (RFP), cyan fluorescent protein (CFP) and blue fluorescent protein (BFP), or any paired combination thereof, provided the paired proteins fluoresce at distinguishable wavelengths.

A reporter gene can be under control of a promoter that is active in cells of the inner ear, including progenitor cells and cells at varying degrees of differentiation, but not in stem cells. Ideally, the promoter is stably upregulated in the differentiated cells or progenitors cells to allow assessment of the partially or fully differentiated phenotype (e.g., expression of the reporter gene and further identification of genes known to be expressed in the inner ear).

Methods for Analyzing Complete or Partial Differentiation

Cells that have been contacted with one or more of the compounds disclosed herein may be analyzed to determine if complete of partial differentiation has occurred. Such a determination can be performed by analyzing the presence or absence of tissue specific genes, as described above (see Cell Selection). Alternatively or in addition, a hair cell can be identified by physiological testing to determine if the cells generate conductance channels characteristic of mature hair or spiral ganglion cells. Such cells can be distinguished from spiral ganglia cells using the markers described above.

Secondary assays can be used to confirm, or provide additional evidence, that a cell has differentiated into a cell of the inner ear. For example, a gene useful as a marker for identifying a cell of the inner ear can be expressed exclusively in a particular cell type (e.g., exclusively in a hair cell or exclusively in cells of the spiral ganglion), or the cell may also be expressed in a few other cell types (preferably not more than one, two, three, four, or five other cell types). For example, ephrinB1 and ephrinB2 are expressed in spiral ganglion cells, and also in retinal cells. Thus detection of ephrinB1 or ephrinB2 expression is not definitive proof that a stem cell has differentiated into a cell of the spiral ganglion. Secondary assays can be used to confirm that a cell has developed into a cell of the spiral ganglion. Such assays include detection of multiple genes known to be expressed in the suspected cell type. For example, a cell that expresses ephrinB1 and/or ephrinB2, can also be assayed for expression of one or more of GATA3, trkB, trkC, BF1, FGF10, FGF3, CSP, GFAP, and Isletl. A determination that these additional genes are expressed is additional evidence that a stem cell has differentiated into a spiral ganglion cell.

Secondary assays also include detection of the absence of gene expression or the absence of proteins that are not typically expressed in hair cells. Such negative markers include the pan-cytokeratin gene, which is not expressed in mature hair cells but is expressed in supporting cells of the inner ear (Li et al., Nat. Med. 9:1293-1299, 2003).

Cells that are confirmed to have undergone complete or partial differentiation towards a inner ear sensory cell, e.g., a hair cell can be transplanted or implanted into a patient.

Implantation Methods

Partially and/or fully differentiated cells, e.g., generated by the methods described above, can be transplanted or implanted, such as in the form of a cell suspension, into the ear by injection, such as into the luminae of the cochlea. Injection can be, for example, through the round window of the ear or through the bony capsule surrounding the cochlea.

The cells can be injected through the round window into the auditory nerve trunk in the internal auditory meatus or into the scala tympani.

To improve the ability of transplanted or implanted cells to engraft, cells can be modified prior to differentiation. For example, the cells can be engineered to overexpress one or more anti-apoptotic genes in the progenitor or differentiated cells. The Fak tyrosine kinase or Akt genes are candidate anti-apoptotic genes that can be useful for this purpose; overexpression of FAK or Akt can prevent cell death in spiral ganglion cells and encourage engraftment when transplanted into another tissue, such as an explanted organ of Corti (see for example, Mangi et al., Nat. Med. 9:1195-201, 2003). Neural progenitor cells overexpressing $\alpha_v\beta_3$ integrin may have an enhanced ability to extend neurites into a tissue explant, as the integrin has been shown to mediate neurite extension from spiral ganglion neurons on laminin substrates (Aletsee et al., Audiol. Neurootol. 6:57-65, 2001). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors et al., J. Comp. Neurol. 462:90-100, 2003). Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie et al., NeuroReport 12:275-279, 2001).

In some embodiments, the cells described herein can be used in a cochlear implant, for example, as described in Edge et al., (U.S. Publication No. 2007/0093878). A cochlear implant is an electronic device that is used to improve hearing in humans who have experienced hearing loss, particularly severe to profound hearing loss. These devices typically include an "external" and an "internal" part. The external part includes a microphone, which can be placed behind the ear, that detects sounds in the environment. The sounds are then digitized and processed by a small computer called a speech processor. The external components may be referred to as a processor unit. In addition to the microphone and speech processor, the external portion of the implant can include a power source, such as a battery and an external antenna transmitter coil. The internal part is an electronic device that is put under the skin in the vicinity of the ear and is commonly referred to as a stimulator/receiver unit (see FIG. 1). The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with the implanted antenna receiver coil provided with the stimulator/receiver unit. The communication is typically provided by a radio frequency (RF) link, but other such links have been proposed and implemented with varying degrees of success.

The implanted stimulator/receiver unit typically includes the antenna receiver coil that receives the coded signal and power from the external processor component, and a stimulator that processes the coded signal and outputs a stimulation signal to an electrode assembly, which applies the electrical stimulation directly to the auditory nerve producing a hearing sensation corresponding to the original detected sound.

An electrode connected to the electronic device is inserted into the inner ear. The electrode can be a bundle of wires that have open contacts spread along the length of the cochlea and represent different frequencies of sounds. The number of electrodes can vary from 1 to about 30 electrodes, such as about 5, 10, 15, 18, 20, 22, 24, 26, or 28 electrodes.

Combination Therapies

In some embodiments, the present invention provides methods for treating a patient with one or more of the compounds described herein using the direct administration and cell therapy methods described above.

Routes of Administration for the Treatment of Abnormal Cell Proliferation

The route of administration will vary depending on the disease being treated. Abnormal cell proliferation and/or cancer can be treated using direct therapy, e.g., using systemic administration and/or local administration according to one or more of the Food and Drug Administration approved methods, for example, as described in CDER Data Standards Manual, version number 004 (which is available at fda.give/cder/dsm/DRG/drg00301.htm).

In some embodiments, the route of administration can be determined by a patient's health care provider or clinician, for example following an evaluation of the patient. In some embodiments, a individual patient's therapy may be customized, e.g., one or more compounds, the routes of administration, and the frequency of administration can be personalized. Alternatively, therapy may be performed using a standard course of treatment, e.g., using one or more preselected compounds and pre-selected routes of administration and frequency of administration.

In some embodiments, one or more of the compounds described herein can be administered to a patient, e.g., a patient identified as being in need of treatment for hair cell loss, using a systemic route of administration. Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops, syrups, suspensions and emulsions; rectal administration, e.g., a rectal suppository or enema; a vaginal suppository; a urethral suppository; transdermal routes of administration; and inhalation (e.g., nasal sprays).

Alternatively or in addition, one or more of the compounds described herein can be administered to a patient, e.g., a patient identified as being in need of treatment for hair cell loss, using a local route of administration. For example, one or more of the compounds can be administered during a surgical procedure, e.g., to remove a tumor and can be performed by injection or topically at one or more site in and around the cancerous site.

Pharmaceutical Formulations

Pharmaceutical compositions containing one or more of the compounds described herein (i.e., as active ingredients) will be formulated according to the intended method of administration.

One or more of the compounds described herein can be formulated as pharmaceutical compositions for direct administration to a subject. Pharmaceutical compositions containing one or more of the compounds described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In some embodiments, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, *Remington's Pharmaceutical Sciences,* 18th Ed., Gennaro, ed., Mack Publishing Co., Easton, Pa., 1990.

One or more of the compounds described herein can be administered, e.g., as a pharmaceutical composition, directly and/or locally by injection or through surgical placement, e.g., to the inner ear and/or the colon. The amount of the pharmaceutical composition may be described as the effective amount or the amount of a cell-based composition may be described as a therapeutically effective amount. Where application over a period of time is advisable or desirable, the compositions of the invention can be placed in sustained released formulations or implantable devices (e.g., a pump).

Alternatively or in addition, the pharmaceutical compositions can be formulated for systemic parenteral administration by injection, for example, by bolus injection or continuous infusion. Such formulations can be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

In addition to the formulations described previously, the compositions can also be formulated as a depot preparation. Such long acting formulations can be administered by implantation (e.g., subcutaneously). Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions formulated for systemic oral administration can take the form of tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

In some embodiments, the pharmaceutical compositions described herein can include one or more of the compounds formulated according to any of the methods described above, and one or more cells obtained to the methods described herein.

Effective/Therapeutic Dose

Toxicity and therapeutic efficacy of the compounds and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. A subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

Generally the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 in *Remington's Pharmaceutical Sciences*, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's *The Pharmacological Basis of Therapeutics*, 9th Ed., Hardman et al., eds., McGraw-Hill, New York, N.Y, 1996).

Kits

The compounds and pharmaceutical compositions described herein can be provided in a kit, as can cells that have been induced to differentiate (e.g., stem cells, progenitor cells, and/or support cells that have differentiated into, for example, hair cells or hair-like cells) and/or that are capable of differentiating into hair cells. The kit can also include combinations of the compounds and pharmaceutical compositions described herein and such cells. The kit can include (a) one or more compounds, such as in a composition that includes the compound, (b) cells that have been induced to differentiate (e.g., stem cells, progenitor cells, and/or support cells that have differentiated into, for example, hair cells or hair-like cells) and/or that are capable of differentiating into hair cells, (c) informational material, and any combination of (a)-(c). In some embodiments, (a) and/or (b) can be provided in a syringe (e.g., a preloaded disposable single dose syringe) suitable for the direct administration of (a) and/or (b) directly into the ear (e.g., the middle or inner ear) of a patient. In some embodiments, (a) and/or (b) can be provided in a catheter and pump system, as described above, suitable for the direct administration of (a) and/or (b) directly into the ear (e.g., the middle or inner ear) of a patient. The informational material can be descriptive, instructional, marketing or other material that relates to the methods described herein and/or to the use of the agent for the methods described herein. For example, the informational material relates to the use of the compound to treat a subject who has, or who is at risk for developing, a auditory hair cell loss hearing and/or abnormal cell proliferation. The kits can also include paraphernalia for administering a differentiation agent to a cell (in culture or in vivo) and/or for administering a cell to a patient.

In one embodiment, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In another embodiment, the informational material can include instructions to administer the pharmaceutical composition to a suitable subject, e.g., a human, e.g., a human having, or at risk for developing, auditory hair cell loss and/or abnormal cell proliferation.

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. Of course, the informational material can also be provided in any combination of formats.

In addition to the differentiation agent, the composition of the kit can include other ingredients, such as a solvent or buffer, a stabilizer, a preservative, a fragrance or other cosmetic ingredient, and/or a second agent for treating a condition or disorder described herein. Alternatively, the other ingredients can be included in the kit, but in different compositions or containers than the agent. In such embodiments, the kit can include instructions for admixing the agent and the other ingredients, or for using one or more compounds together with the other ingredients.

The kit can include one or more containers for the pharmaceutical composition. In some embodiments, the kit contains separate containers, dividers or compartments for the composition and informational material. For example, the composition can be contained in a bottle (e.g., a dropper bottle, such as for administering drops into the ear), vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the pharmaceutical composition. For example, the kit can include a plurality of syringes, ampoules, foil packets, or blister packs, each containing a single unit dose of the pharmaceutical composition. The containers of the kits can be air tight and/or waterproof, and the containers can be labeled for a particular use. For example, a container can be labeled for use to treat a hearing disorder.

As noted above, the kits optionally include a device suitable for administration of the composition (e.g., a syringe, pipette, forceps, dropper (e.g., ear dropper), swab (e.g., a cotton swab or wooden swab), or any such delivery device).

EXAMPLES

The invention is further described in the following examples, which do not limit the scope of the invention described in the claims.

Example 1

High Throughput Screen Optimization

A human embryonic kidney (HEK) cell line stably expressing a Luciferase gene controlled by an Math1 enhancer and minimal promoter was used in a high-throughput screen (HTS) of 144,000 small molecules to identify compounds that increase Math1 expression (i.e., transcription and/or translation). Such compounds can be used to increase the conversion of stem cells, progenitor cells, and support cells to or towards a hair cell. Screens to identify such compounds are described by Li et al., (U.S. Publication No. 2005/0287127) and Li et al., (U.S. application Ser. No. 11/953,797).

The HTS was optimized using 1 µM retinoic acid as a positive control for the activation of the Math1-luciferase reporter construct. Retinoic acid is a well known general inducer of differentiation to mature cell types.

HEK cells stably expressing the Math1 Luciferase reporter were plated onto 384 well plates and cultured overnight in medium containing 10% fetal calf serum (FCS). Activation of the Math1 enhancer was measured by the increase in luminescence on a plate reader following addition of a luciferase detection agent. The assay was optimized for cell number, time of incubation, volume of medium, cell lysis reagent and luciferase reagent. Luminescence levels were compared in cells with the Math1-luciferase construct with and without retinoic acid (1 µM), and/or a luciferase construct with and without the Math1 enhancer and minimal promoter region.

Data indicated that the Math1 luciferase reporter was sensitive to retinoic acid and that the assay had a low background. There was consistently a 1.8-fold increase in luciferase activity in cells treated with 1 µM retinoic acid compared to non-treated cells. Luminescence levels from the promoter without the enhancer were low.

To improve assay sensitivity, and reduce the coefficient of variation (CV), a more sensitive luciferase reagent (BriteLite luciferase reporter assay reagent, Perkin Elmer) was used, and Triton-X-100 was added to the lysis reagent to ensure complete lysis of the cells. Following these changes a CV of 4.2% was recorded. These conditions were used for all high-throughput screens. The luminescence threshold for a compound to be positive was defined as a 2-fold increase above the control (e.g., cells exposed to DMSO).

Time of exposure to the compounds and cell density was optimized as follows. The optimal exposure time was determined to provide the time at which Math1 activity was greatest with minimal cell loss. This was performed using various concentrations of retinoic acid.

Maximal luminescence was observed following a 60 hour incubation in the presence of retinoic acid, however, a significant reduction of signal to 50% was observed at the 72 hour time point. At the 48 hour time point, the luminescence was close to the plateau and has the highest signal-to-background ratio of the times tested. 48 hours was, therefore, selected as the endpoint of the assay.

Optimal cell density was performed by performing a cell titration experiment in which the activity of the Math1 Luciferase reporter was compared in wells seeded with 2000 to 40000 cells per well in a 384-well plate. Cells exposed to retinoic acid were then compared to cells not exposed to retinoic acid. A cell viability assay was also performed to ascertain the viability of the cells expressing the Math1 luciferase reporter.

The cell viability assay showed a linear increase in the number of cells in the range between 2000 and 10000 cells per well. There was no difference in the signal produced in the wells with 8000 and 15000 cells per well, which implied that there may be reduced survival over the course of the experiment at densities greater than 10000 cells per well. The largest difference between untreated and retinoic acid treated cells was observed at a density of 8000 cells per well. Based on these results, assay parameters were selected to be 8000 cells per well, with a 48 hour incubation period in the presence of absence of a test compound or known activator.

Example 2

High Throughput Screening to Identify Activators of Atoh-1 Expression

Cells were seeded on 384 well plates and allowed to attach overnight at 37° C. with 5% $CO_2$ in the absence of growth factors. Math1 activation was measured by the increase in luminescence on a plate reader following addition of a luciferase detection reagent. Luminescence was assessed at 24, 48, and 72 hours. These conditions were used to screen 144,000 compounds contained in the small molecule libraries at Harvard University's Laboratory for Drug Discovery in Neurodegeneration (LDDN).

HTS were performed using HEK-Math1 cells seeded in 384 well plates. One compound was added per well using pin transfer. The final concentration of each compound was 100 µM. Cell were incubated in the presence of a compound for 48 hours at 37° C. with 5% $CO_2$. Cell lysates then were collected and bioluminescence determined. Luminescence values were compared normalized against DMSO.

About 20000 compounds were screened per week in 50 plates of 384 well with the aid of robotic systems (Beckman Biomek FX). Compounds were screened at an average final concentration of 0.7 µM (in 0.04% DMSO) with each plate containing 16 wells of 1 µM retinoic acid, as a positive control, and 16 wells of 0.04% DMSO, as a vehicle control. Percent activation of luminescence in the test compounds was determined for cells treated with the compounds against cells treated with DMSO.

Figure 40:
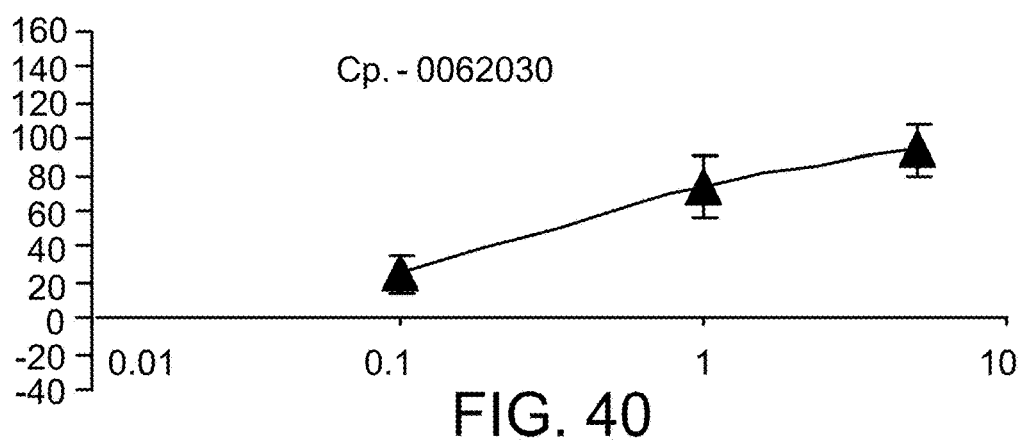
Figure 41:
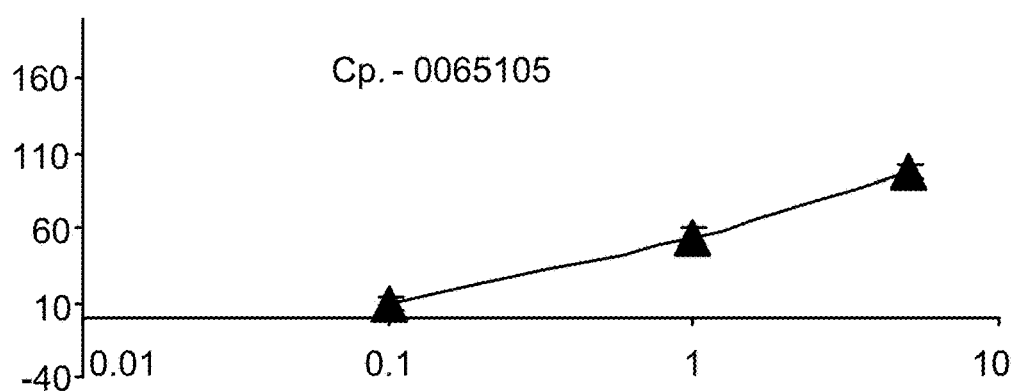
Figure 42:
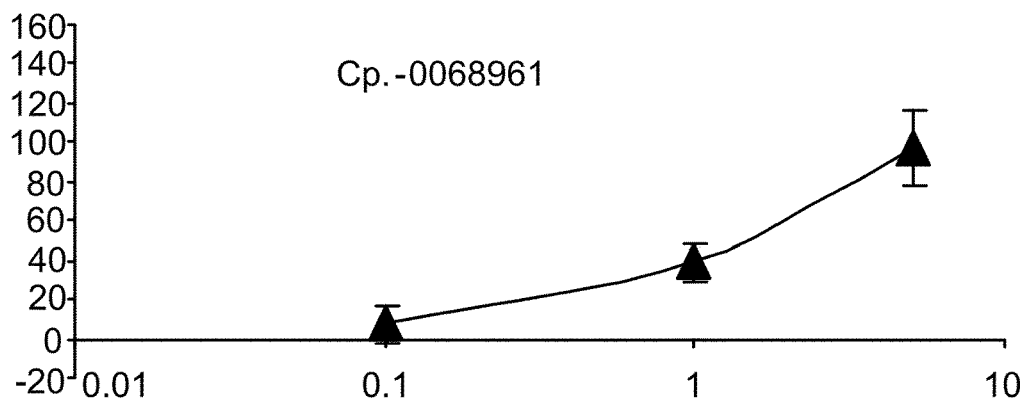
Figure 43:
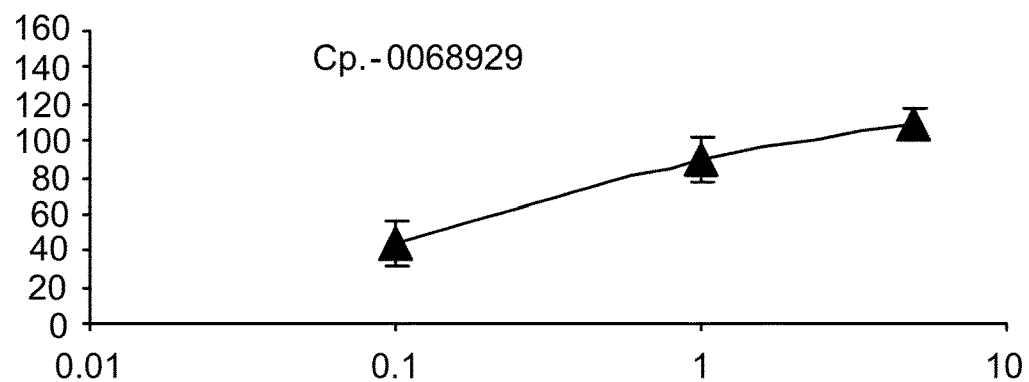
Figure 44:
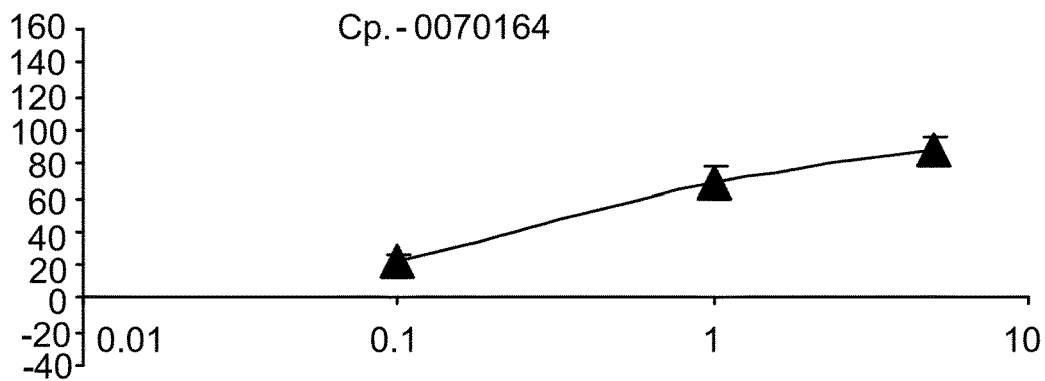
Figure 45:
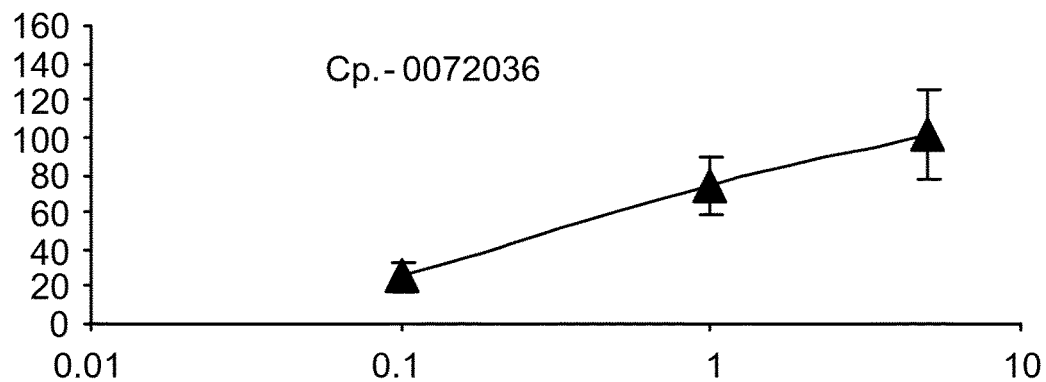
Figure 46:
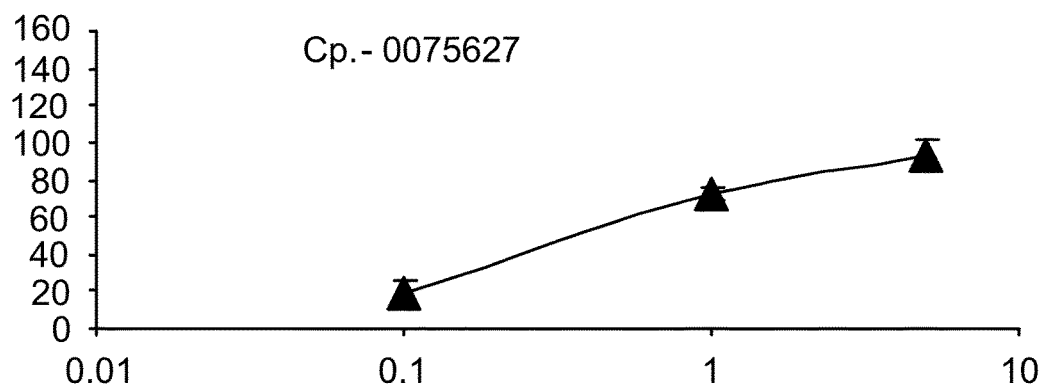
Figure 47:
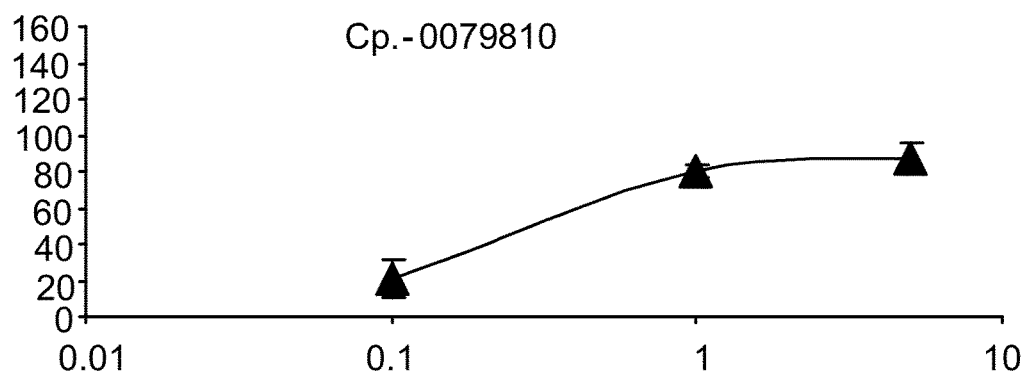
Figure 48:
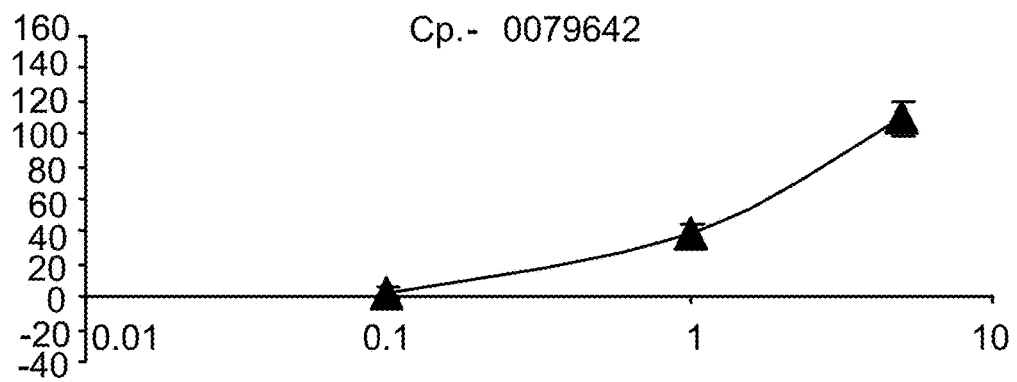
Figure 49:
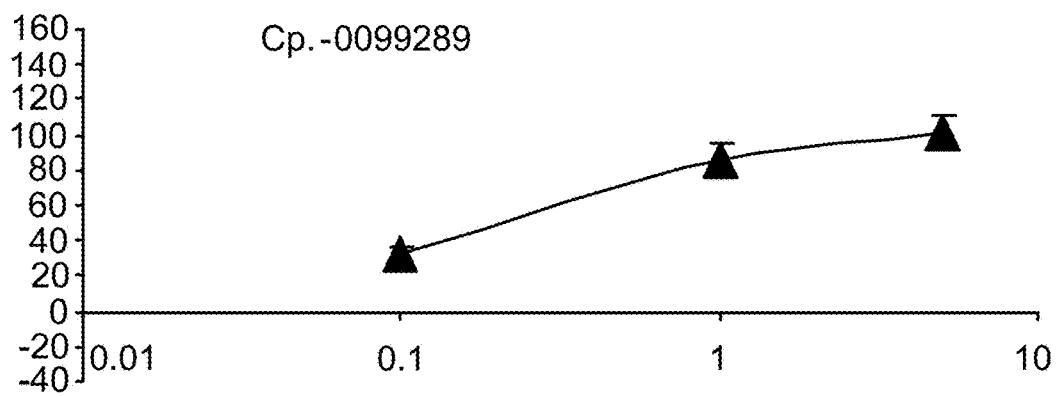
Figure 50:
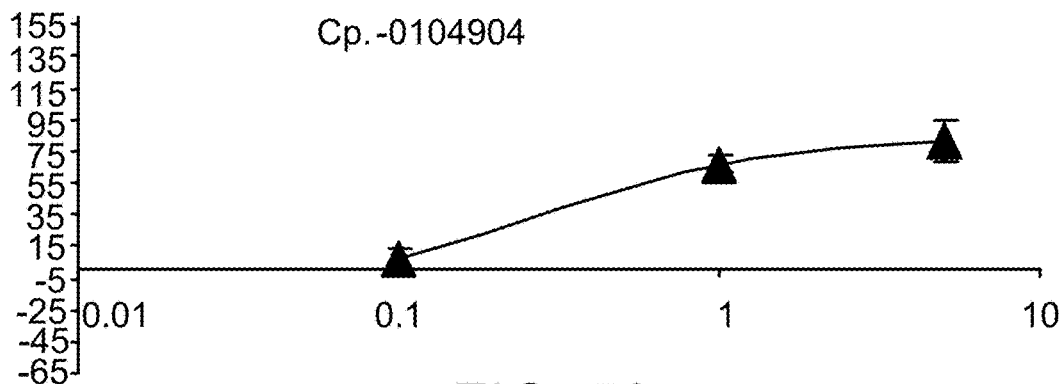
Figure 51:
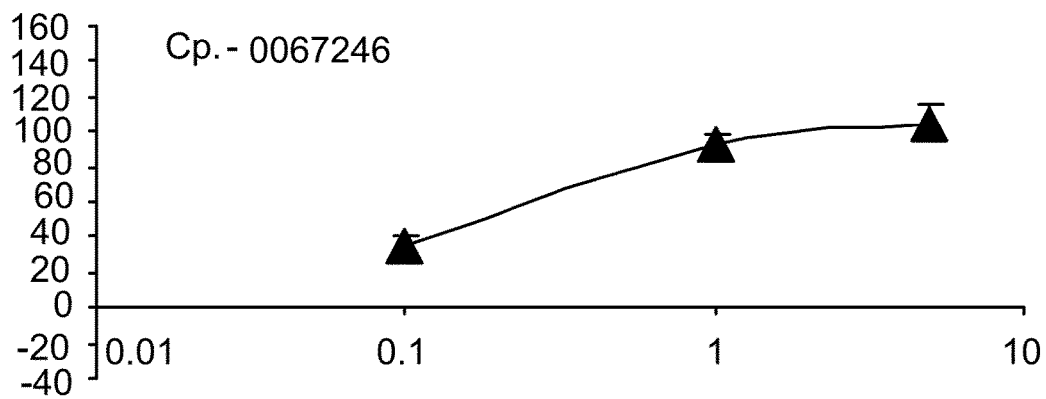
Figure 52:
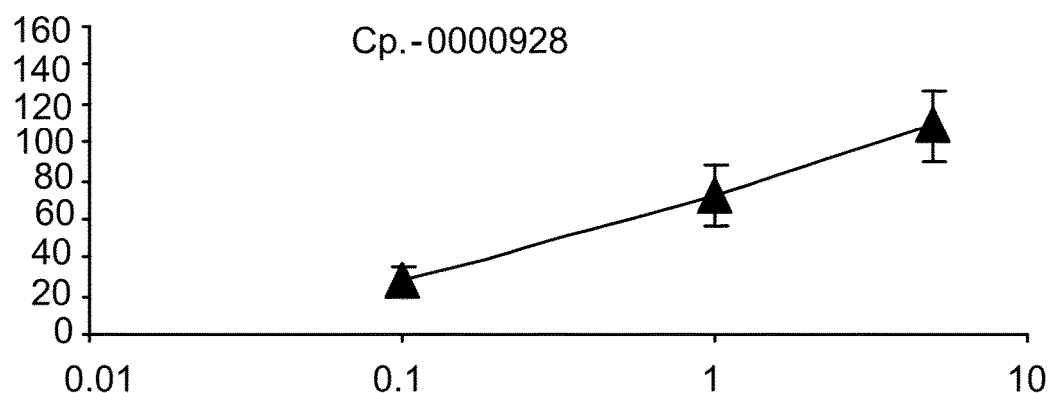
Figure 53:
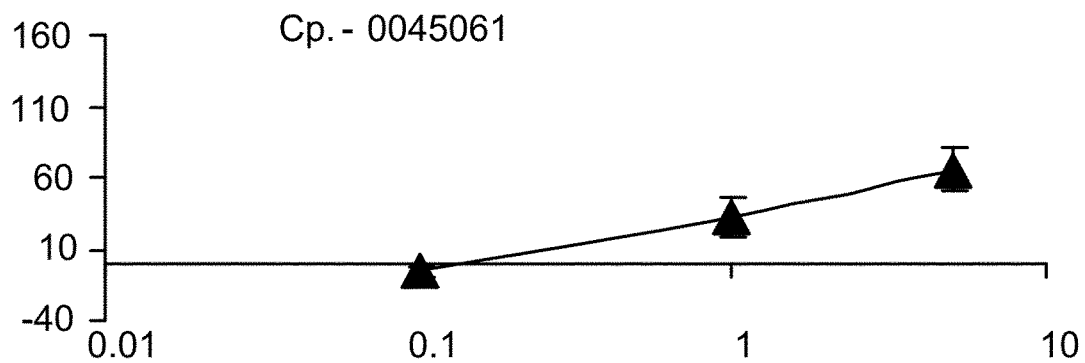
Figure 54:
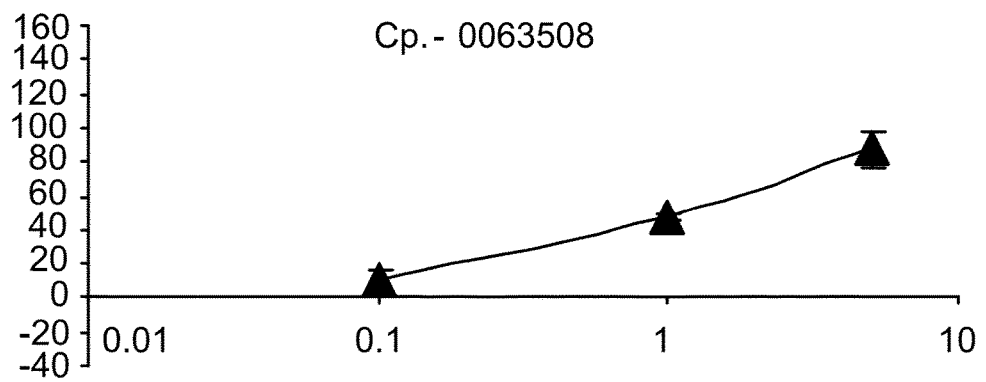
Figure 55:
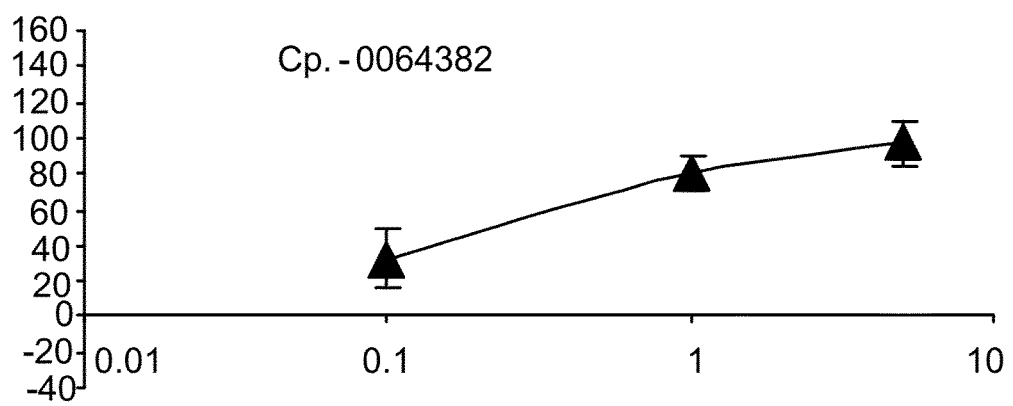
Figure 56:
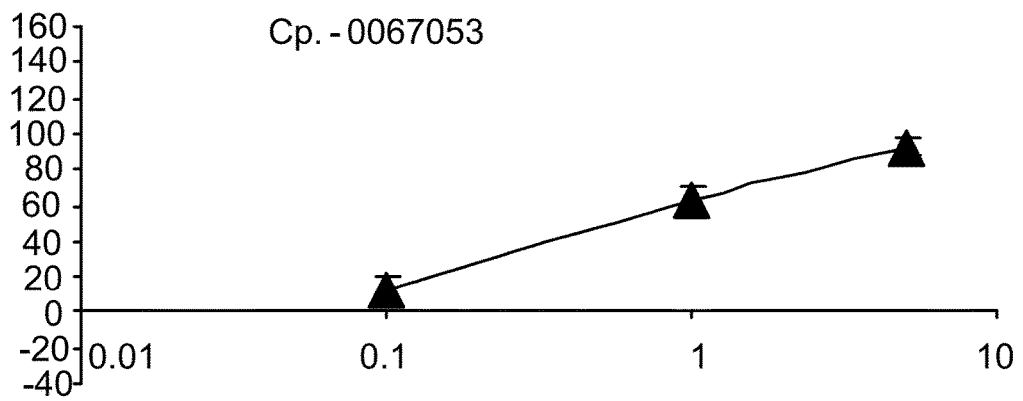
Figure 57:
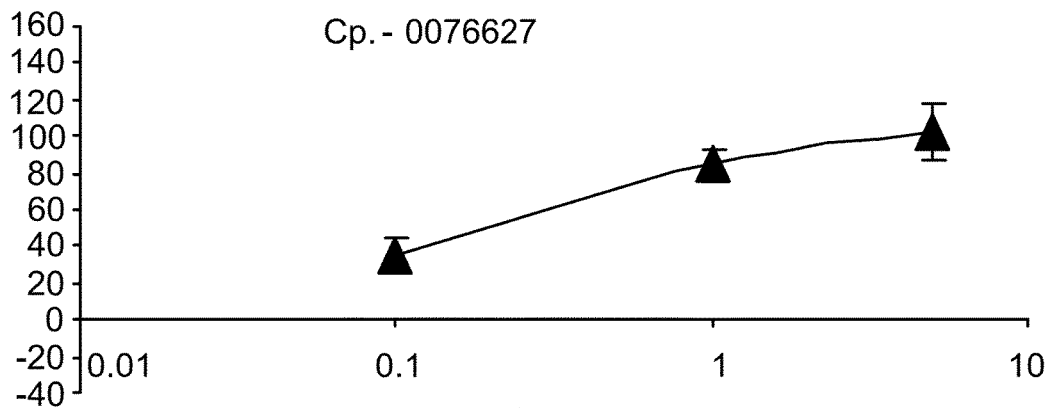
Figure 58:
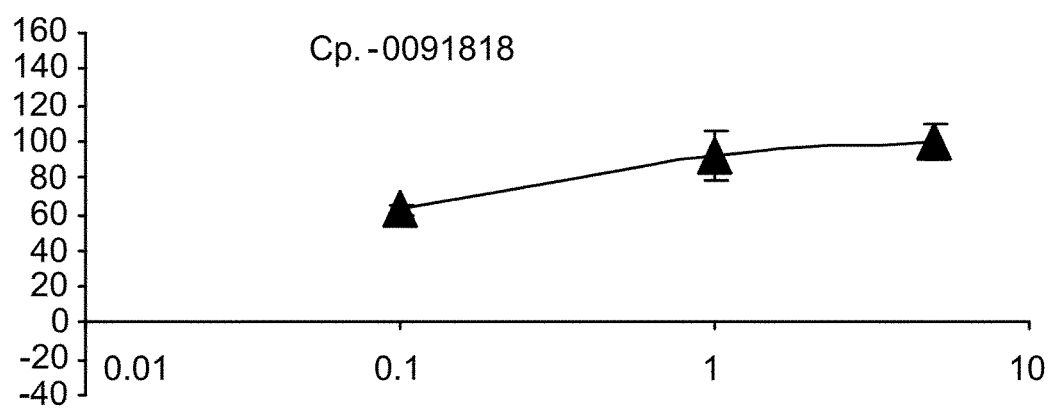
Figure 59:
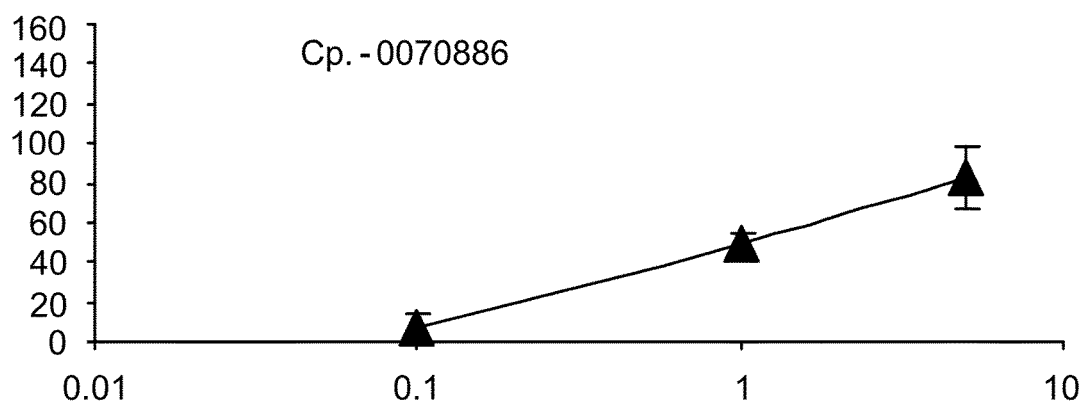
Figure 60:
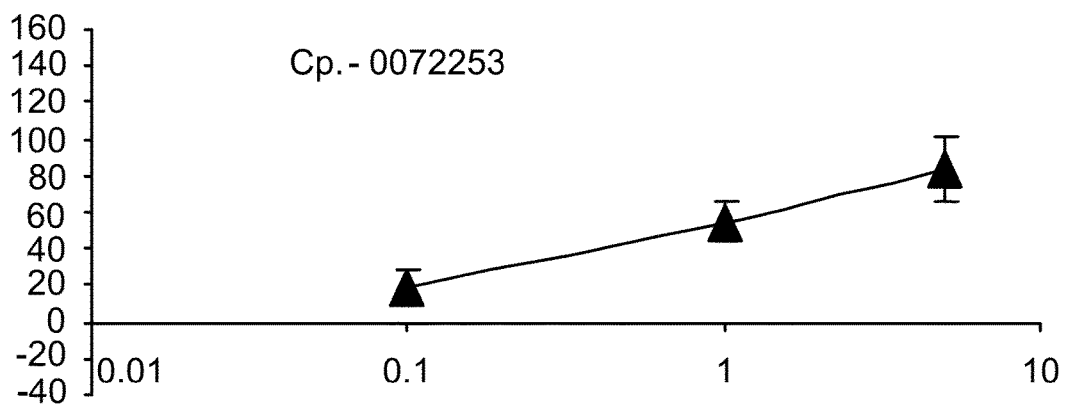
Figure 61:
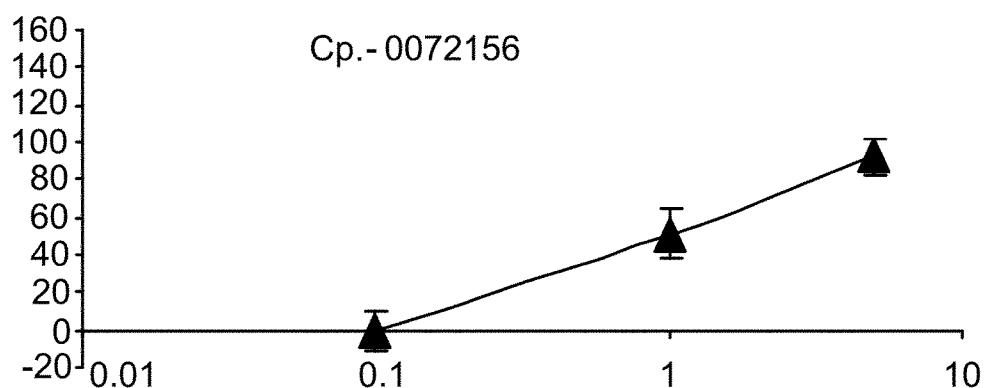
Figure 62:
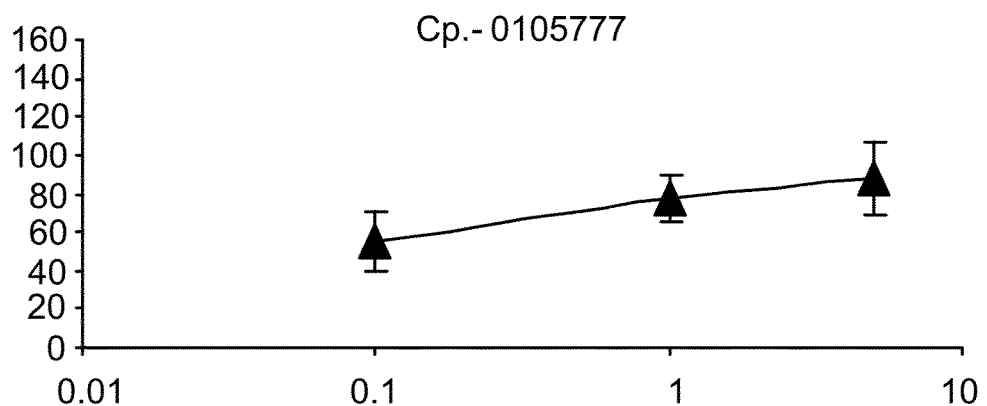
Figure 63:
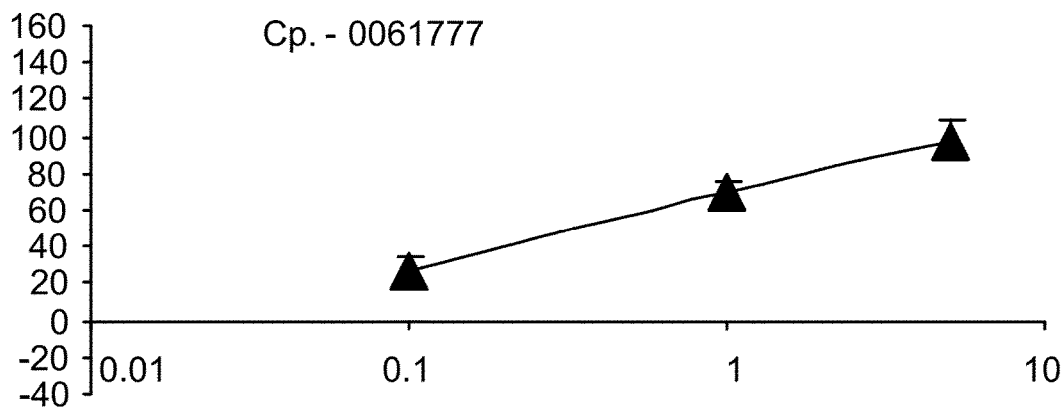
Figure 64:
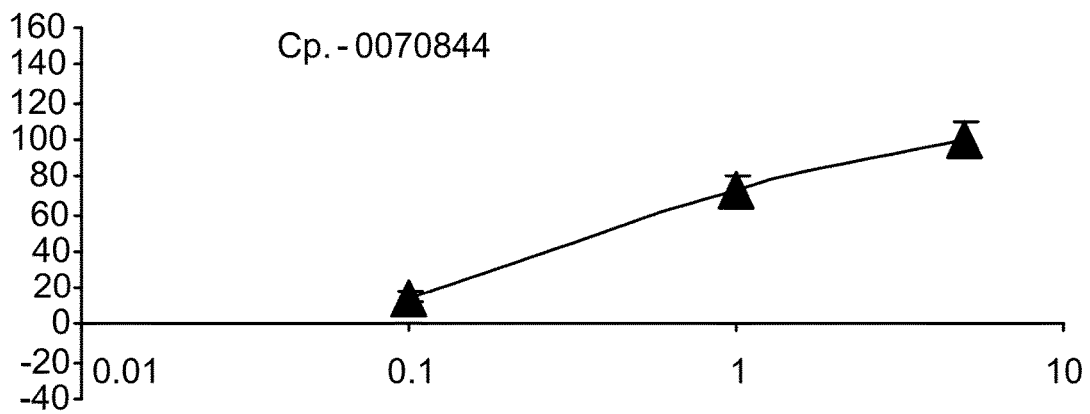
Figure 65:
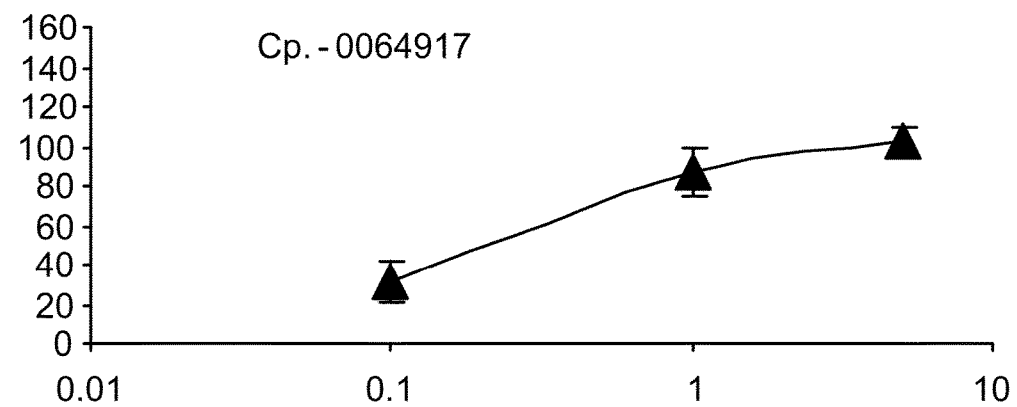
Figure 66:
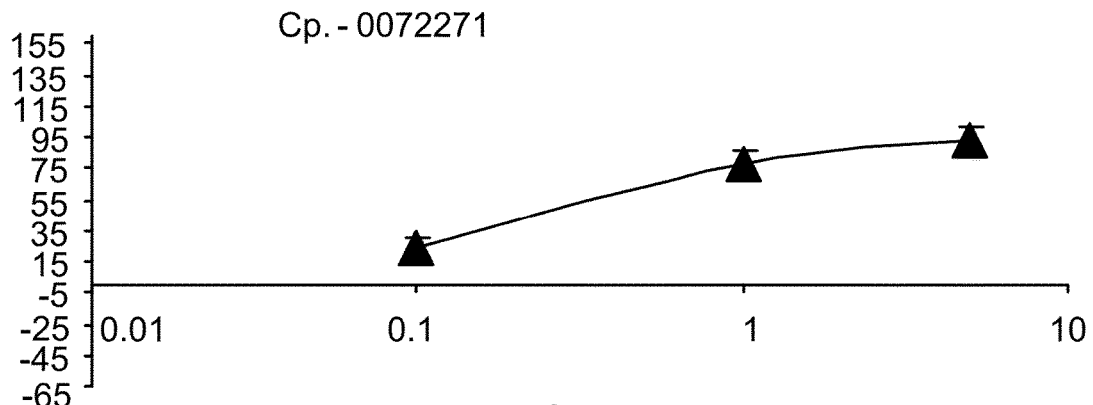
Figure 67:
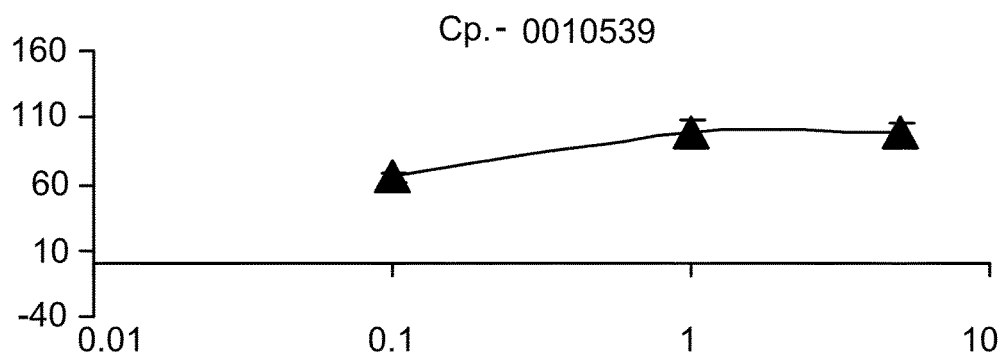
Figure 68:
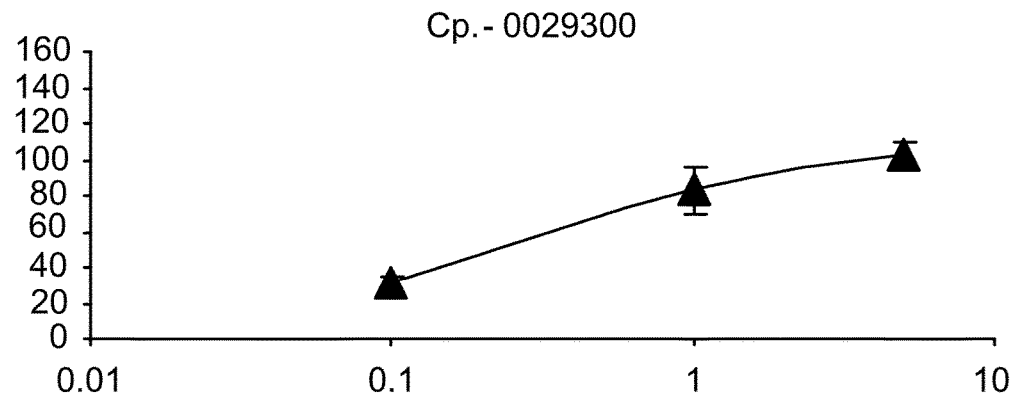
Figure 69:
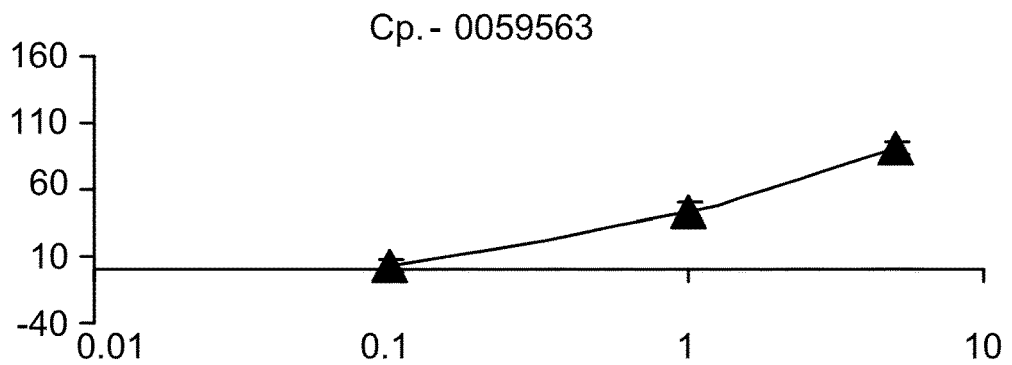
Figure 70:
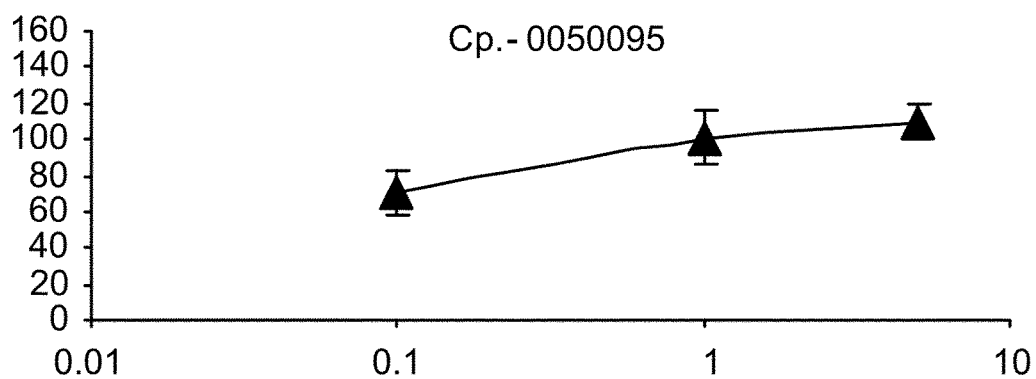
Figure 71:
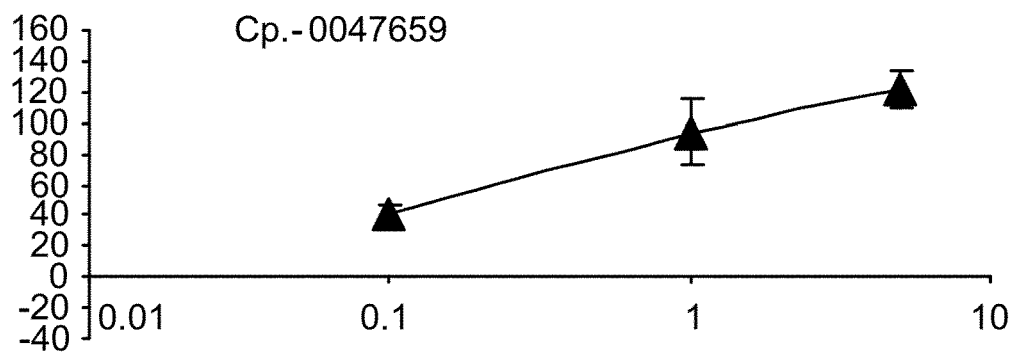
Figure 72:
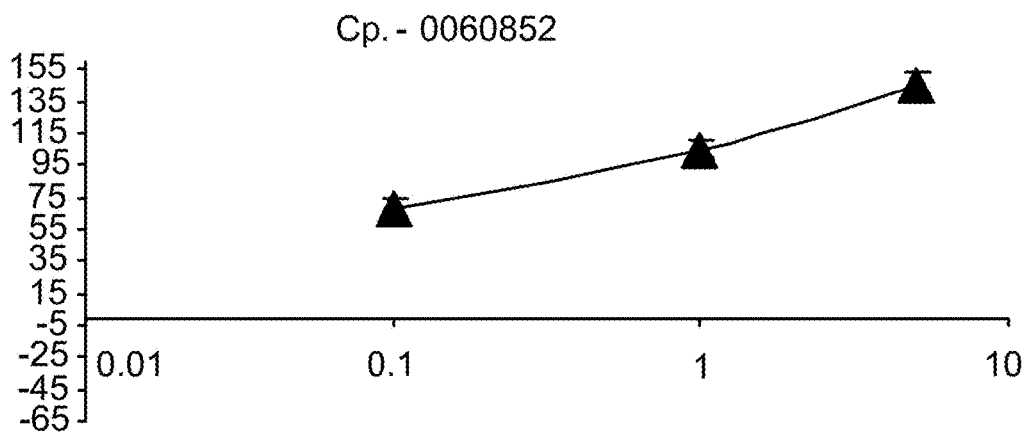
Figure 73:
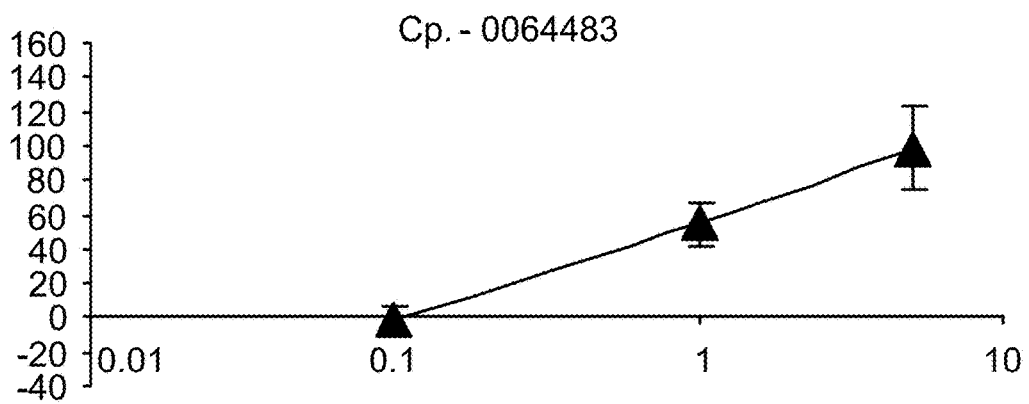
Figure 74:
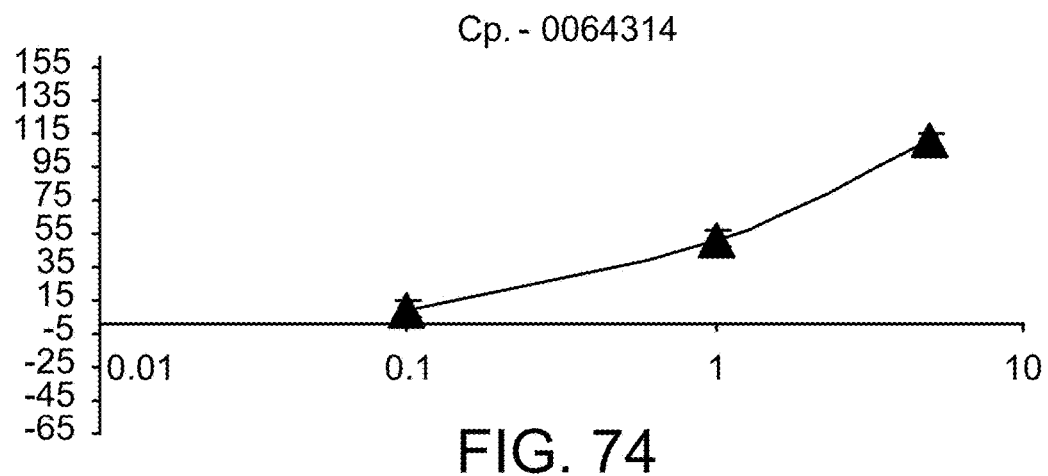
Figure 75:
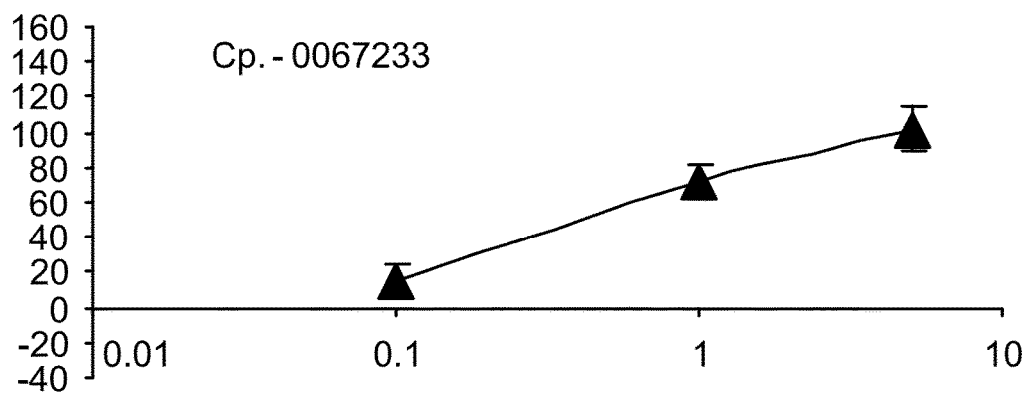
Figure 76:
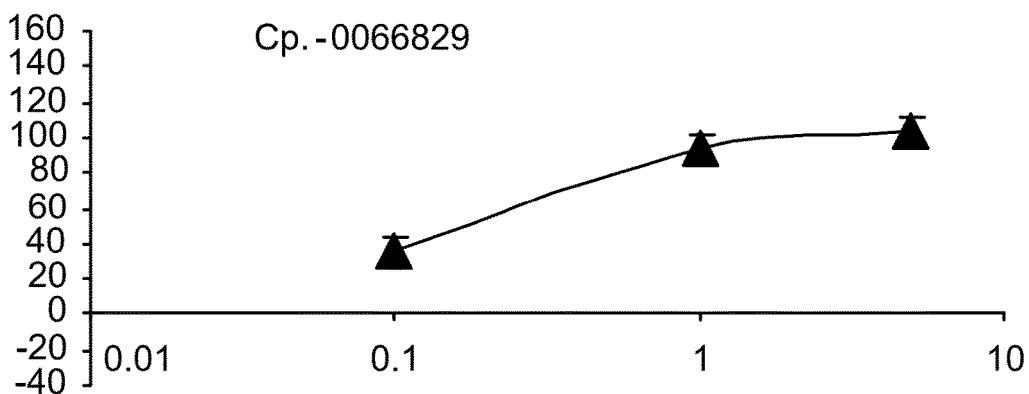
Figure 77:
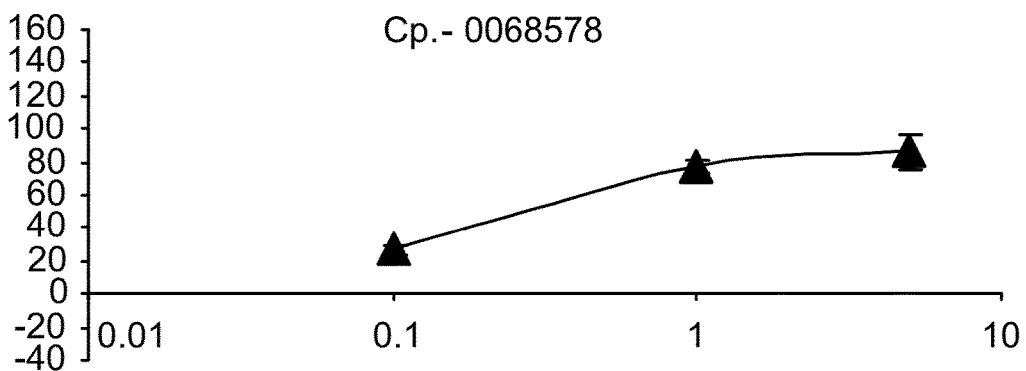
Figure 78:
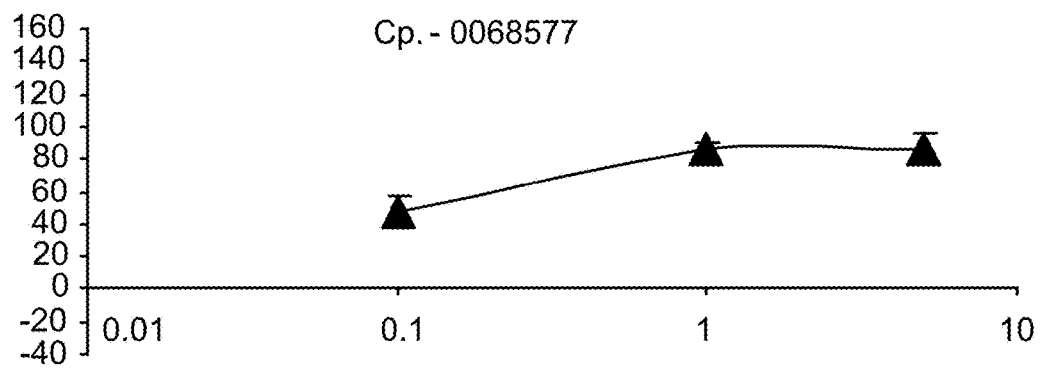
Figure 79:
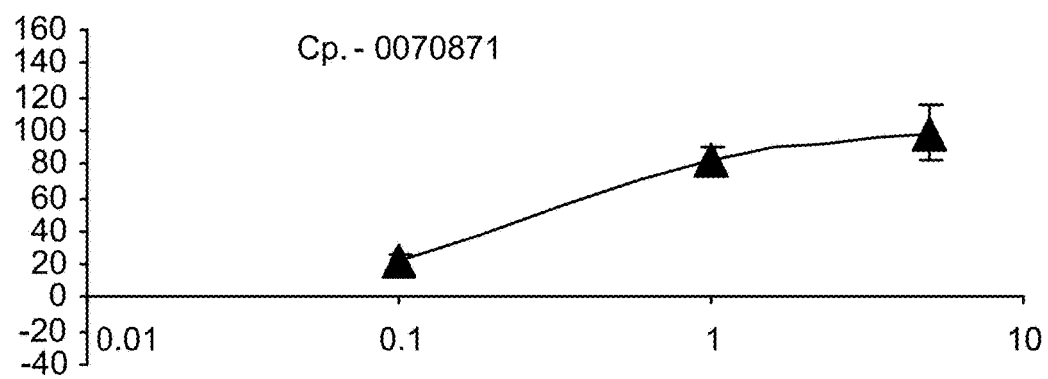
Figure 80:
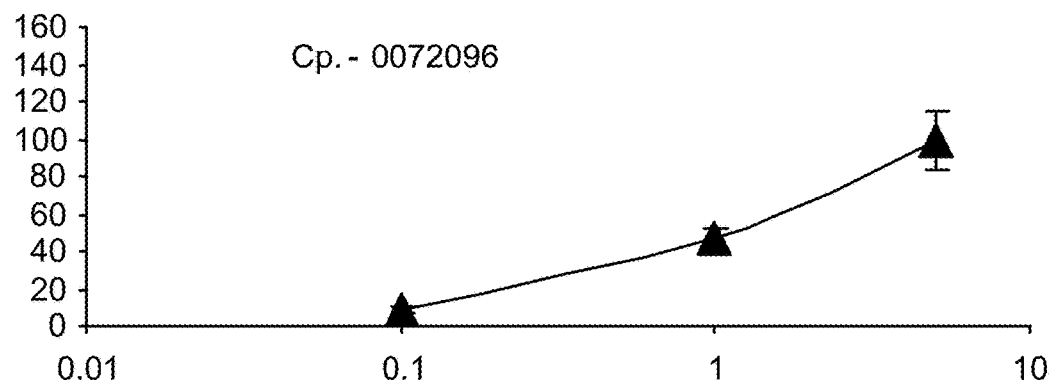
Figure 81:
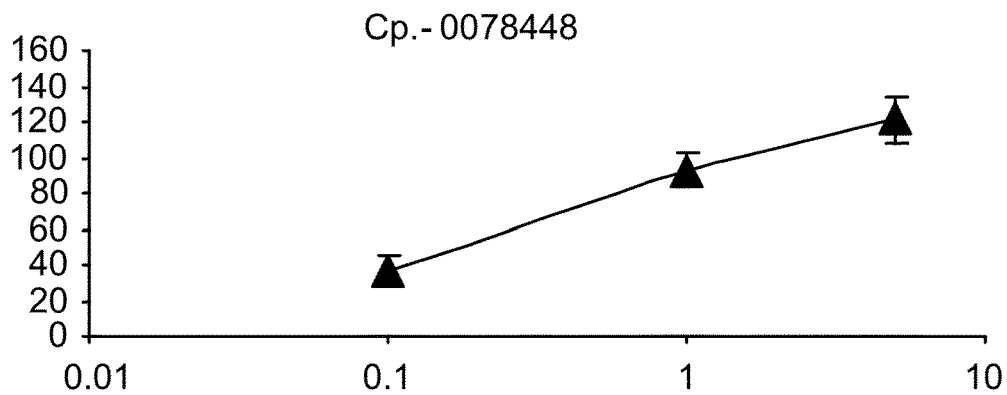
Figure 82:
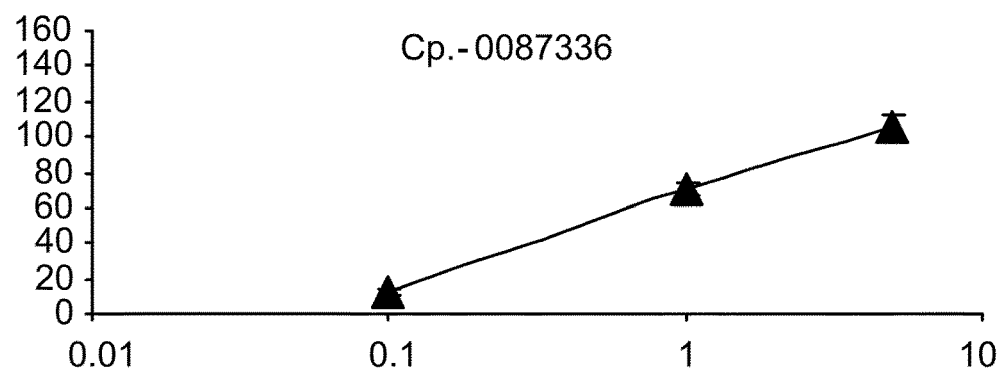
Figure 83:
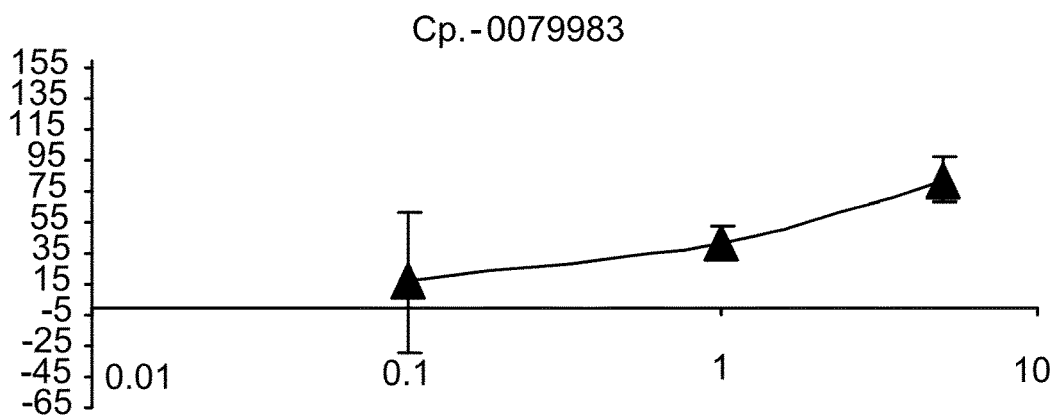
Figure 84:
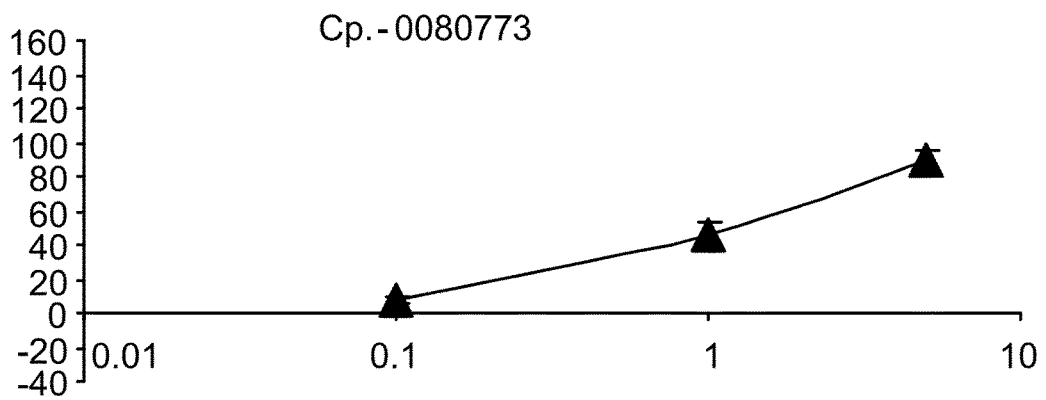
Figure 85:
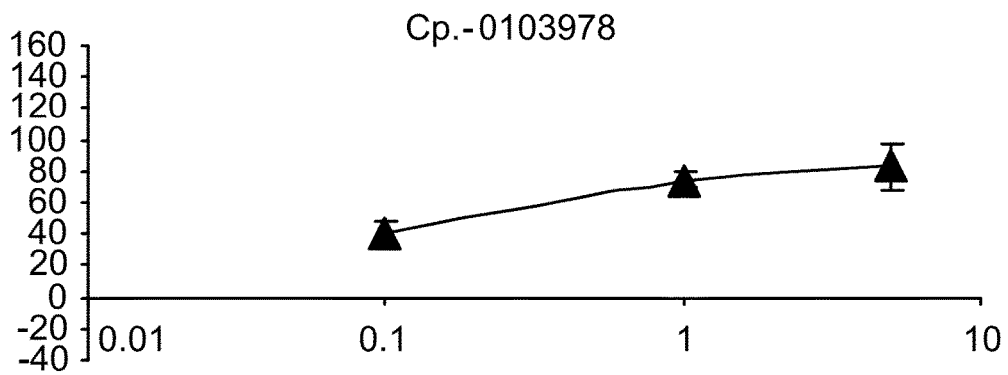
Figure 86:
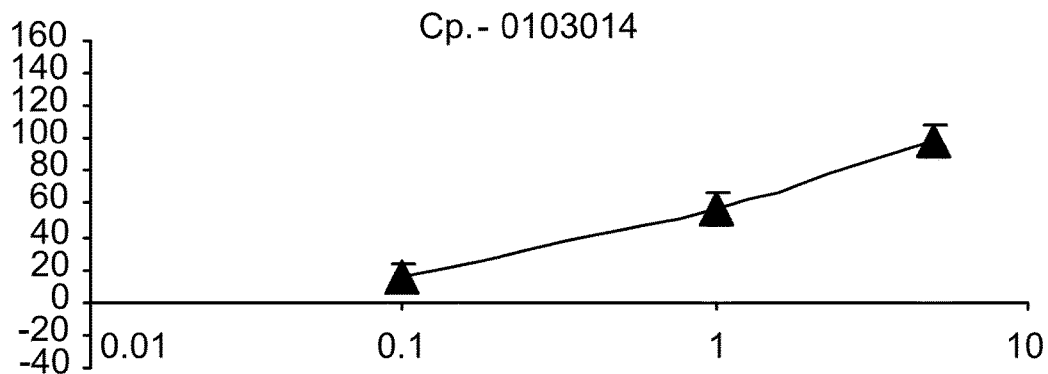
Figure 87:
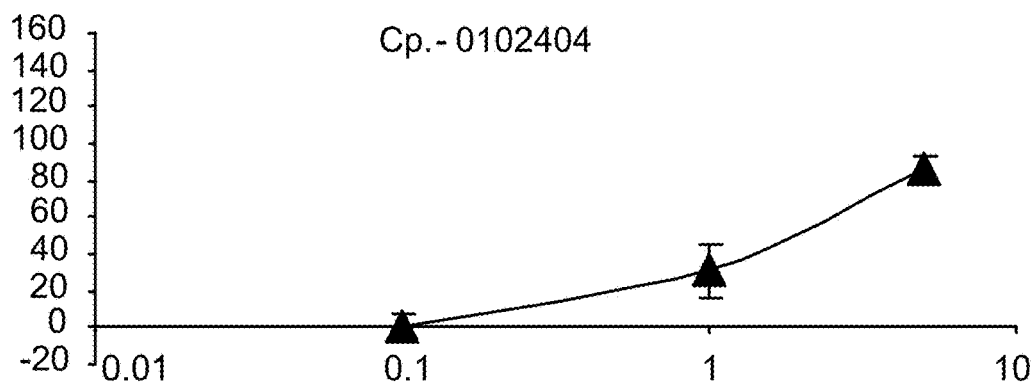
Figure 88:
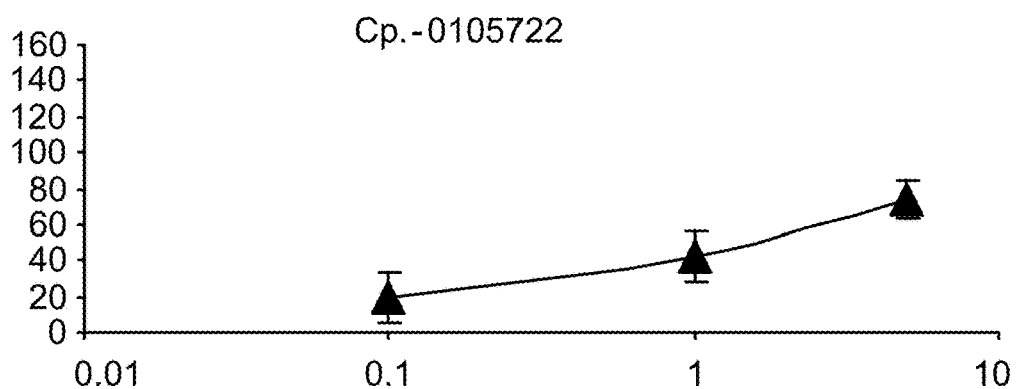
Figure 89:
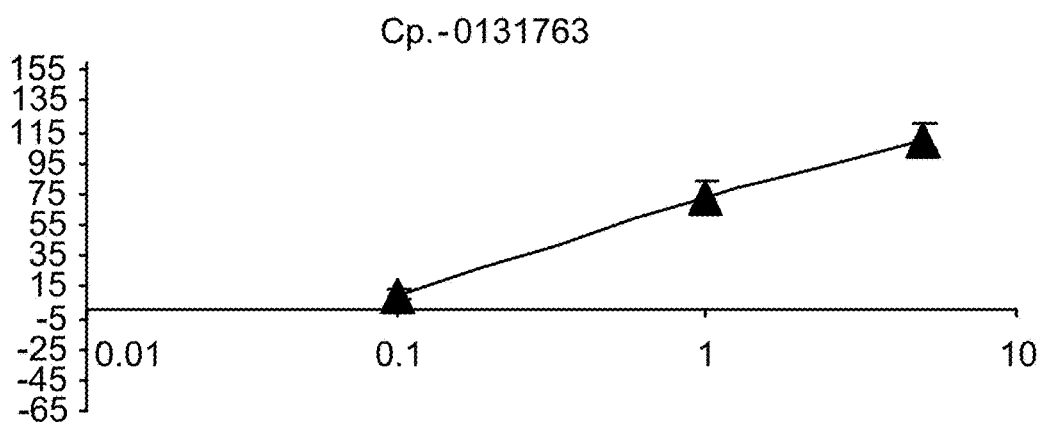
Figure 90:
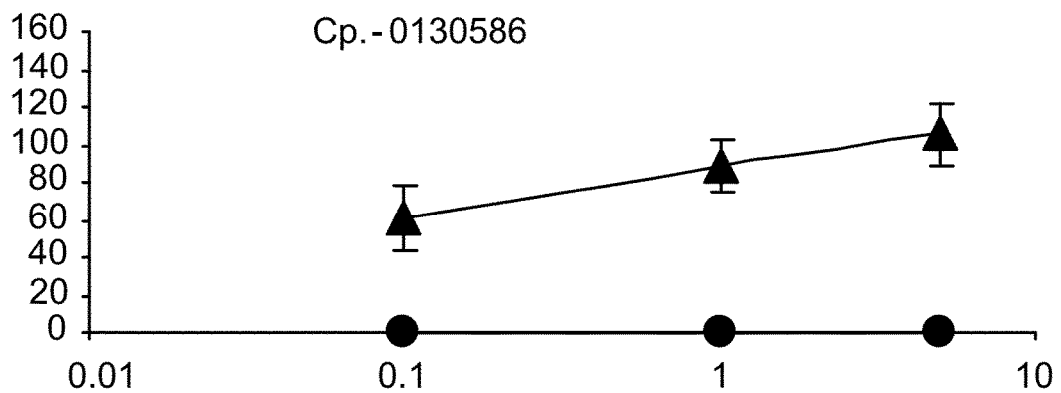
Figure 91:
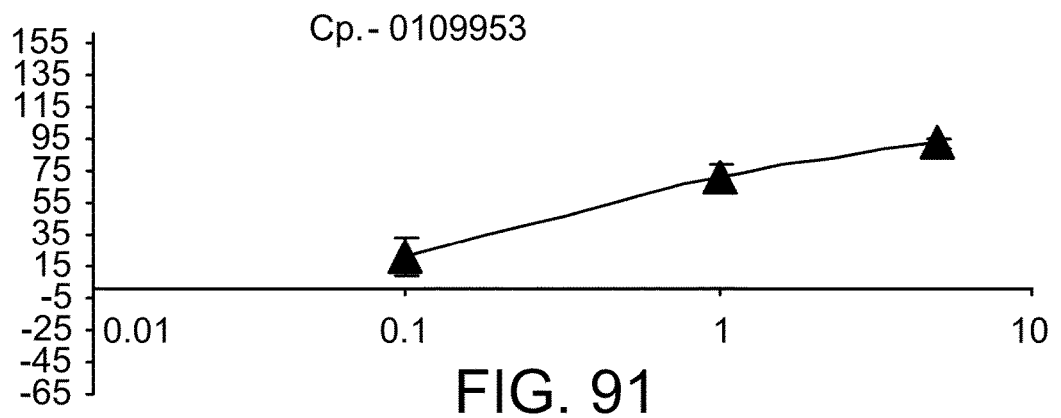
Figure 92:
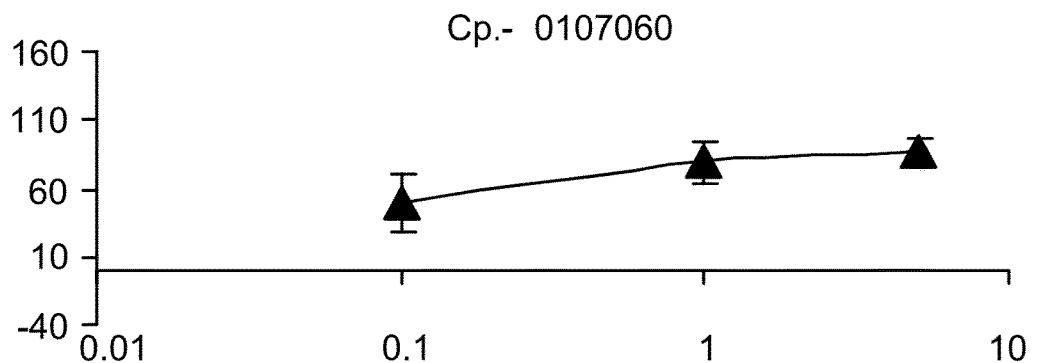
Figure 93:
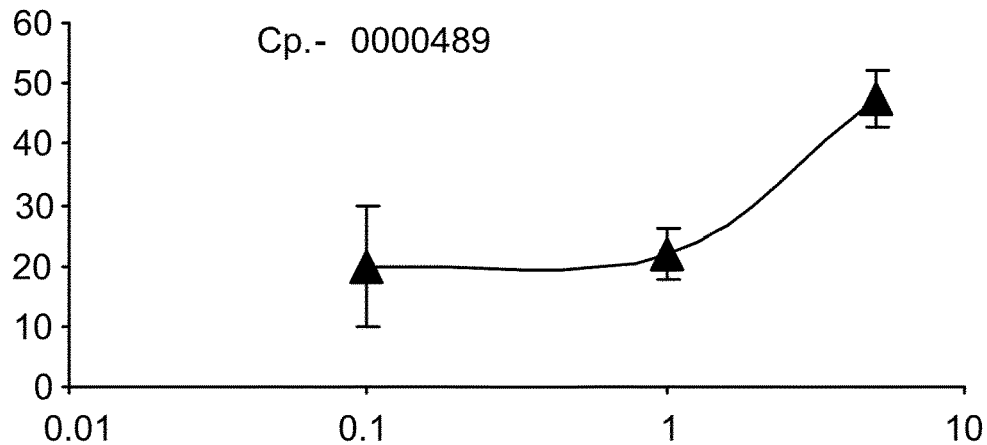
Figure 94:
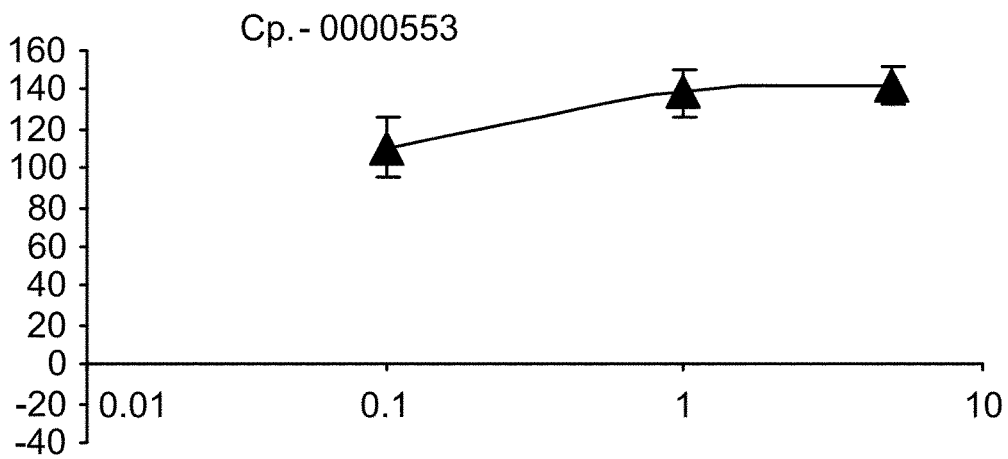
Figure 95:
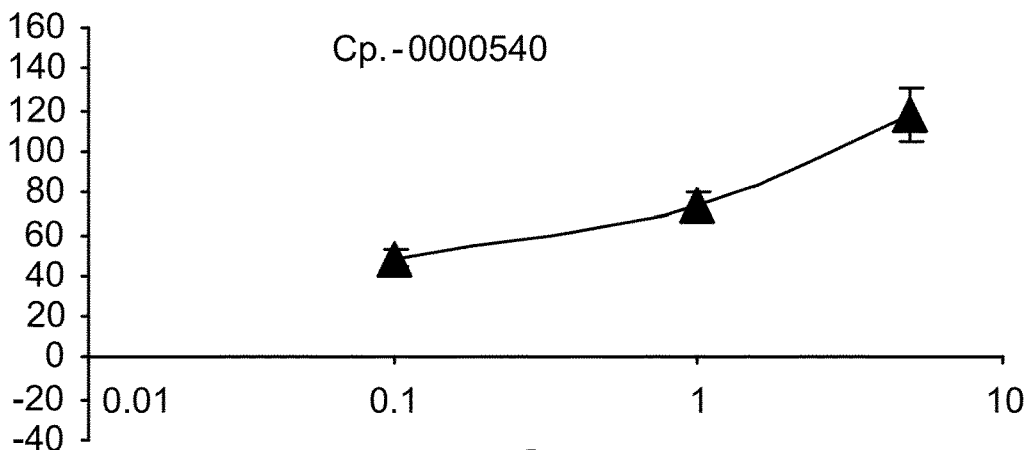
Figure 96:
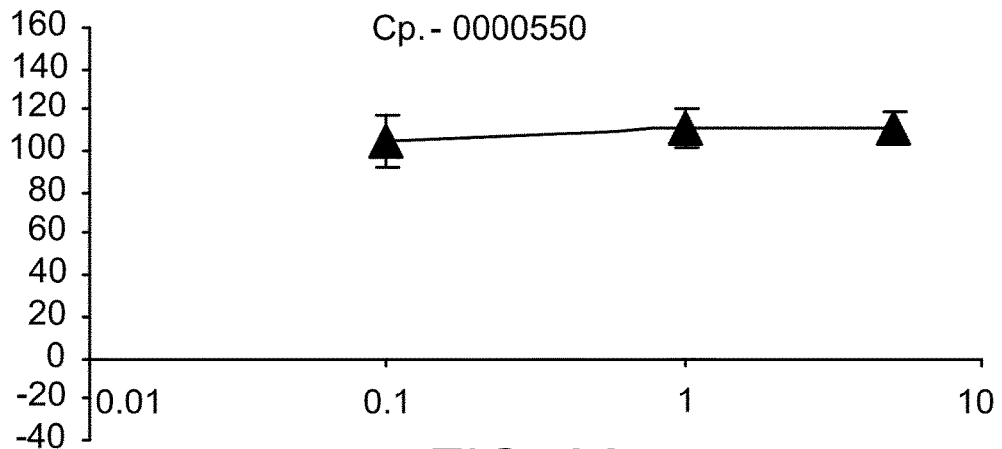
Figure 97:
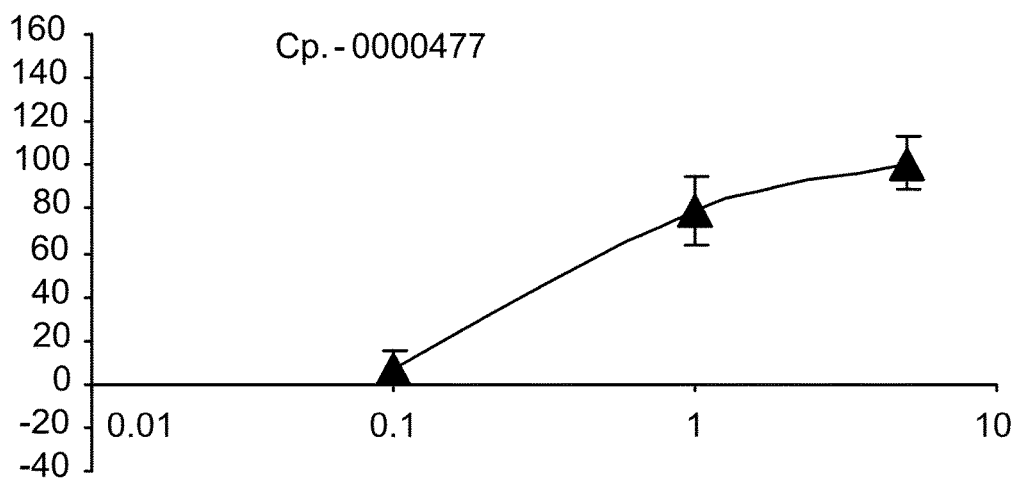
Figure 98:
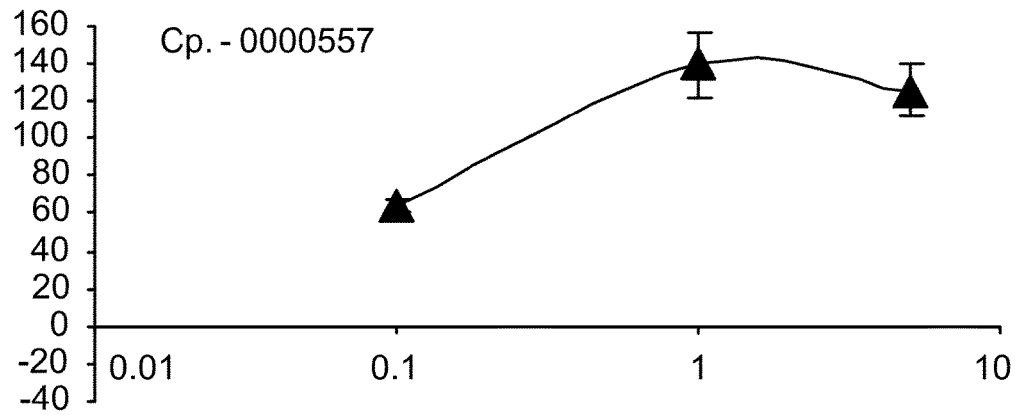
Figure 99:
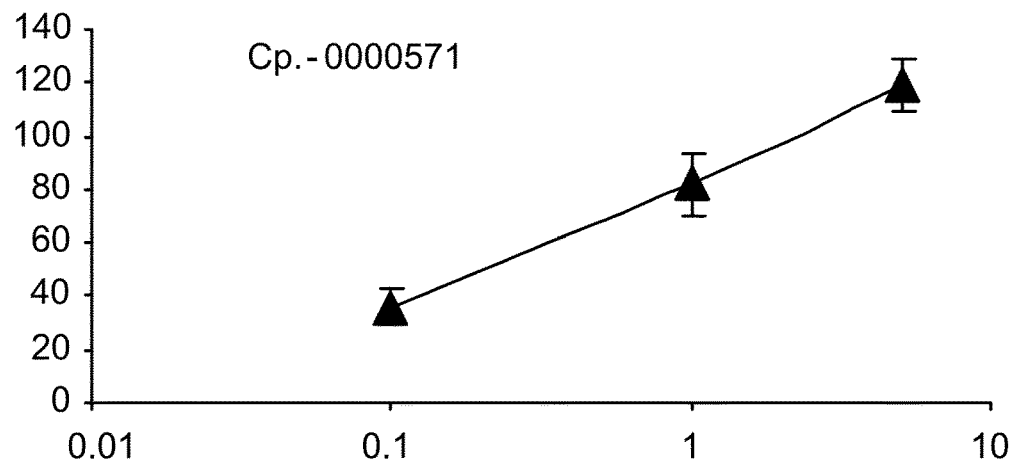
Figure 100:
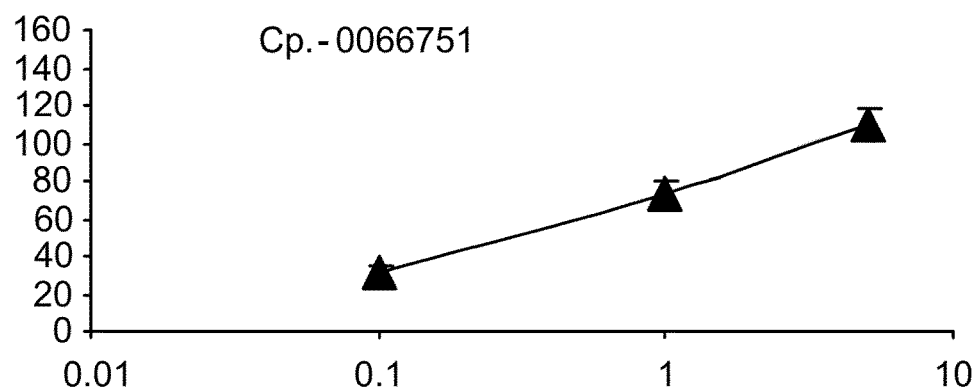
Figure 101:
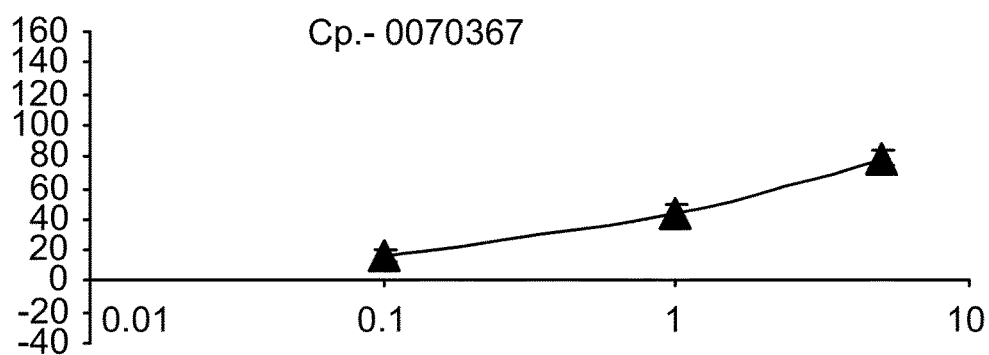
Figure 102:
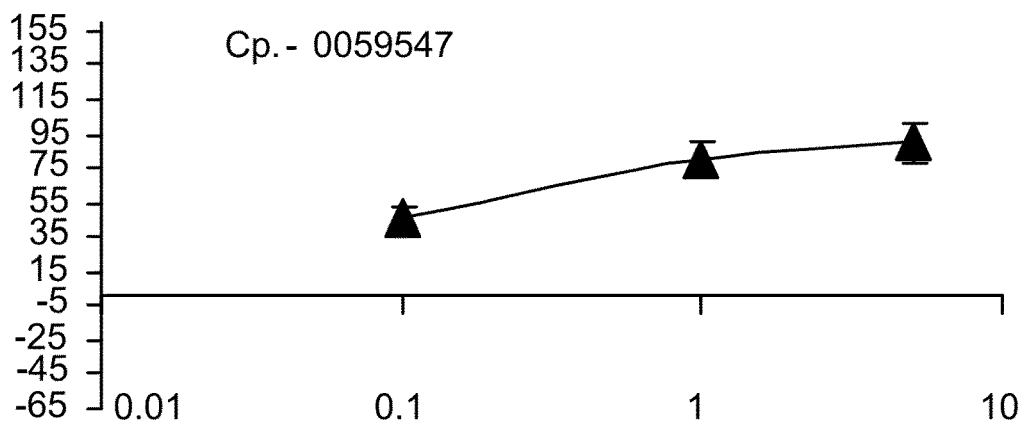
Figure 103:
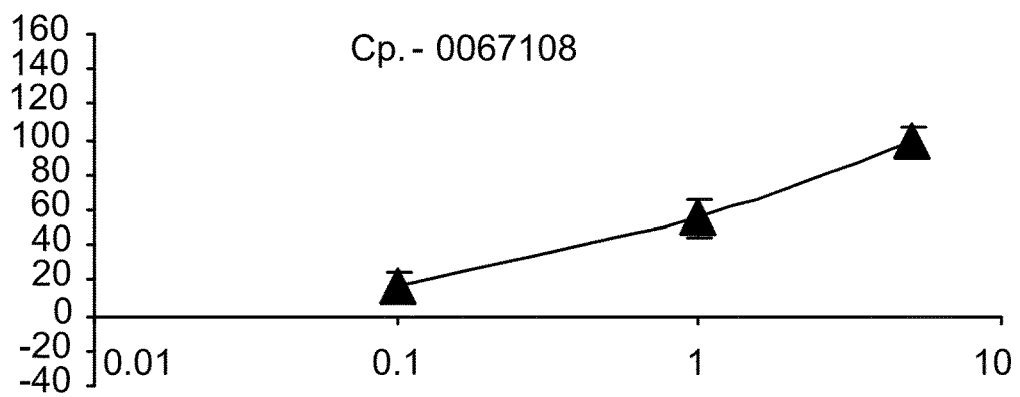
Figure 104:
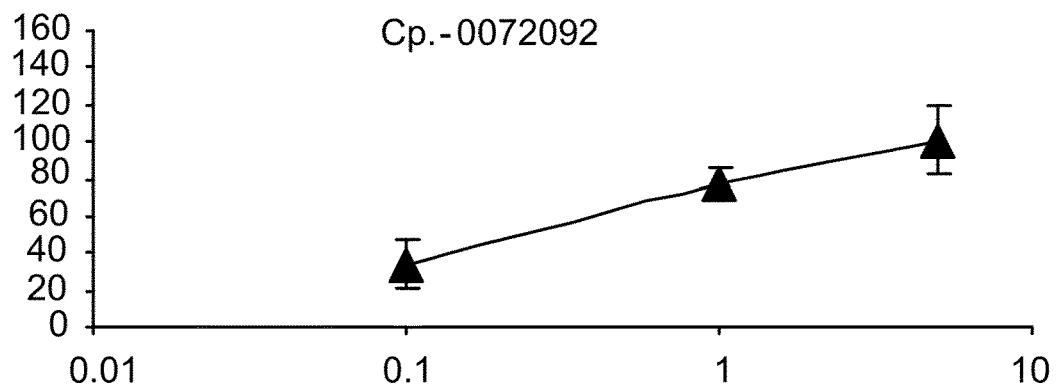
Figure 105:
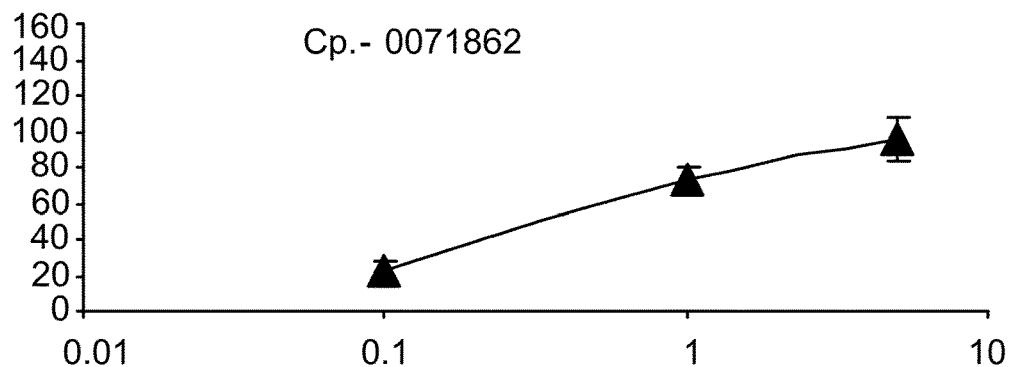
Figure 106:
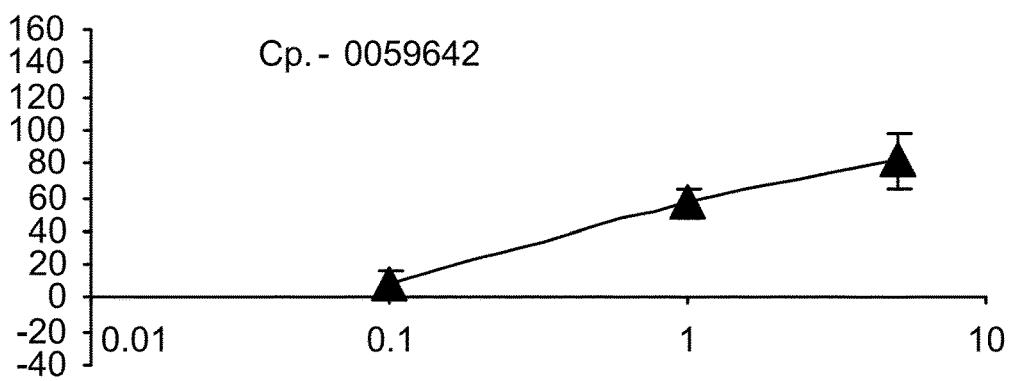
Figure 107:
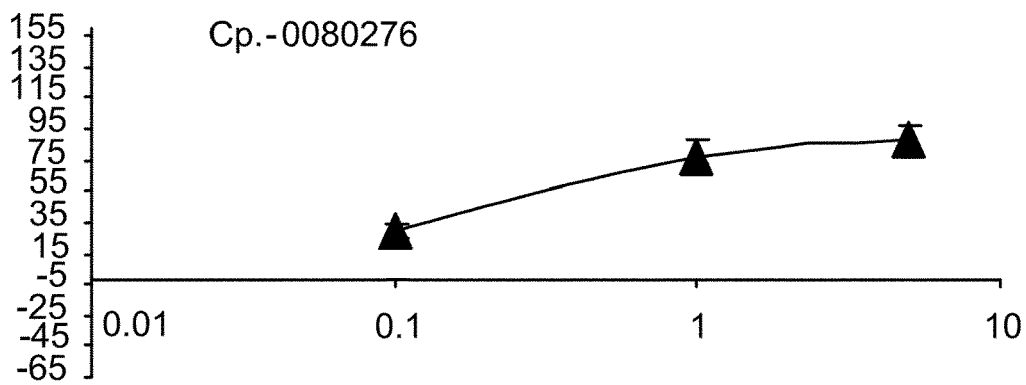
Figure 108:
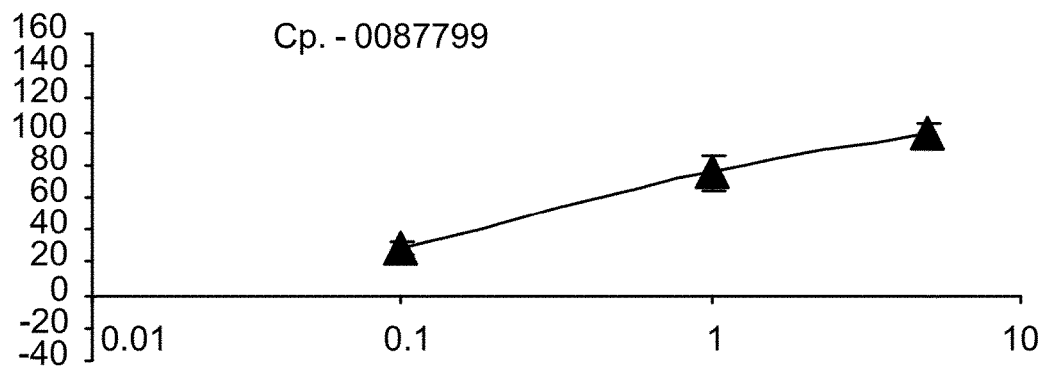
Figure 109:
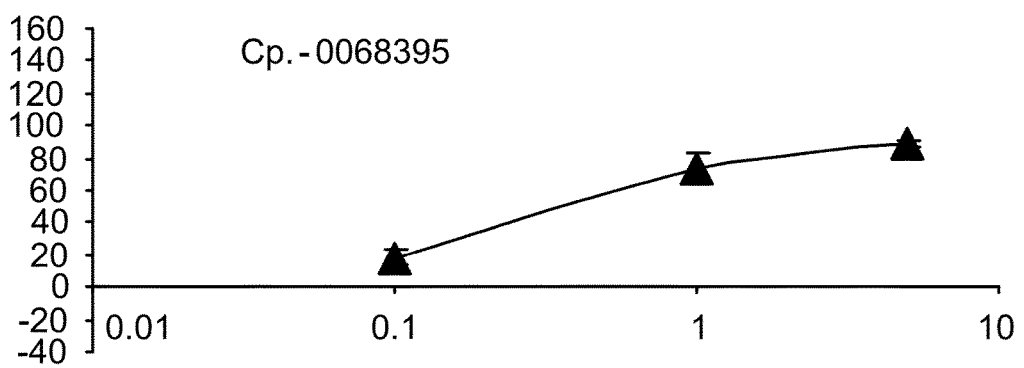
Figure 110:
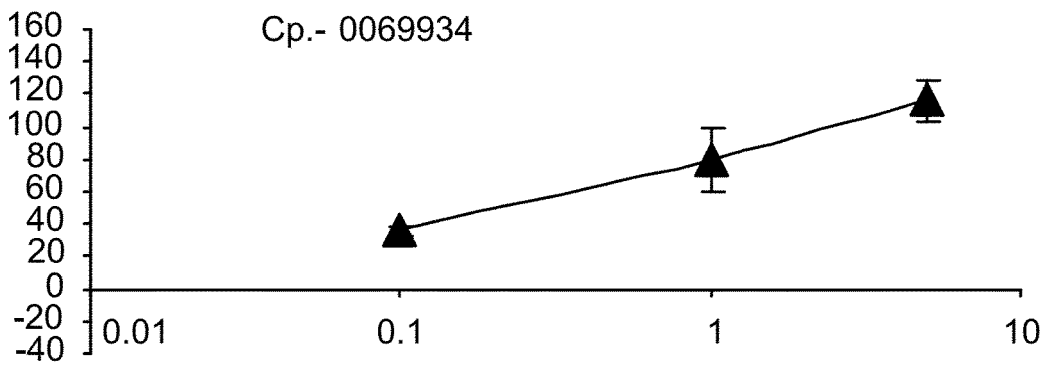
Figure 111:
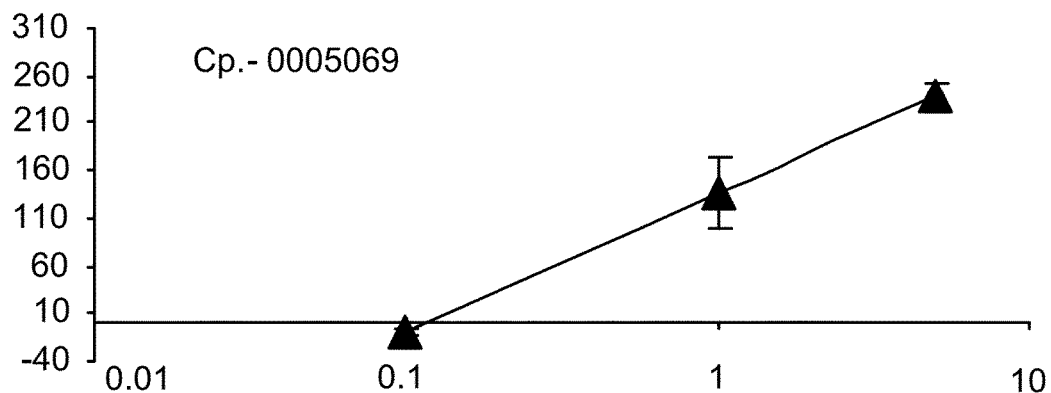
Figure 112:
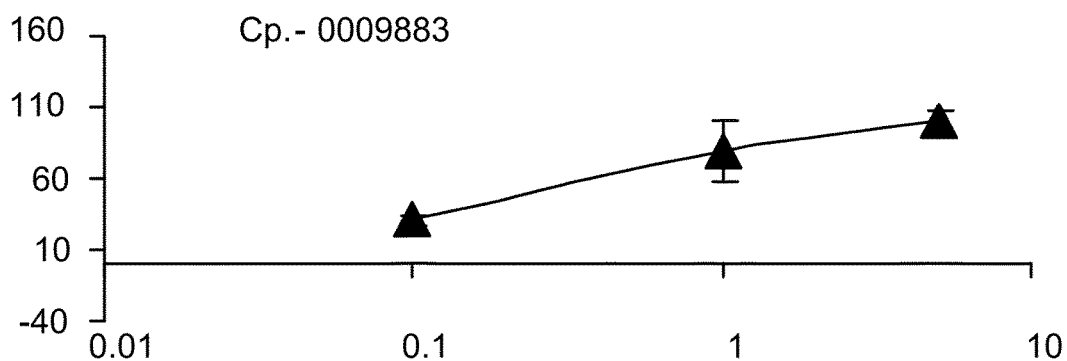
Figure 113:
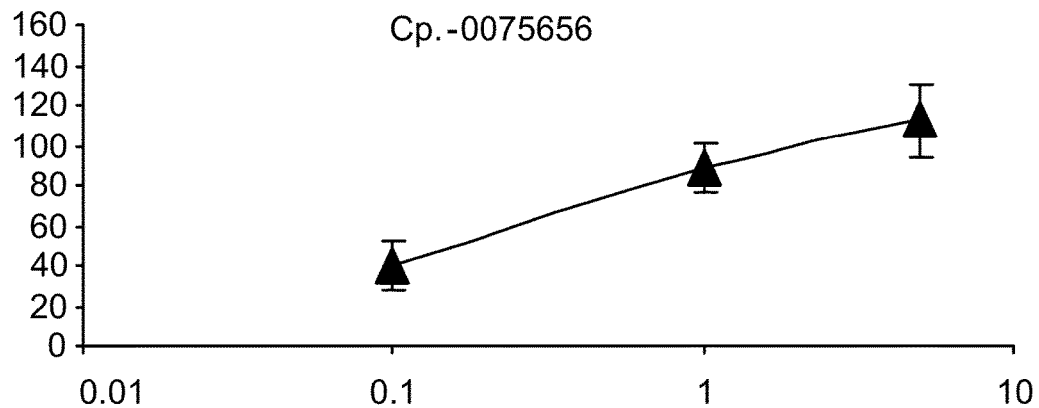
Figure 114:
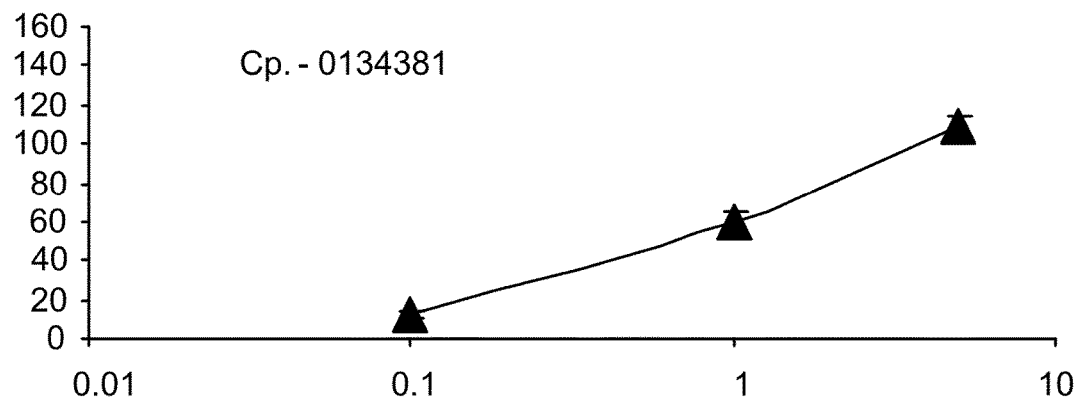
Figure 115:
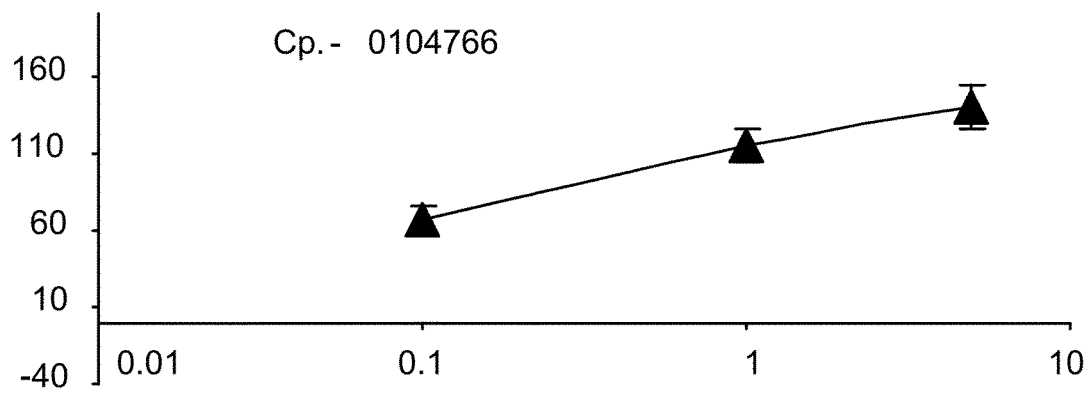
Figure 117A:
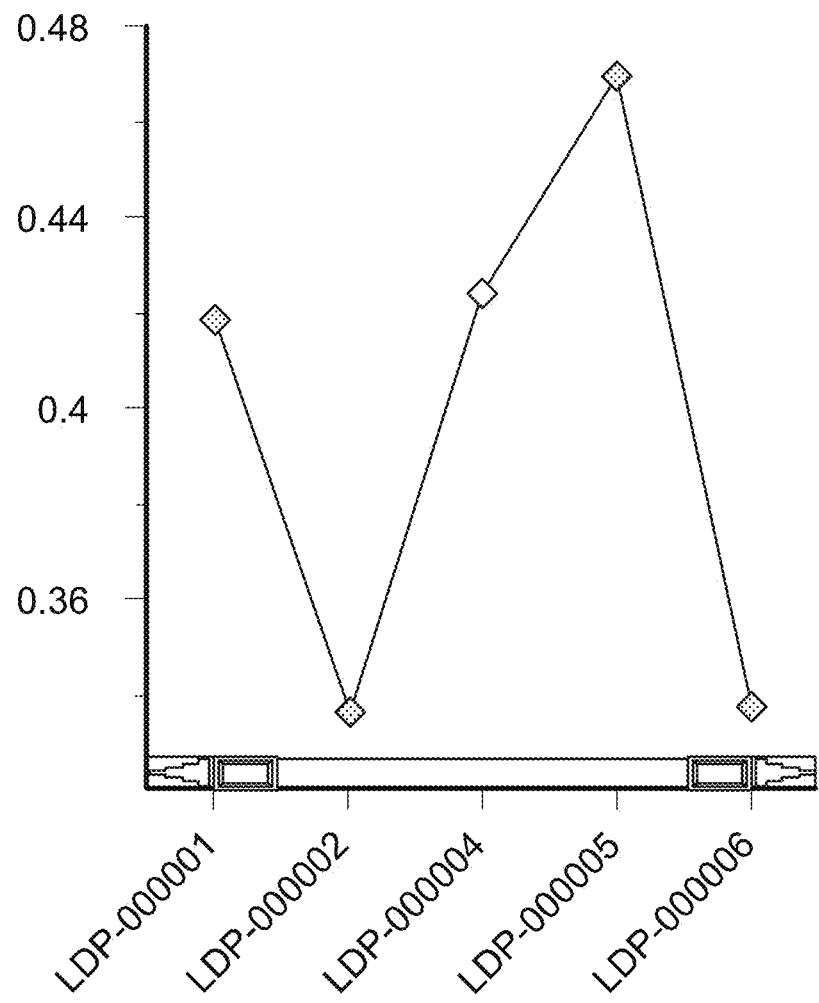
FIGS. 117A and 117B are graphs showing the results of experiments performed to optimize the high throughput screen.
Figure 117B:
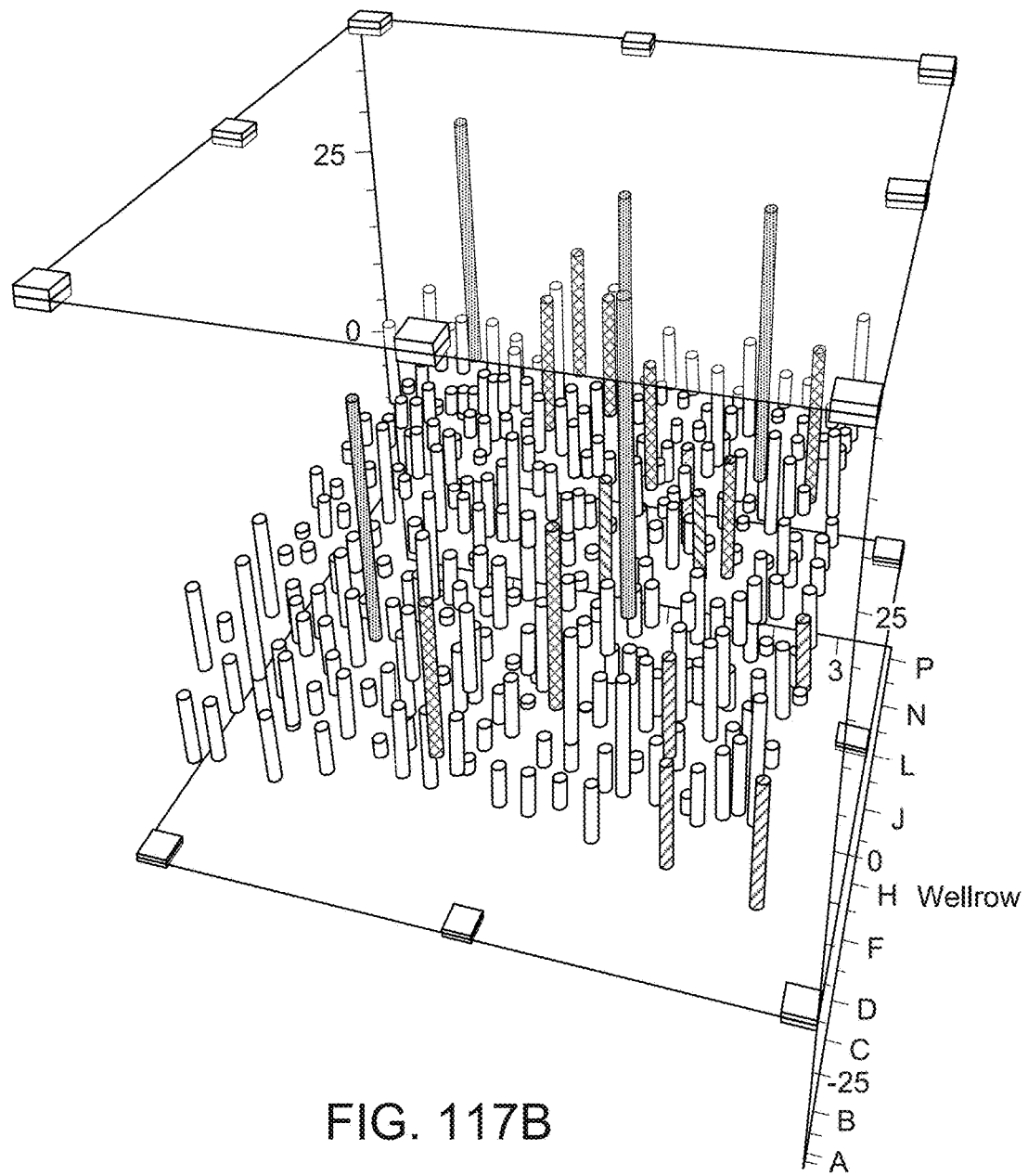

Initial screens were performed using duplicate plates to assay a library of over 10,000 compounds. As shown in FIG. 117B, 40 compounds were observed in to increase Math1 enhancer activity by at least 2-fold, compared to the Math1 expression level observed for DMSO (i.e., 40 compounds were positive). The Z factor for variation among wells with positive control are shown in FIG. 117A. The Z factor is a statistical parameter for HTS that reflects the quality of the data for each assay plate based on the magnitude of the signal window between the positive and negative controls. The signal variability with the controls was then calculated (Zhang et al., *J. Biomol. Screen.* 4:67-73, 1999). Any plate with a Z factor of less than 0.4 were repeated.

Figure 118A:
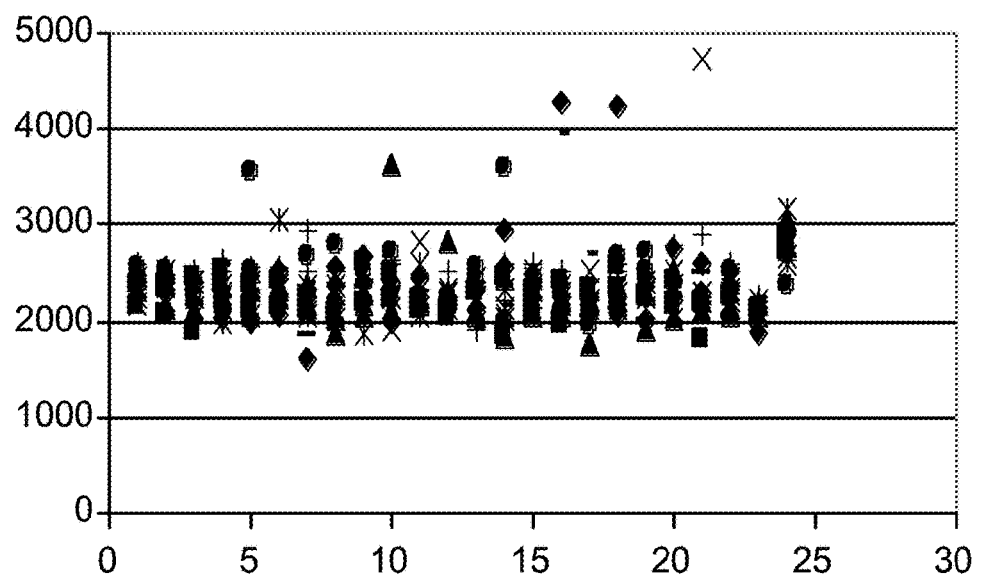
FIGS. 118A and 118B are dot plots showing the a duplicate experiment performed to optimize the high throughput screen.
Figure 118B:
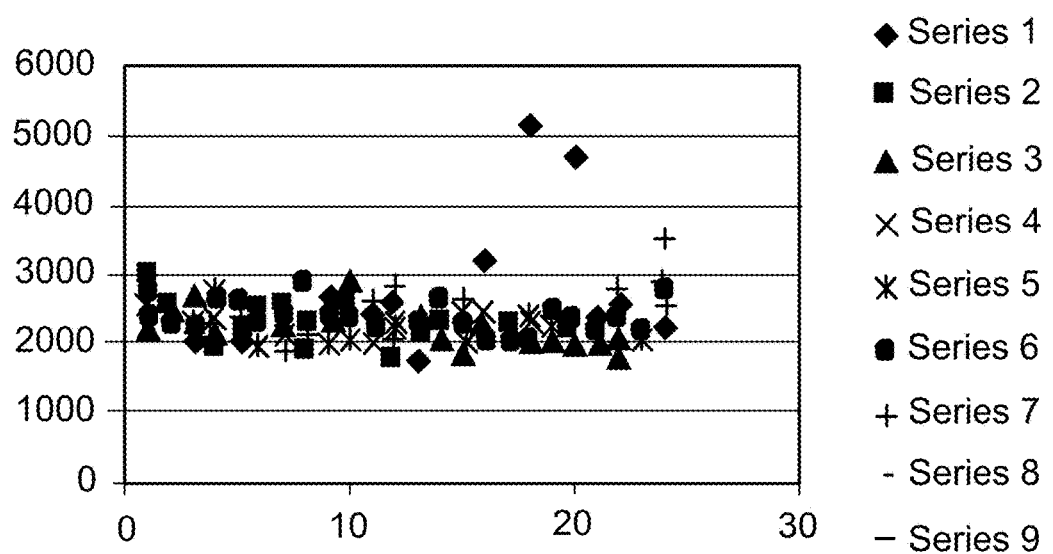

As shown in FIG. 118A and FIG. 118B, similar results were observed in repeat duplicate experiments. This result the reliability and reproducibility of the HTS methods.

Of the 144,000 compounds screened, 921 were found to promote an increase in Math1 Luciferase reporter expression of greater than 60%. The hit rate was 0.47%. The maximum activation observed was 160% (e.g., compared to DMSO).

Each of these compounds were then retested for dose-dependence of response at final assay concentrations of 0.1, 1, and 5 µM. Among the 921 positive compounds identified, 789 compounds evoked a increasing does response at 0.1, 1, and 10 µM concentrations. This observation supports the specificity of the hits. In total, of the 921 compounds tested, 82% reproducibly activated the Math1 Luciferase reporter and 29% showed some toxicity.

Following these experiments, the compounds were re-evaluated and those with good physical chemical properties (i.e., low molecular weight, lack of reactive functional side groups or other undesirable molecular motifs) that exhibited potent activation of Math1-luciferase and no toxicity were further investigated.

Figure 9:
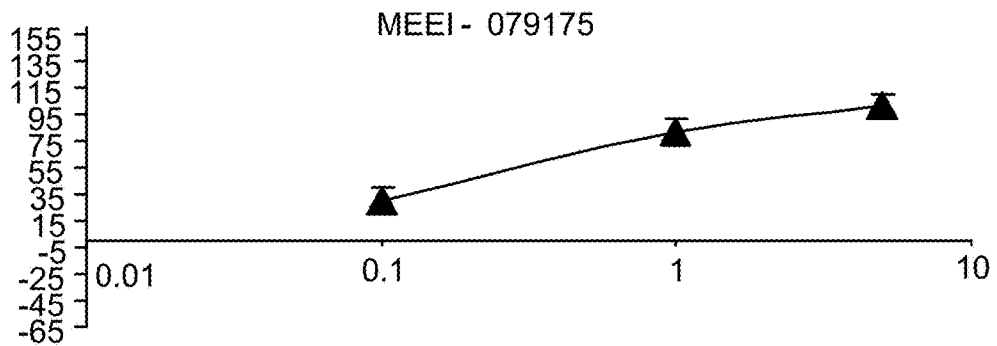
FIGS. 9-116 are line graphs showing Math1 expression in HEK cells with a stably expressed Luciferase gene controlled by a Math1 enhancer and minimal promoter (see Example 1). The compound numbers indicated in the graphs correspond to the compound structures presented in FIG. 1 to FIG. 8. Math1 activation was measured using the high throughput screening methods described in Example 1 and Example 2.
Figure 10:
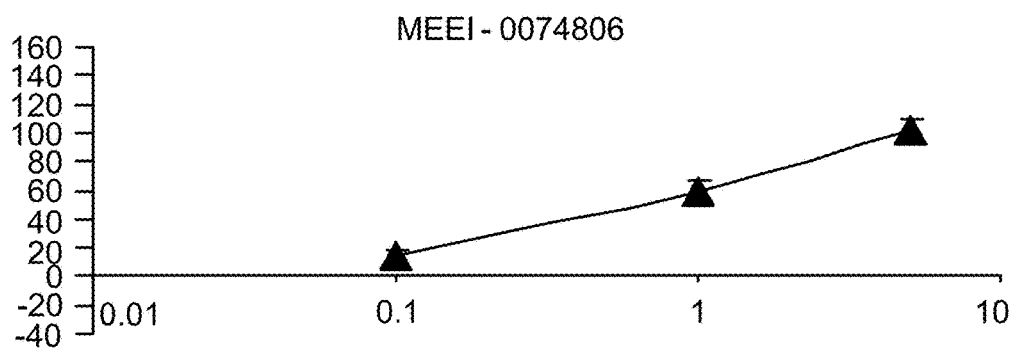
Figure 11:
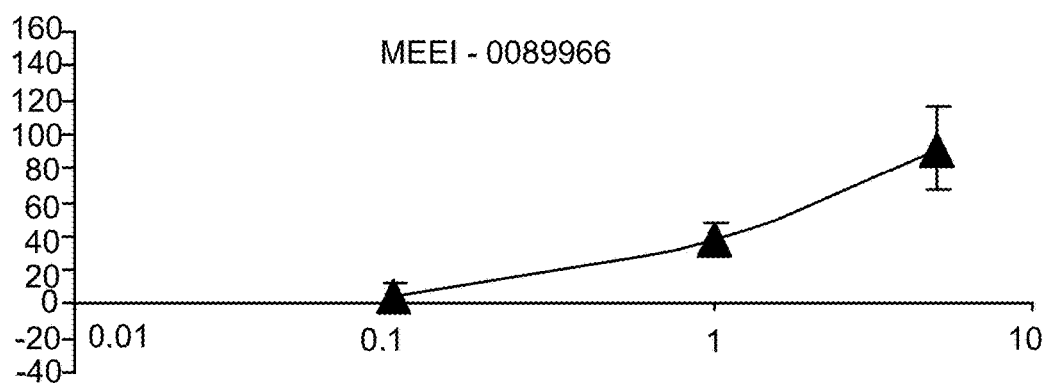
Figure 12:
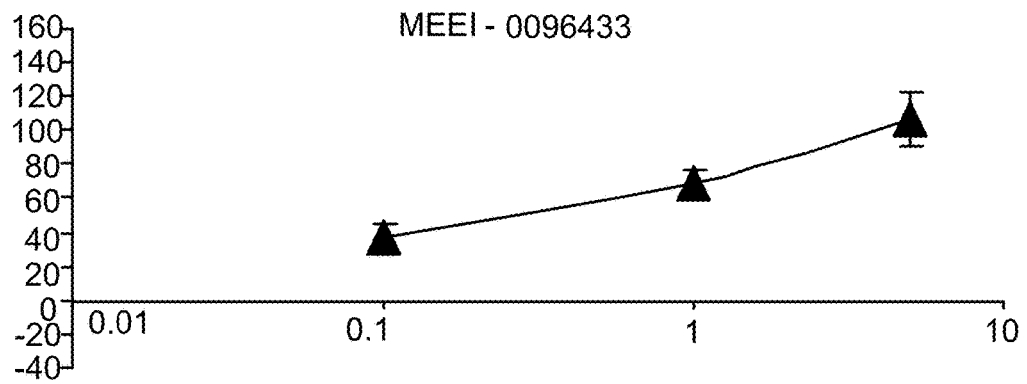
Figure 13:
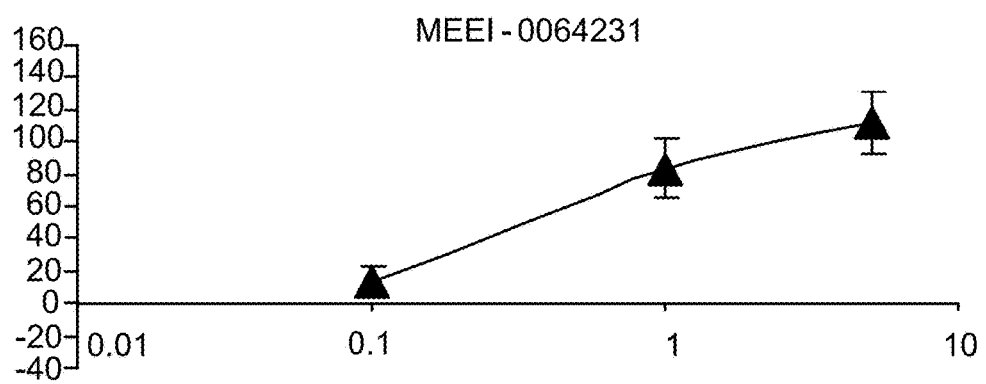
Figure 14:
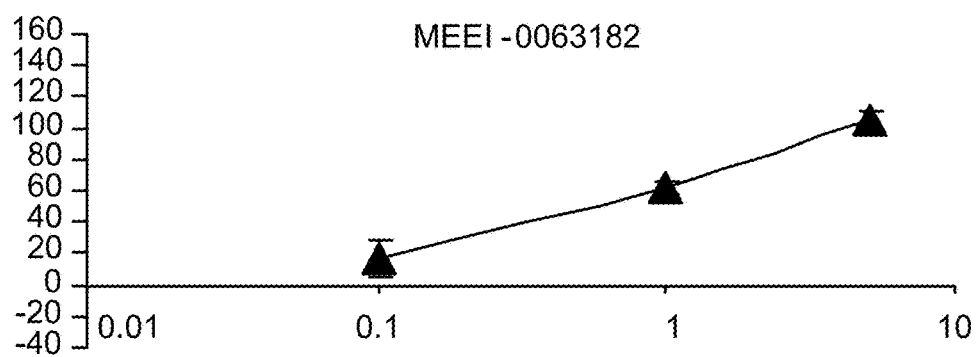
Figure 15:
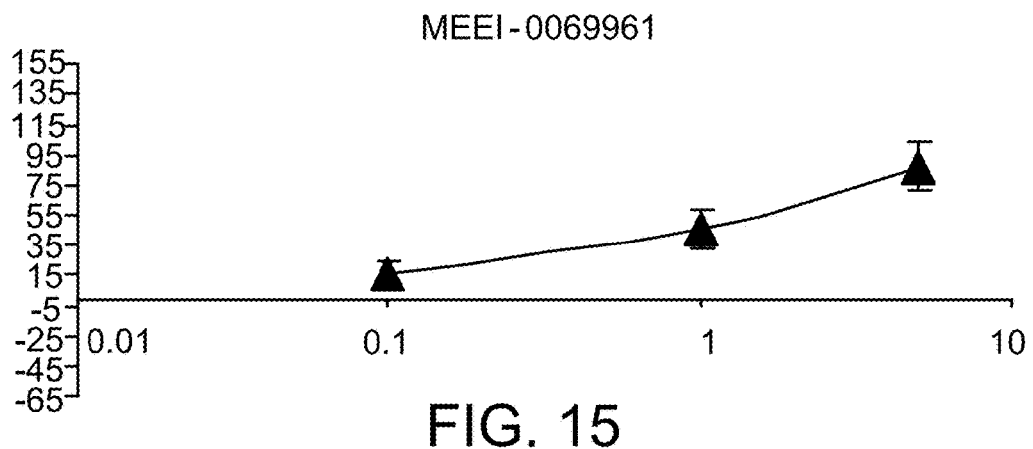
Figure 16:
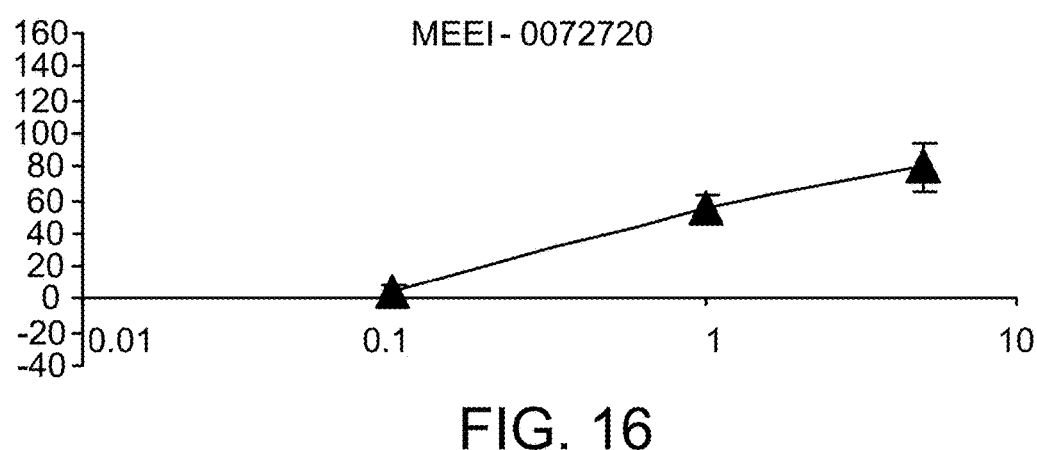
Figure 17:
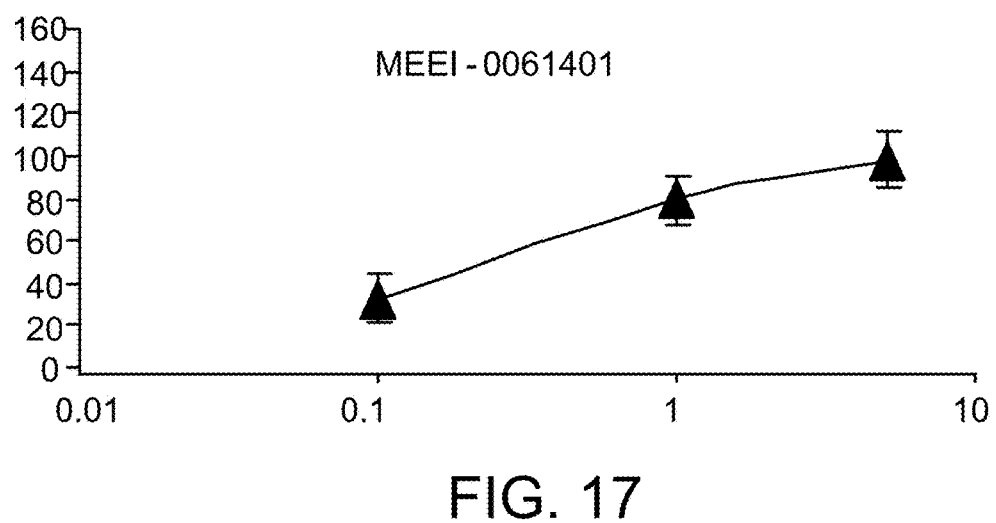
Figure 18:
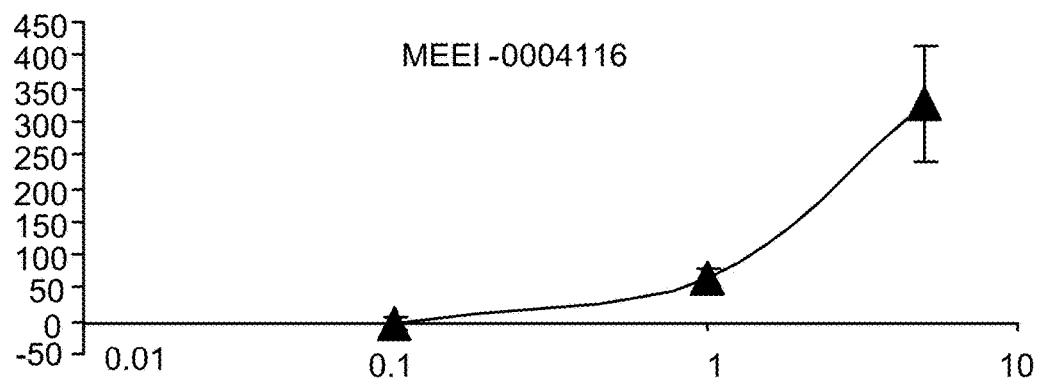
Figure 19:
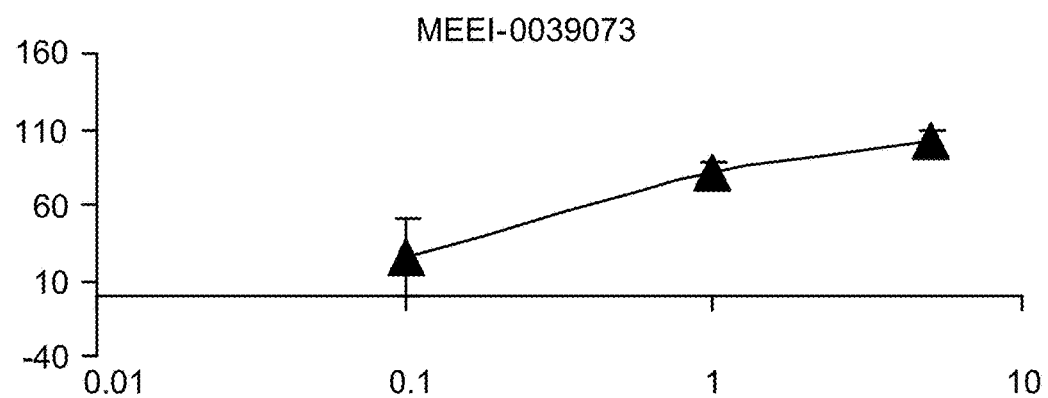
Figure 20:
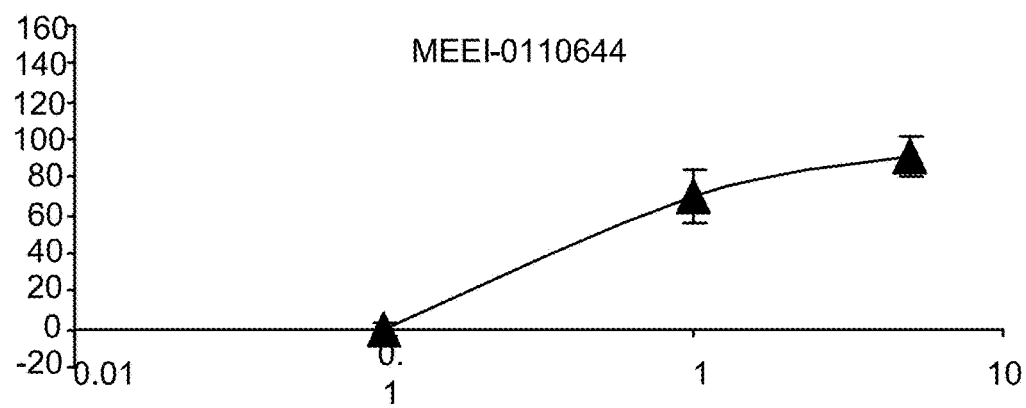
Figure 21:
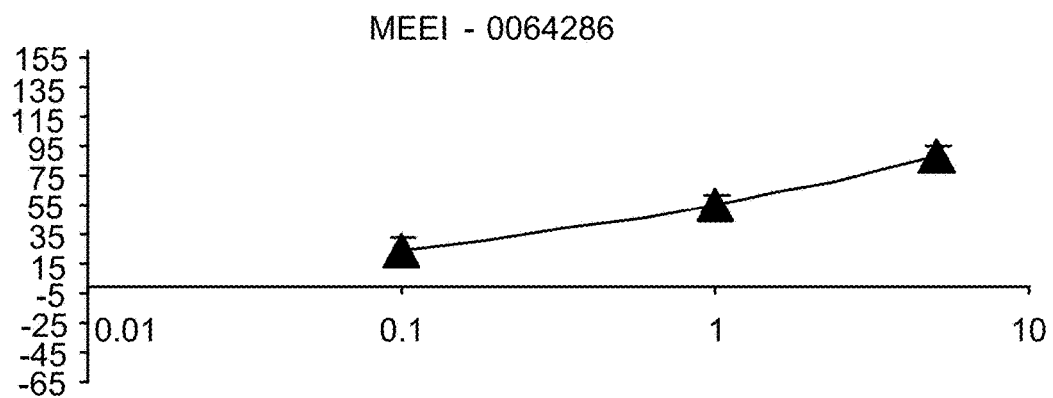
Figure 22:
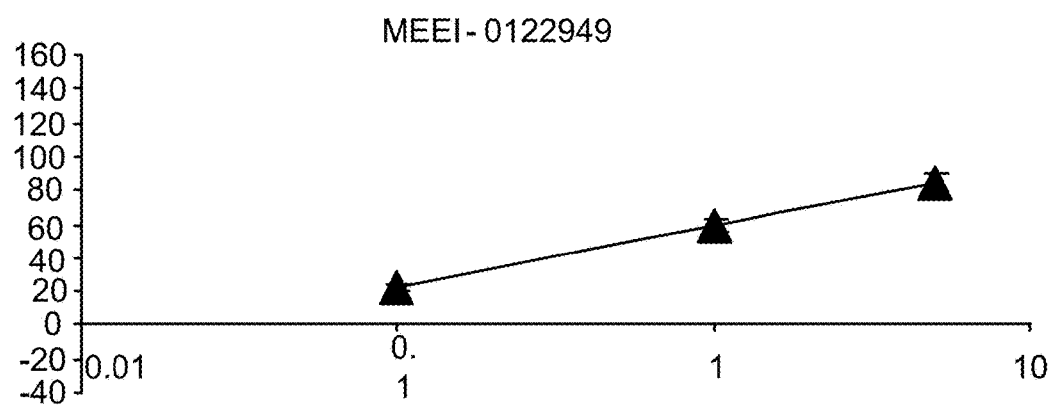
Figure 23:
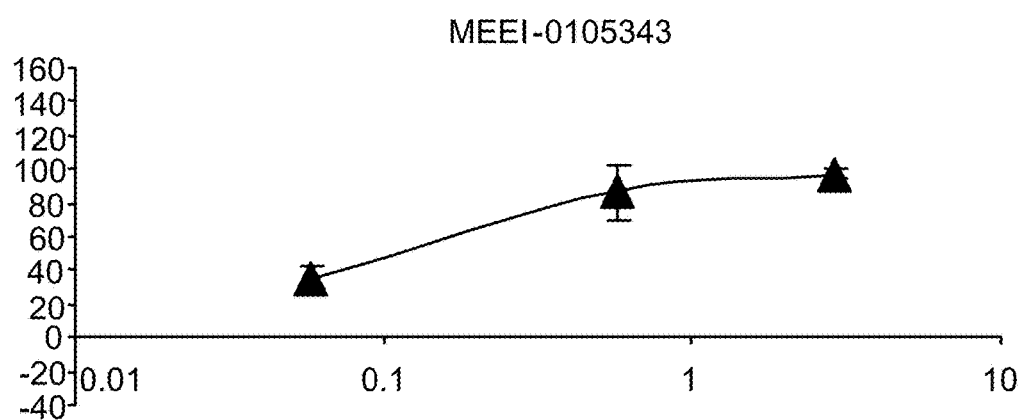
Figure 24:
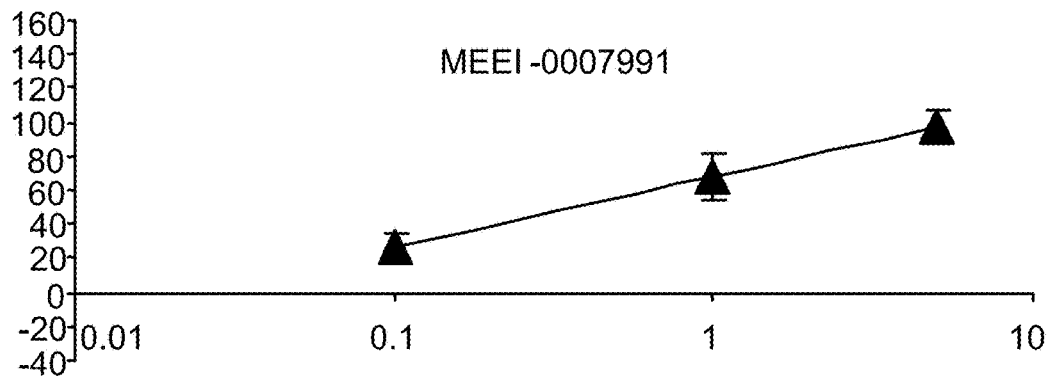
Figure 25:
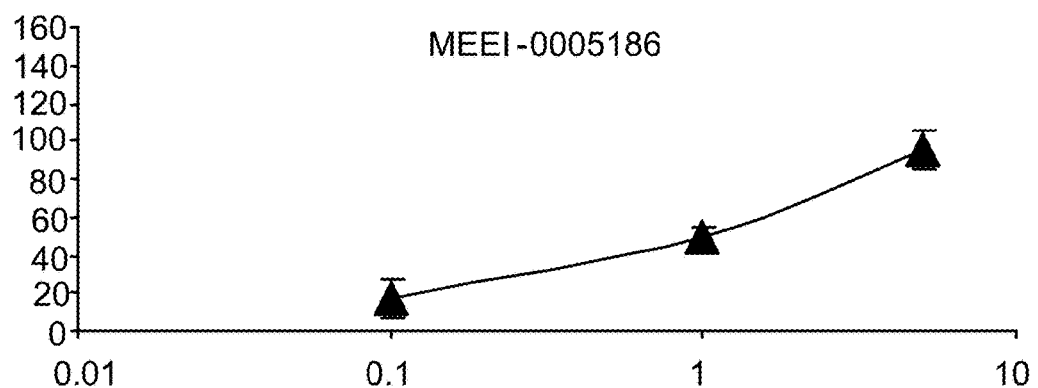
Figure 26:
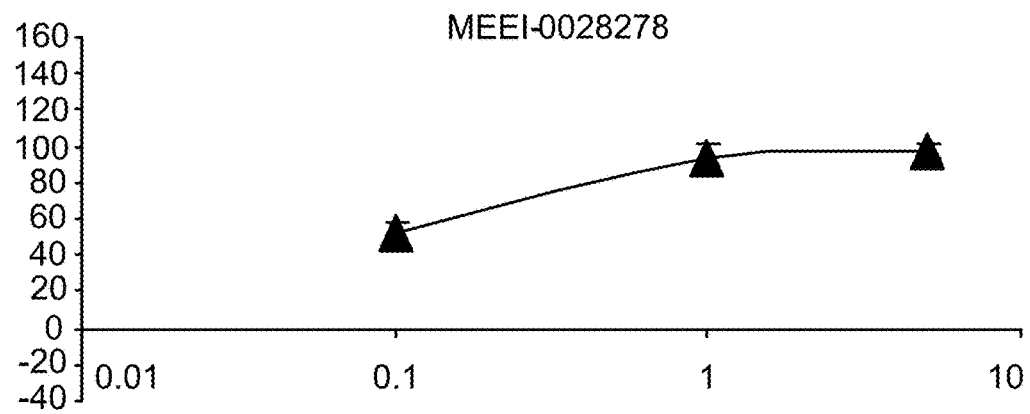
Figure 27:
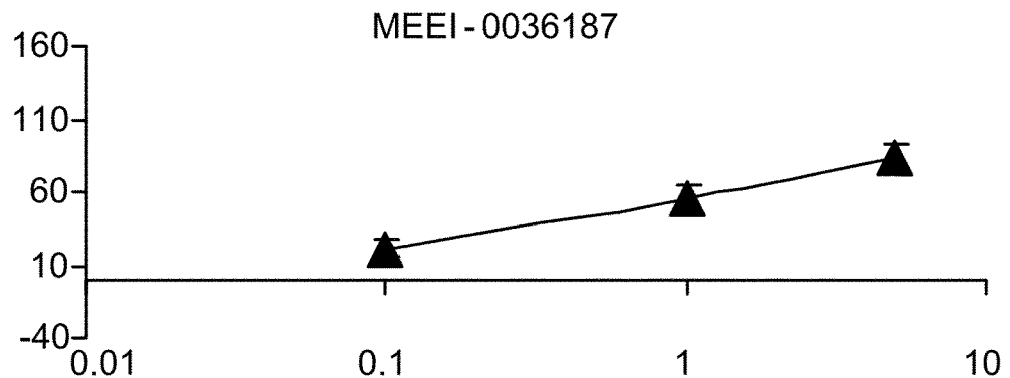
Figure 28:
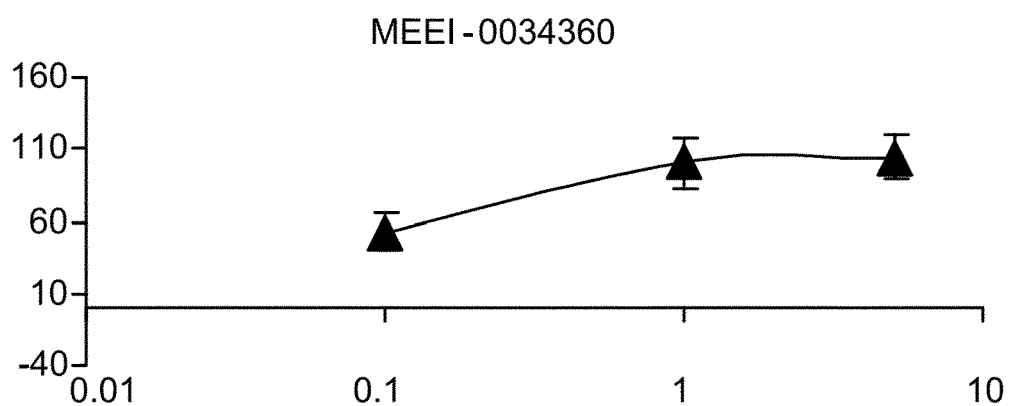
Figure 29:
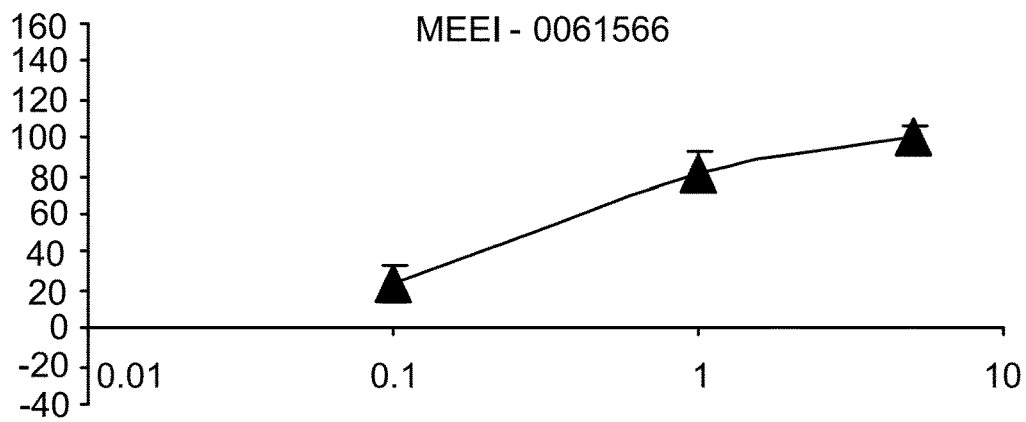
Figure 30:
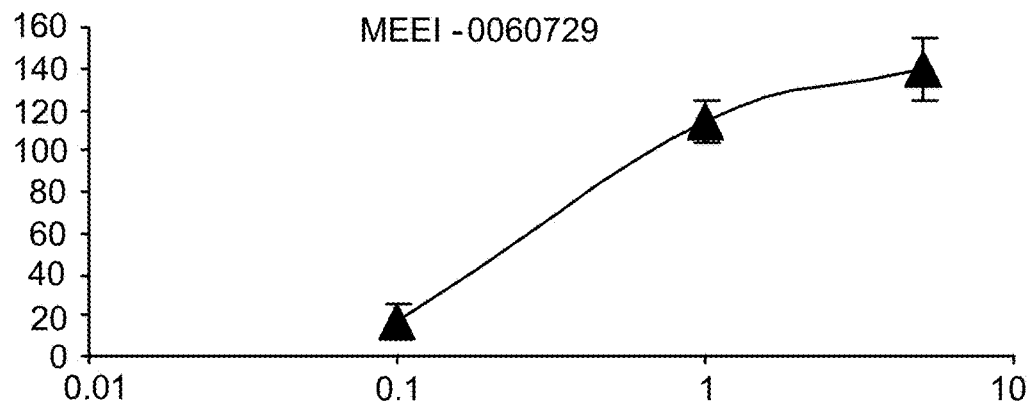
Figure 31:
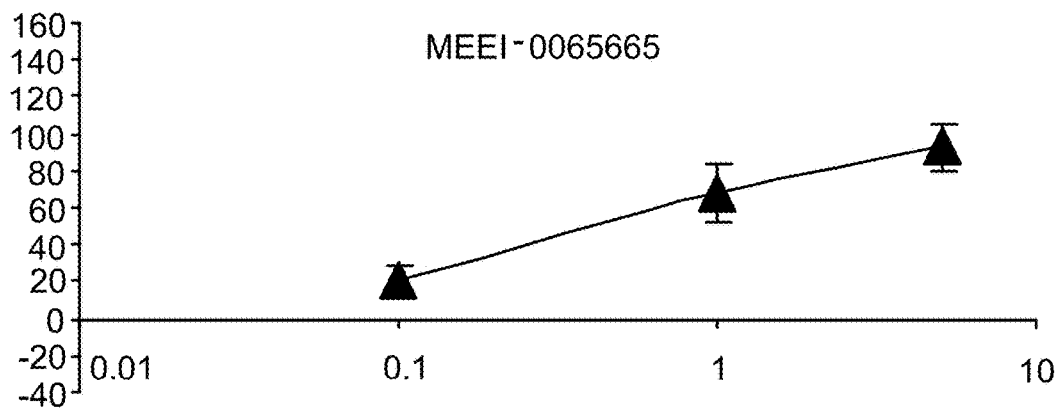
Figure 32:
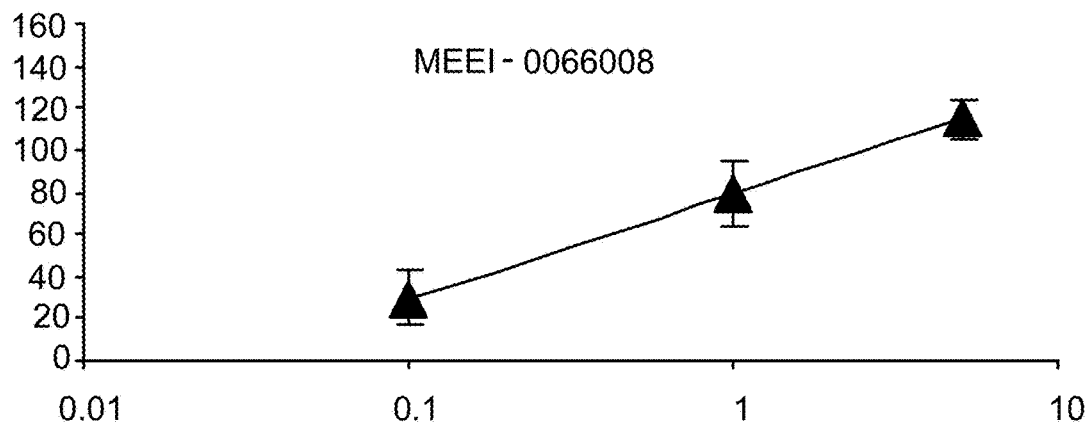
Figure 33:
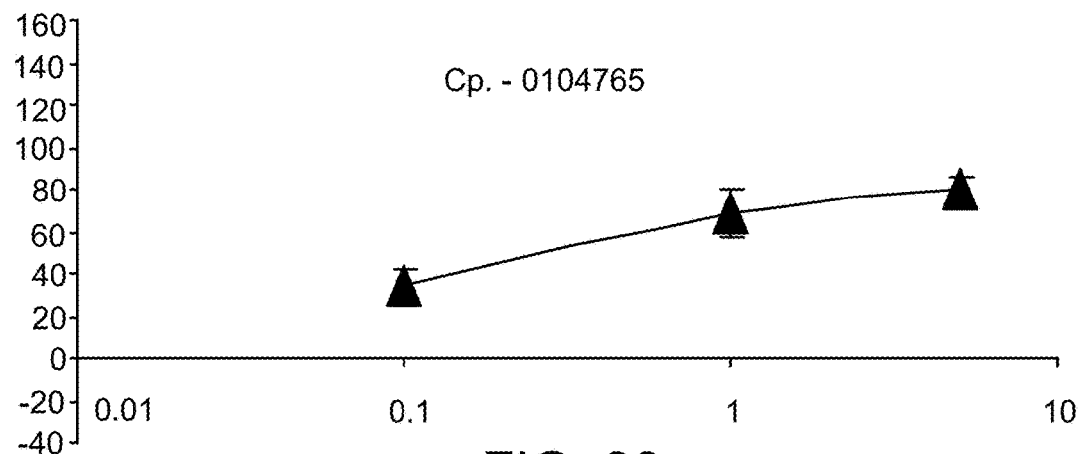
Figure 34:
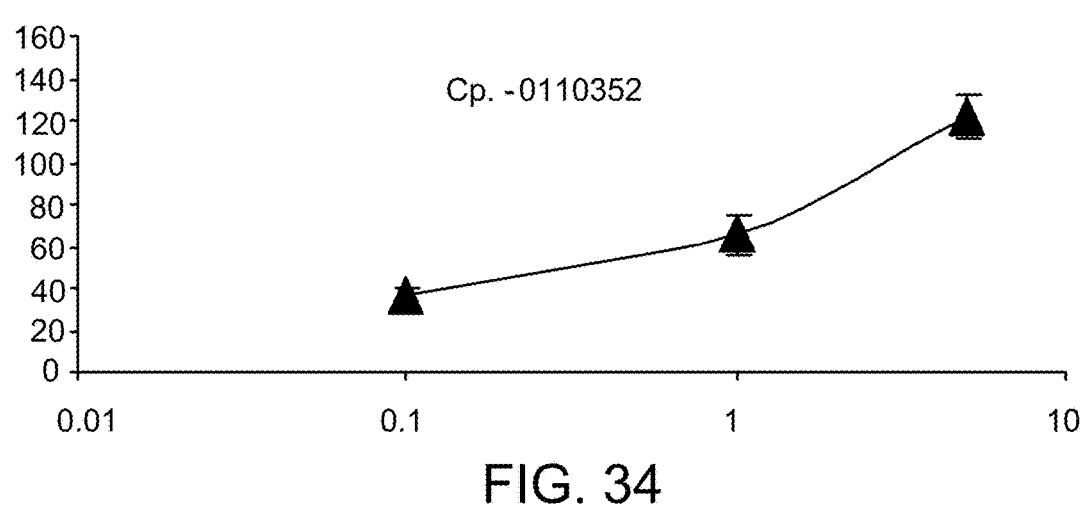
Figure 35:
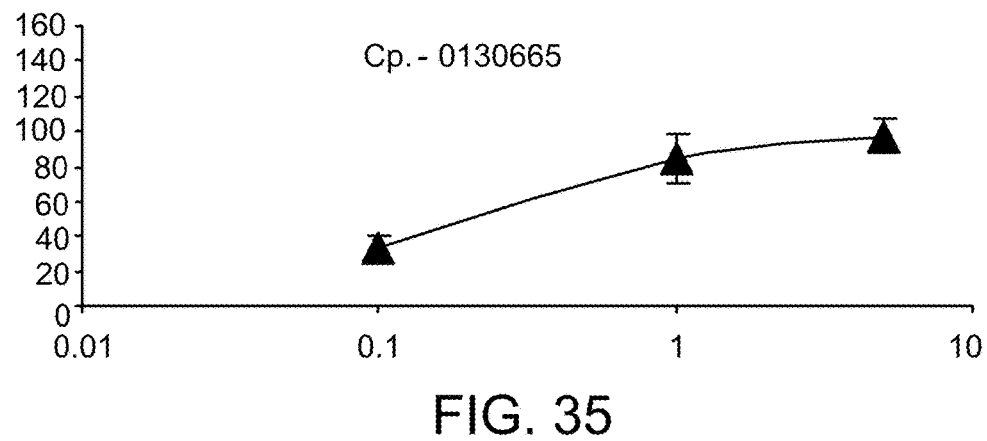
Figure 36:
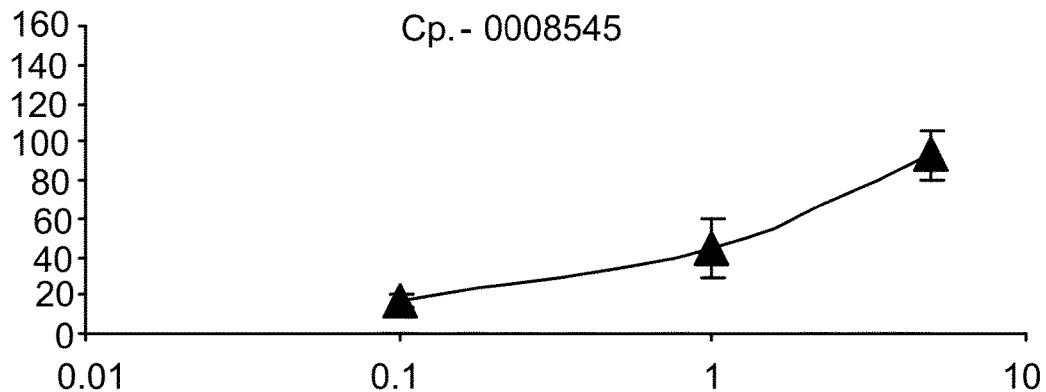
Figure 37:
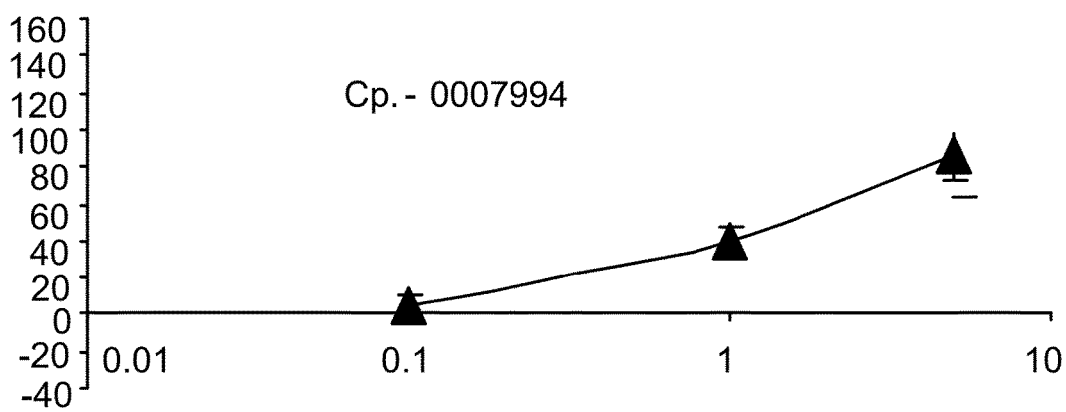
Figure 38:
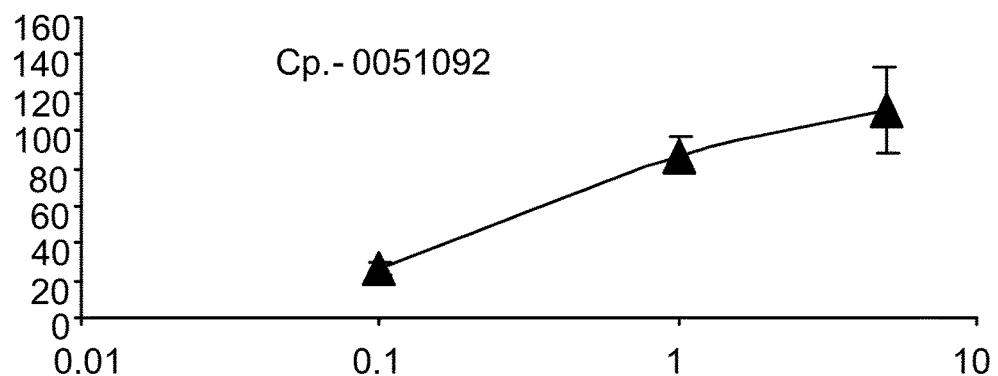
Figure 39:
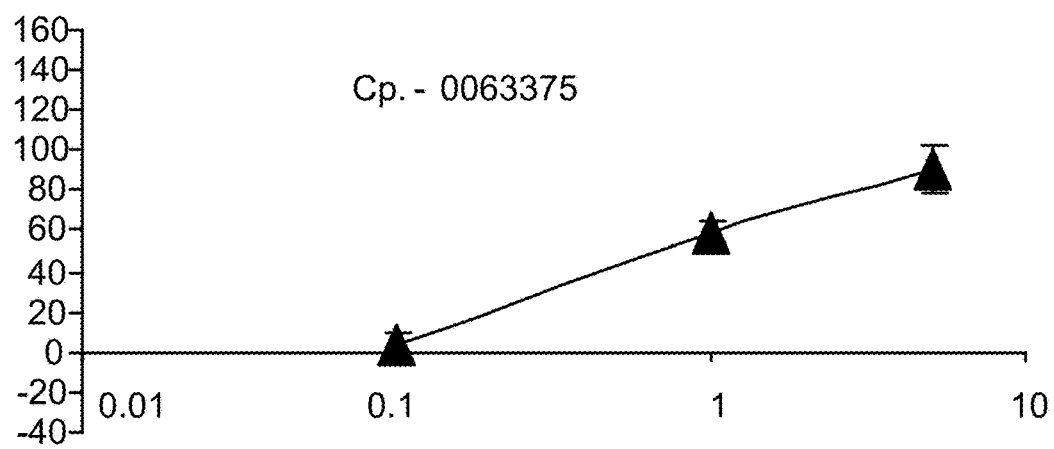
Figure 116:
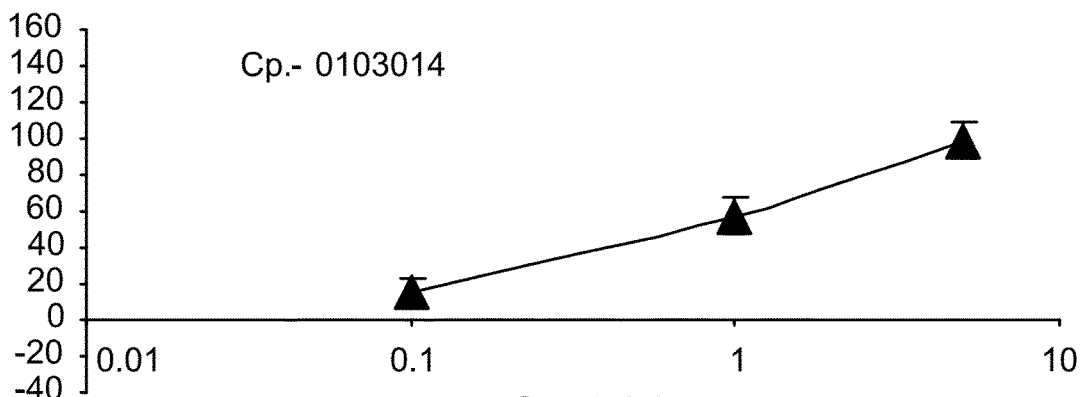

The total number of compounds selected for further evaluation is 110 compounds. The structures of these compounds are shown in FIG. 1 to FIG. 8. The increase in Math1 expression promoted by these compounds is shown in FIGS. 9-116.

Example 3

Evaluation of Positive Compounds by RT-PCR

Ten compounds, randomly selected from the group of 110 compounds identified in Example 2, were further evaluated, as follows. HEK cells were plated on 96 well plates at a density of 100000 cells per well. One day after plating, 0.1, 1, and 5 µM of each positive compound was added per well in a 10% fetal bovine serum (FBS) DMEM solution. Cells were then lysed 48 hours after addition of the compound and Math1 expression was analyzed using a luciferase reporter assay, as described above, and real-time PCR.

Figure 119:
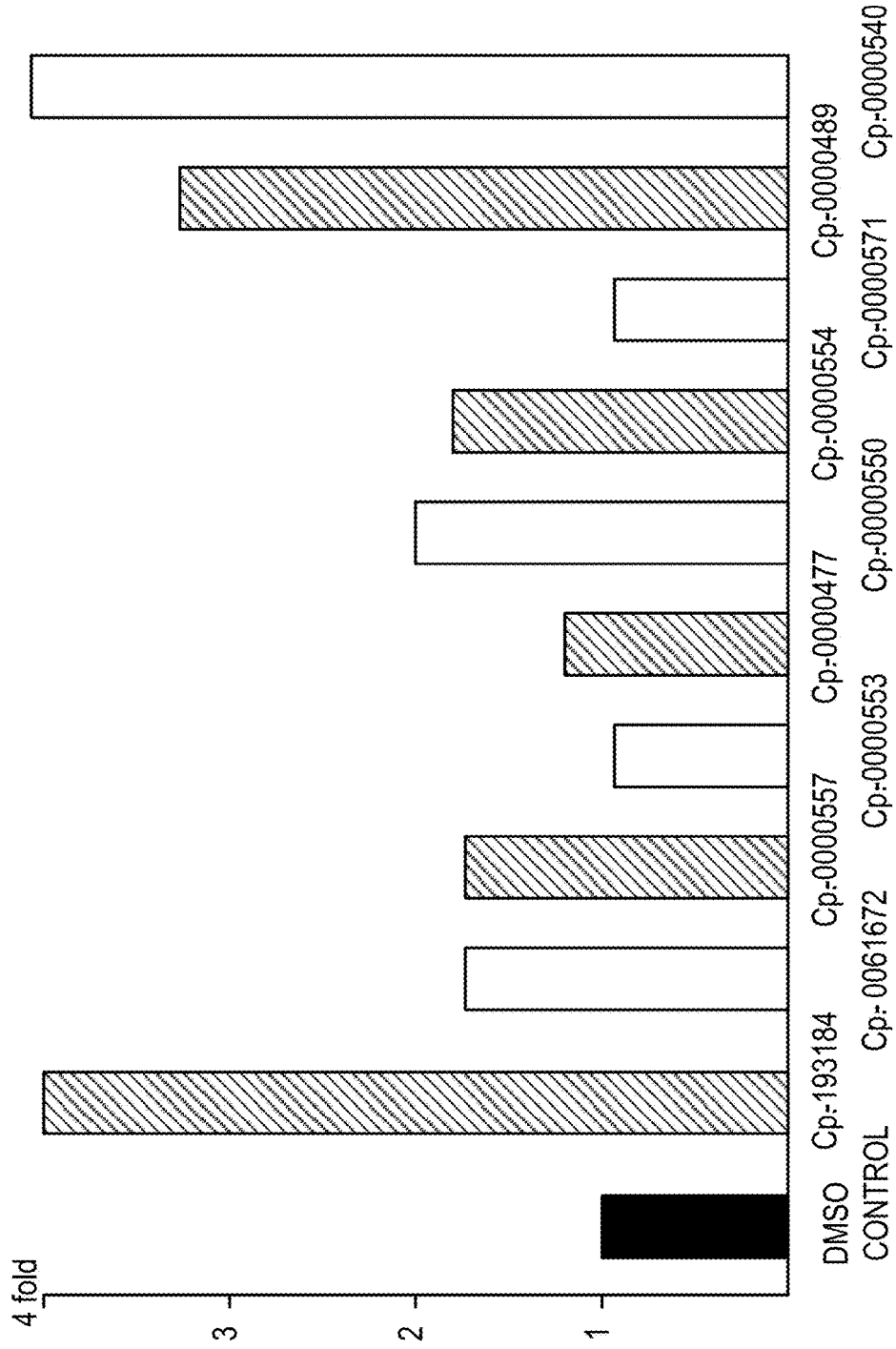
FIG. 119 is a bar graph showing Math1 activation, as assessed using the Math1 Luciferase reporter assay described in Example 1 and Example 2, in cells exposed to the indicated compounds. The structure of these compounds is presented in FIG. 1 to FIG. 8. Initial Atoh1 activation results for these compounds can be found in FIGS. 9-114.

As shown in FIG. 119, four of the ten randomly selected compounds promoted a greater than two fold increase in Math1 expression.

Figure 120A:
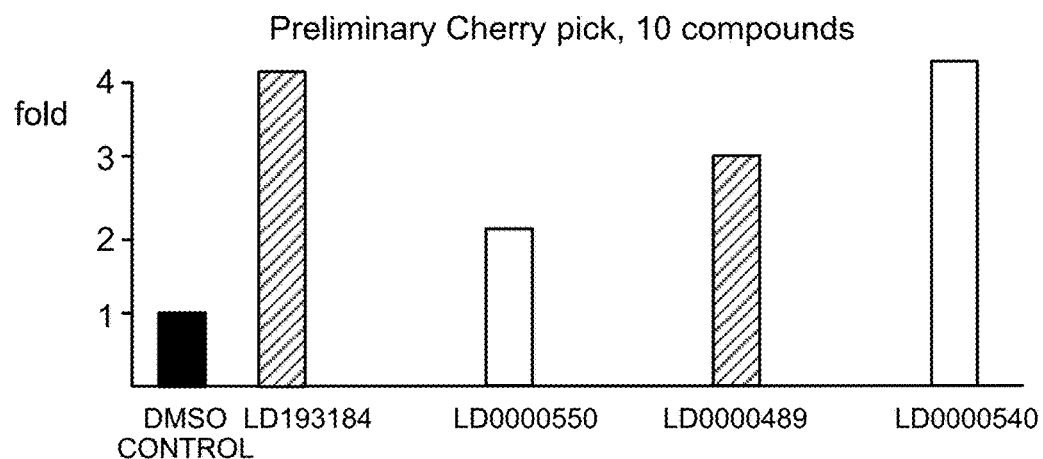
FIG. 120A is a bar graph showing Math1 activation, as assessed using the Math1 Luciferase reporter assay described in Example 1 and Example 2, in cells exposed to the indicated compounds. The structure of these compounds is presented in FIG. 1 to FIG. 8. Initial Math 1 activation results for these compounds can be found in FIGS. 9-114.

As shown in FIG. 120A, in agreement with the HTS, all four randomly selected compounds promoted a greater than 2 fold increase in Math1 expression as determined using the luciferase reporter assay.

Figure 120B:
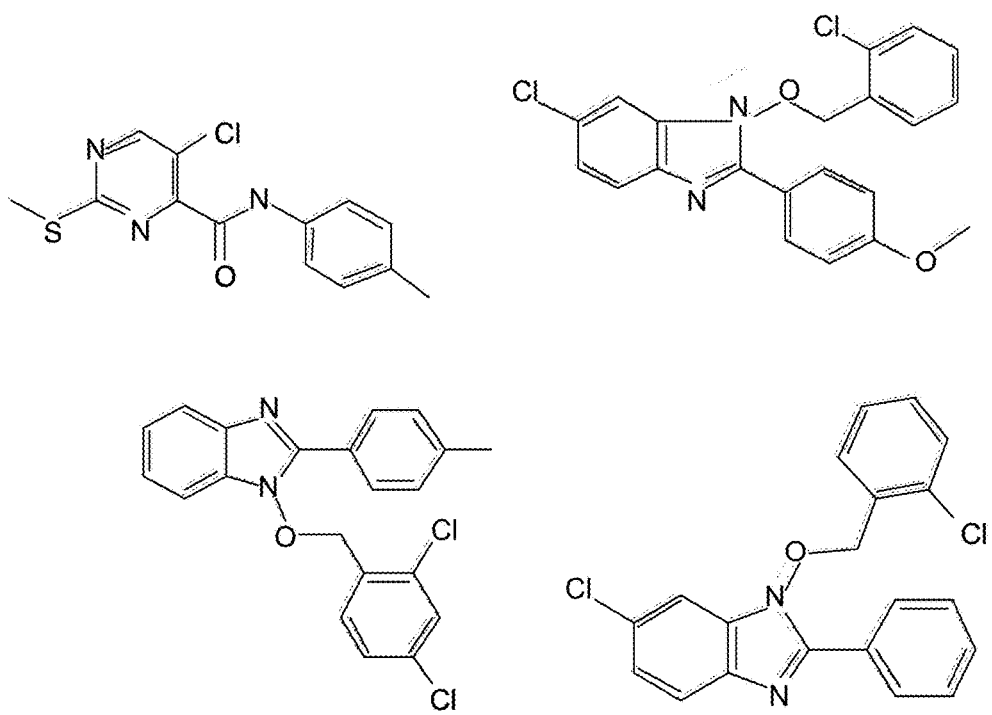
FIG. 120B shows the structures of the compounds indicated in FIG. 117A.
Figure 120C:
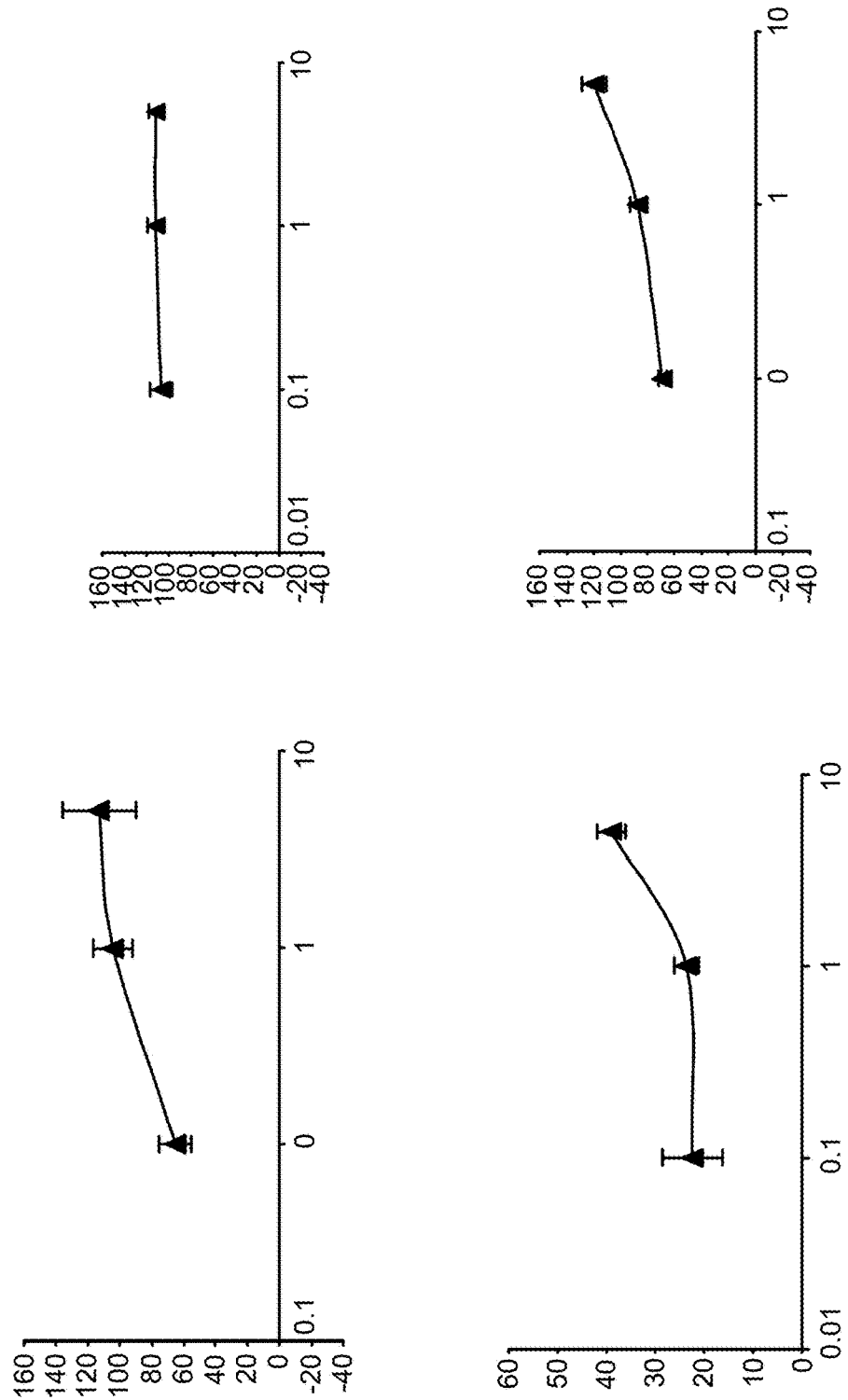
FIG. 120C shows Atoh1 mRNA expression in cells exposed to the indicated compounds.

RNA was also isolated and Math1 transcripts were amplified using high-throughput RT-PCR. As shown in FIG. 120C, all four randomly selected compounds promoted an increase in Math1 mRNA expression by at least 2-fold compared to the DMSO control. CP.-0193184 and CP.-0000540 promoted the highest increase in Math1 mRNA expression. FIG. 120B shows the structures of the four randomly selected samples.

These data confirm the data presented in Example 2.

Example 4

Evaluation of Positive Compounds by Hair Cell Differentiation

Inner ear stem cells were exposed to compound CP.-0000540, which was selected at random from the group of 110 positive compounds described in Example 2.

As shown in FIG. 121B, CP.-0000540 increased the number of cells that co-labeled with hair cell specific markers Math1-GFP and myosin 7a when compared to cells not exposed to compound CP.-0000540, as shown in FIG. 121A. Hair cell differentiation was increased to 5.1% of total cells compared to 1.6% for control.

Example 5

Stage Two Evaluation of Positive Compounds

All positive compounds were assessed for their ability to upregulate Math1 mRNA to confirm the observations made in Example 2.

Math1 mRNA expression levels were analyzed using RT-PCR as described in Example 3.

Example 6

Stage Three Evaluation of Positive Compounds

Positive compounds were assessed for their ability to increase the yield of hair cells from mouse inner ear derived stem cells. Positive compounds are also assessed in vivo in the inner ear of a sensorineural disease mouse model.

Isolated cells were exposed to 0.1, 1, and 5 µM of each positive compound identified in Examples 3, 4, and 5 in vitro.

Compounds are also added to the inner ear of damaged inner ear mouse models, e.g., gentamycin treated mouse models and/or flox caspase transgenic mouse models. These models are used to test the compounds capacity to regenerate hair cells after their loss by toxin damage, as occurs in human deafness.

In vitro results were evaluated by detecting one or more of the hair cell specific markers myosin VIIa, Math1, espin, Brn3.1, F-actin (phalloidin), α-9-acetylcholine receptor, and/or p27kip1. Antibodies were incubate with cultured cells and detected by binding of secondary antibodies coupled to FITC or rhodamine. The fluorescence in individual cells was viewed using confocal microscopy and the percentage of positive cells quantified. The effect of the three different concentrations of each compound was also determined.

Cells are also subjected to physiological testing to identify channels that would be present in mature hair cells were (1) present and (2) active.

In vivo results are assessed at 4, 8, and 12 week time points. Hair cell regeneration is assessed using immunocytochemistry, as described above. Functional recovery is assessed using methods performed routinely in specialized suites for small animal physiology.

Example 7

Evaluation of Inner Ear Progenitor Cell Differentiation

A select number of positive compounds are assessed for their ability to promote differentiation of inner ear progenitor cells derived from bone marrow to hair cells.

Experiments are initially performed using bone marrow derived inner ear progenitor cells (e.g., mesenchymal stem cells (MSCs)), and a luciferase reporter construct in which luciferase expression is driven by a myosin VIII enhancer region and promoter. This is a strong promoter in hair cells. The myosin VIIa enhancer region and promoter was also operably linked to GFP. Positive results are confirmed using RT-PCR and immunocytochemistry using the methods described in Example 3-6, modified for myosin VIIa.

Example 8

Pharmacological Characterization of the Compounds

The half maximal inhibitory concentration ($IC_{50}$) and median lethal dose or Lethal Dose, 50% (LD50) were determined for each of the compounds identified in Example 2 using standard laboratory techniques. $IC_{50}$ is a measure of the effectiveness of a compound in inhibiting biological or biochemical function. LD50 is the amount of a compound required to kill half the members of a tested population.

$IC_{50}$ and LD50 values for each compound are shown in Table 2.

TABLE 2

| Compound | IC50 (µM) | Maximum (Fold DMSO) | LD50 (µM) |
| --- | --- | --- | --- |
| CP-0000477 | 2 | 2 | >30 |
| CP-0000489 | 0.1 | 2.1 | >30 |
| CP-0000540 | 1.3 | 2 | >30 |
| CP-0000550 | 0.03 | 2 | >30 |
| CP-0000553 | 0.01 | 2 | >30 |
| CP-0000554 | 0.4 | 2 | >30 |
| CP-0000557 | 0.02 | 2.6 | 30 |
| CP-0000571 | 0.3 | 2 | >30 |
| CP-0000928 | 0.3 | 2 | >10 |
| CP-0005186 | 1 | 1.8 | >10 |
| CP-0007991 | 0.6 | 2 | >10 |
| CP-0007994 | 1 | 1.9 | >10 |

TABLE 2-continued

| Compound | IC50 (µM) | Maximum (Fold DMSO) | LD50 (µM) |
|---|---|---|---|
| CP-0008545 | 0.4 | 2.5 | >10 |
| CP-0009883 | 2.5 | 2.3 | >10 |
| CP-0010539 | 0.5 | 2.1 | >10 |
| CP-0029278 | 0.5 | 1.9 | >10 |
| CP-0029300 | 1.6 | 2 | >10 |
| CP-0034360 | 1 | 2 | >10 |
| CP-0036187 | 1 | 2.3 | >10 |
| CP-0039073 | 1.5 | 2.4 | >10 |
| CP-0045061 | 3 | 1.9 | >10 |
| CP-0047659 | 1.3 | 2.3 | >10 |
| CP-0050095 | 1.5 | 2.6 | >10 |
| CP-0059547 | 1 | 2 | >10 |
| CP-0059563 | >10 | 1.9 | >10 |
| CP-0059642 | 1 | 2.2 | >10 |
| CP-0060729 | 0.2 | 1.6 | >10 |
| CP-0060852 | 2.5 | 1.8 | >10 |
| CP-0061401 | 0.6 | 1.8 | >10 |
| CP-0061566 | 0.2 | 2 | >10 |
| CP-0061777 | >10 | 2.1 | >10 |
| CP-0062030 | 2 | 1.6 | >10 |
| CP-0063182 | 0.2 | 1.7 | >10 |
| CP-0063375 | 2.2 | 1.9 | >10 |
| CP-0063508 | >10 | 1.7 | >10 |
| CP-0064231 | 1 | 1.5 | >10 |
| CP-0064314 | >10 | 1.7 | >10 |
| CP-0064917 | >10 | 2 | >10 |
| CP-0065665 | 0.8 | 1.7 | >10 |
| CP-0066751 | 1 | 1.9 | >10 |
| CP-0066829 | 1 | 1.8 | >10 |
| CP-0067108 | 3 | 1.8 | >10 |
| CP-0067233 | 2 | 1.8 | >10 |
| CP-0067246 | 1.8 | 1.5 | >10 |
| CP-0068395 | 3 | 1.6 | >10 |
| CP-0068577 | 1 | 1.6 | >10 |
| CP-0068929 | 0.4 | 2 | >10 |
| CP-0069934 | 2 | 1.7 | >10 |
| CP-0069961 | 2 | 1.7 | >10 |
| CP-0070164 | 1.6 | 1.7 | >10 |
| CP-0070367 | 2 | 1.7 | >10 |
| CP-0070844 | 2 | 1.7 | >10 |
| CP-0070871 | 3 | 2 | >10 |
| CP-0070886 | 1 | 2.1 | >10 |
| CP-0071862 | 0.7 | 1.8 | >10 |
| CP-0072036 | 1.5 | 1.7 | >10 |
| CP-0072092 | 1 | 1.7 | >10 |
| CP-0072096 | 6 | 2.2 | >10 |
| CP-0072156 | 2 | 2 | >10 |
| CP-0072253 | 1.3 | 2 | >10 |
| CP-0072271 | 1 | 2.2 | >10 |
| CP-0072720 | 3 | 1.8 | >10 |
| CP-0074806 | 0.7 | 1.8 | >10 |
| CP-0075627 | 8 | 2 | >10 |
| CP-0076627 | 5 | 2.2 | >10 |
| CP-0078448 | >10 | 1.9 | >10 |
| CP-0079810 | 3 | 2.3 | >10 |
| CP-0079983 | 3 | 1.8 | >10 |
| CP-0080276 | 0.3 | 2 | >10 |
| CP-0080773 | >10 | 2.2 | >10 |
| CP-0087336 | 0.08 | 2.2 | >10 |
| CP-0087799 | 1 | 2.1 | >10 |
| CP-0089966 | >10 | 2.2 | >10 |
| CP-0091818 | 0.9 | 2.1 | >10 |
| CP-0096433 | 3 | 2 | >10 |
| CP-0099289 | >10 | 1.6 | >10 |
| CP-0102404 | >10 | 1.6 | >10 |
| CP-0103978 | 1 | 2 | >10 |
| CP-0104765 | 0.4 | 2 | >10 |
| CP-0104766 | 3 | 3 | >10 |
| CP-0104904 | >10 | 2.2 | >10 |
| CP-0105343 | 3 | 2 | >10 |
| CP-0105777 | 0.3 | 2 | >10 |
| CP-0107060 | 0.1 | 2.2 | >10 |
| CP-0109953 | 0.1 | 1.8 | >10 |
| CP-0110352 | 0.05 | 1.8 | >10 |
| CP-0110644 | 1 | 1.8 | >10 |
| CP-0130586 | 0.5 | 2.2 | >10 |
| CP-0130665 | 0.3 | 2 | >10 |
| CP-0131763 | 2 | 2.4 | >10 |
| CP-0134381 | 2 | 2.2 | >10 |
| CP-0193184 | >10 | N/A | >30 |

Example 9

Characterization of Compounds Using Inner Ear Progenitor Cells Isolated from Mouse Cochlea Compounds identified by the methods described in Example 2 are tested for their ability to promote the differentiation of mouse inner ear progenitor cells isolated from mouse cochlea to hair cells.

Cochlear stem cells are isolated from Atoh1-nGFP mice, as previously described (Oshima et al., supra). As described above, these animals express a nuclear version of enhanced green fluorescent protein (GFP) when Atoh1 enhancer elements are activated (Chen et al. and Lumpkin et al., supra). Thus, cells obtained from these animals can be used to track the differentiation of inner ear progenitor cells to hair cells using fluorescence microscopy.

Briefly, inner ear progenitor cells are obtained at 1 to 3 days of age from second or third generation animals. Cells are then seeded at a density of 300 spheres per well (Oshima et al., J Assoc Res Otolaryngol 8:18-31, 2007, and Martinez-Monedero et al., J Neurobiol 66:319-331, 2008) and allowed to attached the surface of 6-well plates and cultured in the presence of growth factors. Cells cultured in DMEM medium containing N2 and B27, but without growth factors, are exposed to the compound and maintained in culture for 3-10 days. Cell differentiation is monitored by examining nuclear GFP expression green fluorescence from the Atoh1 reporter and by staining for the mature hair cell markers myosin VIIa and espin in cultures treated with the compound as compared to controls at 24, 72 m and 108 hour time points.

Positive results are confirmed using RT-PCR and immunocytochemistry using the methods described in Examples 3-6 and 7.

Example 10

Characterization of Compounds Using Mouse Organ of Corti Explants

Compounds identified in Example 2 are tested for their ability to promote new hair cell formation in mouse organ of corti explants.

Briefly, explants are prepared from an Atoh1-GFP mouse by dissection. Organs of corti are cultured on collagen coated plates, and cultured overnight in serum containing medium. Compounds are added to the cultures at the time of plating, as previously described (Shi et al., and Martinez-Monedero et al., supra). Cultures are maintained in DMEM containing B27 supplement (Invitrogen) for 3-10 days prior to analysis.

Hair cell formation arising from the epithelial cells in the cultures outside of the hair cells rows is monitored using quantitative immunohistochemistry using an automated system to detect the appearance of GFP-positive cells.

Example 11

Compound Optimization

Compounds are optimized to provide potency in the nanomolar range and reduced cytotoxicity.

Compounds are modified using the medicinal chemistry methods described above. Absorption, Distribution, Metabolism, and Excretion (ADME) studies are conducted to assess Log P determination, aqueous solubility assessments, mouse liver microsomal stability determinations, and plasma protein binding analyses, as described below.

The following tests are performed using compounds synthesized and purified to at least 95% as determined by 1H NMR. Additional analytical techniques (i.e. 13C NMR, IR, melting point, MS and/or elemental analysis) are also used to determine structure and purity. Optically pure materials are also assessed by chiral stationary-phase HPLC. Compound structures are assessed using 2-D NMR, and x-ray crystallography.

Compound Log P values are determined by adding 15 mL of compound stock solution (10 mM in DMSO) to 750 mL 1-octanol buffer (pH 7.4) in test tubes. 3 mL testosterone (50 mM in DMSO) is used as a control. The samples are rotated at room temperature for 1 hour before allowing samples to stand for 1 hour to allow separation of layers. 400 mL of each layer is removed and placed in separate containers. Serial dilutions of each sample in 50% aqueous methanol are then made. Standard curves of compound and testosterone were prepared using 50% aqueous methanol and samples are analyzed using LC/MS monitoring. The ratio of calculated concentration of test compound in each phase is calculated independently using the least dilute sample from each phase that falls within the standard curve for each of the two replicate experiments. Log P is calculated by taking the $Log_{10}$ of the average of the two calculated ratios.

Aqueous solubility assessments of the compounds is determined by combining a minimum of 1 mg of each test compound with 1 mL of 0.07 M $NaH_2PO_4$ buffer solution adjusted to pH 7.4. Samples are then shaken for 2 hours before being allowed to stand at room temperature for 12 hours. Samples are then filtered through a 0.45 micron nylon syringe filter saturated with the sample. The resulting filtrate is assayed (N=2) by LC/MS using electrospray ionization.

Compound chemical metabolic stability is determined using pooled mouse liver microsomes. Compounds combined with 1 mg/mL microsomal protein and 1 mM NADPH are incubated for 0, 15, 30 and 60 min. Testosterone and propanolol are used as positive controls. Compound and microsomes in the absence of NADPH are used as negative controls. Samples are quenched with acetonitrile and centrifuged for 10 min at 10,000 RPM to precipitate proteins. Sample supernatants are analyzed (N=3) using LC/MS. Standard curves are generated at four concentrations (100%, 30%, 10% and 3%) and the remaining test compound remaining is determined at four time points.

Plasma protein binding studies are performed by preparing solutions containing compound (5 m, 0.5% final DMSO concentration), buffer and 10% plasma (v/v in buffer). 96-well dialysis plates are assembled in which each well is divided in two by a semi-permeable cellulose membrane (molecular weight cut off 10,000). Buffer solutions are added to one side of the membrane and the plasma solution to the other side. The plates are then sealed and placed on an orbital shaker and incubated at 37° C. Standards prepared in plasma and buffer are incubated at 37° C. with the dialysis plate. Corresponding solutions for each compound are analyzed in cassettes by tandem mass spectrometry (LC-MS-MS). Each compound is tested in duplicate.

After equilibration, samples are taken from both sides of the membrane. Solutions for each batch of compounds are combined into two groups (plasma-free and plasma-containing) and cassette analyzed by LC-MS-MS using two sets of calibration standards for plasma-free (6 points) and plasma-containing solutions (7 points). Samples are quantified to determine the amount of compound bound using standard curves prepared in the equivalent matrix.

Example 12

In Vivo Pharmacokinetic, Toxicity, and Formulation Studies

Compounds are administered using intracerebroventricular (icv) injection to the mouse brain and dosing studies are performed to determine the maximal dose of the compound that can be administered via this route.

Pharmacokinetic studies are performed using intraperitoneal (IP) or intra-cochlear administration of 3 mg/kg compound to determine dosing and the concentration of the compound in the cochlea, the relevant tissue. Compound levels are measured in the plasma and cochlear tissue at nine time points spanning 24 hours.

Orally administered compounds are dissolved in a formulation such as 2% hydroxypropyl-beta-cyclodextrin at a concentration of 3 mg/kg body weight. Intra-cochlear administered compounds are administered as previously described (Chen et al., J. Neurosci. Methods, 150:67-73, 2006). Briefly, mice are anesthetized and a tube is inserted into a cochleostomy to provide access to the scala tympani. Compounds in solution are then delivered by a syringe pump at a flow rate of 1 µL per hour over a 6 hour time period. Surgical sites are then closed and the animals are tested at various time points.

Example 13

In Vivo Studies Using Animal Deafness Model

A 10-wk old mouse is exposed to octave-band (8-16 kHz) noise at ~116 dB SPL for 2 hours. In CBA/CaJ mice, this noise dose destroys the outer hair cells throughout the basal half of the cochlea and inner hair cells and supporting cells are destroyed in a more restricted region in the middle of the cochlea (Wang et al., J. Ass. Res. Otolaryngol., 3:248-268, 2002). Further, neurons begin to degenerate within 7 days in the regions in which inner hair cells are destroyed. Such mice are tested for ABRs and DPOAEs after a recovery period. Cochleas were dissected and subjected to immunostaining after cutting of frozen sections or whole mounts. Cell division is assessed in the animals by injecting BrdU and antibody staining frozen sections. Cell death is evaluated by TUNEL. The number of hair cells, supporting cells and spiral ganglion neurons were counted.

Noise treated mice are injected with compounds (1 mg/10 g body weight) one week after noise treatment. Samples are analyzed at 4, 8, 14, and 21 day time points and hair cell counts are performed for the entire length of the cochlear spiral.

Functional assessment is performed using measurements of amplitude versus level functions for DPOAE and ABR, as previously described (Kujawa and Liberman, J. Neurophysiol, 78:3095-3106, 1997; and Maison et al., J. Neurophysiol, 90:2941-2949, 2003).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

---

What is claimed is:

1. A method of treating a subject having a disorder resulting from loss of hair cells, comprising selecting the subject in need of treatment, and administering to the subject a therapeutically effective amount of a compound having the following formula:

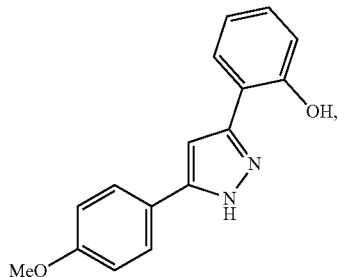 [SMILES: COc1ccc(-c2cc(-c3ccccc3O)n[nH]2)cc1]

wherein the disorder resulting from loss of hair cells is selected from the group consisting of sensorineural hearing loss, hearing impairment, deafness, and a vestibular disorder.

2. The method of claim 1, and wherein the compound is administered locally to the inner ear of the subject.

3. The method of claim 1, wherein the compound increases the number of cells in the subject's inner ear that have characteristics of auditory hair cells.

* * * * *

SEQUENCE LISTING

```
<160> NUMBER OF SEQ ID NOS: 1

<210> SEQ ID NO 1
<211> LENGTH: 6
<212> TYPE: DNA
<213> ORGANISM: Homo sapiens
<220> FEATURE:
<221> NAME/KEY: misc_feature
<222> LOCATION: 3, 4
<223> OTHER INFORMATION: n = A,T,C or G

<400> SEQUENCE: 1 canntg                                                              6
```